(12) United States Patent
Hirvelä et al.

(10) Patent No.: US 10,717,761 B2
(45) Date of Patent: Jul. 21, 2020

(54) THERAPEUTICALLY ACTIVE STEROIDAL DERIVATIVES

(71) Applicant: FORENDO PHARMA LTD, Turku (FI)

(72) Inventors: Leena Hirvelä, Oulu (FI); Marjo Hakola, Kempele (FI); Tero Linnanen, Kaarina (FI); Pasi Koskimies, Turku (FI); Camilla Stjernschantz, Turku (FI)

(73) Assignee: FORENDO PHARMA LTD, Turku (FI)

( * ) Notice: Subject to any disclaimer, the term of this patent is extended or adjusted under 35 U.S.C. 154(b) by 0 days.

(21) Appl. No.: 16/002,227

(22) Filed: Jun. 7, 2018

(65) Prior Publication Data

US 2018/0354984 A1    Dec. 13, 2018

(30) Foreign Application Priority Data

Jun. 8, 2017   (FI) .................................... 20175530

(51) Int. Cl.
| | | |
|---|---|---|
| *C07J 43/00* | (2006.01) | |
| *C07J 41/00* | (2006.01) | |
| *A61K 31/565* | (2006.01) | |
| *A61K 31/58* | (2006.01) | |
| *A61K 45/06* | (2006.01) | |

(52) U.S. Cl.
CPC ........... *C07J 43/003* (2013.01); *A61K 31/565* (2013.01); *A61K 31/58* (2013.01); *A61K 45/06* (2013.01); *C07J 41/0005* (2013.01); *C07J 41/0016* (2013.01); *C07J 41/0044* (2013.01)

(58) Field of Classification Search
None
See application file for complete search history.

(56) References Cited

U.S. PATENT DOCUMENTS

| 2006/0281710 A1 | 12/2006 | Messinger et al. |
| 2018/0265541 A1 | 9/2018 | Hirvelä et al. |

FOREIGN PATENT DOCUMENTS

| EP | 1 685 150 B1 | 9/2008 | |
|---|---|---|---|
| WO | WO 99/46279 | 9/1999 | |
| WO | WO 01/42181 A1 | 6/2001 | |
| WO | WO 03/022835 A1 | 3/2003 | |
| WO | WO 03/033487 A | 4/2003 | |
| WO | WO 04/046111 A1 | 6/2004 | |
| WO | WO 04/060488 A1 | 7/2004 | |
| WO | WO 04/085345 A2 | 10/2004 | |
| WO | WO 04/085457 A2 | 10/2004 | |
| WO | WO 04/089971 A1 | 10/2004 | |
| WO | WO 04/110459 A1 | 12/2004 | |
| WO | WO 05/032527 A2 | 4/2005 | |
| WO | WO 05/047303 A2 | 5/2005 | |
| WO | WO 05/084295 A2 | 9/2005 | |
| WO | WO 06/003012 A1 | 1/2006 | |
| WO | WO 06/003013 A2 | 1/2006 | |
| WO | WO 06/027347 A1 | 3/2006 | |
| WO | WO 06/125800 A1 | 11/2006 | |
| WO | WO 08/034796 A2 | 3/2008 | |
| WO | WO 08/065100 A1 | 6/2008 | |
| WO | WO 08/124922 A1 | 10/2008 | |
| WO | WO 10/059943 A2 | 5/2010 | |
| WO | WO 2012/129673 A1 | 10/2012 | |
| WO | WO 14/207309 A1 | 12/2014 | |
| WO | WO 14/207310 A1 | 12/2014 | |
| WO | WO 14/207311 A1 | 12/2014 | |
| WO | WO 2014/207310 | * 12/2014 | ............. C07J 43/00 |
| WO | WO 16/102776 A1 | 6/2016 | |

(Continued)

OTHER PUBLICATIONS

Das, U.N. (Journal of Inflammation Research, 2010:3, pp. 143-170).*
Hartung, H., et al., "What do we know about the mechanism of action of disease-modifying treatments in MS?" J. Neurol., vol. 251(suppl. 5), pp. V/12-V/29 (2004).*
Wang et al., J. Immunol. 2007, 179, pp. 5958-5965, See Introduction.*
International Search Report dated Dec. 12, 2018.
Furuya, Takeru et al., "Silver Mediated Fluorination of Functionalized Aryl Stannanes," JACS (2009), 131, pp. 1662-1663.

(Continued)

*Primary Examiner* — Alicia L Otton
(74) *Attorney, Agent, or Firm* — Barnes & Thornburg LLP

(57) ABSTRACT

The invention relates to compounds of formula (I) and pharmaceutically acceptable salts thereof

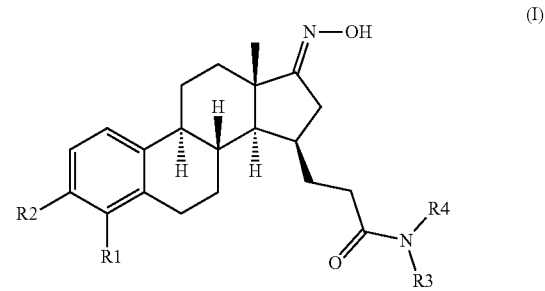

wherein R1 to R4 are as defined in the claims. The invention further relates to their use as inhibitors of 17β-HSD1 and in treatment or prevention of steroid hormone dependent diseases or disorders, such as steroid hormone dependent diseases or disorders requiring the inhibition of the 17β-HSD1 enzyme and/or requiring the lowering of the endogenous estradiol concentration. The present invention also relates to the preparation of the aforementioned compounds and to pharmaceutical compositions comprising as an active ingredient(s) one or more of the aforementioned compounds or pharmaceutically acceptable salts thereof.

20 Claims, No Drawings

(56) References Cited

FOREIGN PATENT DOCUMENTS

WO     WO 2016/102775 A1     6/2016

OTHER PUBLICATIONS

Horwitz, Jerome P. et al., "In Vitro Inhibition of Estrogen Sulfoconjugation by Some 2- and 4-Substituted Estra-1, 3,5(10)-trien-17β-ols[1a]," *J. Med. Chem.* 29 (1986), pp. 692-698.

Kobayashi, Toyoharu et al., "Synthetic study of marine diterpenoid aberrarone: stereocontrolled construction of tetracyclic framework," *Tetrahedron* 71 (2015), pp. 5918-5924.

Messinger, Josef et al., "Estrone C15 derivatives—a new class of 17β-hydroxysteroid dehydrogenase type 1 inhibitors", *Molecular and Cellular Endocrinology* 301 (2009), pp. 216-224.

Pan, Jun et al., "An Improved Palladium-Catalyzed Conversion of Aryl and Vinyl Triflates to Bromides and Chlorides," *Organic Letters* (2011), vol. 13, No. 18, pp. 4974-4976.

Poirier, Donald, "Inhibitors of 17β-Hydroxysteroid Dehydorgenases," *Current Medicinal Chemistry*, (2003), 10, pp. 453-477.

Poirier, Donald, "17β-Hydroxysteroid dehydrogenase inhibitors: a patent review," Expert Opin, Ther. Patents (2010), 20(9), pp. 1123-1145.

Puranen, Terhi J. et al., "Site-directed mutagenesis of the putative active site of human 17β-hydroxysteroid dehydrogenase type 1," Biochem. J. (1994), 304, pp. 289-293.

\* cited by examiner

THERAPEUTICALLY ACTIVE STEROIDAL DERIVATIVES

FIELD OF THE INVENTION

The present invention relates to novel steroidal C-15 derivatives, to their pharmaceutically acceptable salts, and their use in therapy. The invention further relates to pharmaceutical compositions comprising these compounds as active ingredients and to methods for their preparation.

BACKGROUND OF THE INVENTION

17β-hydroxysteroid dehydrogenases (17β-HSDs), also known as 17-ketosteroid reductases (17-KSR) are NAD(H)- and/or NAPD(H)-dependent alcohol oxidoreductase enzymes which catalyse the last and key step in formation of all estrogens and androgens. More specifically 17β-HSDs catalyse the dehydrogenation (oxidation) of 17-hydroxysteroids into corresponding 17-ketosteroids or hydrogenation (reduction) of inactive 17-ketosteroids into corresponding active 17-hydroxysteroids.

As both estrogens and androgens have the highest affinity for their receptors in the 17β-hydroxy form, the 17β-HSD/KSRs regulate the biological activity of the sex hormones. At present, 15 human members of 17β-HSDs have been described (type 1-15). Different types of 17β-HSD/KSRs differ in their substrate and cofactor specificities. The 17KSR activities convert low-activity precursors to more potent forms while 17β-HSD activities decrease the potency of estrogens and androgens and consequently may protect tissues from excessive hormone action.

Each type of 17β-HSD has a selective substrate affinity and a distinctive, although in some cases overlapping, tissue distribution.

Type 1 17β-hydroxysteroid dehydrogenase (17β-HSD1) is most abundantly expressed in the ovarian granulosa cells of the developing follicles in ovaries and in human placenta, both being estrogen biosynthetic tissues. In addition, 17β-HSD1 is expressed in estrogen target tissues, including breast, endometrium and bone. The human 17β-HSD1 is specific to estrogenic substrates and in vivo catalyzes the reduction of estrone to estradiol.

Type 2 17β-hydroxysteroid dehydrogenase (17β-HSD2) on the other hand converts estradiol, testosterone and 5a-dihydrotestrosterone to their less active forms estrone, androstenedione and 5a-androstanedione, respectively. Due to its wide and abundant expression in number of various estrogen and androgen target tissues, such as uterus, placenta, liver and the gastrointestinal and urinary tracts, it has been suggested that type 2 enzyme protects tissues from excessive steroid actions.

Estradiol (E2) is about 10 times as potent as estrone (E1) and about 80 times as potent as estratriol (E3) in its estrogenic effect. In contrast to certain other estrogens, estradiol binds well to both estrogen receptors ERα and ERβ, and thus regulates the expression of a variety of genes.

Although both 17β-HSD1 and 17β-HSD2 are present in healthy pre-menopausal humans, increased ratio of 17β-HSD1 to 17-HSD2 in the tumors of postmenopausal patients with hormone-dependent breast cancer has been shown in several studies. 17HSD1 gene amplification and loss of heterozygosity of 17HSD2 allele are potential mechanisms involved to increased reductive estrogen synthesis pathway in breast tumors. Increased ratio of type 1 enzyme to type 2 enzyme results in an increased level of estradiol that then promotes the proliferation of the cancerous tissue via the estrogen receptors (ER). High levels of estrogen thus support certain cancers such as breast cancer and cancer of the uterine lining i.e. endometrial cancer and uterine cancer.

Similarly it has been suggested that 17β-HSD2 is down-regulated in endometriosis while both aromatase and 17β-HSD1 are expressed or upregulated in comparison with normal endometrium. This again results in the presence of high concentration of estradiol (E2) which drives the proliferation of the tissue. Similar mechanism has been elucidated in uterine leiomyoma (uterine fibroids) and endometrial hyperplasia.

Reduction of the endogenous estradiol concentration in affected tissues will result in reduced or impaired proliferation of 17β-estradiol cells in said tissues and may thus be utilized in prevention and treatment of malign and benign estradiol dependent pathologies. Due to the proposed involvement of 17β-estradiol in a number of malign and benign pathologies, inhibitors of 17β-hydroxysteroid dehydrogenases, that can be used to impair endogenous production of estradiol from estrone, can have therapeutic value in the prevention or the treatment of such disorders or diseases are in great demand.

Some small-molecule inhibitors of 17β-HSD1 enzyme have been identified and reviewed in Poirier D. (2003) Curr Med Chem 10: 453-77 and Poirier D. (2010) Expert Opin. Ther. Patents 20(9): 1123-1145. Further, small molecule inhibitors of 17β-HSD's have been disclosed in WO 2001/42181, WO 2003/022835, WO 2003/033487, WO 2004/046111, WO 2004/060488, WO 2004/110459, WO 2005/032527, and WO 2005/084295.

WO2004/085457 discloses steroidal compounds capable of inhibiting 17β-hydroxysteroid dehydrogenase. WO2006/003012 discloses 2-substituted D-homo-estriene derivatives suitable for the treatment of estrogendependent diseases that can be influenced by the inhibition of the 17β-hydroxysteroid dehydrogenase type 1. Similarly WO2006/003013 presents 2-substituted estratrienones usable for preventing and treating estrogendependent diseases influenced by inhibiting 17β-hydroxysteroid dehydrogenase type 1.

15-substituted estradiol analogues acting as locally active estrogens are presented in WO2004/085345. WO2006/027347 discloses 15b-substituted estradiol derivatives having selective estrogenic activity for the treatment or prevention of estrogen receptor-related diseases and physiological conditions. Further, WO2005/047303 discloses 3,15 substituted estrone derivatives capable of inhibiting the 17β-hydroxysteroid dehydrogenase type 1.

International application WO2008/034796 relates to estratrien triazoles suitable for use in treatment and prevention of steroid hormone dependent diseases or disorders requiring the inhibition of a 17β-hydroxysteroid dehydrogenases such as 17β-HSD type 1, type 2 or type 3 enzyme. Inhibitors of 17β-HSD type 3 enzyme have been disclosed in WO99/46279.

International applications WO2014/207309, WO2014/207310 and WO2014/207311 relate to estrone C-15 thiazole derivatives, estrone C-17 ketimine C-15 thiazole derivatives and estradiol C-15 thiazole derivatives, respectively, as well as their use in therapy.

BRIEF DESCRIPTION OF THE INVENTION

An object of the present invention is to provide compounds useful in treating disorders and diseases associated with increased level of estradiol and/or treatable by inhibition of 17β-HSD1 enzyme. It is further an object of the present invention to provide compounds that show little or no inhibitory effect on 17β-HSD2 enzyme.

One of the problems associated with the known 17β-HSD1 inhibitors is the disposition, in particular the metabolic stability, of the compounds. It is therefore yet a further object of the present invention to provide compounds with improved metabolic stability.

One further problem associated with the known 17β-HSD1 inhibitors is the formation of conjugative metabolites and species selectivity of the compounds. It is therefore yet a further object of the present invention to provide compounds with improved properties in these parameters.

The present invention provides novel compounds of formula (I)

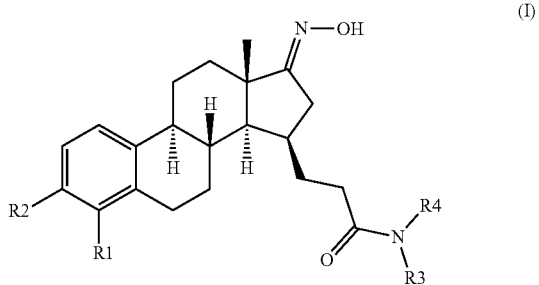

wherein R1 and R2 are each independently selected from the group consisting of H, and halogen;

(i) R3 is selected from the group consisting of H, and C1-3-alkyl, and

R4 is selected from the group consisting of

C1-3-alkyl, 4 to 6 membered unsubstituted saturated heterocycle comprising 1 heteroatom selected from the group consisting of nitrogen, sulfur, and oxygen, 5 membered partially unsaturated heterocycle comprising 1 nitrogen atom and optionally 1 to 2 further heteroatom(s) selected from the group consisting of nitrogen, sulfur, and oxygen, and being optionally substituted with one or two substituents selected from the group consisting of halogen, CN, C1-3-alkyl, C1-3-(per)haloalkyl, OH, C1-3-alkoxy, C(O)N(C1-3-alkyl)$_2$, and 6 membered saturated heterocycle comprising 1 to 2 heteroatom(s) independently selected from the group consisting of nitrogen, oxygen and sulfur and being optionally substituted with one or two substituent(s) independently selected from the group consisting of halogen, CN, C1-3-alkyl, C1-3-(per)haloalkyl, OH, and C1-3-alkoxy, 5 membered unsubstituted unsaturated or aromatic heterocycle comprising 1 nitrogen atom and 1 to 2 further heteroatom(s) independently selected from the group consisting of nitrogen, sulfur, and oxygen, 5 membered unsaturated or aromatic heterocycle comprising 1 nitrogen atom and optionally 1 to 2 further heteroatom(s) independently selected from the group consisting of nitrogen, and oxygen, and being optionally substituted with one or two substituent(s) independently selected from the group consisting of halogen, CN, C1-3-alkyl, C1-3-(per)haloalkyl, OH, C1-3-alkoxy, C(O)N(C1-3-alkyl)$_2$, and 6 membered saturated heterocycle containing 1 to 2 heteroatom(s) independently selected from the group consisting of nitrogen, oxygen and sulfur and being optionally substituted with one or two substituent(s) independently selected from the group consisting of halogen, CN, C1-3-alkyl, C1-3-(per)haloalkyl, OH, and C1-3-alkoxy, and 6 membered unsaturated or aromatic heterocycle comprising 1 nitrogen atom and optionally 1 to 2 further heteroatom(s) independently selected from the group consisting of nitrogen, sulfur, and oxygen, and being optionally substituted with one or two substituent(s) independently selected from the group consisting of halogen, CN, C1-3-alkyl, C1-3-(per)haloalkyl, OH, oxo, C1-3-alkoxy, C(O)N(C1-3-alkyl)$_2$, and 6 membered saturated heterocycle comprising 1 to 2 heteroatom(s) independently selected from the group consisting of nitrogen, oxygen and sulfur and being optionally substituted with one or two substituent(s) independently selected from the group consisting of halogen, CN, C1-3-alkyl, C1-3-(per)haloalkyl, OH, and C1-3-alkoxy, or two adjacent substituents may form a 5 or 6 membered saturated fused ring;

or (ii) R3 and R4 form together with the nitrogen atom they are attached to form a group selected from a 5 to 6 membered saturated heterocycle comprising said nitrogen atom and being optionally substituted with a substituent selected from the group consisting of halogen, CN, C1-3-alkyl, C1-3-(per)haloalkyl, OH, C1-3-alkoxy, and (CH$_2$)—C1-3-alkoxy; and an unsubstituted bicyclic spirocyclic or fused heterocycle containing said nitrogen atom and optionally 1 or 2 further heteroatom(s) selected from a group consisting of nitrogen, oxygen and sulfur;

and pharmaceutically acceptable salts thereof.

The present invention further provides compounds of formula (II)

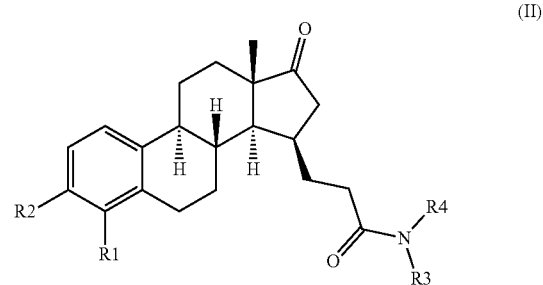

wherein R1, R2, R3 and R4 are as defined for compounds of formula (I) as starting materials for providing compound of formula (I), Compounds of formula (I) of the present invention may be useful in therapy, especially in the treatment or prevention of steroid hormone dependent diseases or disorders requiring the lowering of the endogenous estradiol concentration or the inhibition of 17β-HSD enzymes, in animals, in particular mammals, and humans. In particular, compounds of formula (I) represent inhibitors of the 17β-HSD1 enzyme, possessing pharmacological properties for the treatment and/or prophylaxis of steroid dependent diseases and conditions that include, but are not limited to, breast cancer, prostate carcinoma, ovarian cancer, uterine cancer, endometrial cancer, endometrial hyperplasia, endometriosis, uterine fibroids, adenomyosis, polycystic ovarian syndrome, dysmenorrhea, menorrhagia, metrorrhagia, contraception, prostadynia, benign prostatic hyperplasia, urinary dysfunction, lower urinary tract symptoms, chronic prostatitis/chronic pelvic pain syndrome (CP/CPPS), systemic lupus erythematosus (SLE), multiple sclerosis, obesity, rheumatoid arthritis, chronic obstructive pulmonary disease (COPD), lung cancer, colon cancer, tissue wounds, skin wrinkles and cataracts.

The compounds of formula (I) of the present invention typically have an inhibitory activity at the 17-β-HSD1 enzyme in the IC50 range of 0.1 nM to 1 μM. The inhibitory activity can be measured as explained in context of the experimental examples.

The invention also relates to pharmaceutical compositions comprising an effective amount of one or more compound(s) of formula (I).

Further the invention relates to a compound of formula (I) or a pharmaceutically acceptable salt thereof for use as a medicament.

The invention also relates to a compounds of formula (I) and pharmaceutically acceptable salts thereof for use in the treatment of estradiol dependent malign or benign diseases and disorders.

Finally the invention provides a method for the preparation of compounds of formula (I).

DETAILED DESCRIPTION OF THE INVENTION

Compounds of the invention contain steroidal core structure having a defined stereochemistry that is the natural configuration of estrogens.

Compounds of the invention bear a side chain at C15, which, together with the specific substitution pattern of the A ring, provides the inventive properties of the compounds of the present invention. Also, the C-17 carbonyl group of the native steroidal core may also be masked as a C-17 ketimine to further enhance the metabolic and/or inhibitory properties of the compounds of the present invention.

The term "halogen" as used herein and hereafter by itself or as part of other groups refers to the Group VIIa elements and includes F, Cl, Br and I groups.

The term "alkyl" as used herein and hereafter is an aliphatic linear, branched or cyclic, especially linear or branched, hydrocarbon group having the indicated number of carbon atoms, for example C1-6-alkyl has 1 to 6 carbon atoms in the alkyl moiety and thus, for example, C1-4-alkyl includes methyl, ethyl, n-propyl, isopropyl, n-butyl, sec-butyl, isobutyl, tert-butyl and C1-6-alkyl additionally includes branched and straight chain pentyl and hexyl.

The term "(per)haloalkyl" as used herein and hereafter refers to any of the above alkyl groups where one or more hydrogen atoms are replaced by halogen(s): in particular I, Br, F or Cl. Examples of haloalkyl groups include without limitation chloromethyl, fluoromethyl and —CH$_2$CF$_3$. The term "perhaloalkyl" is understood to refer to an alkyl group, in which all the hydrogen atoms are replaced by halogen atoms. Preferred examples include trifluoromethyl (—CF$_3$) and trichloromethyl (—CCl$_3$).

The term "C1-3-alkoxy" as used herein and hereafter refers to a —O—(C$_{1-3}$-alkyl) group where the "C$_{1-3}$-alkyl" has the above-defined meaning. Examples of preferred alkoxy groups include, but are not limited to, methoxy, ethoxy, and iso-propyloxy.

The term "6 membered saturated heterocycle containing 1 to 2 heteroatom(s) independently selected from the group consisting of nitrogen, oxygen and sulfur", refers to a monocyclic ring, which is saturated and has 4 to 6 ring atoms, and comprises 1 heteroatom selected from N, S and O while the remaining ring atoms are carbon atoms. It may be substituted with one or two substituent(s) as denoted, in particular one, at any suitable ring atom, including N.

Preferred substitutent groups include, but are not limited to halogen, in particular fluoro, CN, methoxy, and methyl.

The term "4 to 6 membered unsubstituted saturated heterocycle containing 1 heteroatom selected from the group consisting of nitrogen, sulfur, and oxygen", refers to a monocyclic ring, which is saturated and has 4 to 6 ring atoms, and comprises 1 heteroatom selected from N, S and O while the remaining ring atoms are carbon atoms. The ring is unsubstituted. Representing groups include oxetanyl, pyrrolidinyl, piperidinyl, and tetrahydropyranyl, in particular oxetanyl and tetrahydropyranyl.

The term "5 membered partially unsaturated heterocycle comprising 1 nitrogen atom and optionally 1 to 2 further heteroatom(s) selected from the group consisting of nitrogen, sulfur, and oxygen" refers to a monocyclic ring which is partially unsaturated with 5 ring atoms comprising at least one double bond between the ring atoms and containing 1 nitrogen atom and optionally 1 to 2 further heteroatom(s) selected from the group consisting of N, S and O, while the remaining ring atoms are carbon atoms. It may be substituted with one or two substituents as denoted, in particular one, at any suitable ring atom, including N. Preferred substitutent groups include, but are not limited to halogen, in particular fluoro, CN, methoxy, and methyl. Representing groups include dihydrothiazolyl.

The term "5 membered unsubstituted unsaturated or aromatic heterocycle containing 1 nitrogen atom and 1 to 2 further heteroatom(s) independently selected from the group consisting of nitrogen, sulfur, and oxygen" refers to a monocyclic ring with 5 ring atoms and which may be aromatic or unsaturated and which contains 1 nitrogen atom and 1 to 2 further heteroatom(s) independently selected from N, S and O, while the remaining ring atoms are carbon atoms. The ring is unsubstituted. Representing groups include thiadiazolyl.

The term "5 membered unsaturated or aromatic heterocycle" refers to a monocyclic ring with 5 ring atoms and which may be aromatic or unsaturated and comprises 1 nitrogen atom and optionally 1 to 2 further heteroatom(s) independently selected from the group consisting of N, and O, while the remaining ring atoms are carbon atoms. It may be substituted with one or two substituents as denoted, in particular one, at any suitable ring atom, including N. Preferred substitutent groups include, but are not limited to halogen, in particular fluoro, CN, methoxy, and methyl. Representing groups include oxazolyl and methyloxazolyl.

The term "6 membered unsaturated or aromatic heterocycle comprising 1 nitrogen atom and optionally 1 to 2 further heteroatom(s) independently selected from the group consisting of nitrogen, and oxygen" refers to a monocyclic ring with 6 ring atoms and which may be aromatic or unsaturated containing 1 nitrogen atom and optionally 1 to 2 further heteroatom(s) independently selected from the group consisting of N, S, and O, while the remaining ring atoms are carbon atoms. It may be substituted with one or two, preferably one, substituents as denoted, in particular one, at any suitable ring atom, including N. Preferred substitutent groups include, but are not limited to halogen, in particular fluoro, CN, methoxy, and methyl. Advantageously the substituent is at the para-position of the ring. Representing groups include pyridinyl, fluoropyridinyl, cyanopyridinyl, methylpyridinyl, dimethylpyridinyl, isopropylpyridinyl, hydroxypyridinyl, methoxypyridinyl, morpholinopyridinyl, methylpiperazinylpyridinyl, pyrazinyl, methylpyridazinyl, and methoxypyridazinyl; in particular fluoropyridinyl, methoxypyridinyl, methylpyridazinyl, and methoxypyridazinyl.

The term "a 5 to 6 membered saturated heterocycle comprising nitrogen atom", refers to a saturated monocyclic ring with 6 ring atoms and contains 1 nitrogen atom while the remaining ring atoms are carbon atoms. It may be substituted with one or two substituent(s) as denoted, in particular one, at any suitable ring atom, including N. Preferred substitutent groups include, but are not limited to halogen, in particular fluoro, CN, methoxy, and methyl. Representing groups include pyrrolidinyl, and methoxymethylpyrrolidinyl.

The term "an unsubstituted bicyclic spirocyclic or fused heterocycle comprising said nitrogen atom and optionally 1 or 2 further heteroatom(s) selected from a group consisting of nitrogen, oxygen and sulfur" refers to a bicyclic ring system where the rings may be joined together as a spirocyclic system or as a fused system, preferably as a spirocyclic system, and contains a nitrogen atom and optionally 1 or 2 further heteroatom(s) selected from N, O and S as indicated while the remaining ring atoms are carbon atoms. The ring system is unsubstituted. Representing groups include oxaazaspiro[4.5]decanyl.

The term "a 5 or 6 membered saturated fused ring" refers to a fused ring, which is saturated or partly unsaturated and adds 3 to 4, accordingly, additional ring atoms to the original ring into which is fused and optionally comprises 1 to 2 heteroatoms each independently selected from N, S and O while the remaining ring atoms are carbon atoms.

The term "optionally substituted" as used herein and hereafter in context of a phenyl group denotes phenyl that is either unsubstituted or substituted independently with one or more, in particular 1, 2, or 3, substituent(s) attached at any available atom to produce a stable compound, e.g. pyridinyl may be substituted once with a denoted substituent attached to any suitably position of the pyridinyl ring. In general "substituted" refers to a substituent group as defined herein in which one or more bonds to a hydrogen atom contained therein are replaced by a bond to a non-hydrogen atom unless otherwise denoted. In particular the substituent groups are each independently selected from the group consisting of halogen, in particular F; $C_{1-4}$-alkyl, in particular methyl; OH; $C_{1-4}$-alkoxy, in particular methoxy; and CN.

"Optional" or "optionally" denotes that the subsequently described event or circumstance may but need not occur, and that the description includes instances where the event or circumstance occurs and instances in which it does not. "Comprises" or "comprising" denotes that the subsequently described set may but need not include other elements.

The expression "pharmaceutically acceptable" represents being useful in the preparation a pharmaceutical composition that is generally safe, non-toxic, and neither biologically nor otherwise undesirable, and includes being useful for both veterinary use as well as human pharmaceutical use.

The expression "acid addition salt" includes any non-toxic organic and inorganic acid addition salts that compounds of formula (I) can form. Illustrative inorganic acids, which form suitable salts, include, but are not limited to, hydrogen chloride, hydrogen bromide, sulphuric and phosphoric acids. Illustrative organic acids, which form suitable salts, include, but are not limited to, acetic acid, lactic acid, malonic acid, succinic acid, glutaric acid, fumaric acid, malic acid, tartaric acid, citric acid, ascorbic acid, maleic acid, benzoic acid, phenylacetic acid, cinnamic acid, methane sulfonic acid, salicylic acid, and the like. The term "acid addition salt" as used herein also comprises solvates which the compounds and salts thereof are able to form, such as, for example, hydrates, alcoholates, and the like. These salts also include salts useful for the chiral resolution of racemates.

The expression "base addition salt" includes any non-toxic base addition salts that the compound of formula (I) can form. Suitable base salts include, but are not limited to, those derived from inorganic bases such as aluminum, ammonium, calcium, copper, iron, lithium, magnesium, manganese, potassium, sodium, and zinc salts, in particular sodium and ammonium salts. Further examples of organic base addition salt include salts of trialkylamines, such as triethyl amine and trimethyl amine, and choline salts.

The present invention relates to novel compounds of formula (I)

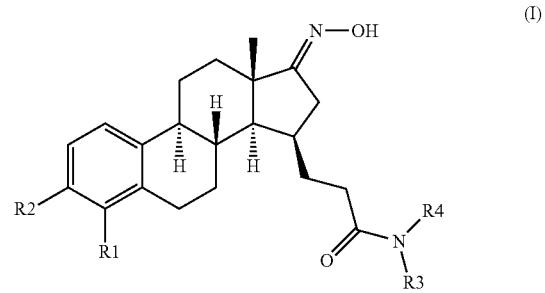

wherein R1 and R2 are each independently selected from the group consisting of H, and halogen;

(i) R3 is selected from the group consisting of H, and C1-3-alkyl; and

R4 is selected from the group consisting of

C1-3-alkyl, 4 to 6 membered unsubstituted saturated heterocycle comprising 1 heteroatom selected from the group consisting of nitrogen, sulfur, and oxygen, 5 membered partially unsaturated heterocycle comprising 1 nitrogen atom and optionally 1 to 2 further heteroatom(s) selected from the group consisting of nitrogen, sulfur, and oxygen, and being optionally substituted with one or two substituents selected from the group consisting of halogen, CN, C1-3-alkyl, C1-3-(per)haloalkyl, OH, C1-3-alkoxy, C(O)N(C1-3-alkyl)$_2$, and 6 membered saturated heterocycle comprising 1 to 2 heteroatom(s) independently selected from the group consisting of nitrogen, oxygen and sulfur and being optionally substituted with one or two substituent(s) independently selected from the group consisting of halogen, CN, C1-3-alkyl, C1-3-(per)haloalkyl, OH, and C1-3-alkoxy, 5 membered unsubstituted unsaturated or aromatic heterocycle comprising 1 nitrogen atom and 1 to 2 further heteroatom(s) independently selected from the group consisting of nitrogen, sulfur, and oxygen, 5 membered unsaturated or aromatic heterocycle comprising 1 nitrogen atom and optionally 1 to 2 further heteroatom(s) independently selected from the group consisting of nitrogen, and oxygen, and being optionally substituted with one or two substituent(s) independently selected from the group consisting of halogen, CN, C1-3-alkyl, C1-3-(per)haloalkyl, OH, C1-3-alkoxy, C(O)N(C1-3-alkyl)$_2$, and 6 membered saturated heterocycle containing 1 to 2 heteroatom(s) independently selected from the group consisting of nitrogen, oxygen and sulfur and being optionally substituted with one or two substituent(s) independently selected from the group consisting of halogen, CN, C1-3-alkyl, C1-3-(per) haloalkyl, OH, and C1-3-alkoxy, and 6 membered unsaturated or aromatic heterocycle comprising 1 nitrogen atom and optionally 1 to 2 further heteroatom(s) independently selected from the group consisting of nitrogen, sulfur, and oxygen, and being optionally substituted with one or two substituent(s) independently selected from the group consisting of halogen, CN, C1-3-alkyl, C1-3-(per)haloalkyl, OH, oxo, C1-3-alkoxy, C(O)N (C1-3-alkyl)$_2$, and 6 membered saturated heterocycle comprising 1 to 2 heteroatom(s) independently selected from the group consisting of nitrogen, oxygen and sulfur and being optionally substituted with one or two substituent(s) independently selected from the group consisting of halogen, CN, C1-3-alkyl, C1-3-(per)haloalkyl, OH, and C1-3-alkoxy, or two adjacent substituents may form a 5 or 6 membered saturated fused ring;

or (ii) R3 and R4 form together with the nitrogen atom they are attached to form a group selected from a 5 to 6 membered saturated heterocycle comprising said nitrogen atom and being optionally substituted with a substituent selected from the group consisting of halogen, CN, C1-3-alkyl, C1-3-(per)haloalkyl, OH, C1-3-alkoxy, and (CH$_2$)—C1-3-alkoxy; and an unsubstituted bicyclic spirocyclic or fused heterocycle containing said nitrogen atom and optionally 1 or 2 further heteroatom(s) selected from a group consisting of nitrogen, oxygen and sulfur;

and pharmaceutically acceptable salts thereof.

In the compounds of the present invention the C-17 carbonyl group of the native estrone core may is masked as a C-17 ketimine to enhance the metabolic and/or inhibitory properties of the compounds of formula (I) of the present invention.

The desirably active compounds of the present invention can be readily made from the respective compound bearing the C-17 carbonyl group of the native estrone core. Accordingly provided herein are compounds of formula (II)

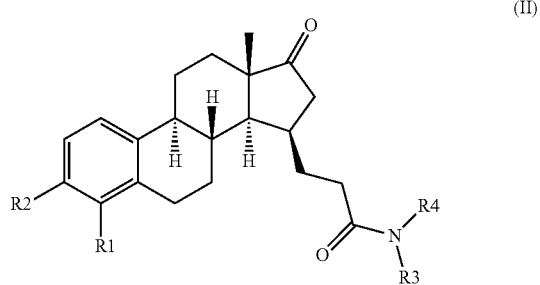

(II)

wherein R1, R2, R3 and R4 are as defined for compounds of formula (I). These compounds are direct starting materials for the preparation of compounds of formula (I). Accordingly the below presented examples of substituents R1 to R4 of compounds of formula (I) apply for compounds of formula (II) as well.

Selection of the substituents of the A ring, that is substituents R1 and R2, is particularly important for attaining the desired properties of the compounds of the present invention.

In first example of the present invention R1 and R2 are each independently selected from the group consisting of H, F and Cl, preferably F and Cl. In second example of the present invention one of R1 and R2 is H and the other is F or Cl, preferably F. In a third example of the present invention both R1 and R are H.

Thus in a further example of compounds of formula (I) of the present invention R1 is as defined above, particularly halogen, preferably F or Cl, more preferably F, and R2 is H. In an alternative example of the present invention R1 is H and R2 is as defined above, particularly halogen, preferably F or Cl, more preferably F.

Accordingly the present invention provides compounds of formula (Ia)

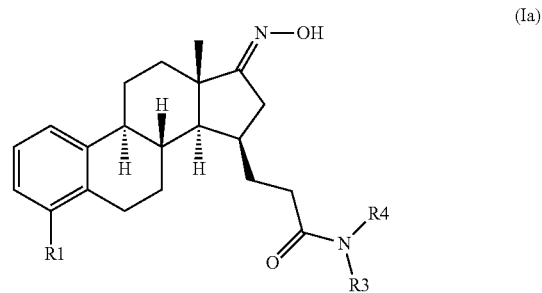

(Ia)

wherein R1, R3, and R4 are as defined above.

Furthermore, selection of the substituents R3 and R4 is particularly important for attaining the desired properties of the compounds of the present invention.

In an aspect of the present invention R3 is H or methyl, in particular H, and R4 is selected from a group consisting of 5 membered unsubstituted unsaturated or aromatic heterocycle comprising 1 nitrogen atom and 1 to 2 further heteroatom(s) independently selected from the group consisting of nitrogen, sulfur, and oxygen, 5 membered unsaturated or aromatic heterocycle comprising 1 nitrogen atom and optionally 1 to 2 further heteroatom(s) independently selected from the group consisting of nitrogen, and oxygen, and being optionally substituted with one or two substituent(s) independently selected from the group consisting of halogen, CN, C1-3-alkyl, C1-3-(per) haloalkyl, OH, C1-3-alkoxy, C(O)N(C1-3-alkyl)$_2$, and 6 membered saturated heterocycle containing 1 to 2 heteroatom(s) independently selected from the group consisting of nitrogen, oxygen and sulfur and being optionally substituted with one or two substituent(s) independently selected from the group consisting of halogen, CN, C1-3-alkyl, C1-3-(per) haloalkyl, OH, and C1-3-alkoxy, and 6 membered unsaturated or aromatic heterocycle comprising 1 nitrogen atom and optionally 1 to 2 further heteroatom(s) independently selected from the group consisting of nitrogen, sulfur, and oxygen, and being optionally substituted with one or two substituent(s) independently selected from the group consisting of halogen, CN, C1-3-alkyl, C1-3-(per)haloalkyl, OH, oxo, C1-3-alkoxy, C(O)N (C1-3-alkyl)$_2$, and 6 membered saturated heterocycle comprising 1 to 2 heteroatom(s) independently selected from the group consisting of nitrogen, oxygen and sulfur and being optionally substituted with one or two substituent(s) independently selected from the group consisting of halogen, CN, C1-3-alkyl, C1-3-(per)haloalkyl, OH, and C1-3-alkoxy, or two adjacent substituents may form a 5 or 6 membered saturated fused ring.

In a further aspect of the present invention R3 is H or methyl, in particular H, and R4 is selected from the group consisting of oxetanyl, pyrrolidinyl, piperidinyl, tetrahydropyranyl, dihydrothiazolyl, thiadiazolyl, oxazolyl, methyloxazolyl, pyridinyl, fluoropyridinyl, cyanopyridinyl, methylpyridinyl, dimethylpyridinyl, isopropylpyridinyl, hydroxypyridinyl, methoxypyridinyl, morpholinopyridinyl, methylpiperazinylpyridinyl, pyrazinyl, methylpyridazinyl, and methoxypyridazinyl; in particular from the group consisting of oxetanyl and tetrahydropyranyl, dihydrothiazolyl, thiadiazolyl, oxazolyl, methyloxazolyl, fluoropyridinyl, methoxypyridinyl, methylpyridazinyl, and methoxypyridazinyl.

In an alternative aspect of the present invention R3 and R4 form together with the nitrogen they are attached to a ring selected from the group consisting of pyrrolidinyl, and methoxymethylpyrrolidinyl, and oxaazaspiro[4.5]decanyl.

In a particular aspect of compounds of formula (Ia),
R1 is halogen, preferably F;
R3 is H, and
R4 is selected from the group consisting of 5 membered unsubstituted unsaturated or aromatic heterocycle comprising 1 nitrogen atom and 1 to 2 further heteroatom(s) independently selected from the group consisting of nitrogen, sulfur, and oxygen, 5 membered unsaturated or aromatic heterocycle comprising 1 nitrogen atom and optionally 1 to 2 further heteroatom(s) independently selected from the group consisting of nitrogen, and oxygen, and being optionally substituted with one or two substituent(s) independently selected from the group consisting of halogen, CN, C1-3-alkyl, C1-3-(per)haloalkyl, OH, C1-3-alkoxy, C(O)N(C1-3-alkyl)$_2$, and 6 membered saturated heterocycle containing 1 to 2 heteroatom(s) independently selected from the group consisting of nitrogen, oxygen and sulfur and being optionally substituted with one or two substituent(s) independently selected from the group consisting of halogen, CN, C1-3-alkyl, C1-3-(per)haloalkyl, OH, and C1-3-alkoxy, and 6 membered unsaturated or aromatic heterocycle comprising 1 nitrogen atom and optionally 1 to 2 further heteroatom(s) independently selected from the group consisting of nitrogen, sulfur, and oxygen, and being optionally substituted with one or two substituent(s) independently selected from the group consisting of halogen, CN, C1-3-alkyl, C1-3-(per)haloalkyl, OH, oxo, C1-3-alkoxy, C(O)N(C1-3-alkyl)$_2$, and 6 membered saturated heterocycle comprising 1 to 2 heteroatom(s) independently selected from the group consisting of nitrogen, oxygen and sulfur and being optionally substituted with one or two substituent(s) independently selected from the group consisting of halogen, CN, C1-3-alkyl, C1-3-(per)haloalkyl, OH, and C1-3-alkoxy, or two adjacent substituents may form a 5 or 6 membered saturated fused ring;

and pharmaceutically acceptable salts thereof.

The present invention accordingly provides compounds of formula (I) wherein R2 and R3 are H, and the compounds have formula (Ib)

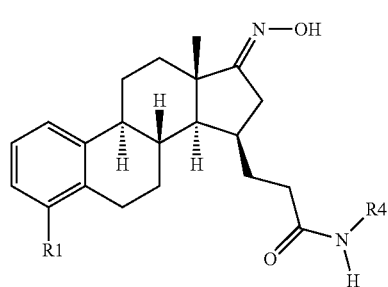

(Ib)

wherein R1 and R4 are as defined above.

In examples of compounds of formula (I), (Ia) and (Ib) R4 is a 6 membered aromatic heterocycle of formula (A

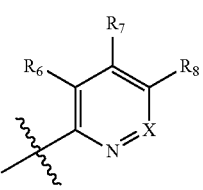

(A)

wherein
X is CR9 or N;
one of R6, R7, R8 is H, and the others are independently selected from a group consisting of H, halogen, CN, C1-3-alkyl, C1-3-(per)haloalkyl, OH, C1-3-alkoxy, and morpholine ring; and
R9 is H or C1-3-alkyl.

In a particularly advantageous aspect of the present invention R4 is a 6 membered aromatic heterocycle of formula (A), wherein R6 and R7 are both H and has the formula (B)

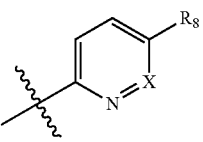

(B)

wherein
X is CH or N, preferably CH; and
R8 is selected from a group consisting of H, halogen, CN, C1-3-alkyl, C1-3-(per)haloalkyl, OH, C1-3-alkoxy, and morpholine ring.

In one aspect R8 is selected from a group consisting of halogen, preferably F, methyl, methoxy. Most preferably R8 is F.

In another examples of compounds of formula (I), (Ia) and (Ib) R4 is a 6 membered aromatic heterocycle of formula (B), wherein R6 and R8 are both H and has the formula (C)

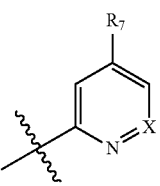

(C)

wherein
X is CH or N, preferably CH; and
R7 is selected from a group consisting of H, halogen, CN, C1-3-alkyl, C1-3-(per)haloalkyl, OH, C1-3-alkoxy, and morpholine ring.

In one aspect R7 is selected from a group consisting of halogen, preferably F, OH, methyl, methoxy. Most preferably R7 is methoxy and methyl.

In aspect further example of the present invention the compounds of formula (I) are those presented in Table 1.

In a typical example of the present invention the compounds of formula (I) are selected from the group consisting of:

3-((13S,15R,E)-4-fluoro-17-(hydroxyimino)-13-methyl-7,
8,9,11,12,13,14,15,16,17-decahydro-6H-cyclopenta[a]
phenanthren-15-yl)-N-(5-methylisoxazol-3-yl)propanamide;

3-((13S,15R,E)-4-fluoro-17-(hydroxyimino)-13-methyl-7,
8,9,11,12,13,14,15,16,17-decahydro-6H-cyclopenta[a]
phenanthren-15-yl)-N-(6-methoxypyridazin-3-yl)propanamide;

3-((13S,15R,E)-4-fluoro-17-(hydroxyimino)-13-methyl-7,
8,9,11,12,13,14,15,16,17-decahydro-6H-cyclopenta[a]
phenanthren-15-yl)-N-(5-methoxypyridin-2-yl)propanamide;

3-((13S,15R,E)-4-fluoro-17-(hydroxyimino)-13-methyl-7,
8,9,11,12,13,14,15,16,17-decahydro-6H-cyclopenta[a]
phenanthren-15-yl)-N-(5-fluoropyridin-2-yl)propanamide;

3-((13S,15R,E)-4-fluoro-17-(hydroxyimino)-13-methyl-7,
8,9,11,12,13,14,15,16,17-decahydro-6H-cyclopenta[a]
phenanthren-15-yl)-N-(oxetan-3-yl)propanamide;

3-((13S,15R,E)-4-fluoro-17-(hydroxyimino)-13-methyl-7,
8,9,11,12,13,14,15,16,17-decahydro-6H-cyclopenta[a]
phenanthren-15-yl)-N-methyl-(oxetan-3-yl)propanamide;

3-((13S,15R,E)-4-fluoro-17-(hydroxyimino)-13-methyl-7,
8,9,11,12,13,14,15,16,17-decahydro-6H-cyclopenta[a]
phenanthren-15-yl)-1-(pyrrolidin-1-yl)propan-1-one;

3-((13S,15R,E)-4-fluoro-17-(hydroxyimino)-13-methyl-7,
8,9,11,12,13,14,15,16,17-decahydro-6H-cyclopenta[a]
phenanthren-15-yl)-N-(6-methylpyridazin-3-yl)propanamide;

3-((13S,15R,E)-4-fluoro-17-(hydroxyimino)-13-methyl-7,
8,9,11,12,13,14,15,16,17-decahydro-6H-cyclopenta[a]
phenanthren-15-yl)-N-(1,3,4-thiadiazol-2-yl)propanamide;

3-((13S,15R,E)-4-fluoro-17-(hydroxyimino)-13-methyl-7,
8,9,10,11,12,13,14,15,16,17-decahydro-6H-cyclopenta
[a]phenanthren-15-yl)-N-(pyridazine-3-yl)propanamide;

N-(4,5-dihydrothiazol-2-yl)-3-((13S,15R,E)-4-fluoro-17-
(hydroxyimino)-13-methyl-7,8,9,11,12,13,14,15,16,17-
decahydro-6H-cyclopenta[a]phenanthren-15-yl)propanamide;

N,N-diethyl-3-((13S,15R,E)-4-fluoro-17-(hydroxyimino)-
13-methyl-7,8,9,11,12,13,14,15,16,17-decahydro-6H-cyclopenta[a]phenanthren-15-yl)propanamide;

3-((13S,15R,E)-3-fluoro-17-(hydroxyimino)-13-methyl-7,
8,9,11,12,13,14,15,16,17-decahydro-6H-cyclopenta[a]
phenanthren-15-yl)-N-(5-fluoropyridin-2-yl)propanamide;

3-((13S,15R,E)-3-fluoro-17-(hydroxyimino)-13-methyl-7,
8,9,11,12,13,14,15,16,17-decahydro-6H-cyclopenta[a]
phenanthren-15-yl)-N-(5-methoxypyridin-2-yl)propanamide;

3-((13S,15R,E)-3-fluoro-17-(hydroxyimino)-13-methyl-7,
8,9,11,12,13,14,15,16,17-decahydro-6H-cyclopenta[a]
phenanthren-15-yl)-N-(6-methoxypyridazin-3-yl)propanamide;

3-((13S,15R,E)-3-fluoro-17-(hydroxyimino)-13-methyl-7,
8,9,11,12,13,14,15,16,17-decahydro-6H-cyclopenta[a]
phenanthren-15-yl)-N-(6-methylpyridazin-3-yl)propanamide;

3-((13S,15R,E)-3-fluoro-17-(hydroxyimino)-13-methyl-7,
8,9,11,12,13,14,15,16,17-decahydro-6H-cyclopenta[a]
phenanthren-15-yl)-N-(pyridazin-3-yl)propanamide;

3-((13S,15R,E)-3-fluoro-17-(hydroxyimino)-13-methyl-7,
8,9,11,12,13,14,15,16,17-decahydro-6H-cyclopenta[a]
phenanthren-15-yl)-N-methyl-N-(oxetan-3-yl)propanamide;

3-((13S,15R,E)-3-fluoro-17-(hydroxyimino)-13-methyl-7,
8,9,11,12,13,14,15,16,17-decahydro-6H-cyclopenta[a]
phenanthren-15-yl)-N-(1,3,4-thiadiazol-2-yl)propanamide;

N,N-diethyl-3-((13S,15R,E)-3-fluoro-17-(hydroxyimino)-
13-methyl-7,8,9,11,12,13,14,15,16,17-decahydro-6H-cyclopenta[a]phenanthren-15-yl)propanamide;

3-((13S,15R,E)-3-fluoro-17-(hydroxyimino)-13-methyl-7,
8,9,11,12,13,14,15,16,17-decahydro-6H-cyclopenta[a]
phenanthren-15-yl)-N-(5-isopropylpyridin-2-yl)propanamide;

3-((13S,15R,E)-3-chloro-17-(hydroxyimino)-13-methyl-7,
8,9,11,12,13,14,15,16,17-decahydro-6H-cyclopenta[a]
phenanthren-15-yl)-N-(pyridazine-3-yl)propanamide;

3-((13S,15R,E)-3-chloro-17-(hydroxyimino)-13-methyl-7,
8,9,11,12,13,14,15,16,17-decahydro-6H-cyclopenta[a]
phenanthren-15-yl)-N-(4,5-dihydrothiazol-2-yl)propanamide;

3-((13S,15R,E)-3-chloro-17-(hydroxyimino)-13-methyl-7,
8,9,11,12,13,14,15,16,17-decahydro-6H-cyclopenta[a]
phenanthren-15-yl)-1-(8-oxa-2-azaspiro[4.5]decan-2-yl)
propan-1-one;

3-((13S,15R,E)-3-chloro-17-(hydroxyimino)-13-methyl-7,
8,9,11,12,13,14,15,16,17-decahydro-6H-cyclopenta[a]
phenanthren-15-yl)-N-(6-methoxypyridazin-3-yl)propanamide;

3-((13S,15R,E)-3-chloro-17-(hydroxyimino)-13-methyl-7,
8,9,11,12,13,14,15,16,17-decahydro-6H-cyclopenta[a]
phenanthren-15-yl)-N,N-diethylpropanamide;

3-((13S,15R,E)-3-chloro-17-(hydroxyimino)-13-methyl-7,
8,9,11,12,13,14,15,16,17-decahydro-6H-cyclopenta[a]
phenanthren-15-yl)-N-(5-methylisoxazol-3-yl)propanamide;

3-((13S,15R,E)-3-chloro-17-(hydroxyimino)-13-methyl-7,
8,9,11,12,13,14,15,16,17-decahydro-6H-cyclopenta[a]
phenanthren-15-yl)-N-(4-methoxypyridin-2-yl)propanamide;

3-((13S,15R,E)-3-chloro-17-(hydroxyimino)-13-methyl-7,
8,9,11,12,13,14,15,16,17-decahydro-6H-cyclopenta[a]
phenanthren-15-yl)-N-(5-fluoropyridin-2-yl)propanamide;

3-((13S,15R,E)-3-chloro-17-(hydroxyimino)-13-methyl-7,
8,9,11,12,13,14,15,16,17-decahydro-6H-cyclopenta[a]
phenanthren-15-yl)-N-(3-methylpyridin-2-yl)propanamide;

3-((13S,15R,E)-3-chloro-17-(hydroxyimino)-13-methyl-7,
8,9,11,12,13,14,15,16,17-decahydro-6H-cyclopenta[a]
phenanthren-15-yl)-N-(3-fluoropyridin-2-yl)propanamide;

3-((13S,15R,E)-3-chloro-17-(hydroxyimino)-13-methyl-7,
8,9,11,12,13,14,15,16,17-decahydro-6H-cyclopenta[a]
phenanthren-15-yl)-N-(5-methyloxazol-2-yl)propanamide;

3-((13S,15R,E)-3-chloro-17-(hydroxyimino)-13-methyl-7,
8,9,11,12,13,14,15,16,17-decahydro-6H-cyclopenta[a]
phenanthren-15-yl)-N-(5-methoxypyridin-2-yl)propanamide;

3-((13S,15R,E)-3-chloro-17-(hydroxyimino)-13-methyl-7,
8,9,11,12,13,14,15,16,17-decahydro-6H-cyclopenta[a]
phenanthren-15-yl)-N-(pyridin-2-yl)propanamide;

3-((13S,15R,E)-3-chloro-17-(hydroxyimino)-13-methyl-7,
8,9,11,12,13,14,15,16,17-decahydro-6H-cyclopenta[a]
phenanthren-15-yl)-N-(4-methylpyridin-2-yl)propanamide;

3-((13S,15R,E)-3-chloro-17-(hydroxyimino)-13-methyl-7,8,9,11,12,13,14,15,16,17-decahydro-6H-cyclopenta[a]phenanthren-15-yl)-N-(5-cyanopyridin-2-yl)propanamide;

3-((13S,15R,E)-3-chloro-17-(hydroxyimino)-13-methyl-7,8,9,11,12,13,14,15,16,17-decahydro-6H-cyclopenta[a]phenanthren-15-yl)-N-(pyrazin-2-yl)propanamide;

3-((13S,15R,E)-3-chloro-17-(hydroxyimino)-13-methyl-7,8,9,11,12,13,14,15,16,17-decahydro-6H-cyclopenta[a]phenanthren-15-yl)-N-(6-methylpyridazin-3-yl)propanamide;

3-((13S,15R,E)-3-chloro-17-(hydroxyimino)-13-methyl-7,8,9,11,12,13,14,15,16,17-decahydro-6H-cyclopenta[a]phenanthren-15-yl)-N-(5-morpholinopyridin-2-yl)propanamide;

3-((13S,15R,E)-17-(hydroxyimino)-13-methyl-7,8,9,11,12,13,14,15,16,17-decahydro-6H-cyclopenta[a]phenanthren-15-yl)-N-methyl-N-(tetrahydro-2H-pyran-4-yl)propanamide;

3-((13S,15R,E)-17-(hydroxyimino)-13-methyl-7,8,9,11,12,13,14,15,16,17-decahydro-6H-cyclopenta[a]phenanthren-15-yl)-N-(pyridazin-3-yl)propanamide;

3-((13S,15R,E)-17-(hydroxyimino)-13-methyl-7,8,9,11,12,13,14,15,16,17-decahydro-6H-cyclopenta[a]phenanthren-15-yl)-N-(5-methoxypyridin-2-yl)propanamide;

3-((13S,15R,E)-17-(hydroxyimino)-13-methyl-7,8,9,11,12,13,14,15,16,17-decahydro-6H-cyclopenta[a]phenanthren-15-yl)-N-(5-(4-methylpiperazin-1-yl)pyridin-2-yl)propanamide;

3-((13S,15R,E)-17-(hydroxyimino)-13-methyl-7,8,9,11,12,13,14,15,16,17-decahydro-6H-cyclopenta[a]phenanthren-15-yl)-N-(4-methylpyridin-2-yl)propanamide;

3-((13S,15R,E)-17-(hydroxyimino)-13-methyl-7,8,9,11,12,13,14,15,16,17-decahydro-6H-cyclopenta[a]phenanthren-15-yl)-N-(5-morpholinopyridin-2-yl)propanamide;

6-(3-((13S,15R,E)-17-(hydroxyimino)-13-methyl-7,8,9,11,12,13,14,15,16,17-decahydro-6H-cyclopenta[a]phenanthren-15-yl)propanamido)-N,N-dimethylnicotinamide;

3-((13S,15R,E)-17-(hydroxyimino)-13-methyl-7,8,9,11,12,13,14,15,16,17-decahydro-6H-cyclopenta[a]phenanthren-15-yl)-N-(2-oxo-1,2,5,6,7,8-hexahydroquinolin-3-yl)propanamide;

3-((13S,15R,E)-17-(hydroxyimino)-13-methyl-7,8,9,11,12,13,14,15,16,17-decahydro-6H-cyclopenta[a]phenanthren-15-yl)-N-(5-isopropylpyridin-2-yl)propanamide;

N-(5-fluoropyridin-2-yl)-3-((13S,15R,E)-17-(hydroxyimino)-13-methyl-7,8,9,11,12,13,14,15,16,17-decahydro-6H-cyclopenta[a]phenanthren-15-yl)propanamide;

N-(5-cyanopyridin-2-yl)-3-((13S,15R,E)-17-(hydroxyimino)-13-methyl-7,8,9,11,12,13,14,15,16,17-decahydro-6H-cyclopenta[a]phenanthren-15-yl)propanamide;

3-((13S,15R,E)-17-(hydroxyimino)-13-methyl-7,8,9,11,12,13,14,15,16,17-decahydro-6H-cyclopenta[a]phenanthren-15-yl)-N-(3-hydroxypyridin-2-yl)propanamide;

3-((13S,15R,E)-17-(hydroxyimino)-13-methyl-7,8,9,11,12,13,14,15,16,17-decahydro-6H-cyclopenta[a]phenanthren-15-yl)-N-(pyridin-2-yl)propanamide;

3-((13S,15R,E)-17-(hydroxyimino)-13-methyl-7,8,9,11,12,13,14,15,16,17-decahydro-6H-cyclopenta[a]phenanthren-15-yl)-N-(4-methoxypyridin-2-yl)propanamide;

3-((13S,15R,E)-17-(hydroxyimino)-13-methyl-7,8,9,11,12,13,14,15,16,17-decahydro-6H-cyclopenta[a]phenanthren-15-yl)-N-(5-methyloxazol-2-yl)propanamide;

3-((13S,15R,E)-17-(hydroxyimino)-13-methyl-7,8,9,11,12,13,14,15,16,17-decahydro-6H-cyclopenta[a]phenanthren-15-yl)-N-(5-methylisoxazol-3-yl)propanamide;

3-((13S,15R,E)-4-fluoro-17-(hydroxyimino)-13-methyl-7,8,9,11,12,13,14,15,16,17-decahydro-6H-cyclopenta[a]phenanthren-15-yl)-N-(5-isopropylpyridin-2-yl)propanamide;

3-((13S,15R,E)-4-fluoro-17-(hydroxyimino)-13-methyl-7,8,9,11,12,13,14,15,16,17-decahydro-6H-cyclopenta[a]phenanthren-15-yl)-N-(5-morpholinopyridin-2-yl)propanamide;

3-((13S,15R,E)-4-fluoro-17-(hydroxyimino)-13-methyl-7,8,9,11,12,13,14,15,16,17-decahydro-6H-cyclopenta[a]phenanthren-15-yl)-N-(5-(4-methylpiperazin-1-yl)pyridin-2-yl)propanamide;

3-((13S,15R,E)-4-fluoro-17-(hydroxyimino)-13-methyl-7,8,9,11,12,13,14,15,16,17-decahydro-6H-cyclopenta[a]phenanthren-15-yl)-N-methylpropanamide;

3-((13S,15R,E)-4-fluoro-17-(hydroxyimino)-13-methyl-7,8,9,11,12,13,14,15,16,17-decahydro-6H-cyclopenta[a]phenanthren-15-yl)-N,N-dimethylpropanamide;

3-((13S,15R,E)-4-fluoro-17-(hydroxyimino)-13-methyl-7,8,9,11,12,13,14,15,16,17-decahydro-6H-cyclopenta[a]phenanthren-15-yl)-N-(tetrahydro-2H-pyran-4-yl)propanamide;

N-Cyclohexyl-3-((13S,15R,E)-4-fluoro-17-(hydroxyimino)-13-methyl-7,8,9,11,12,13,14,15,16,17-decahydro-6H-cyclopenta[a]phenanthren-15-yl)propanamide;

3-((13S,15R,E)-4-fluoro-17-(hydroxyimino)-13-methyl-7,8,9,11,12,13,14,15,16,17-decahydro-6H-cyclopenta[a]phenanthren-15-yl)-N-(pyrazin-2-yl)propanamide;

3-((13S,15R,E)-4-fluoro-17-(hydroxyimino)-13-methyl-7,8,9,11,12,13,14,15,16,17-decahydro-6H-cyclopenta[a]phenanthren-15-yl)-1-(8-oxa-2-azaspiro[4.5]decan-2-yl)propan-1-one;

3-((13S,15R,E)-4-fluoro-17-(hydroxyimino)-13-methyl-7,8,9,11,12,13,14,15,16,17-decahydro-6H-cyclopenta[a]phenanthren-15-yl)-N-(4-methylpyridin-2-yl)propanamide;

3-((13S,15R,E)-4-fluoro-17-(hydroxyimino)-13-methyl-7,8,9,11,12,13,14,15,16,17-decahydro-6H-cyclopenta[a]phenanthren-15-yl)-N-(4-methoxypyridin-2-yl)propanamide;

3-((13S,15R,E)-3-fluoro-17-(hydroxyimino)-13-methyl-7,8,9,11,12,13,14,15,16,17-decahydro-6H-cyclopenta[a]phenanthren-15-yl)-N-(5-methylisoxazol-3-yl)propanamide;

3-((13S,15R,E)-4-fluoro-17-(hydroxyimino)-13-methyl-7,8,9,11,12,13,14,15,16,17-decahydro-6H-cyclopenta[a]phenanthren-15-yl)-1-morpholinopropan-1-one;

3-((13S,15R,E)-4-fluoro-17-(hydroxyimino)-13-methyl-7,8,9,11,12,13,14,15,16,17-decahydro-6H-cyclopenta[a]phenanthren-15-yl)-N-(pyridin-2-yl)propanamide;

3-((13S,15R,E)-4-fluoro-17-(hydroxyimino)-13-methyl-7,8,9,11,12,13,14,15,16,17-decahydro-6H-cyclopenta[a]phenanthren-15-yl)-N-(4-fluoropyridin-2-yl)propanamide;

3-((13S,15R,E)-4-fluoro-17-(hydroxyimino)-13-methyl-7,8,9,11,12,13,14,15,16,17-decahydro-6H-cyclopenta[a]phenanthren-15-yl)-N-(3-fluoropyridin-2-yl)propanamide;

3-((13S,15R,E)-4-fluoro-17-(hydroxyimino)-13-methyl-7,8,9,11,12,13,14,15,16,17-decahydro-6H-cyclopenta[a]phenanthren-15-yl)-N-(6-fluoropyridin-2-yl)propanamide;

N-(3,5-difluoropyridin-2-yl)-3-((13S,15R,E)-4-fluoro-17-(hydroxyimino)-13-methyl-7,8,9,11,12,13,14,15,16,17-decahydro-6H-cyclopenta[a]phenanthren-15-yl)propanamide;

N-(5-cyanopyridin-2-yl)-3-((13S,15R,E)-4-fluoro-17-(hydroxyimino)-13-methyl-7,8,9,11,12,13,14,15,16,17-decahydro-6H-cyclopenta[a]phenanthren-15-yl)propanamide;

3-((13S,15R,E)-3-fluoro-17-(hydroxyimino)-13-methyl-7,8,9,11,12,13,14,15,16,17-decahydro-6H-cyclopenta[a]phenanthren-15-yl)-N-(3-fluoropyridin-2-yl)propanamide;

N-(3,5-difluoropyridin-2-yl)-3-((13S,15R, E)-3-fluoro-17-(hydroxyimino)-13-methyl-7,8,9,11,12,13,14,15,16,17-decahydro-6H-cyclopenta[a]phenanthren-15-yl)propanamide;

3-((13S,15R,E)-3-fluoro-17-(hydroxyimino)-13-methyl-7,8,9,11,12,13,14,15,16,17-decahydro-6H-cyclopenta[a]phenanthren-15-yl)-N-(5-morpholinopyridin-2-yl)propanamide;

3-((13S,15R,E)-3-chloro-17-(hydroxyimino)-13-methyl-7,8,9,11,12,13,14,15,16,17-decahydro-6H-cyclopenta[a]phenanthren-15-yl)-N-(4-fluoropyridin-2-yl)propanamide;

N-(4-fluoropyridin-2-yl)-3-((13S,15R,E)-17-(hydroxyimino)-13-methyl-7,8,9,11,12,13,14,15,16,17-decahydro-6H-cyclopenta[a]phenanthren-15-yl)propanamide;

N-(3-fluoropyridin-2-yl)-3-((13S,15R,E)-17-(hydroxyimino)-13-methyl-7,8,9,11,12,13,14,15,16,17-decahydro-6H-cyclopenta[a]phenanthren-15-yl)propanamide;

3-((13S,15R,E)-3-chloro-17-(hydroxyimino)-13-methyl-7,8,9,11,12,13,14,15,16,17-decahydro-6H-cyclopenta[a]phenanthren-15-yl)-N-(3-fluoropyridin-2-yl)propanamide;

3-((13S,15R,E)-3-chloro-17-(hydroxyimino)-13-methyl-7,8,9,11,12,13,14,15,16,17-decahydro-6H-cyclopenta[a]phenanthren-15-yl)-N-(3,5-difluoropyridin-2-yl)propanamide;

N-(3,5-difluoropyridin-2-yl)-3-((13S,15R,E)-17-(hydroxyimino)-13-methyl-7,8,9,11,12,13,14,15,16,17-decahydro-6H-cyclopenta[a]phenanthren-15-yl)propanamide;

N-(6-fluoropyridin-2-yl)-3-((13S,15R,E)-17-(hydroxyimino)-13-methyl-7,8,9,11,12,13,14,15,16,17-decahydro-6H-cyclopenta[a]phenanthren-15-yl)propanamide;

3-((13S,15R,E)-3-chloro-17-(hydroxyimino)-13-methyl-7,8,9,11,12,13,14,15,16,17-decahydro-6H-cyclopenta[a]phenanthren-15-yl)-N-(6-fluoropyridin-2-yl)propanamide;

6-(3-((13S,15R,E)-3-chloro-17-(hydroxyimino)-13-methyl-7,8,9,11,12,13,14,15,16,17-decahydro-6H-cyclopenta[a]phenanthren-15-yl)propanamido)-N,N-dimethylnicotinamide;

3-((13S,15R,E)-3-chloro-17-(hydroxyimino)-13-methyl-7,8,9,11,12,13,14,15,16,17-decahydro-6H-cyclopenta[a]phenanthren-15-yl)-N-(2-oxo-1,2,5,6,7,8-hexahydroquinolin-3-yl)propanamide;

6-(3-((13S,15R,E)-4-fluoro-17-(hydroxyimino)-13-methyl-7,8,9,11,12,13,14,15,16,17-decahydro-6H-cyclopenta[a]phenanthren-15-yl)propanamido)-N,N-dimethylnicotinamide;

3-((13S,15R,E)-4-fluoro-17-(hydroxyimino)-13-methyl-7,8,9,11,12,13,14,15,16,17-decahydro-6H-cyclopenta[a]phenanthren-15-yl)-N-(2-oxo-1,2,5,6,7,8-hexahydroquinolin-3-yl)propanamide;

and pharmaceutically acceptable salts thereof.

In a preferred aspect of the present invention the compounds of formula (I) are selected from the group consisting of:

3-((13S,15R,E)-4-fluoro-17-(hydroxyimino)-13-methyl-7,8,9,11,12,13,14,15,16,17-decahydro-6H-cyclopenta[a]phenanthren-15-yl)-N-(5-methoxypyridin-2-yl)propanamide;

3-((13S,15R,E)-4-fluoro-17-(hydroxyimino)-13-methyl-7,8,9,11,12,13,14,15,16,17-decahydro-6H-cyclopenta[a]phenanthren-15-yl)-N-(5-fluoropyridin-2-yl)propanamide;

and pharmaceutically acceptable salts thereof.

In a particularly advantageous aspect of the present invention the compounds of formula (II) are selected from the group consisting of:

3-((13S,15R)-4-fluoro-13-methyl-17-oxo-7,8,9,11,12,13,14,15,16,17-decahydro-6H-cyclopenta[a]phenanthren-15-yl)-N-(5-methylisoxazol-3-yl)propanamide;

3-((13S,15R)-4-fluoro-13-methyl-17-oxo-7,8,9,11,12,13,14,15,16,17-decahydro-6H-cyclopenta[a]phenanthren-15-yl)-N-(6-methoxypyridazin-3-yl)propanamide;

3-((13S,15R)-4-fluoro-13-methyl-17-oxo-7,8,9,11,12,13,14,15,16,17-decahydro-6H-cyclopenta[a]phenanthren-15-yl)-N-(5-methoxypyridin-2-yl)propanamide;

3-((13S,15R)-4-fluoro-13-methyl-17-oxo-7,8,9,11,12,13,14,15,16,17-decahydro-6H-cyclopenta[a]phenanthren-15-yl)-N-(5-fluoropyridin-2-yl)propanamide;

3-((13S,15R)-4-fluoro-13-methyl-17-oxo-7,8,9,11,12,13,14,15,16,17-decahydro-6H-cyclopenta[a]phenanthren-15-yl)-N-(oxetan-3-yl)propanamide 3-((13S,15R)-4-fluoro-13-methyl-17-oxo-7,8,9,11,12,13,14,15,16,17-decahydro-6H-cyclopenta[a]phenanthren-15-yl)-N-methyl-(oxetan-3-yl)propanamide;

(13S,15R)-4-fluoro-13-methyl-15-(3-oxo-3-(pyrrolidin-1-yl)propyl)-6,7,8,9,11,12,13,14,15,16-decahydro-17H-cyclopenta[a]phenanthren-17-one 3-((13S,15R)-4-fluoro-13-methyl-17-oxo-7,8,9,11,12,13,14,15,16,17-decahydro-6H-cyclopenta[a]phenanthren-15-yl)-N-(6-methylpyridazin-3-yl)propanamide;

3-((13S,15R)-4-fluoro-13-methyl-17-oxo-7,8,9,11,12,13,14,15,16,17-decahydro-6H-cyclopenta[a]phenanthren-15-yl)-N-(1,3,4-thiadiazol-2-yl)propanamide;

N-(4,5-dihydrothiazol-2-yl)-3-((13S,15R)-4-fluoro-13-methyl-17-oxo-7,8,9,11,12,13,14,15,16,17-decahydro-6H-cyclopenta[a]phenanthren-15-yl)propanamide;

N,N-diethyl-3-((13S,15R)-4-fluoro-13-methyl-17-oxo-7,8,9,11,12,13,14,15,16,17-decahydro-6H-cyclopenta[a]phenanthren-15-yl)propanamide;

is 3-((13S,15R)-4-fluoro-13-methyl-17-oxo-7,8,9,11,12,13,14,15,16,17-decahydro-6H-cyclopenta[a]phenanthren-15-yl)-N-(5-isopropylpyridin-2-yl)propanamide;

3-((13S,15R)-4-fluoro-13-methyl-17-oxo-7,8,9,11,12,13,14,15,16,17-decahydro-6H-cyclopenta[a]phenanthren-15-yl)-N-(5-morpholinopyridin-2-yl)propanamide;

3-((13S,15R)-4-fluoro-13-methyl-17-oxo-7,8,9,11,12,13,14,15,16,17-decahydro-6H-cyclopenta[a]phenanthren-15-yl)-N-(5-(4-methylpiperazin-1-yl)pyridin-2-yl)propanamide;

3-((13S,15R)-4-fluoro-13-methyl-17-oxo-7,8,9,11,12,13,14,15,16,17-decahydro-6H-cyclopenta[a]phenanthren-15-yl)-N-methylpropanamide;

3-((13S,15R)-4-fluoro-13-methyl-17-oxo-7,8,9,11,12,13,14,15,16,17-decahydro-6H-cyclopenta[a]phenanthren-15-yl)-N,N-dimethylpropanamide;

3-((13S,15R)-4-fluoro-13-methyl-17-oxo-7,8,9,11,12,13,14,15,16,17-decahydro-6H-cyclopenta[a]phenanthren-15-yl)-N-(tetrahydro-2H-pyran-4-yl)propanamide;

N-cyclohexyl-3-((13S,15R)-4-fluoro-13-methyl-17-oxo-7,8,9,11,12,13,14,15,16,17-decahydro-6H-cyclopenta[a]phenanthren-15-yl)propanamide;

3-((13S,15R)-4-fluoro-13-methyl-17-oxo-7,8,9,11,12,13,14,15,16,17-decahydro-6H-cyclopenta[a]phenanthren-15-yl)-N-(pyrazin-2-yl)propanamide;

(13S,15R)-4-fluoro-13-methyl-15-(3-oxo-3-(8-oxa-2-azaspiro[4.5]decan-2-yl)propyl)-6,7,8,9,11,12,13,14,15,16-decahydro-17H-cyclopenta[a]phenanthren-17-one;
3-((13S,15R)-4-fluoro-13-methyl-17-oxo-7,8,9,11,12,13,14,15,16,17-decahydro-6H-cyclopenta[a]phenanthren-15-yl)-N-(4-methylpyridin-2-yl)propanamide;
3-((13S,15R)-4-fluoro-13-methyl-17-oxo-7,8,9,11,12,13,14,15,16,17-decahydro-6H-cyclopenta[a]phenanthren-15-yl)-N-(4-methoxypyridin-2-yl)propanamide;
3-((13S,15R)-3-fluoro-13-methyl-17-oxo-7,8,9,11,12,13,14,15,16,17-decahydro-6H-cyclopenta[a]phenanthren-15-yl)-N-(5-methylisoxazol-3-yl)propanamide;
(13S,15R)-4-fluoro-13-methyl-15-(3-morpholino-3-oxopropyl)-6,7,8,9,11,12,13,14,15,16-decahydro-17H-cyclopenta[a]phenanthren-17-one;
is 3-((13S,15R)-4-fluoro-13-methyl-17-oxo-7,8,9,11,12,13,14,15,16,17-decahydro-6H-cyclopenta[a]phenanthren-15-yl)-N-(pyridin-2-yl)propanamide;
3-((13S,15R)-4-fluoro-13-methyl-17-oxo-7,8,9,11,12,13,14,15,16,17-decahydro-6H-cyclopenta[a]phenanthren-15-yl)-N-(4-fluoropyridin-2-yl)propanamide;
3-((13S,15R)-4-fluoro-13-methyl-17-oxo-7,8,9,11,12,13,14,15,16,17-decahydro-6H-cyclopenta[a]phenanthren-15-yl)-N-(3-fluoropyridin-2-yl)propanamide;
3-((13S,15R)-4-fluoro-13-methyl-17-oxo-7,8,9,11,12,13,14,15,16,17-decahydro-6H-cyclopenta[a]phenanthren-15-yl)-N-(6-fluoropyridin-2-yl)propanamide;
N-(3,5-difluoropyridin-2-yl)-3-((13S,15R)-4-fluoro-13-methyl-17-oxo-7,8,9,11,12,13,14,15,16,17-decahydro-6H-cyclopenta[a]phenanthren-15-yl)propanamide;
N-(5-cyanopyridin-2-yl)-3-((13S,15R)-4-fluoro-13-methyl-17-oxo-7,8,9,11,12,13,14,15,16,17-decahydro-6H-cyclopenta[a]phenanthren-15-yl)propanamide;
3-((13S,15R)-3-fluoro-13-methyl-17-oxo-7,8,9,11,12,13,14,15,16,17-decahydro-6H-cyclopenta[a]phenanthren-15-yl)-N-(3-fluoropyridin-2-yl)propanamide;
N-(3,5-difluoropyridin-2-yl)-3-((13S,15R)-3-fluoro-13-methyl-17-oxo-7,8,9,11,12,13,14,15,16,17-decahydro-6H-cyclopenta[a]phenanthren-15-yl)propanamide;
3-((13S,15R)-3-fluoro-13-methyl-17-oxo-7,8,9,11,12,13,14,15,16,17-decahydro-6H-cyclopenta[a]phenanthren-15-yl)-N-(5-morpholinopyridin-2-yl)propanamide;
3-((13S,15R)-3-chloro-13-methyl-17-oxo-7,8,9,11,12,13,14,15,16,17-decahydro-6H-cyclopenta[a]phenanthren-15-yl)-N-(4-fluoropyridin-2-yl)propanamide;
N-(4-fluoropyridin-2-yl)-3-((13S,15R)-13-methyl-17-oxo-7,8,9,11,12,13,14,15,16,17-decahydro-6H-cyclopenta[a]phenanthren-15-yl)propanamide;
N-(3-fluoropyridin-2-yl)-3-((13S,15R)-13-methyl-17-oxo-7,8,9,11,12,13,14,15,16,17-decahydro-6H-cyclopenta[a]phenanthren-15-yl)propanamide;
3-((13S,15R)-3-chloro-13-methyl-17-oxo-7,8,9,11,12,13,14,15,16,17-decahydro-6H-cyclopenta[a]phenanthren-15-yl)-N-(3-fluoropyridin-2-yl)propanamide;
3-((13S,15R)-3-chloro-13-methyl-17-oxo-7,8,9,11,12,13,14,15,16,17-decahydro-6H-cyclopenta[a]phenanthren-15-yl)-N-(3,5-difluoropyridin-2-yl)propanamide;
N-(3,5-difluoropyridin-2-yl)-3-((13S,15R)-13-methyl-17-oxo-7,8,9,11,12,13,14,15,16,17-decahydro-6H-cyclopenta[a]phenanthren-15-yl)propanamide;
N-(6-fluoropyridin-2-yl)-3-((13S,15R)-13-methyl-17-oxo-7,8,9,11,12,13,14,15,16,17-decahydro-6H-cyclopenta[a]phenanthren-15-yl)propanamide;
3-((13S,15R)-3-chloro-13-methyl-17-oxo-7,8,9,11,12,13,14,15,16,17-decahydro-6H-cyclopenta[a]phenanthren-15-yl)-N-(6-fluoropyridin-2-yl)propanamide;
6-(3-((13S,15R)-3-chloro-13-methyl-17-oxo-7,8,9,11,12,13,14,15,16,17-decahydro-6H-cyclopenta[a]phenanthren-15-yl)propanamido)-N,N-dimethylnicotinamide;
3-((13S,15R)-3-chloro-13-methyl-17-oxo-7,8,9,11,12,13,14,15,16,17-decahydro-6H-cyclopenta[a]phenanthren-15-yl)-N-(2-oxo-1,2,5,6,7,8-hexahydroquinolin-3-yl)propanamide;
6-(3-((13S,15R)-4-fluoro-13-methyl-17-oxo-7,8,9,11,12,13,14,15,16,17-decahydro-6H-cyclopenta[a]phenanthren-15-yl)propanamido)-N,N-dimethylnicotinamide;
3-((13S,15R)-4-fluoro-13-methyl-17-oxo-7,8,9,11,12,13,14,15,16,17-decahydro-6H-cyclopenta[a]phenanthren-15-yl)-N-(2-oxo-1,2,5,6,7,8-hexahydroquinolin-3-yl)propanamide;
and pharmaceutically acceptable salts thereof.

The invention further relates to a method for the preparation of a compound of the present invention, comprising the steps of:

reacting a compound of formula (III)

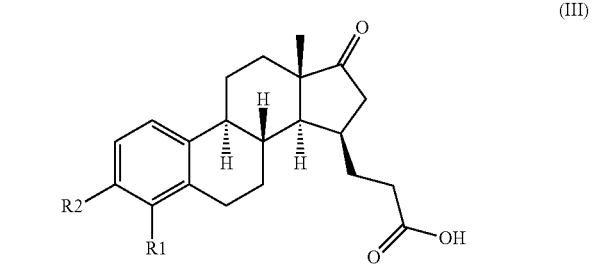

(III)

wherein R1 and R2 are each independently selected from the group consisting of H, and halogen;
with compound of formula (IV)

NR3R4     (IV)

wherein R3 and R4 are as defined for compound of formula (I),
in the presence of amide bond forming reagents, in particular $T_3P$ and a base, preferably pyridine,
to obtain a compound of formula (II), and reacting the obtained compound with

NH$_2$—OH     (V)

or hydrogen halide thereof,
in the presence of a base, preferably pyridine,
to obtain a compound of formula (I);
and optionally converting the compound of formula (I) to a pharmaceutically acceptable salt thereof.

ENUMERATED EMBODIMENTS

1. A compound of formula (I)

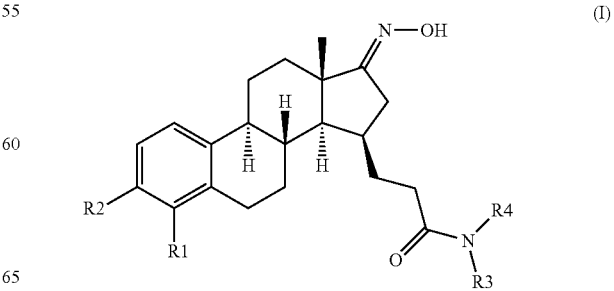

(I)

wherein R1 and R2 are each independently selected from the group consisting of H and halogen;

(i) R3 is selected from the group consisting of H and C1-3-alkyl; and

R4 is selected from the group consisting of

C1-3-alkyl, 4 to 6 membered unsubstituted saturated heterocycle comprising 1 heteroatom selected from the group consisting of nitrogen, sulfur, and oxygen, 5 membered partially unsaturated heterocycle comprising 1 nitrogen atom and optionally 1 to 2 further heteroatom(s) selected from the group consisting of nitrogen, sulfur, and oxygen, and being optionally substituted with one or two substituents selected from the group consisting of halogen, CN, C1-3-alkyl, C1-3-(per)haloalkyl, OH, C1-3-alkoxy, C(O)N(C1-3-alkyl)$_2$, and 6 membered saturated heterocycle comprising 1 to 2 heteroatom(s) independently selected from the group consisting of nitrogen, oxygen and sulfur and being optionally substituted with one or two substituent(s) independently selected from the group consisting of halogen, CN, C1-3-alkyl, C1-3-(per)haloalkyl, OH, and C1-3-alkoxy, 5 membered unsubstituted unsaturated or aromatic heterocycle comprising 1 nitrogen atom and 1 to 2 further heteroatom(s) independently selected from the group consisting of nitrogen, sulfur, and oxygen, 5 membered unsaturated or aromatic heterocycle comprising 1 nitrogen atom and optionally 1 to 2 further heteroatom(s) independently selected from the group consisting of nitrogen, and oxygen, and being optionally substituted with one or two substituent(s) independently selected from the group consisting of halogen, CN, C1-3-alkyl, C1-3-(per)haloalkyl, OH, C1-3-alkoxy, C(O)N(C1-3-alkyl)$_2$, and 6 membered saturated heterocycle containing 1 to 2 heteroatom(s) independently selected from the group consisting of nitrogen, oxygen and sulfur and being optionally substituted with one or two substituent(s) independently selected from the group consisting of halogen, CN, C1-3-alkyl, C1-3-(per)haloalkyl, OH, and C1-3-alkoxy, and 6 membered unsaturated or aromatic heterocycle comprising 1 nitrogen atom and optionally 1 to 2 further heteroatom(s) independently selected from the group consisting of nitrogen, sulfur, and oxygen, and being optionally substituted with one or two substituent(s) independently selected from the group consisting of halogen, CN, C1-3-alkyl, C1-3-(per)haloalkyl, OH, oxo, C1-3-alkoxy, C(O)N(C1-3-alkyl)$_2$, and 6 membered saturated heterocycle comprising 1 to 2 heteroatom(s) independently selected from the group consisting of nitrogen, oxygen and sulfur and being optionally substituted with one or two substituent(s) independently selected from the group consisting of halogen, CN, C1-3-alkyl, C1-3-(per)haloalkyl, OH, and C1-3-alkoxy, or two adjacent substituents may form a 5 or 6 membered saturated fused ring;

or (ii) R3 and R4 form together with the nitrogen atom they are attached to form a group selected from a 5 to 6 membered saturated heterocycle comprising said nitrogen atom and being optionally substituted with a substituent selected from the group consisting of halogen, CN, methyl, C1-3-(per)haloalkyl, OH, and methoxy; and an unsubstituted bicyclic spirocyclic or fused heterocycle containing said nitrogen atom and optionally 1 or 2 further heteroatom(s) selected from a group consisting of nitrogen, oxygen and sulfur;

or a pharmaceutically acceptable salt thereof.

2. A compound as recited in embodiment 1, having formula (Ia)

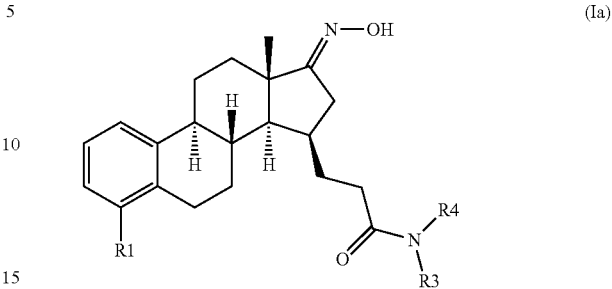

wherein R1, R2, R3, and R4 are as defined in embodiment 1.

3. A compound as recited in embodiment 2, wherein R1 is selected from the group consisting of H, F and Cl, preferably F and Cl.

4. A compound as recited in any one of embodiments 1 to 3, wherein R3 is H or methyl.

5. A compound as recited in embodiment 4, wherein R3 is H.

6. A compound as recited in any one of embodiments 1 to 5, where in R4 is selected from a group consisting of 5 membered unsubstituted unsaturated or aromatic heterocycle comprising 1 nitrogen atom and 1 to 2 further heteroatom(s) independently selected from the group consisting of nitrogen, sulfur, and oxygen, 5 membered unsaturated or aromatic heterocycle comprising 1 nitrogen atom and optionally 1 to 2 further heteroatom(s) independently selected from the group consisting of nitrogen, and oxygen, and being optionally substituted with one or two substituent(s) independently selected from the group consisting of halogen, CN, C1-3-alkyl, C1-3-(per)haloalkyl, OH, C1-3-alkoxy, C(O)N(C1-3-alkyl)$_2$, and 6 membered saturated heterocycle containing 1 to 2 heteroatom(s) independently selected from the group consisting of nitrogen, oxygen and sulfur and being optionally substituted with one or two substituent(s) independently selected from the group consisting of halogen, CN, C1-3-alkyl, C1-3-(per)haloalkyl, OH, and C1-3-alkoxy, and 6 membered unsaturated or aromatic heterocycle comprising 1 nitrogen atom and optionally 1 to 2 further heteroatom(s) independently selected from the group consisting of nitrogen, sulfur, and oxygen, and being optionally substituted with one or two substituent(s) independently selected from the group consisting of halogen, CN, C1-3-alkyl, C1-3-(per)haloalkyl, OH, oxo, C1-3-alkoxy, C(O)N(C1-3-alkyl)$_2$, and 6 membered saturated heterocycle comprising 1 to 2 heteroatom(s) independently selected from the group consisting of nitrogen, oxygen and sulfur and being optionally substituted with one or two substituent(s) independently selected from the group consisting of halogen, CN, C1-3-alkyl, C1-3-(per)haloalkyl, OH, and C1-3-alkoxy, or two adjacent substituents may form a 5 or 6 membered saturated fused ring.

7. A compound as recited in any one of embodiments 1 to 5, wherein R4 is selected from the group consisting of oxetanyl, pyrrolidinyl, piperidinyl, tetrahydropyranyl, dihydrothiazolyl, thiadiazolyl, oxazolyl, methyloxazolyl, pyridinyl, fluoropyridinyl, cyanopyridinyl, methylpyridinyl, dimethylpyridinyl, isopropylpyridinyl, hydroxypyridinyl, methoxypyridinyl, morpholinopyridinyl, methylpiperazinylpyridinyl, pyrazinyl, methylpyridazinyl, and methoxypyridazinyl; in particular from the group consisting of oxetanyl and tetrahydropyranyl, dihydrothiazolyl, thiadiazolyl, oxazolyl, methyloxazolyl, fluoropyridinyl, methoxypyridinyl, methylpyridazinyl, and methoxypyridazinyl.

8. A compound as recited in any one of embodiments 1 to 4, wherein R3 and R4 form together with the nitrogen they are attached to a ring selected from the group consisting of pyrrolidinyl, methoxymethylpyrrolidinyl, and oxaazaspiro[4.5]decanyl.

9. A compound as recited in embodiment 3, wherein the compound has formula (Ib)

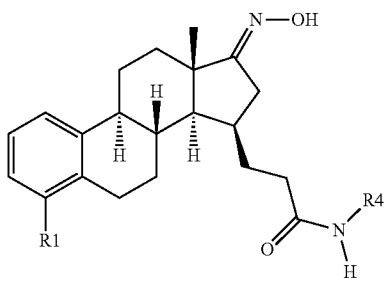

(Ib)

wherein R1 and R4 are as defined in embodiment 1.

10. A compound as recited in embodiment 9, wherein R4 is a 6 membered aromatic heterocycle of formula (A)

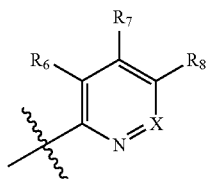

(A)

wherein
X is CR9 or N;
one of R6, R7, R8 is H, and the others are independently selected from a group consisting of H, halogen, CN, C1-3-alkyl, C1-3-(per)haloalkyl, OH, C1-3-alkoxy, and morpholine ring; and
R9 is H or C1-3-alkyl.

11. The compound as recited in embodiment 1 selected from the group consisting of:
3-((13S,15R,E)-4-fluoro-17-(hydroxyimino)-13-methyl-7,8,9,11,12,13,14,15,16,17-decahydro-6H-cyclopenta[a]phenanthren-15-yl)-N-(5-methylisoxazol-3-yl)propanamide;
3-((13S,15R,E)-4-fluoro-17-(hydroxyimino)-13-methyl-7,8,9,11,12,13,14,15,16,17-decahydro-6H-cyclopenta[a]phenanthren-15-yl)-N-(6-methoxypyridazin-3-yl)propanamide;
3-((13S,15R,E)-4-fluoro-17-(hydroxyimino)-13-methyl-7,8,9,11,12,13,14,15,16,17-decahydro-6H-cyclopenta[a]phenanthren-15-yl)-N-(5-methoxypyridin-2-yl)propanamide;
3-((13S,15R,E)-4-fluoro-17-(hydroxyimino)-13-methyl-7,8,9,11,12,13,14,15,16,17-decahydro-6H-cyclopenta[a]phenanthren-15-yl)-N-(5-fluoropyridin-2-yl)propanamide;
3-((13S,15R,E)-4-fluoro-17-(hydroxyimino)-13-methyl-7,8,9,11,12,13,14,15,16,17-decahydro-6H-cyclopenta[a]phenanthren-15-yl)-N-(oxetan-3-yl)propanamide;
3-((13S,15R,E)-4-fluoro-17-(hydroxyimino)-13-methyl-7,8,9,11,12,13,14,15,16,17-decahydro-6H-cyclopenta[a]phenanthren-15-yl)-N-methyl-(oxetan-3-yl)propanamide;
3-((13S,15R,E)-4-fluoro-17-(hydroxyimino)-13-methyl-7,8,9,11,12,13,14,15,16,17-decahydro-6H-cyclopenta[a]phenanthren-15-yl)-1-(pyrrolidin-1-yl)propan-1-one;
3-((13S,15R,E)-4-fluoro-17-(hydroxyimino)-13-methyl-7,8,9,11,12,13,14,15,16,17-decahydro-6H-cyclopenta[a]phenanthren-15-yl)-N-(6-methylpyridazin-3-yl)propanamide;
3-((13S,15R,E)-4-fluoro-17-(hydroxyimino)-13-methyl-7,8,9,11,12,13,14,15,16,17-decahydro-6H-cyclopenta[a]phenanthren-15-yl)-N-(1,3,4-thiadiazol-2-yl)propanamide;
3-((13S,15R,E)-4-fluoro-17-(hydroxyimino)-13-methyl-7,8,9,11,12,13,14,15,16,17-decahydro-6H-cyclopenta[a]phenanthren-15-yl)-N-(pyridazine-3-yl)propanamide;
N-(4,5-dihydrothiazol-2-yl)-3-((13S,15R,E)-4 fluoro-17-(hydroxyimino)-13-methyl-7,8,9,11,12,13,14,15,16,17-decahydro-6H-cyclopenta[a]phenanthren-15-yl)propanamide;
N,N-diethyl-3-((13S,15R,E)-4-fluoro-17-(hydroxyimino)-13-methyl-7,8,9,11,12,13,14,15,16,17-decahydro-6H-cyclopenta[a]phenanthren-15-yl)propanamide;
3-((13S,15R,E)-3-fluoro-17-(hydroxyimino)-13-methyl-7,8,9,11,12,13,14,15,16,17-decahydro-6H-cyclopenta[a]phenanthren-15-yl)-N-(5-fluoropyridin-2-yl)propanamide;
3-((13S,15R,E)-3-fluoro-17-(hydroxyimino)-13-methyl-7,8,9,11,12,13,14,15,16,17-decahydro-6H-cyclopenta[a]phenanthren-15-yl)-N-(5-methoxypyridin-2-yl)propanamide;
3-((13S,15R,E)-3-fluoro-17-(hydroxyimino)-13-methyl-7,8,9,11,12,13,14,15,16,17-decahydro-6H-cyclopenta[a]phenanthren-15-yl)-N-(6-methoxypyridazin-3-yl)propanamide;
3-((13S,15R,E)-3-fluoro-17-(hydroxyimino)-13-methyl-7,8,9,11,12,13,14,15,16,17-decahydro-6H-cyclopenta[a]phenanthren-15-yl)-N-(6-methylpyridazin-3-yl)propanamide;
3-((13S,15R,E)-3-fluoro-17-(hydroxyimino)-13-methyl-7,8,9,11,12,13,14,15,16,17-decahydro-6H-cyclopenta[a]phenanthren-15-yl)-N-(pyridazin-3-yl)propanamide;
3-((13S,15R,E)-3-fluoro-17-(hydroxyimino)-13-methyl-7,8,9,11,12,13,14,15,16,17-decahydro-6H-cyclopenta[a]phenanthren-15-yl)-N-methyl-N-(oxetan-3-yl)propanamide;
3-((13S,15R,E)-3-fluoro-17-(hydroxyimino)-13-methyl-7,8,9,11,12,13,14,15,16,17-decahydro-6H-cyclopenta[a]phenanthren-15-yl)-N-(1,3,4-thiadiazol-2-yl)propanamide;
N,N-diethyl-3-((13S,15R,E)-3-fluoro-17-(hydroxyimino)-13-methyl-7,8,9,11,12,13,14,15,16,17-decahydro-6H-cyclopenta[a]phenanthren-15-yl)propanamide;
3-((13S,15R,E)-3-fluoro-17-(hydroxyimino)-13-methyl-7,8,9,11,12,13,14,15,16,17-decahydro-6H-cyclopenta[a]phenanthren-15-yl)-N-(5-isopropylpyridin-2-yl)propanamide;
3-((13S,15R,E)-3-chloro-17-(hydroxyimino)-13-methyl-7,8,9,11,12,13,14,15,16,17-decahydro-6H-cyclopenta[a]phenanthren-15-yl)-N-(pyridazine-3-yl)propanamide;

3-((13S,15R,E)-3-chloro-17-(hydroxyimino)-13-methyl-7,
8,9,11,12,13,14,15,16,17-decahydro-6H-cyclopenta[a]
phenanthren-15-yl)-N-(4,5-dihydrothiazol-2-yl)propana-
mide;
3-((13S,15R,E)-3-chloro-17-(hydroxyimino)-13-methyl-7,
8,9,11,12,13,14,15,16,17-decahydro-6H-cyclopenta[a]
phenanthren-15-yl)-1-(8-oxa-2-azaspiro[4.5]decan-2-yl)
propan-1-one;
3-((13S,15R,E)-3-chloro-17-(hydroxyimino)-13-methyl-7,
8,9,11,12,13,14,15,16,17-decahydro-6H-cyclopenta[a]
phenanthren-15-yl)-N-(6-methoxypyridazin-3-yl)pro-
panamide;
3-((13S,15R,E)-3-chloro-17-(hydroxyimino)-13-methyl-7,
8,9,11,12,13,14,15,16,17-decahydro-6H-cyclopenta[a]
phenanthren-15-yl)-N,N-diethylpropanamide;
3-((13S,15R,E)-3-chloro-17-(hydroxyimino)-13-methyl-7,
8,9,11,12,13,14,15,16,17-decahydro-6H-cyclopenta[a]
phenanthren-15-yl)-N-(5-methylisoxazol-3-yl)propana-
mide;
3-((13S,15R,E)-3-chloro-17-(hydroxyimino)-13-methyl-7,
8,9,11,12,13,14,15,16,17-decahydro-6H-cyclopenta[a]
phenanthren-15-yl)-N-(4-methoxypyridin-2-yl)propana-
mide;
3-((13S,15R,E)-3-chloro-17-(hydroxyimino)-13-methyl-7,
8,9,11,12,13,14,15,16,17-decahydro-6H-cyclopenta[a]
phenanthren-15-yl)-N-(5-fluoropyridin-2-yl)propana-
mide;
3-((13S,15R,E)-3-chloro-17-(hydroxyimino)-13-methyl-7,
8,9,11,12,13,14,15,16,17-decahydro-6H-cyclopenta[a]
phenanthren-15-yl)-N-(3-methylpyridin-2-yl)propana-
mide;
3-((13S,15R,E)-3-chloro-17-(hydroxyimino)-13-methyl-7,
8,9,11,12,13,14,15,16,17-decahydro-6H-cyclopenta[a]
phenanthren-15-yl)-N-(3-fluoropyridin-2-yl)propana-
mide;
3-((13S,15R,E)-3-chloro-17-(hydroxyimino)-13-methyl-7,
8,9,11,12,13,14,15,16,17-decahydro-6H-cyclopenta[a]
phenanthren-15-yl)-N-(5-methyloxazol-2-yl)propana-
mide;
3-((13S,15R,E)-3-chloro-17-(hydroxyimino)-13-methyl-7,
8,9,11,12,13,14,15,16,17-decahydro-6H-cyclopenta[a]
phenanthren-15-yl)-N-(5-methoxypyridin-2-yl)propana-
mide;
3-((13S,15R,E)-3-chloro-17-(hydroxyimino)-13-methyl-7,
8,9,11,12,13,14,15,16,17-decahydro-6H-cyclopenta[a]
phenanthren-15-yl)-N-(pyridin-2-yl)propanamide;
3-((13S,15R,E)-3-chloro-17-(hydroxyimino)-13-methyl-7,
8,9,11,12,13,14,15,16,17-decahydro-6H-cyclopenta[a]
phenanthren-15-yl)-N-(4-methylpyridin-2-yl)propana-
mide;
3-((13S,15R,E)-3-chloro-17-(hydroxyimino)-13-methyl-7,
8,9,11,12,13,14,15,16,17-decahydro-6H-cyclopenta[a]
phenanthren-15-yl)-N-(5-cyanopyridin-2-yl)propana-
mide;
3-((13S,15R,E)-3-chloro-17-(hydroxyimino)-13-methyl-7,
8,9,11,12,13,14,15,16,17-decahydro-6H-cyclopenta[a]
phenanthren-15-yl)-N-(pyrazin-2-yl)propanamide;
3-((13S,15R,E)-3-chloro-17-(hydroxyimino)-13-methyl-7,
8,9,11,12,13,14,15,16,17-decahydro-6H-cyclopenta[a]
phenanthren-15-yl)-N-(6-methylpyridazin-3-yl)propana-
mide;
3-((13S,15R,E)-3-chloro-17-(hydroxyimino)-13-methyl-7,
8,9,11,12,13,14,15,16,17-decahydro-6H-cyclopenta[a]
phenanthren-15-yl)-N-(5-morpholinopyridin-2-yl)pro-
panamide;

3-((13S,15R,E)-17-(hydroxyimino)-13-methyl-7,8,9,11,12,
13,14,15,16,17-decahydro-6H-cyclopenta[a]phenan-
thren-15-yl)-N-methyl-N-(tetrahydro-2H-pyran-4-yl)pro-
panamide;
3-((13S,15R,E)-17-(hydroxyimino)-13-methyl-7,8,9,11,12,
13,14,15,16,17-decahydro-6H-cyclopenta[a]phenan-
thren-15-yl)-N-(pyridazin-3-yl)propanamide;
3-((13S,15R,E)-17-(hydroxyimino)-13-methyl-7,8,9, 11,12,
13,14,15,1617-decahydro-6H-cyclopenta[a]phenanthren-
15-yl)-N-(5-methoxypyridin-2-yl)propanamide;
3-((13S,15R,E)-17-(hydroxyimino)-13-methyl-7,8,9,11,12,
13,14,15,16,17-decahydro-6H-cyclopenta[a]phenan-
thren-15-yl)-N-(5-(4-methylpiperazin-1-yl)pyridin-2-yl)
propanamide;
3-((13S,15R,E)-17-(hydroxyimino)-13-methyl-7,8,9,11,12,
13,14,15,16,17-decahydro-6H-cyclopenta[a]phenan-
thren-15-yl)-N-(4-methylpyridin-2-yl)propanamide;
3-((13S,15R,E)-17-(hydroxyimino)-13-methyl-7,8,9,11,12,
13,14,15,16,17-decahydro-6H-cyclopenta[a]phenan-
thren-15-yl)-N-(5-morpholinopyridin-2-yl)propanamide;
6-(3-((13S,15R,E)-17-(hydroxyimino)-13-methyl-7,8,9,11,
12,13,14,15,16,17-decahydro-6H-cyclopenta[a]phenan-
thren-15-yl)propanamido)-N,N-dimethylnicotinamide;
3-((13S,15R,E)-17-(hydroxyimino)-13-methyl-7,8,9,11,12,
13,14,15,16,17-decahydro-6H-cyclopenta[a]phenan-
thren-15-yl)-N-(2-oxo-1,2,5,6,7,8-hexahydroquinolin-3-
yl)propanamide;
3-((13S,15R,E)-17-(hydroxyimino)-13-methyl-7,8,9,11,12,
13,14,15,16,17-decahydro-6H-cyclopenta[a]phenan-
thren-15-yl)-N-(5-isopropylpyridin-2-yl)propanamide;
N-(5-fluoropyridin-2-yl)-3-((13S,15R,E)-17-(hydroxy-
imino)-13-methyl-7,8,9,11,12,13,14,15,16,17-decahydro-
6H-cyclopenta[a]phenanthren-15-yl)propanamide;
N-(5-cyanopyridin-2-yl)-3-((13S,15R,E)-17-(hydroxy-
imino)-13-methyl-7,8,9,11,12,13,14,15,16,17-decahydro-
6H-cyclopenta[a]phenanthren-15-yl)propanamide;
3-((13S,15R,E)-17-(hydroxyimino)-13-methyl-7,8,9,11,12,
13,14,15,16,17-decahydro-6H-cyclopenta[a]phenan-
thren-15-yl)-N-(3-hydroxypyridin-2-yl)propanamide;
3-((13S,15R,E)-17-(hydroxyimino)-13-methyl-7,8,9,11,12,
13,14,15,16,17-decahydro-6H-cyclopenta[a]phenan-
thren-15-yl)-N-(pyridin-2-yl)propanamide;
3-((13S,15R,E)-17-(hydroxyimino)-13-methyl-7,8,9,11,12,
13,14,15,16,17-decahydro-6H-cyclopenta[a]phenan-
thren-15-yl)-N-(4-methoxypyridin-2-yl)propanamide;
3-((13S,15R,E)-17-(hydroxyimino)-13-methyl-7,8,9,11,12,
13,14,15,16,17-decahydro-6H-cyclopenta[a]phenan-
thren-15-yl)-N-(5-methyloxazol-2-yl)propanamide;
3-((13S,15R,E)-17-(hydroxyimino)-13-methyl-7,8,9,11,12,
13,14,15,16,17-decahydro-6H-cyclopenta[a]phenan-
thren-1-yl)-N-(5-methylisoxazol-3-yl)propanamide;
3-((13S,15R,E)-4-fluoro-17-(hydroxyimino)-13-methyl-7,
8,9,11,12,13,14,15,16,17-decahydro-6H-cyclopenta[a]
phenanthren-15-yl)-N-(5-isopropylpyridin-2-yl)propana-
mide;
3-((13S,15R,E)-4-fluoro-17-(hydroxyimino)-13-methyl-7,
8,9,11,12,13,14,15,16,17-decahydro-6H-cyclopenta[a]
phenanthren-15-yl)-N-(5-morpholinopyridin-2-yl)pro-
panamide;
3-((13S,15R,E)-4-fluoro-17-(hydroxyimino)-13-methyl-7,
8,9,11,12,13,14,15,16,17-decahydro-6H-cyclopenta[a]
phenanthren-15-yl)-N-(5-(4-methylpiperazin-1-yl)pyri-
din-2-yl)propanamide;
3-((13S,15R,E)-4-fluoro-17-(hydroxyimino)-13-methyl-7,
8,9,11,12,13,14,15,16,17-decahydro-6H-cyclopenta[a]
phenanthren-15-yl)-N-methylpropanamide;

3-((13S,15R,E)-4-fluoro-17-(hydroxyimino)-13-methyl-7,8,9,11,12,13,14,15,16,17-decahydro-6H-cyclopenta[a]phenanthren-15-yl)-N,N-dimethylpropanamide;

3-((13S,15R,E)-4-fluoro-17-(hydroxyimino)-13-methyl-7,8,9,11,12,13,14,15,16,17-decahydro-6H-cyclopenta[a]phenanthren-15-yl)-N-(tetrahydro-2H-pyran-4-yl)propanamide;

N-Cyclohexyl-3-((13S,15R,E)-4-fluoro-17-(hydroxyimino)-13-methyl-7,8,9,11,12,13,14,15,16,17-decahydro-6H-cyclopenta[a]phenanthren-15-yl)propanamide;

3-((13S,15R,E)-4-fluoro-17-(hydroxyimino)-13-methyl-7,8,9,11,12,13,14,15,16,17-decahydro-6H-cyclopenta[a]phenanthren-15-yl)-N-(pyrazin-2-yl)propanamide;

3-((13S,15R,E)-4-fluoro-17-(hydroxyimino)-13-methyl-7,8,9,11,12,13,14,15,16,17-decahydro-6H-cyclopenta[a]phenanthren-15-yl)-1-(8-oxa-2-azaspiro[4.5]decan-2-yl)propan-1-one;

3-((13S,15R,E)-4-fluoro-17-(hydroxyimino)-13-methyl-7,8,9,11,12,13,14,15,16,17-decahydro-6H-cyclopenta[a]phenanthren-15-yl)-N-(4-methylpyridin-2-yl)propanamide;

3-((13S,15R,E)-4-fluoro-17-(hydroxyimino)-13-methyl-7,8,9,11,12,13,14,15,16,17-decahydro-6H-cyclopenta[a]phenanthren-15-yl)-N-(4-methoxypyridin-2-yl)propanamide;

3-((13S,15R,E)-3-fluoro-17-(hydroxyimino)-13-methyl-7,8,9,11,12,13,14,15,16,17-decahydro-6H-cyclopenta[a]phenanthren-15-yl)-N-(5-methylisoxazol-3-yl)propanamide;

3-((13S,15R,E)-4-fluoro-17-(hydroxyimino)-13-methyl-7,8,9,11,12,13,14,15,16,17-decahydro-6H-cyclopenta[a]phenanthren-15-yl)-1-morpholinopropan-1-one;

3-((13S,15R,E)-4-fluoro-17-(hydroxyimino)-13-methyl-7,8,9,11,12,13,14,15,16,17-decahydro-6H-cyclopenta[a]phenanthren-15-yl)-N-(pyridin-2-yl)propanamide;

3-((13S,15R,E)-4-fluoro-17-(hydroxyimino)-13-methyl-7,8,9,11,12,13,14,15,16,17-decahydro-6H-cyclopenta[a]phenanthren-15-yl)-N-(4-fluoropyridin-2-yl)propanamide;

3-((13S,15R,E)-4-fluoro-17-(hydroxyimino)-13-methyl-7,8,9,11,12,13,14,15,16,17-decahydro-6H-cyclopenta[a]phenanthren-15-yl)-N-(3-fluoropyridin-2-yl)propanamide;

3-((13S,15R,E)-4-fluoro-17-(hydroxyimino)-13-methyl-7,8,9,11,12,13,14,15,16,17-decahydro-6H-cyclopenta[a]phenanthren-15-yl)-N-(6-fluoropyridin-2-yl)propanamide;

N-(3,5-difluoropyridin-2-yl)-3-((13S,15R,E)-4-fluoro-17-(hydroxyimino)-13-methyl-7,8,9,11,12,13,14,15,16,17-decahydro-6H-cyclopenta[a]phenanthren-15-yl)propanamide;

N-(5-cyanopyridin-2-yl)-3-((13S,15R,E)-4-fluoro-17-(hydroxyimino)-13-methyl-7,8,9,11,12,13,14,15,16,17-decahydro-6H-cyclopenta[a]phenanthren-15-yl)propanamide;

3-((13S,15R,E)-3-fluoro-17-(hydroxyimino)-13-methyl-7,8,9,11,12,13,14,15,16,17-decahydro-6H-cyclopenta[a]phenanthren-15-yl)-N-(3-fluoropyridin-2-yl)propanamide;

N-(3,5-difluoropyridin-2-yl)-3-((13S,15R,E)-3-fluoro-17-(hydroxyimino)-13-methyl-7,8,9,11,12,13,14,15,16,17-decahydro-6H-cyclopenta[a]phenanthren-15-yl)propanamide;

3-((13S,15R,E)-3-fluoro-17-(hydroxyimino)-13-methyl-7,8,9,11,12,13,14,15,16,17-decahydro-6H-cyclopenta[a]phenanthren-15-yl)-N-(5-morpholinopyridin-2-yl)propanamide;

3-((13S,15R,E)-3-chloro-17-(hydroxyimino)-13-methyl-7,8,9,11,12,13,14,15,16,17-decahydro-6H-cyclopenta[a]phenanthren-15-yl)-N-(4-fluoropyridin-2-yl)propanamide;

N-(4-fluoropyridin-2-yl)-3-((13S,15R,E)-17-(hydroxyimino)-13-methyl-7,8,9,11,12,13,14,15,16,17-decahydro-6H-cyclopenta[a]phenanthren-15-yl)propanamide;

N-(3-fluoropyridin-2-yl)-3-((13S,15R,E)-17-(hydroxyimino)-13-methyl-7,8,9,11,12,13,14,15,16,17-decahydro-6H-cyclopenta[a]phenanthren-15-yl)propanamide;

3-((13S,15R,E)-3-chloro-17-(hydroxyimino)-13-methyl-7,8,9,11,12,13,14,15,16,17-decahydro-6H-cyclopenta[a]phenanthren-15-yl)-N-(3-fluoropyridin-2-yl)propanamide;

3-((13S,15R,E)-3-chloro-17-(hydroxyimino)-13-methyl-7,8,9,11,12,13,14,15,16,17-decahydro-6H-cyclopenta[a]phenanthren-15-yl)-N-(3,5-difluoropyridin-2-yl)propanamide;

N-(3,5-difluoropyridin-2-yl)-3-((13S,15R,E)-17-(hydroxyimino)-13-methyl-7,8,9,11,12,13,14,15,16,17-decahydro-6H-cyclopenta[a]phenanthren-15-yl)propanamide;

N-(6-fluoropyridin-2-yl)-3-((13S,15R,E)-17-(hydroxyimino)-13-methyl-7,8,9,11,12,13,14,15,16,17-decahydro-6H-cyclopenta[a]phenanthren-15-yl)propanamide;

3-((13S,15R,E)-3-chloro-17-(hydroxyimino)-13-methyl-7,8,9,11,12,13,14,15,16,17-decahydro-6H-cyclopenta[a]phenanthren-15-yl)-N-(6-fluoropyridin-2-yl)propanamide;

6-(3-((13S,15R,E)-3-chloro-17-(hydroxyimino)-13-methyl-7,8,9,11,12,13,14,15,16,17-decahydro-6H-cyclopenta[a]phenanthren-15-yl)propanamido)-N,N-dimethylnicotinamide;

3-((13S,15R,E)-3-chloro-17-(hydroxyimino)-13-methyl-7,8,9,11,12,13,14,15,16,17-decahydro-6H-cyclopenta[a]phenanthren-15-yl)-N-(2-oxo-1,2,5,6,7,8-hexahydroquinolin-3-yl)propanamide;

6-(3-((13S,15R,E)-4-fluoro-17-(hydroxyimino)-13-methyl-7,8,9,11,12,13,14,15,16,17-decahydro-6H-cyclopenta[a]phenanthren-15-yl)propanamido)-N,N-dimethylnicotinamide;

3-((13S,15R,E)-4-fluoro-17-(hydroxyimino)-13-methyl-7,8,9,11,12,13,14,15,16,17-decahydro-6H-cyclopenta[a]phenanthren-15-yl)-N-(2-oxo-1,2,5,6,7,8-hexahydroquinolin-3-yl)propanamide;

or a pharmaceutically acceptable salt thereof.

12. The compound as recited in embodiment 11 selected from the group consisting of:

3-((13S,15R,E)-4-fluoro-17-(hydroxyimino)-13-methyl-7,8,9,11,12,13,14,15,16,17-decahydro-6H-cyclopenta[a]phenanthren-15-yl)-N-(5-methoxypyridin-2-yl)propanamide;

3-((13S,15R,E)-4-fluoro-17-(hydroxyimino)-13-methyl-7,8,9,11,12,13,14,15,16,17-decahydro-6H-cyclopenta[a]phenanthren-15-yl)-N-(5-fluoropyridin-2-yl)propanamide;

or a pharmaceutically acceptable salt thereof.

13. A compound of formula (II)

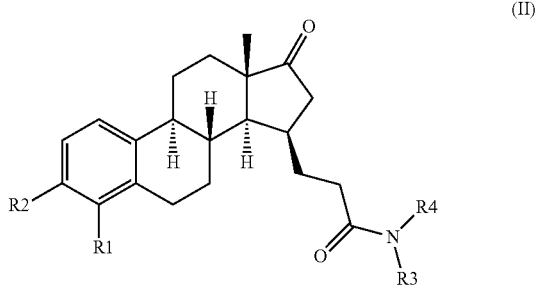

(II)

wherein R1, R2, R3, and R4 are as defined in embodiment 1.

14. A compound as recited in embodiment 13, wherein R1 and R2 are each independently selected from the group consisting of H and halogen, preferably F and Cl.

15. A compound as recited in any one of embodiments 13 to 14, wherein R3 is H or methyl.

16. A compound as recited in any one of embodiments 13 to 15, wherein R4 is selected from a group consisting of 5 membered unsubstituted unsaturated or aromatic heterocycle comprising 1 nitrogen atom and 1 to 2 further heteroatom(s) independently selected from the group consisting of nitrogen, sulfur, and oxygen, 5 membered unsaturated or aromatic heterocycle comprising 1 nitrogen atom and optionally 1 to 2 further heteroatom(s) independently selected from the group consisting of nitrogen, and oxygen, and being optionally substituted with one or two substituent(s) independently selected from the group consisting of halogen, CN, C1-3-alkyl, C1-3-(per) haloalkyl, OH, C1-3-alkoxy, C(O)N(C1-3-alkyl)$_2$, and 6 membered saturated heterocycle containing 1 to 2 heteroatom(s) independently selected from the group consisting of nitrogen, oxygen and sulfur and being optionally substituted with one or two substituent(s) independently selected from the group consisting of halogen, CN, C1-3-alkyl, C1-3-(per) haloalkyl, OH, and C1-3-alkoxy, and 6 membered unsaturated or aromatic heterocycle comprising 1 nitrogen atom and optionally 1 to 2 further heteroatom(s) independently selected from the group consisting of nitrogen, sulfur, and oxygen, and being optionally substituted with one or two substituent(s) independently selected from the group consisting of halogen, CN, C1-3-alkyl, C1-3-(per)haloalkyl, OH, oxo, C1-3-alkoxy, C(O)N(C1-3-alkyl)$_2$, and 6 membered saturated heterocycle comprising 1 to 2 heteroatom(s) independently selected from the group consisting of nitrogen, oxygen and sulfur and being optionally substituted with one or two substituent(s) independently selected from the group consisting of halogen, CN, C1-3-alkyl, C1-3-(per)haloalkyl, OH, and C1-3-alkoxy, or two adjacent substituents may form a 5 or 6 membered saturated fused ring.

17. A compound as recited in any one of embodiments 13 to 16, wherein R4 is selected from the group consisting of oxetanyl, pyrrolidinyl, piperidinyl, tetrahydropyranyl, dihydrothiazolyl, thiadiazolyl, oxazolyl, methyloxazolyl, pyridinyl, fluoropyridinyl, cyanopyridinyl, methylpyridinyl, dimethylpyridinyl, isopropylpyridinyl, hydroxypyridinyl, methoxypyridinyl, morpholinopyridinyl, methylpiperazinylpyridinyl, pyrazinyl, methylpyridazinyl, and methoxypyridazinyl; in particular from the group consisting of oxetanyl and tetrahydropyranyl, dihydrothiazolyl, thiadiazolyl, oxazolyl, methyloxazolyl, fluoropyridinyl, methoxypyridinyl, methylpyridazinyl, and methoxypyridazinyl.

18. A compound as recited in any one of embodiments 13 to 14, wherein R3 and R4 form together with the nitrogen they are attached to a ring selected from the group consisting of pyrrolidinyl, methoxymethylpyrrolidinyl, and oxaazaspiro[4.5]decanyl.

19. The compound as recited in embodiment 13 selected from the group consisting of:

3-((13S,15R)-4-fluoro-13-methyl-17-oxo-7,8,9,11,12,13,14,15,16,17-decahydro-6H-cyclopenta[a]phenanthren-15-yl)-N-(5-methylisoxazol-3-yl)propanamide;

3-((13S,15R)-4-fluoro-13-methyl-17-oxo-7,8,9,11,12,13,14,15,16,17-decahydro-6H-cyclopenta[a]phenanthren-15-yl)-N-(6-methoxypyridazin-3-yl)propanamide;

3-((13S,15R)-4-fluoro-13-methyl-17-oxo-7,8,9,11,12,13,14,15,16,17-decahydro-6H-cyclopenta[a]phenanthren-15-yl)-N-(5-methoxypyridin-2-yl)propanamide;

3-((13S,15R)-4-fluoro-13-methyl-17-oxo-7,8,9,11,12,13,14,15,16,17-decahydro-6H-cyclopenta[a]phenanthren-15-yl)-N-(5-fluoropyridin-2-yl)propanamide;

3-((13S,15R)-4-fluoro-13-methyl-17-oxo-7,8,9,11,12,13,14,15,16,17-decahydro-6H-cyclopenta[a]phenanthren-15-yl)-N-(oxetan-3-yl)propanamide 3-((13S,15R)-4-fluoro-13-methyl-17-oxo-7,8,9,11,12,13,14,15,16,17-decahydro-6H-cyclopenta[a]phenanthren-15-yl)-N-methyl-(oxetan-3-yl)propanamide;

(13S,15R)-4-fluoro-13-methyl-15-(3-oxo-3-(pyrrolidin-1-yl)propyl)-6,7,8,9,11,12,13,14,15,16-decahydro-17H-cyclopenta[a]phenanthren-17-one 3-((13S,15R)-4-fluoro-13-methyl-17-oxo-7,8,9,11,12,13,14,15,16,17-decahydro-6H-cyclopenta[a]phenanthren-15-yl)-N-(6-methylpyridazin-3-yl)propanamide;

3-((13S,15R)-4-fluoro-13-methyl-17-oxo-7,8,9,11,12,13,14,15,16,17-decahydro-6H-cyclopenta[a]phenanthren-15-yl)-N-(1,3,4-thiadiazol-2-yl)propanamide;

N-(4,5-dihydrothiazol-2-yl)-3-((13S,15R)-4-fluoro-13-methyl-17-oxo-7,8,9,11,12,13,14,15,16,17-decahydro-6H-cyclopenta[a]phenanthren-15-yl)propanamide;

N,N-diethyl-3-((13S,15R)-4-fluoro-13-methyl-17-oxo-7,8,9,11,12,13,14,15,16,17-decahydro-6H-cyclopenta[a]phenanthren-15-yl)propanamide;

3-((13S,15R)-4-fluoro-13-methyl-17-oxo-7,8,9,11,12,13,14,15,16,17-decahydro-6H-cyclopenta[a]phenanthren-15-yl)-N-(5-isopropylpyridin-2-yl)propanamide;

3-((13S,15R)-4-fluoro-13-methyl-17-oxo-7,8,9,11,12,13,14,15,16,17-decahydro-6H-cyclopenta[a]phenanthren-15-yl)-N-(5-morpholinopyridin-2-yl)propanamide;

3-((13S,15R)-4-fluoro-13-methyl-17-oxo-7,8,9,11,12,13,14,15,16,17-decahydro-6H-cyclopenta[a]phenanthren-15-yl)-N-(5-(4-methylpiperazin-1-yl)pyridin-2-yl)propanamide;

3-((13S,15R)-4-fluoro-13-methyl-17-oxo-7,8,9,11,12,13,14,15,16,17-decahydro-6H-cyclopenta[a]phenanthren-15-yl)-N-methylpropanamide;

3-((13S,15R)-4-fluoro-13-methyl-17-oxo-7,8,9,11,12,13,14,15,16,17-decahydro-6H-cyclopenta[a]phenanthren-15-yl)-N,N-dimethylpropanamide;

3-((13S,15R)-4-fluoro-13-methyl-17-oxo-7,8,9,11,12,13,14,15,16,17-decahydro-6H-cyclopenta[a]phenanthren-15-yl)-N-(tetrahydro-2H-pyran-4-yl)propanamide;

N-cyclohexyl-3-((13S,15R)-4-fluoro-13-methyl-17-oxo-7,8,9,11,12,13,14,15,16,17-decahydro-6H-cyclopenta[a]phenanthren-15-yl)propanamide;

3-((13S,15R)-4-fluoro-13-methyl-17-oxo-7,8,9,11,12,13,14,15,16,17-decahydro-6H-cyclopenta[a]phenanthren-15-yl)-N-(pyrazin-2-yl)propanamide;

(13S,15R)-4-fluoro-13-methyl-15-(3-oxo-3-(8-oxa-2-azaspiro[4.5]decan-2-yl)propyl)-6,7,8,9,11,12,13,14,15,16-decahydro-17H-cyclopenta[a]phenanthren-17-one;

3-((13S,15R)-4-fluoro-13-methyl-17-oxo-7,8,9,11,12,13,14,15,16,17-decahydro-6H-cyclopenta[a]phenanthren-15-yl)-N-(4-methylpyridin-2-yl)propanamide;

is 3-((13S,15R)-4-fluoro-13-methyl-17-oxo-7,8,9,11,12,13,14,15,16,17-decahydro-6H-cyclopenta[a]phenanthren-15-yl)-N-(4-methoxypyridin-2-yl)propanamide;

3-((13S,15R)-3-fluoro-13-methyl-17-oxo-7,8,9,11,12,13,14,15,16,17-decahydro-6H-cyclopenta[a]phenanthren-15-yl)-N-(5-methylisoxazol-3-yl)propanamide;

(13S,15R)-4-fluoro-13-methyl-15-(3-morpholino-3-oxopropyl)-6,7,8,9,11,12,13,14,15,16-decahydro-17H-cyclopenta[a]phenanthren-17-one;

3-((13S,15R)-4-fluoro-13-methyl-17-oxo-7,8,9,11,12,13,14,15,16,17-decahydro-6H-cyclopenta[a]phenanthren-15-yl)-N-(pyridin-2-yl)propanamide;

3-((13S,15R)-4-fluoro-13-methyl-17-oxo-7,8,9,11,12,13,14,15,16,17-decahydro-6H-cyclopenta[a]phenanthren-15-yl)-N-(4-fluoropyridin-2-yl)propanamide;

3-((13S,15R)-4-fluoro-13-methyl-17-oxo-7,8,9,11,12,13,14,15,16,17-decahydro-6H-cyclopenta[a]phenanthren-15-yl)-N-(3-fluoropyridin-2-yl)propanamide;

3-((13S,15R)-4-fluoro-13-methyl-17-oxo-7,8,9,11,12,13,14,15,16,17-decahydro-6H-cyclopenta[a]phenanthren-15-yl)-N-(6-fluoropyridin-2-yl)propanamide;

N-(3,5-difluoropyridin-2-yl)-3-((13S,15R)-4-fluoro-13-methyl-17-oxo-7,8,9,11,12,13,14,15,16,17-decahydro-6H-cyclopenta[a]phenanthren-15-yl)propanamide;

N-(5-cyanopyridin-2-yl)-3-((13S,15R)-4-fluoro-13-methyl-17-oxo-7,8,9,11,12,13,14,15,16,17-decahydro-6H-cyclopenta[a]phenanthren-15-yl)propanamide;

3-((13S,15R)-3-fluoro-13-methyl-17-oxo-7,8,9,11,12,13,14,15,16,17-decahydro-6H-cyclopenta[a]phenanthren-15-yl)-N-(3-fluoropyridin-2-yl)propanamide;

N-(3,5-difluoropyridin-2-yl)-3-((13S,15R)-3-fluoro-13-methyl-17-oxo-7,8,9,11,12,13,14,15,16,17-decahydro-6H-cyclopenta[a]phenanthren-15-yl)propanamide;

3-((13S,15R)-3-fluoro-13-methyl-17-oxo-7,8,9,11,12,13,14,15,16,17-decahydro-6H-cyclopenta[a]phenanthren-15-yl)-N-(5-morpholinopyridin-2-yl)propanamide;

3-((13S,15R)-3-chloro-13-methyl-17-oxo-7,8,9,11,12,13,14,15,16,17-decahydro-6H-cyclopenta[a]phenanthren-15-yl)-N-(4-fluoropyridin-2-yl)propanamide;

N-(4-fluoropyridin-2-yl)-3-((13S,15R)-13-methyl-17-oxo-7,8,9,11,12,13,14,15,16,17-decahydro-6H-cyclopenta[a]phenanthren-15-yl)propanamide;

N-(3-fluoropyridin-2-yl)-3-((13S,15R)-13-methyl-17-oxo-7,8,9,11,12,13,14,15,16,17-decahydro-6H-cyclopenta[a]phenanthren-15-yl)propanamide;

3-((13S,15R)-3-chloro-13-methyl-17-oxo-7,8,9,11,12,13,14,15,16,17-decahydro-6H-cyclopenta[a]phenanthren-15-yl)-N-(3-fluoropyridin-2-yl)propanamide;

3-((13S,15R)-3-chloro-13-methyl-17-oxo-7,8,9,11,12,13,14,15,16,17-decahydro-6H-cyclopenta[a]phenanthren-15-yl)-N-(3,5-difluoropyridin-2-yl)propanamide;

N-(3,5-difluoropyridin-2-yl)-3-((13S,15R)-13-methyl-17-oxo-7,8,9,11,12,13,14,15,16,17-decahydro-6H-cyclopenta[a]phenanthren-15-yl)propanamide;

N-(6-fluoropyridin-2-yl)-3-((13S,15R)-13-methyl-17-oxo-7,8,9,11,12,13,14,15,16,17-decahydro-6H-cyclopenta[a]phenanthren-15-yl)propanamide;

3-((13S,15R)-3-chloro-13-methyl-17-oxo-7,8,9,11,12,13,14,15,16,17-decahydro-6H-cyclopenta[a]phenanthren-15-yl)-N-(6-fluoropyridin-2-yl)propanamide;

6-(3-((13S,15R)-3-chloro-13-methyl-17-oxo-7,8,9,11,12,13,14,15,16,17-decahydro-6H-cyclopenta[a]phenanthren-15-yl)propanamido)-N,N-dimethylnicotinamide;

3-((13S,15R)-3-chloro-13-methyl-17-oxo-7,8,9,11,12,13,14,15,16,17-decahydro-6H-cyclopenta[a]phenanthren-15-yl)-N-(2-oxo-1,2,5,6,7,8-hexahydroquinolin-3-yl)propanamide;

6-(3-((13S,15R)-4-fluoro-13-methyl-17-oxo-7,8,9,11,12,13,14,15,16,17-decahydro-6H-cyclopenta[a]phenanthren-15-yl)propanamido)-N,N-dimethylnicotinamide, and 3-((13S,15R)-4-fluoro-13-methyl-17-oxo-7,8,9,11,12,13,14,15,16,17-decahydro-6H-cyclopenta[a]phenanthren-15-yl)-N-(2-oxo-1,2,5,6,7,8-hexahydroquinolin-3-yl)propanamide.

20. A compound as recited in any one of embodiments 1 to 12, for use as a medicament.

21. A compound as recited in any one of embodiments 1 to 12 for use in treatment or prevention of a disease selected from a group consisting of breast cancer, prostate carcinoma, ovarian cancer, uterine cancer, endometrial cancer, endometrial hyperplasia, endometriosis, uterine fibroids, adenomyosis, polycystic ovarian syndrome, dysmenorrhea, menorrhagia, metrorrhagia, contraception, prostadynia, benign prostatic hyperplasia, urinary dysfunction, lower urinary tract symptoms, chronic prostatitis/chronic pelvic pain syndrome (CP/CPPS), systemic lupus erythematosus (SLE), multiple sclerosis, obesity, rheumatoid arthritis, chronic obstructive pulmonary disease (COPD), lung cancer, colon cancer, tissue wounds, skin wrinkles and cataracts.

22. A compound as recited in any one of embodiments 1 to 12 for use in treatment of a disease selected from a group consisting of breast cancer, prostate carcinoma, ovarian cancer, uterine cancer, endometrial cancer, endometrial hyperplasia, endometriosis, uterine fibroids, adenomyosis, polycystic ovarian syndrome, dysmenorrhea, menorrhagia, metrorrhagia, contraception, prostadynia, benign prostatic hyperplasia, urinary dysfunction, lower urinary tract symptoms, chronic prostatitis/chronic pelvic pain syndrome (CP/CPPS), systemic lupus erythematosus (SLE), multiple sclerosis, obesity, rheumatoid arthritis, chronic obstructive pulmonary disease (COPD), lung cancer, colon cancer, tissue wounds, skin wrinkles and cataracts.

23. A pharmaceutical composition comprising an effective amount of one or more compounds as recited in any one of embodiments 1 to 12, together with one or more pharmaceutically acceptable excipient(s).

24. A pharmaceutical composition as recited in embodiment 23 comprising one or more compounds as recited in any one of embodiments 1 to 12 in combination with one or more other active ingredients.

25. A method for the preparation of a compound of formula (I) as defined in any one of embodiments 1 to 12, comprising the steps of:
reacting a compound of formula (III)

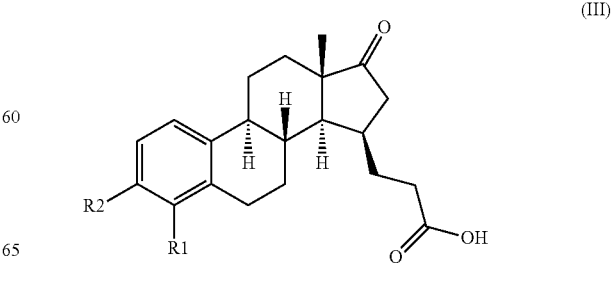

(III)

wherein R1 and R2 are each independently selected from the group consisting of H and halogen;
with compound of formula (IV)

NR3R4 (IV)

wherein R3 and R4 are as defined for compound of formula (I),
in the presence of amide bond forming reagents, in particular T₃P and a base, preferably pyridine,
to obtain a compound of formula (II), and reacting the obtained compound with

NH₂—OH (V)

or hydrogen halide thereof,
in the presence of a base, preferably pyridine,
to obtain a compound of formula (I); and optionally converting the compound of formula (I) to a pharmaceutically acceptable salt thereof.

EXAMPLES OF THE INVENTION

Representative examples of compounds of formula (I) and (II) are shown in Table 1.

TABLE 1

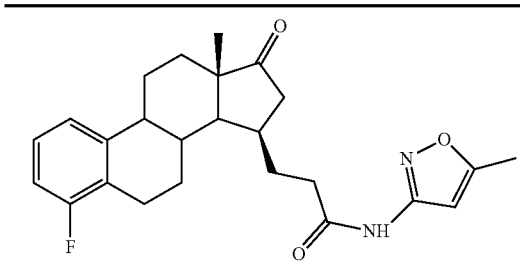
1

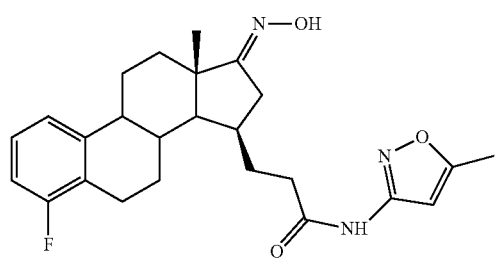 [SMILES: Cc1cc(NC(=O)CC[C@@H]2C/C(=N\O)[C@@]3(C)CCC4c5cccc(F)c5CCC4C23)no1]
2

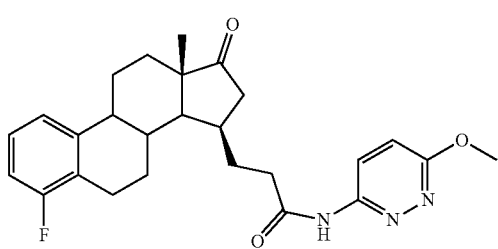 [SMILES: COc1ccc(NC(=O)CC[C@@H]2CC(=O)[C@@]3(C)CCC4c5cccc(F)c5CCC4C23)nn1]
3

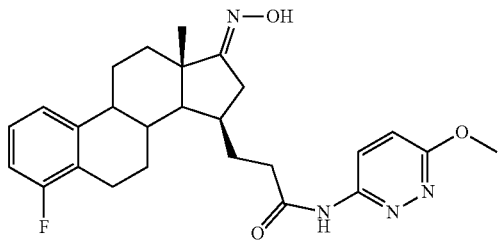
4

TABLE 1-continued

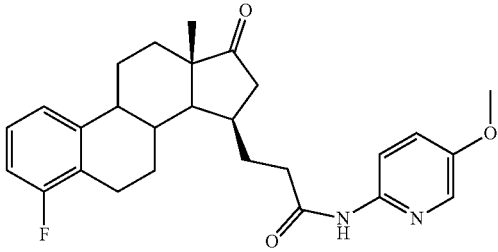 [SMILES: COc1ccc(NC(=O)CC[C@@H]2CC(=O)[C@@]3(C)CCC4c5cccc(F)c5CCC4C23)nc1]
5

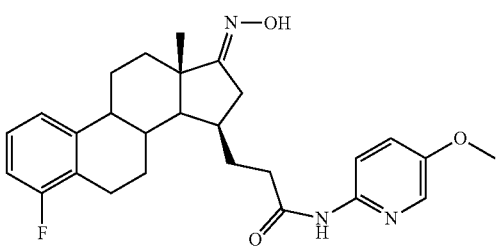
6

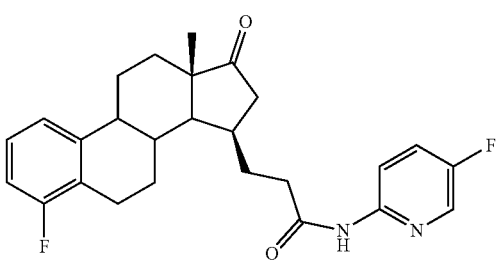 [SMILES: C[C@]12CCC3c4cccc(F)c4CCC3C1[C@H](CCC(=O)Nc1ccc(F)cn1)CC2=O]
7

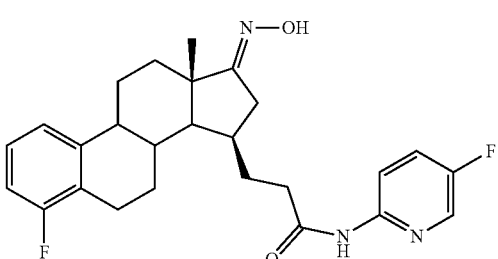
8

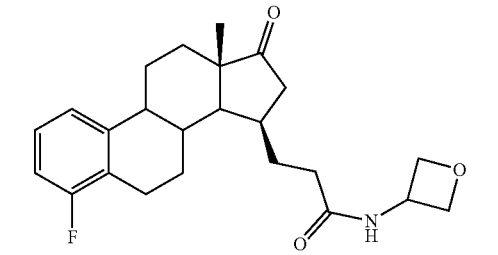 [SMILES: C[C@]12CCC3c4cccc(F)c4CCC3C1[C@H](CCC(=O)NC1COC1)CC2=O]
9

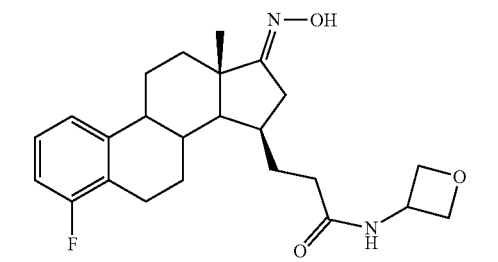 [SMILES: C[C@]12CCC3c4cccc(F)c4CCC3C1[C@H](CCC(=O)NC1COC1)C/C2=N\O]
10

TABLE 1-continued
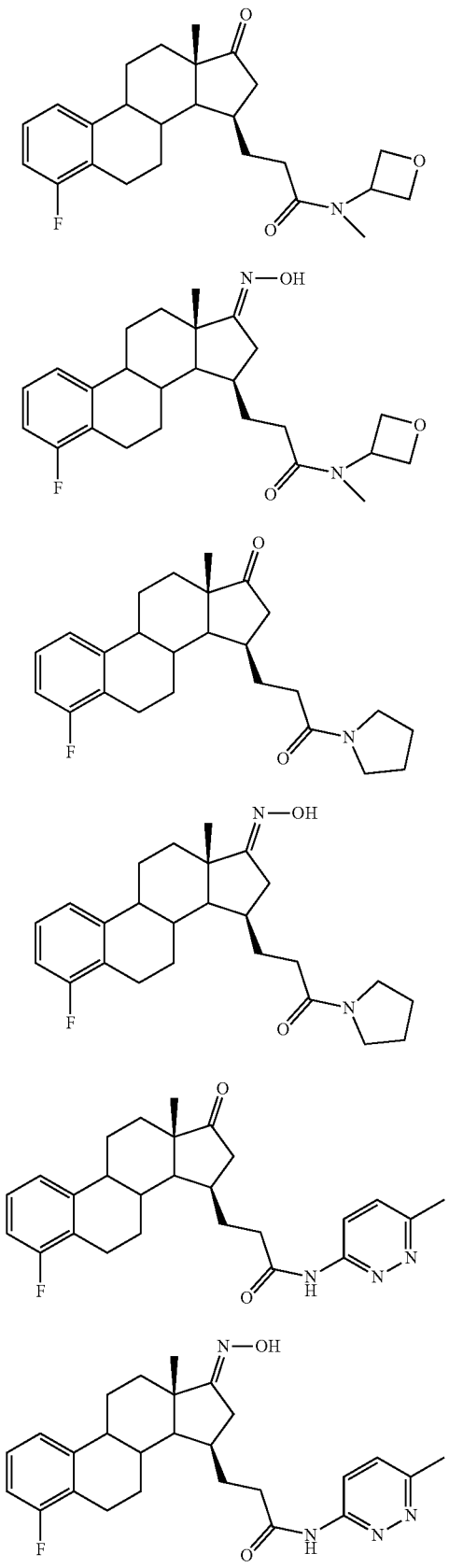
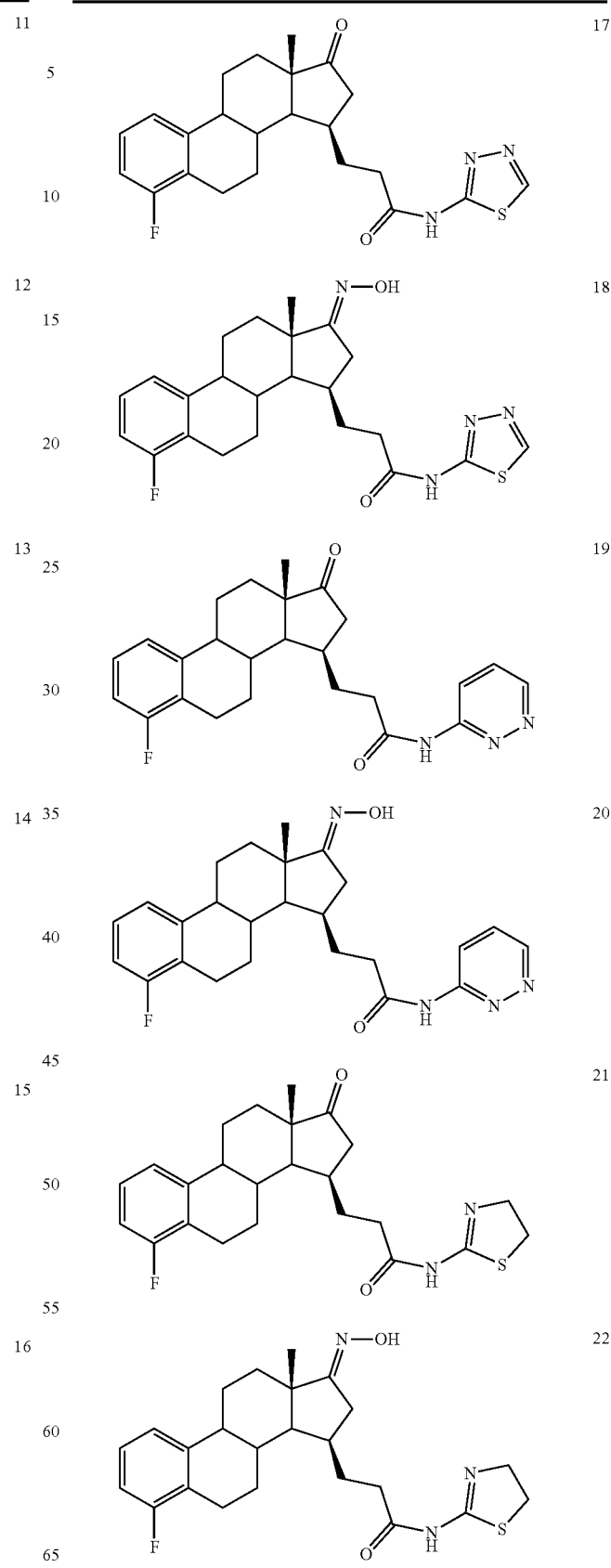

TABLE 1-continued
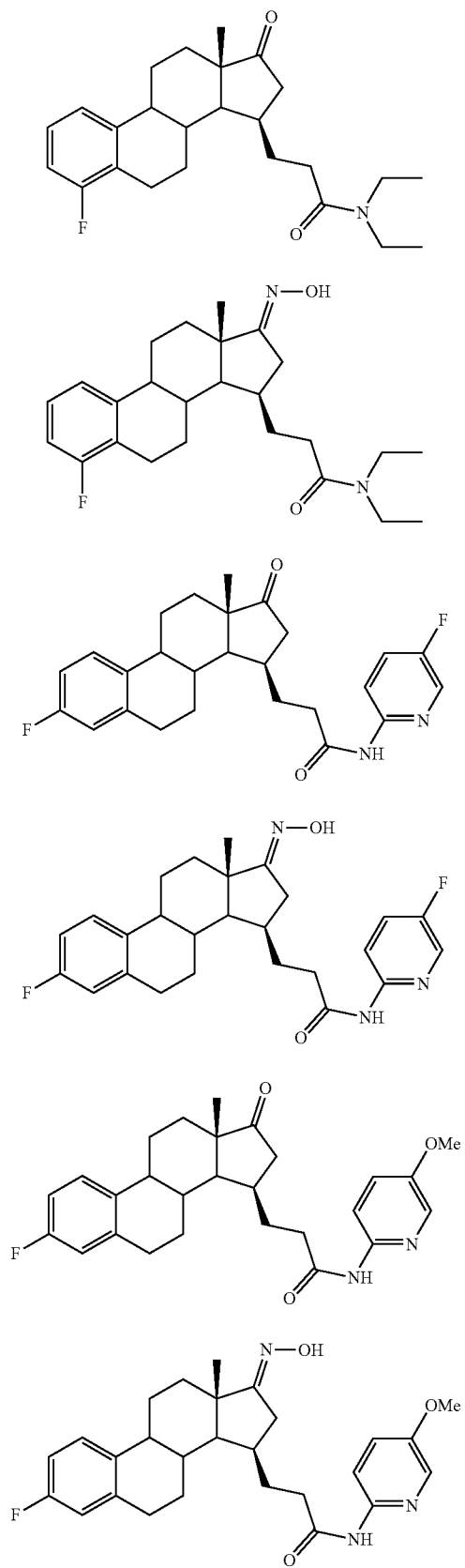
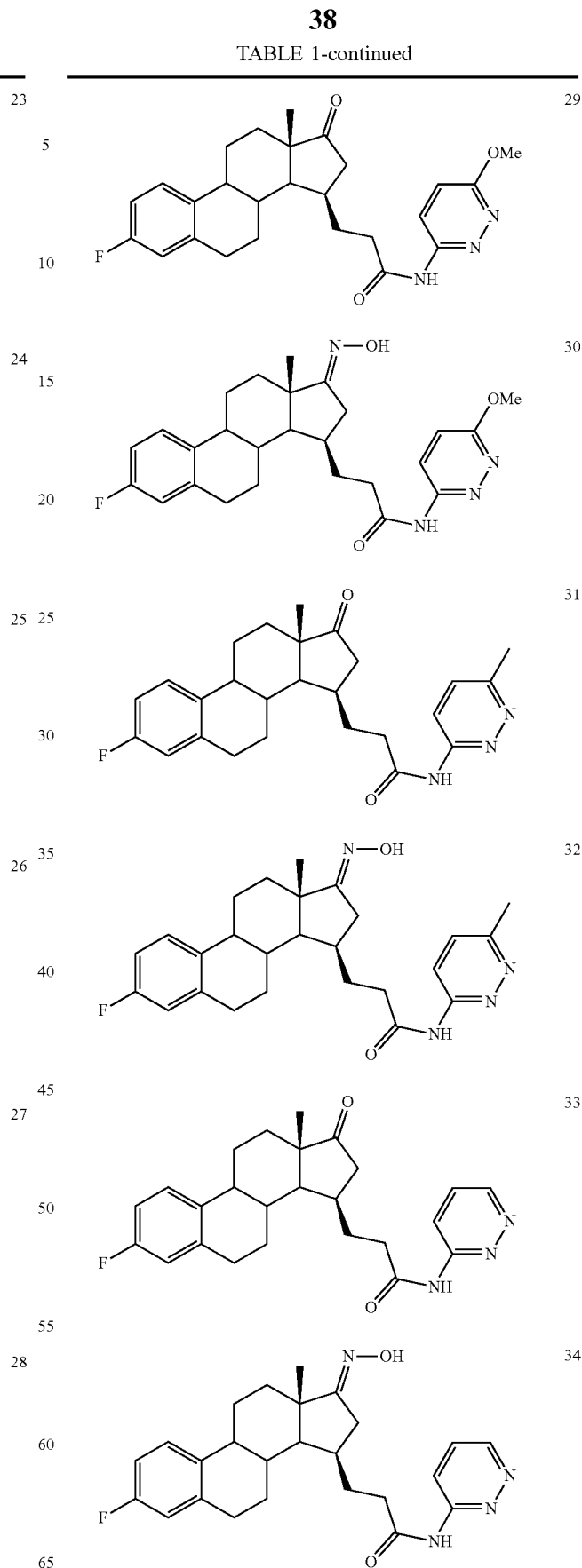

TABLE 1-continued
| | |
|---|---|
| 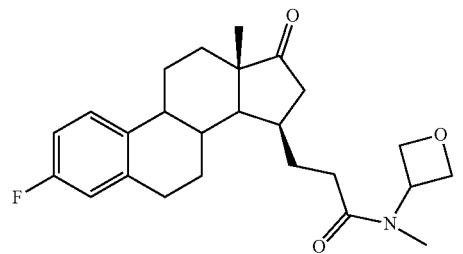 [SMILES: CN(C(=O)CC[C@@H]1CC(=O)[C@@]2(C)CCC3c4ccc(F)cc4CCC3C12)C1COC1] 35 | 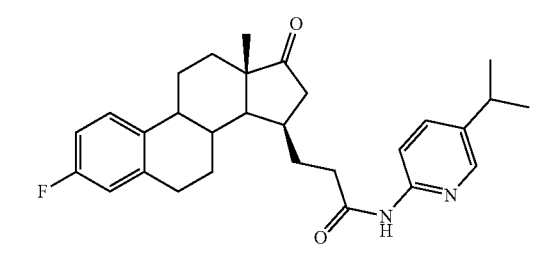 41 |
| 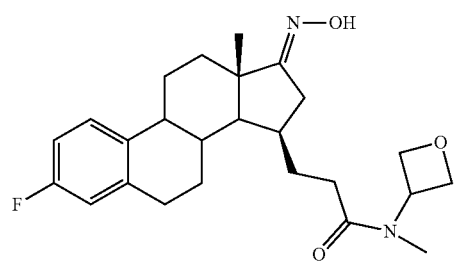 [SMILES: CN(C(=O)CC[C@@H]1C/C(=N\O)[C@@]2(C)CCC3c4ccc(F)cc4CCC3C12)C1COC1] 36 | 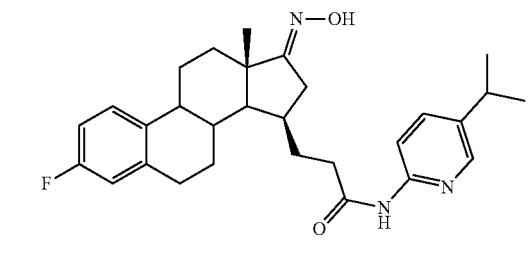 42 |
| 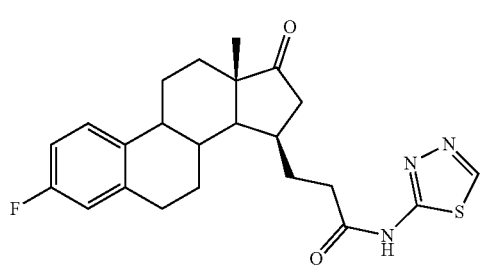 [SMILES: C[C@]12CCC3c4ccc(F)cc4CCC3C1[C@H](CCC(=O)Nc1nncs1)CC2=O] 37 | 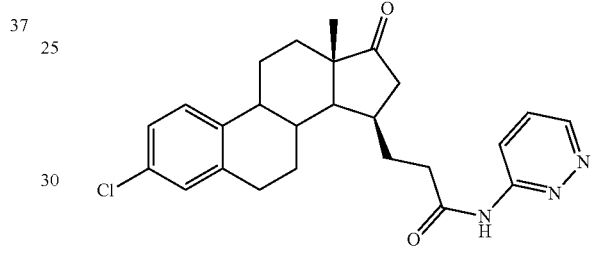 43 |
| 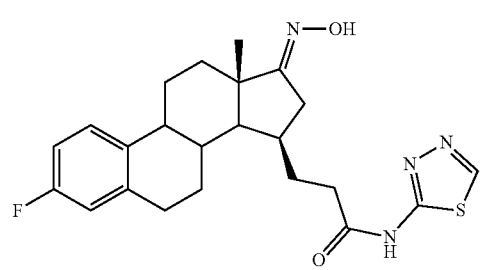 [SMILES: C[C@]12CCC3c4ccc(F)cc4CCC3C1[C@H](CCC(=O)Nc1nncs1)C/C2=N\O] 38 | 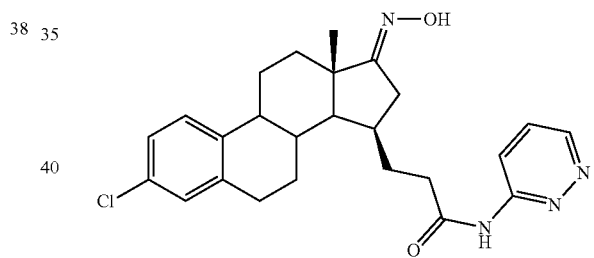 44 |
| 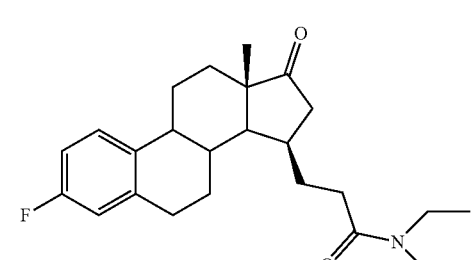 39 | 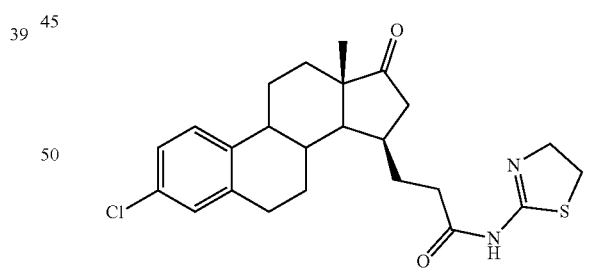 45 |
| 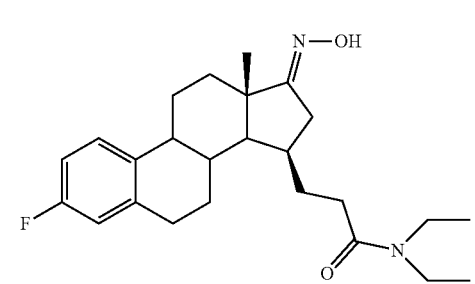 [SMILES: CCN(CC)C(=O)CC[C@@H]1C/C(=N\O)[C@@]2(C)CCC3c4ccc(F)cc4CCC3C12] 40 | 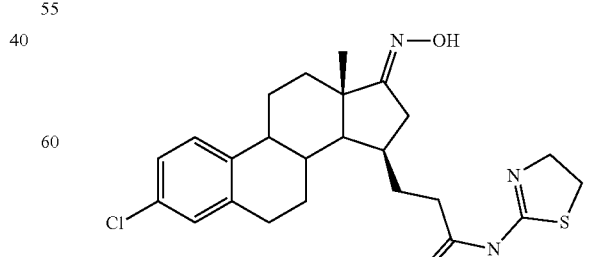 46 |

TABLE 1-continued
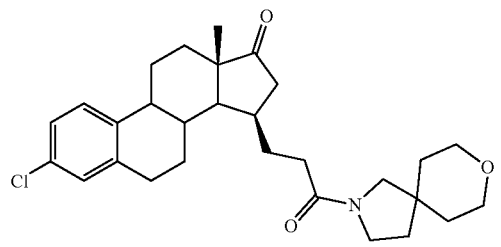 [SMILES: C[C@]12CCC3c4ccc(Cl)cc4CCC3C1[C@H](CCC(=O)N1CCC3(CCOCC3)C1)CC2=O] 47
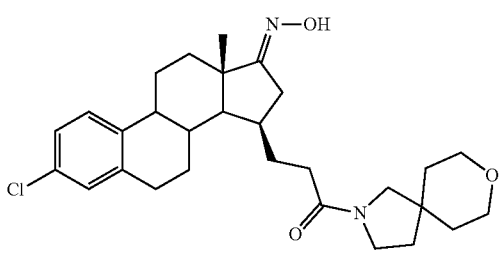 [SMILES: C[C@]12CCC3c4ccc(Cl)cc4CCC3C1[C@H](CCC(=O)N1CCC3(CCOCC3)C1)C/C2=N\O] 48
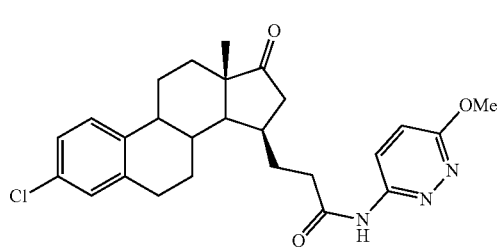 [SMILES: COc1ccc(NC(=O)CC[C@@H]2CC(=O)[C@@]3(C)CCC4c5ccc(Cl)cc5CCC4C23)nn1] 49
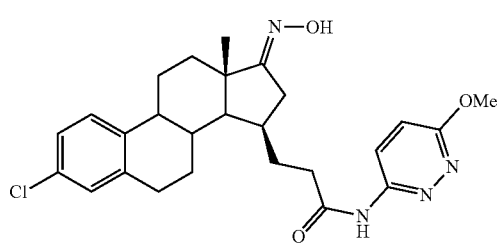 [SMILES: COc1ccc(NC(=O)CC[C@@H]2C/C(=N\O)[C@@]3(C)CCC4c5ccc(Cl)cc5CCC4C23)nn1] 50
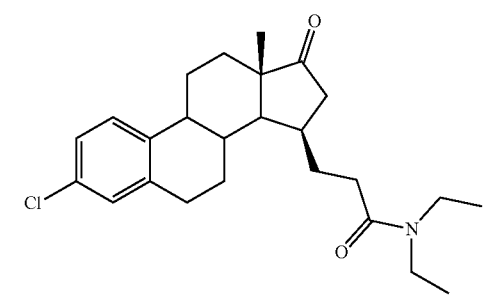 [SMILES: CCN(CC)C(=O)CC[C@@H]1CC(=O)[C@@]2(C)CCC3c4ccc(Cl)cc4CCC3C12] 51
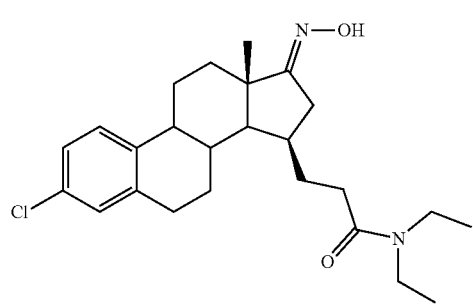 [SMILES: CCN(CC)C(=O)CC[C@@H]1C/C(=N\O)[C@@]2(C)CCC3c4ccc(Cl)cc4CCC3C12] 52
TABLE 1-continued
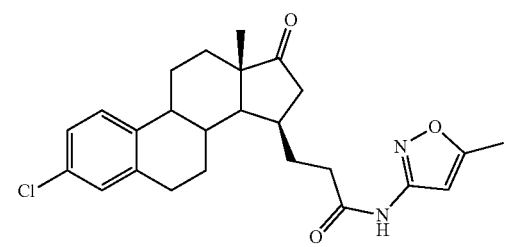 [SMILES: Cc1cc(NC(=O)CC[C@@H]2CC(=O)[C@@]3(C)CCC4c5ccc(Cl)cc5CCC4C23)no1] 53
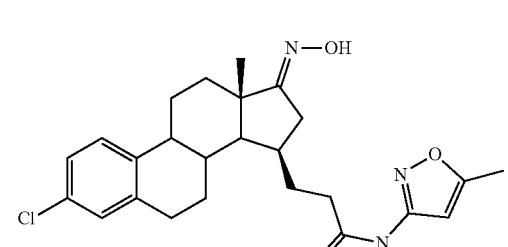 54
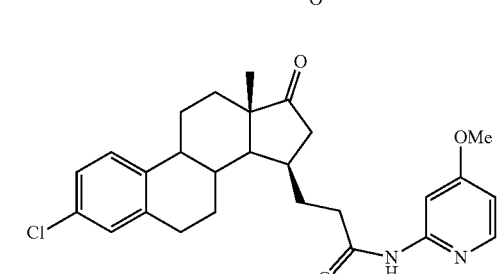 55
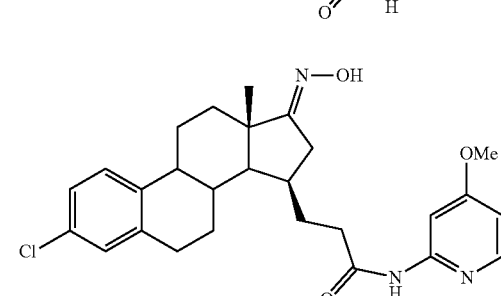 56
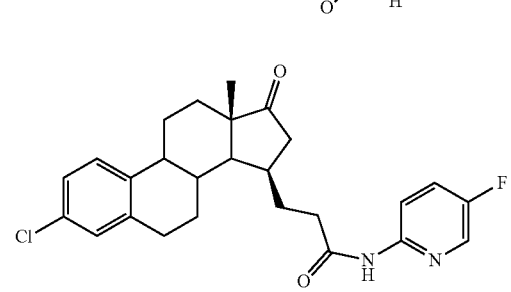 57
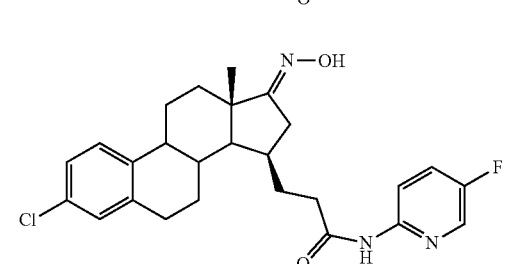 58

TABLE 1-continued
59
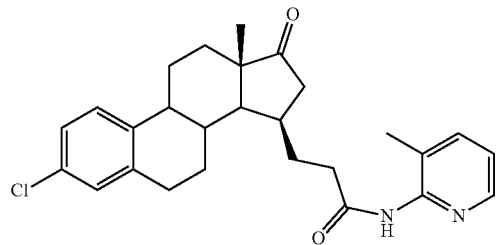 [SMILES: Cc1cccnc1NC(=O)CC[C@@H]1CC(=O)[C@@]2(C)CCC3c4ccc(Cl)cc4CCC3C12]
60
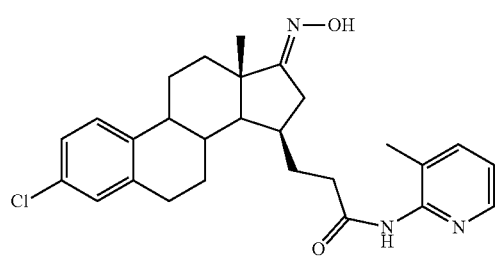 [SMILES: Cc1cccnc1NC(=O)CC[C@@H]1C/C(=N\O)[C@@]2(C)CCC3c4ccc(Cl)cc4CCC3C12]
61
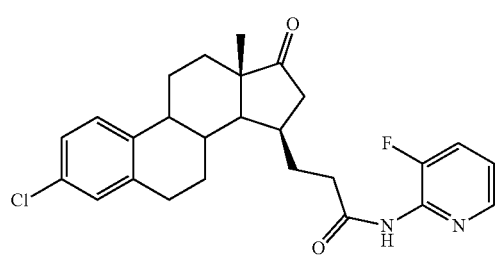 [SMILES: C[C@]12CCC3c4ccc(Cl)cc4CCC3C1[C@H](CCC(=O)Nc1ncccc1F)CC2=O]
62
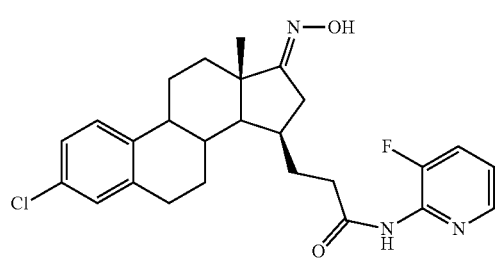 [SMILES: C[C@]12CCC3c4ccc(Cl)cc4CCC3C1[C@H](CCC(=O)Nc1ncccc1F)C/C2=N\O]
63
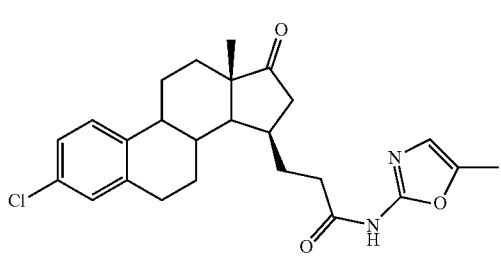 [SMILES: Cc1cnc(NC(=O)CC[C@@H]2CC(=O)[C@@]3(C)CCC4c5ccc(Cl)cc5CCC4C23)o1]
64
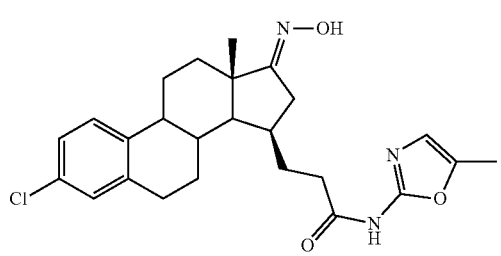 [SMILES: Cc1cnc(NC(=O)CC[C@@H]2C/C(=N\O)[C@@]3(C)CCC4c5ccc(Cl)cc5CCC4C23)o1]
TABLE 1-continued
65
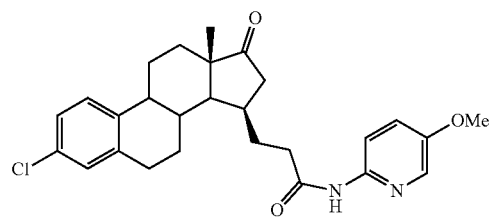 [SMILES: COc1ccc(NC(=O)CC[C@@H]2CC(=O)[C@@]3(C)CCC4c5ccc(Cl)cc5CCC4C23)nc1]
66
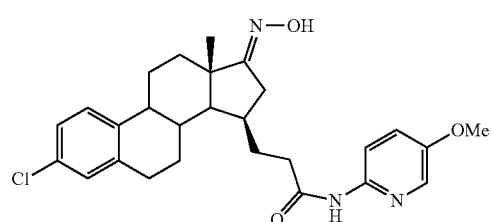
67
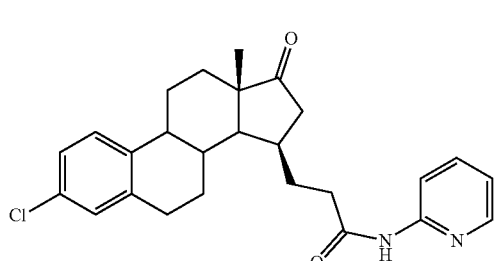
68
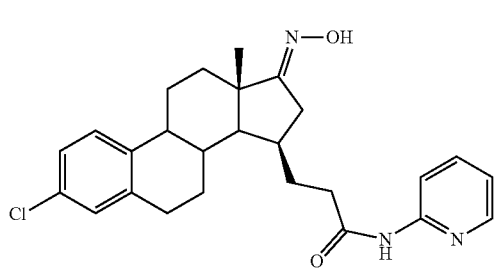 [SMILES: C[C@]12CCC3c4ccc(Cl)cc4CCC3C1[C@H](CCC(=O)Nc1ccccn1)C/C2=N\O]
69
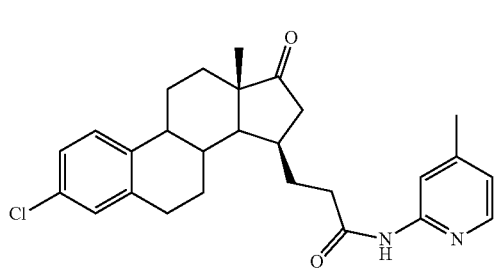 [SMILES: Cc1ccnc(NC(=O)CC[C@@H]2CC(=O)[C@@]3(C)CCC4c5ccc(Cl)cc5CCC4C23)c1]
70
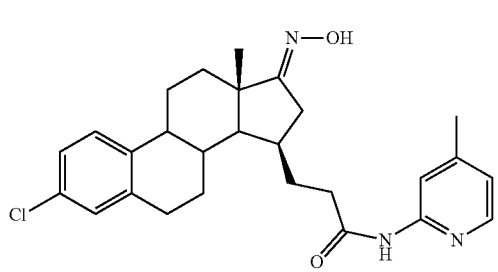 [SMILES: Cc1ccnc(NC(=O)CC[C@@H]2C/C(=N\O)[C@@]3(C)CCC4c5ccc(Cl)cc5CCC4C23)c1]

TABLE 1-continued
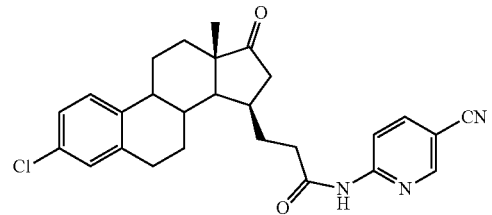 [SMILES: C[C@]12CCC3c4ccc(Cl)cc4CCC3C1[C@H](CCC(=O)Nc1ccc(C#N)cn1)CC2=O]
71
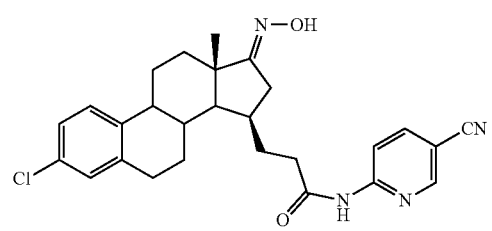 [SMILES: C[C@]12CCC3c4ccc(Cl)cc4CCC3C1[C@H](CCC(=O)Nc1ccc(C#N)cn1)C/C2=N\O]
72
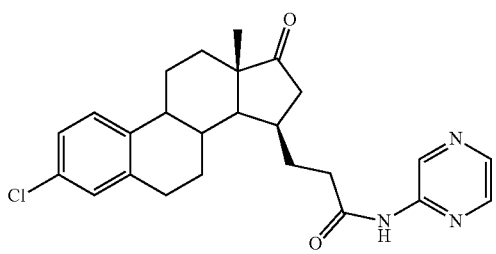 [SMILES: C[C@]12CCC3c4ccc(Cl)cc4CCC3C1[C@H](CCC(=O)Nc1cnccn1)CC2=O]
73
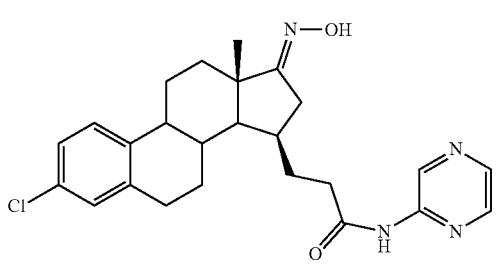 [SMILES: C[C@]12CCC3c4ccc(Cl)cc4CCC3C1[C@H](CCC(=O)Nc1cnccn1)C/C2=N\O]
74
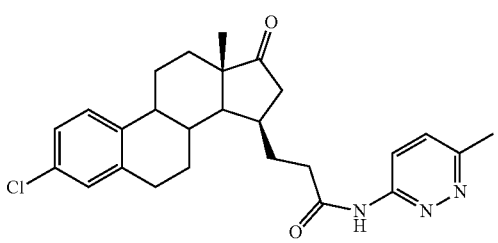 [SMILES: Cc1ccc(NC(=O)CC[C@@H]2CC(=O)[C@@]3(C)CCC4c5ccc(Cl)cc5CCC4C23)nn1]
75
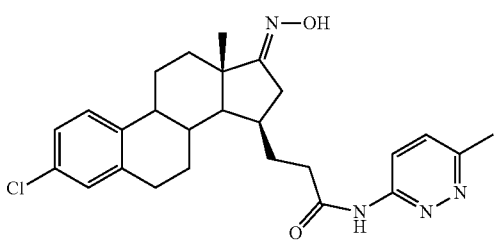 [SMILES: Cc1ccc(NC(=O)CC[C@@H]2C/C(=N\O)[C@@]3(C)CCC4c5ccc(Cl)cc5CCC4C23)nn1]
76
TABLE 1-continued
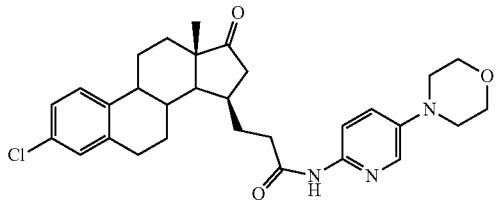 [SMILES: C[C@]12CCC3c4ccc(Cl)cc4CCC3C1[C@H](CCC(=O)Nc1ccc(N3CCOCC3)cn1)CC2=O]
77
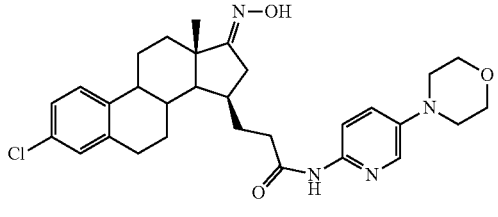 [SMILES: C[C@]12CCC3c4ccc(Cl)cc4CCC3C1[C@H](CCC(=O)Nc1ccc(N3CCOCC3)cn1)C/C2=N\O]
78
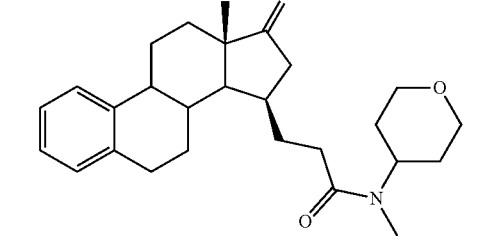
79
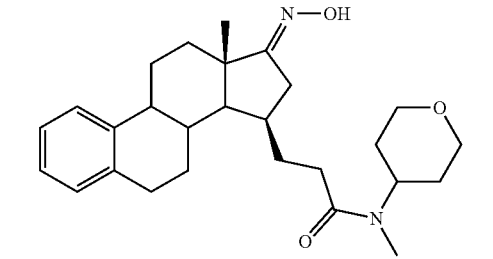 [SMILES: CN(C(=O)CC[C@@H]1C/C(=N\O)[C@@]2(C)CCC3c4ccccc4CCC3C12)C1CCOCC1]
80
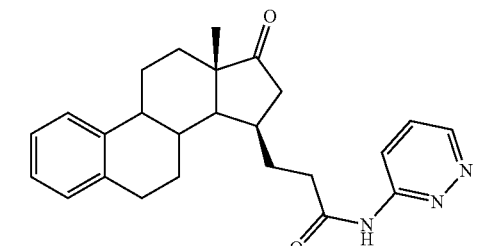
81
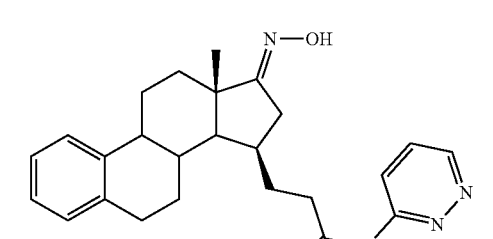
82

TABLE 1-continued
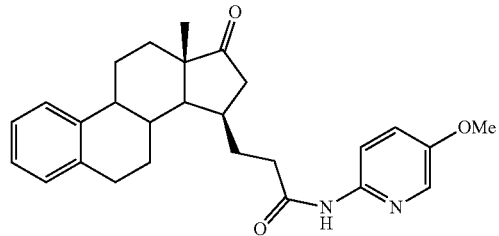 [SMILES: COc1ccc(NC(=O)CC[C@@H]2CC(=O)[C@@]3(C)CCC4c5ccccc5CCC4C23)nc1] 83
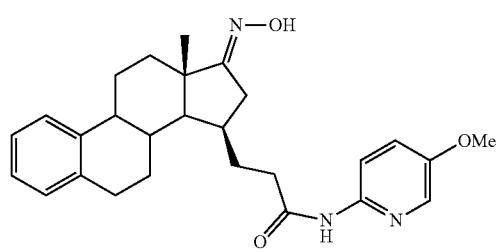 [SMILES: COc1ccc(NC(=O)CC[C@@H]2C/C(=N\O)[C@@]3(C)CCC4c5ccccc5CCC4C23)nc1] 84
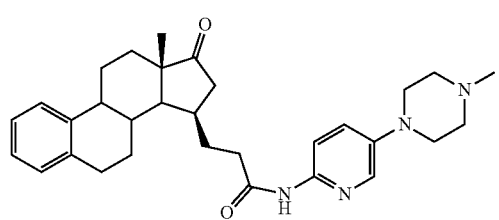 85
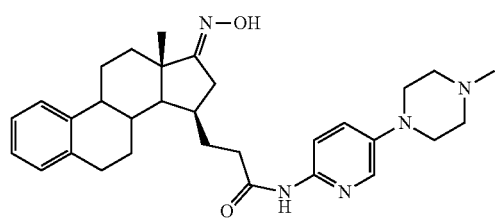 [SMILES: CN1CCN(c2ccc(NC(=O)CC[C@@H]3C/C(=N\O)[C@@]4(C)CCC5c6ccccc6CCC5C34)nc2)CC1] 86
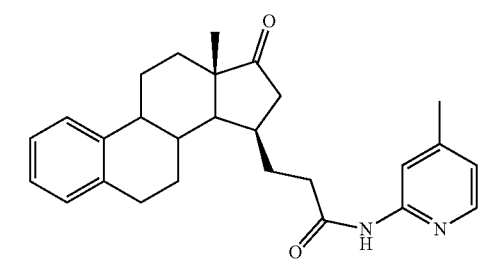 [SMILES: Cc1ccnc(NC(=O)CC[C@@H]2CC(=O)[C@@]3(C)CCC4c5ccccc5CCC4C23)c1] 87
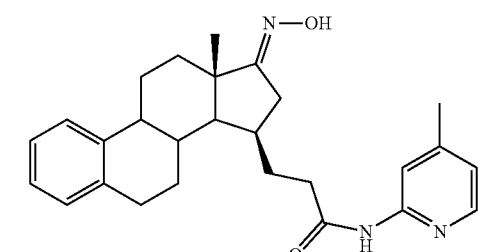 88
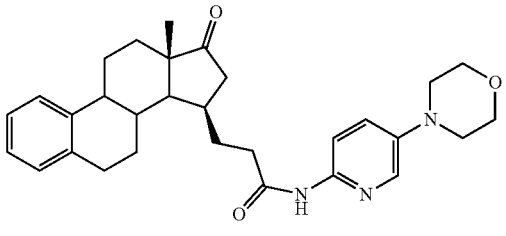 89
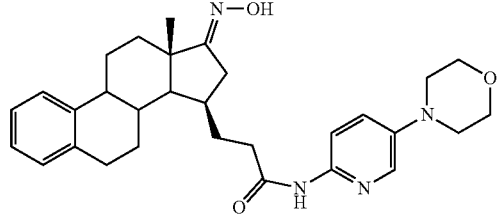 [SMILES: C[C@]12CCC3c4ccccc4CCC3C1[C@H](CCC(=O)Nc1ccc(N3CCOCC3)cn1)C/C2=N\O] 90
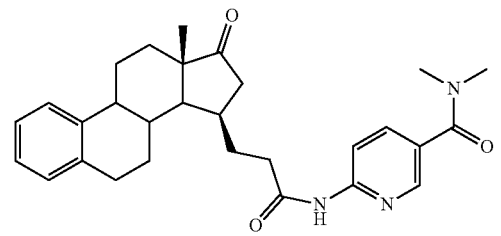 [SMILES: CN(C)C(=O)c1ccc(NC(=O)CC[C@@H]2CC(=O)[C@@]3(C)CCC4c5ccccc5CCC4C23)nc1] 91
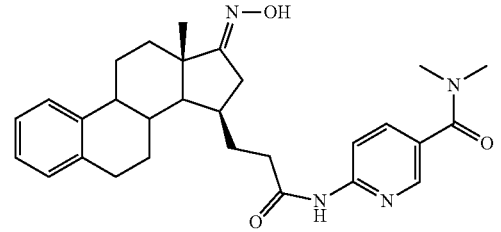 [SMILES: CN(C)C(=O)c1ccc(NC(=O)CC[C@@H]2C/C(=N\O)[C@@]3(C)CCC4c5ccccc5CCC4C23)nc1] 92
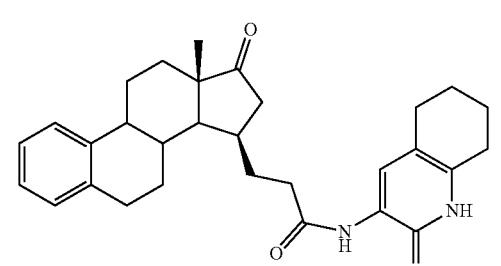 93
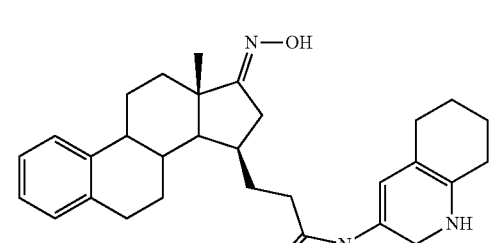 94

TABLE 1-continued
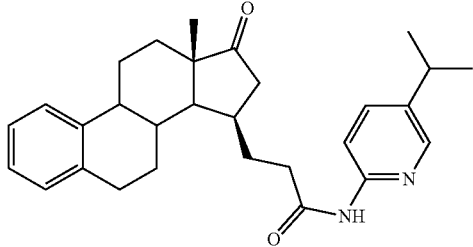 [SMILES: CC(C)c1ccc(NC(=O)CC[C@@H]2CC(=O)[C@@]3(C)CCC4c5ccccc5CCC4C23)nc1] 95
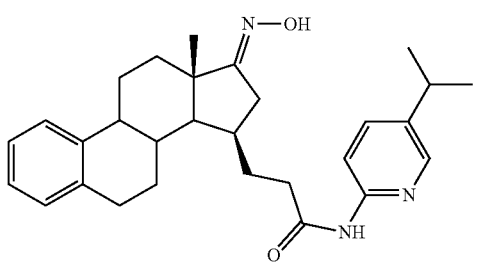 [SMILES: CC(C)c1ccc(NC(=O)CC[C@@H]2C/C(=N\O)[C@@]3(C)CCC4c5ccccc5CCC4C23)nc1] 96
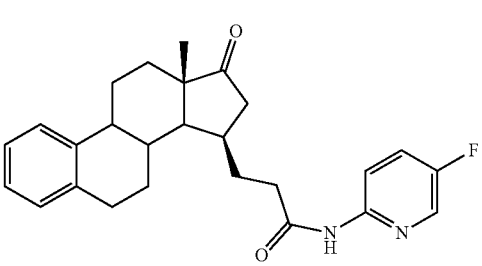 [SMILES: C[C@]12CCC3c4ccccc4CCC3C1[C@H](CCC(=O)Nc1ccc(F)cn1)CC2=O] 97
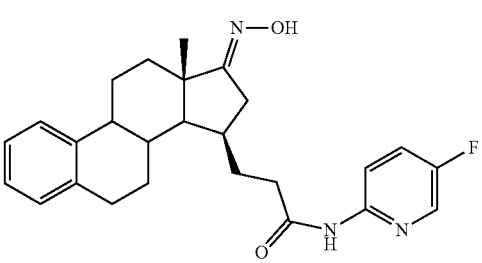 [SMILES: C[C@]12CCC3c4ccccc4CCC3C1[C@H](CCC(=O)Nc1ccc(F)cn1)C/C2=N\O] 98
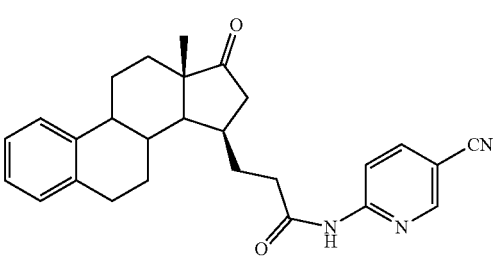 [SMILES: C[C@]12CCC3c4ccccc4CCC3C1[C@H](CCC(=O)Nc1ccc(C#N)cn1)CC2=O] 99
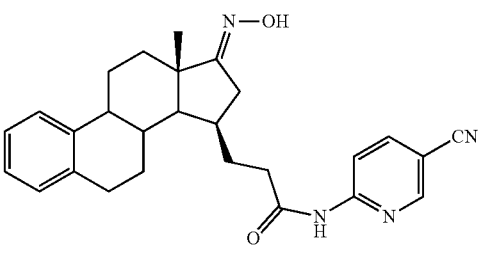 [SMILES: C[C@]12CCC3c4ccccc4CCC3C1[C@H](CCC(=O)Nc1ccc(C#N)cn1)C/C2=N\O] 100
TABLE 1-continued
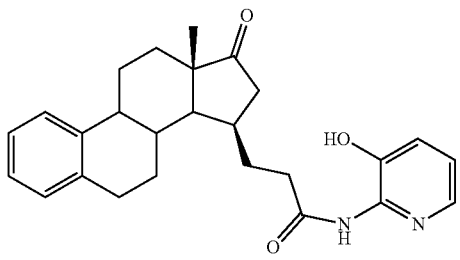 [SMILES: C[C@]12CCC3c4ccccc4CCC3C1[C@H](CCC(=O)Nc1ncccc1O)CC2=O] 101
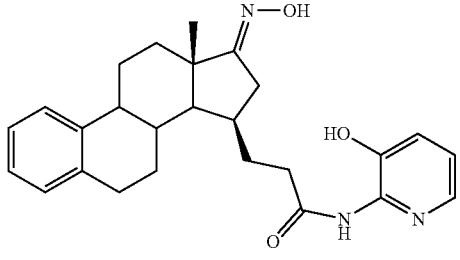 [SMILES: C[C@]12CCC3c4ccccc4CCC3C1[C@H](CCC(=O)Nc1ncccc1O)C/C2=N\O] 102
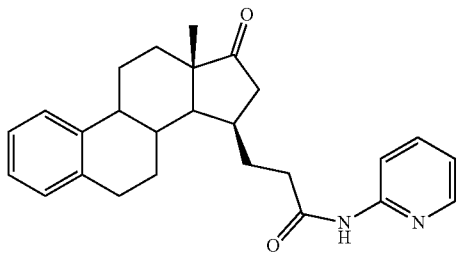 [SMILES: C[C@]12CCC3c4ccccc4CCC3C1[C@H](CCC(=O)Nc1ccccn1)CC2=O] 103
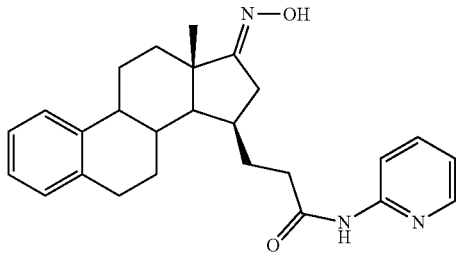 [SMILES: C[C@]12CCC3c4ccccc4CCC3C1[C@H](CCC(=O)Nc1ccccn1)C/C2=N\O] 104
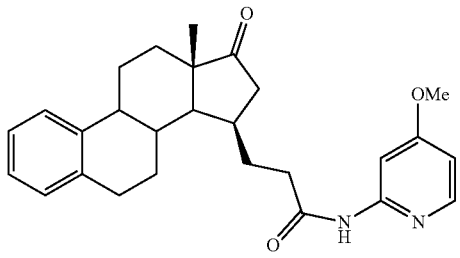 [SMILES: COc1ccnc(NC(=O)CC[C@@H]2CC(=O)[C@@]3(C)CCC4c5ccccc5CCC4C23)c1] 105
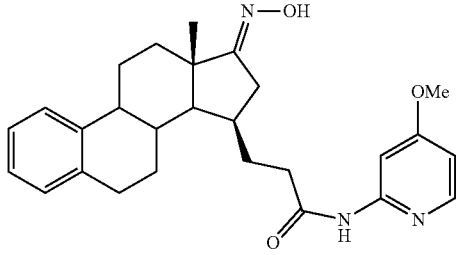 [SMILES: COc1ccnc(NC(=O)CC[C@@H]2C/C(=N\O)[C@@]3(C)CCC4c5ccccc5CCC4C23)c1] 106

TABLE 1-continued
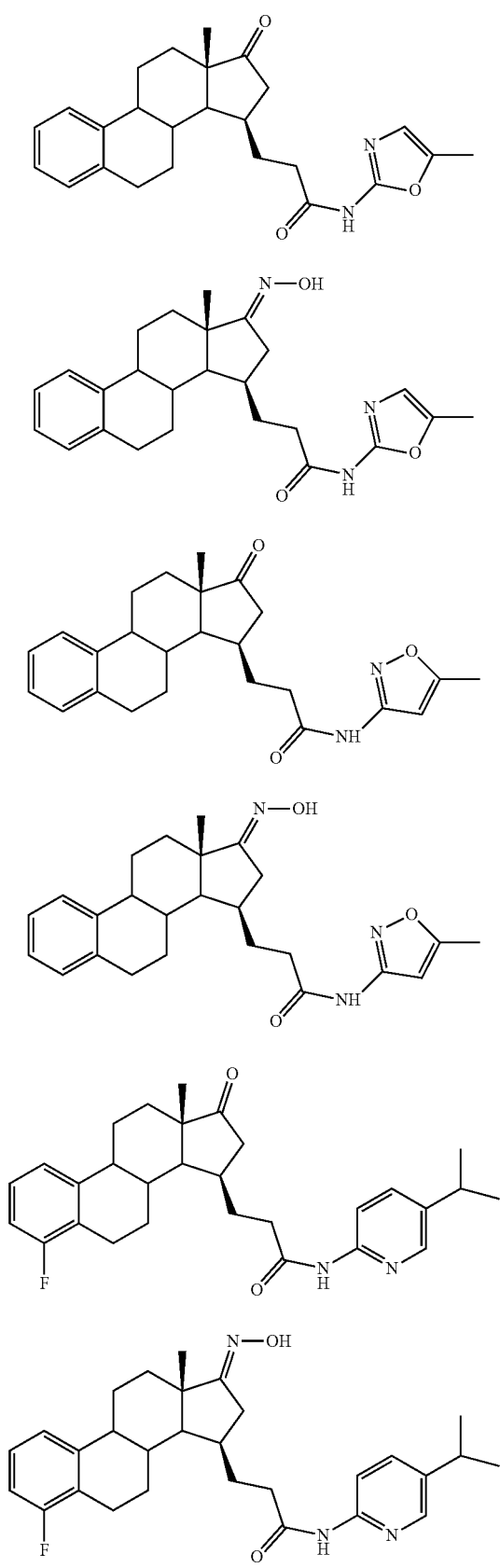
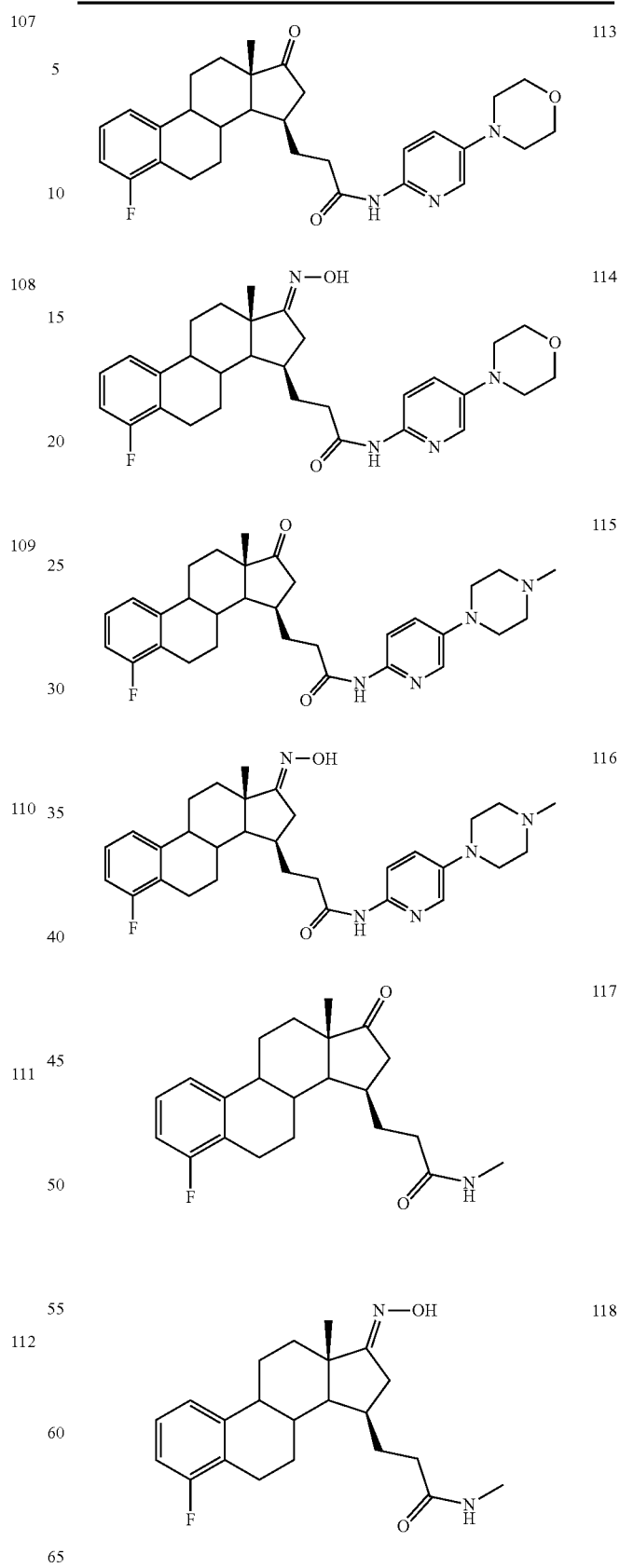

TABLE 1-continued
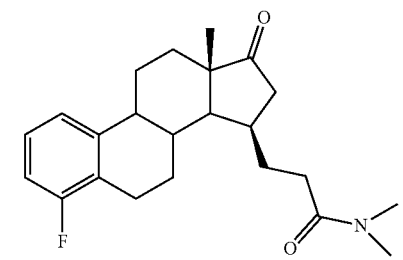 [SMILES: CN(C)C(=O)CC[C@@H]1CC(=O)[C@@]2(C)CCC3c4cccc(F)c4CCC3C12] 119
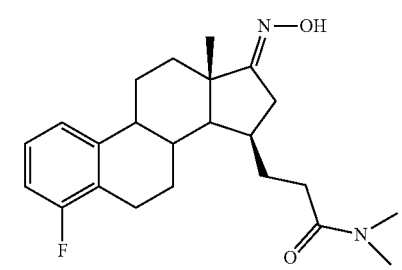 [SMILES: CN(C)C(=O)CC[C@@H]1C/C(=N\O)[C@@]2(C)CCC3c4cccc(F)c4CCC3C12] 120
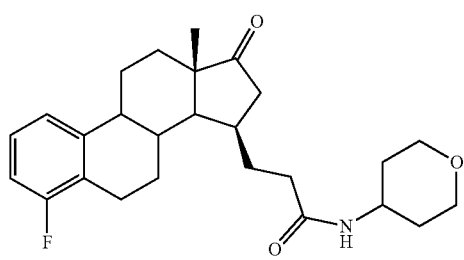 [SMILES: C[C@]12CCC3c4cccc(F)c4CCC3C1[C@H](CCC(=O)NC1CCOCC1)CC2=O] 121
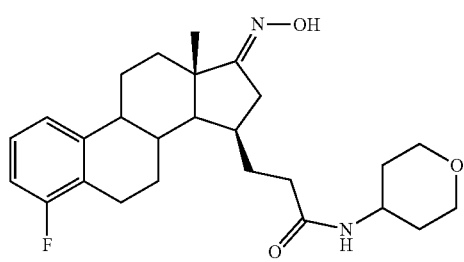 [SMILES: C[C@]12CCC3c4cccc(F)c4CCC3C1[C@H](CCC(=O)NC1CCOCC1)C/C2=N\O] 122
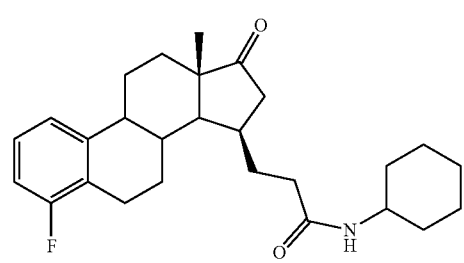 [SMILES: C[C@]12CCC3c4cccc(F)c4CCC3C1[C@H](CCC(=O)NC1CCCCC1)CC2=O] 123
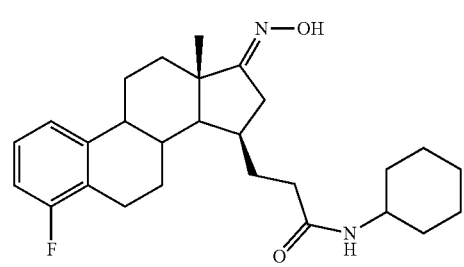 [SMILES: C[C@]12CCC3c4cccc(F)c4CCC3C1[C@H](CCC(=O)NC1CCCCC1)C/C2=N\O] 124
TABLE 1-continued
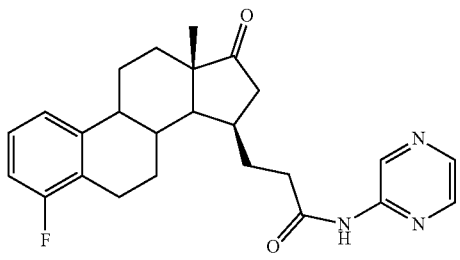 [SMILES: C[C@]12CCC3c4cccc(F)c4CCC3C1[C@H](CCC(=O)Nc1cnccn1)CC2=O] 125
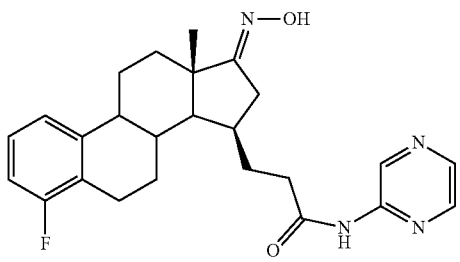 [SMILES: C[C@]12CCC3c4cccc(F)c4CCC3C1[C@H](CCC(=O)Nc1cnccn1)C/C2=N\O] 126
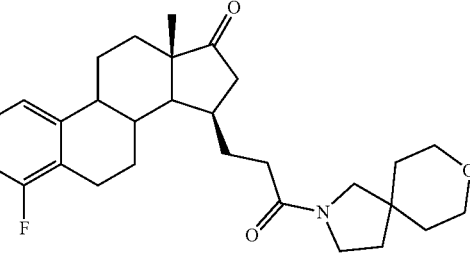 127
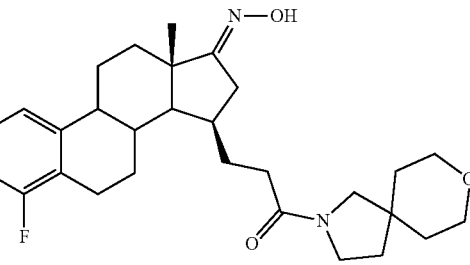 128
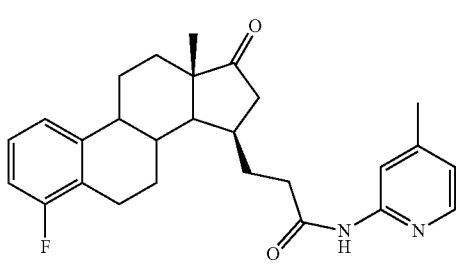 [SMILES: Cc1ccnc(NC(=O)CC[C@@H]2CC(=O)[C@@]3(C)CCC4c5cccc(F)c5CCC4C23)c1] 129
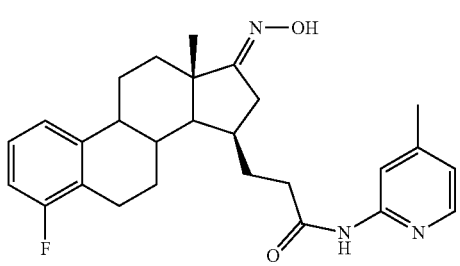 [SMILES: Cc1ccnc(NC(=O)CC[C@@H]2C/C(=N\O)[C@@]3(C)CCC4c5cccc(F)c5CCC4C23)c1] 130

TABLE 1-continued
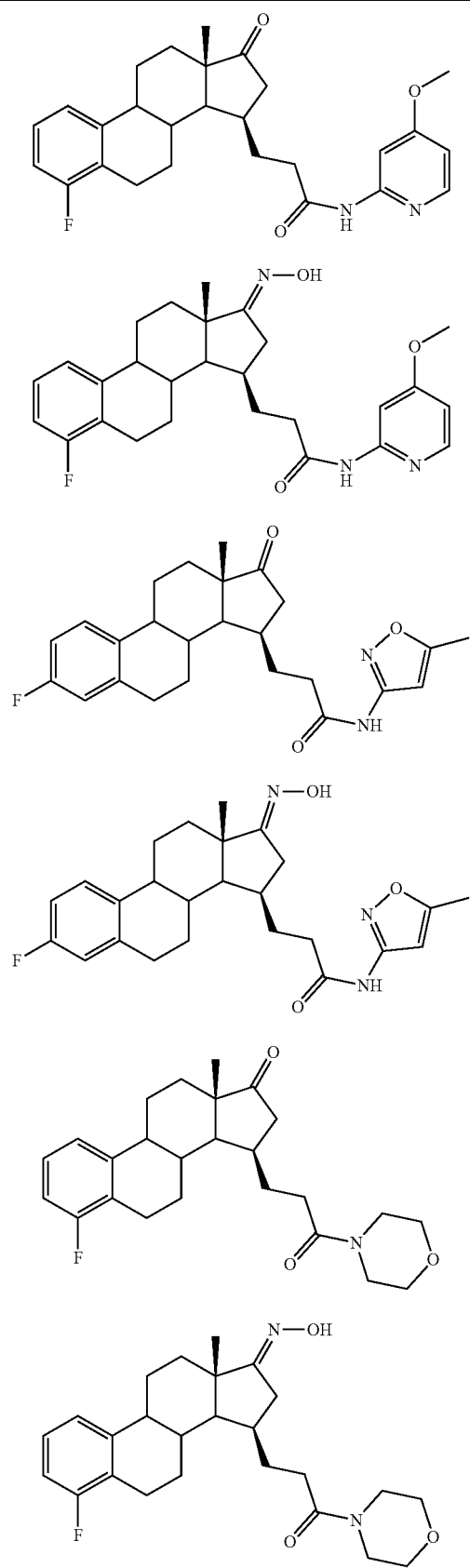
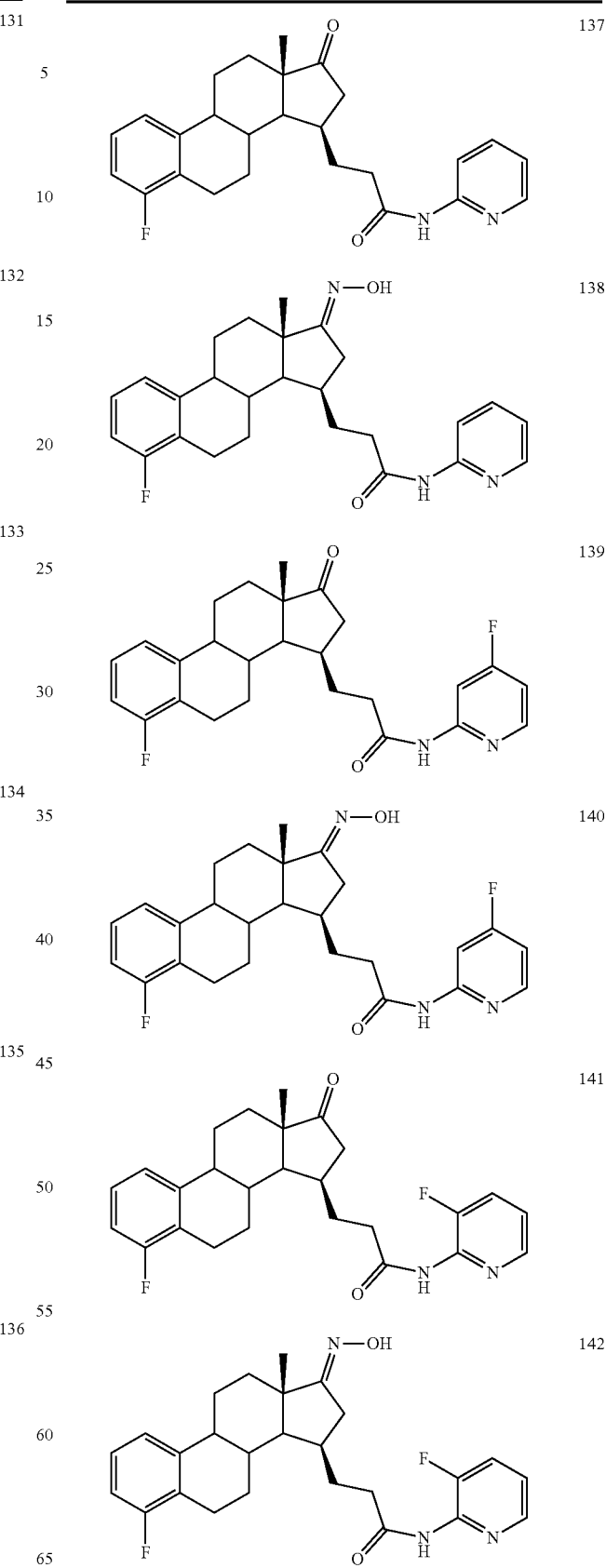

TABLE 1-continued
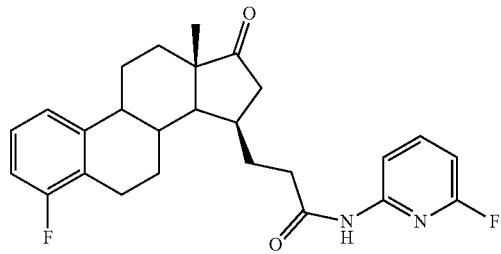 [SMILES: C[C@]12CCC3c4cccc(F)c4CCC3C1[C@H](CCC(=O)Nc1cccc(F)n1)CC2=O] 143
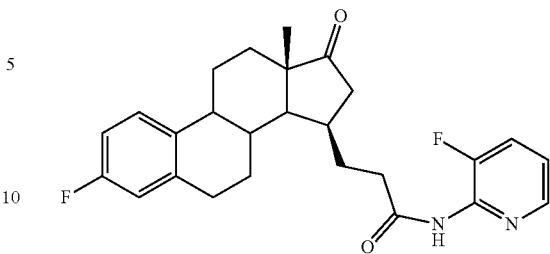 149
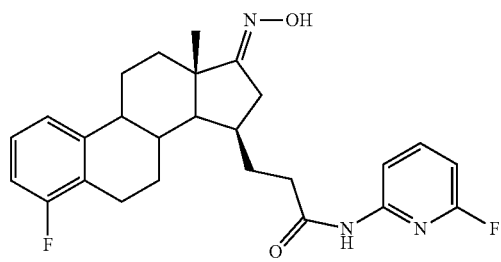 [SMILES: C[C@]12CCC3c4cccc(F)c4CCC3C1[C@H](CCC(=O)Nc1cccc(F)n1)C/C2=N\O] 144
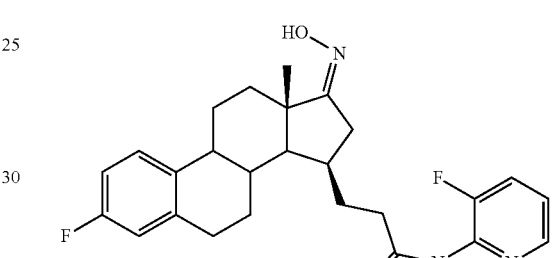 150a
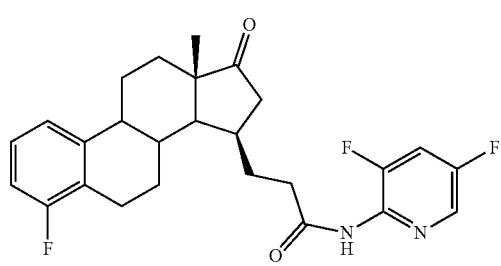 [SMILES: C[C@]12CCC3c4cccc(F)c4CCC3C1[C@H](CCC(=O)Nc1ncc(F)cc1F)CC2=O] 145
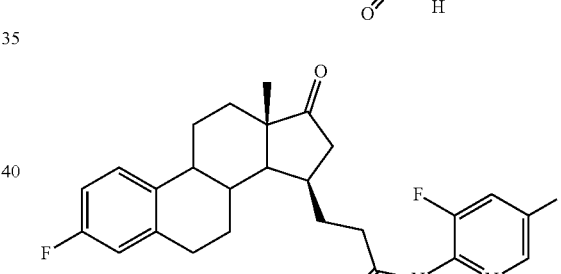 150b
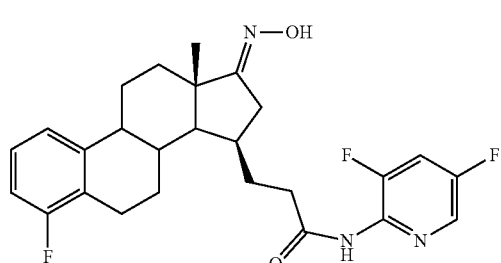 146
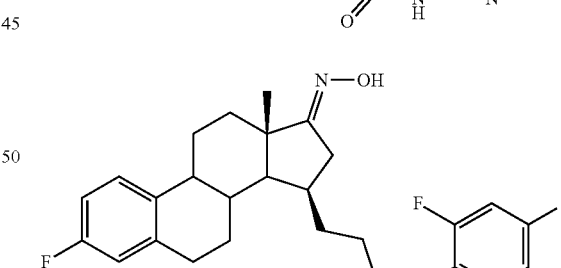 151
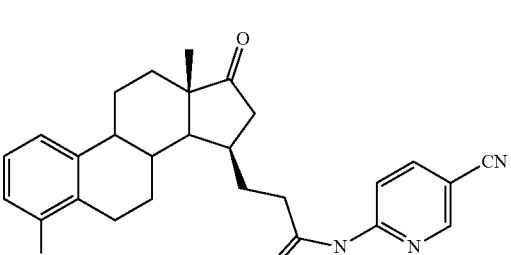 147
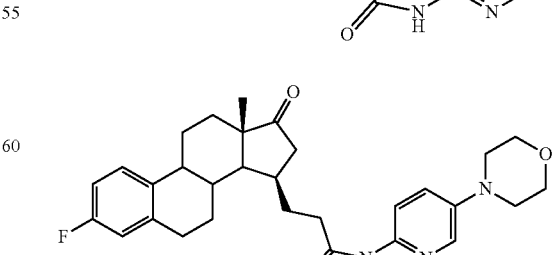 152
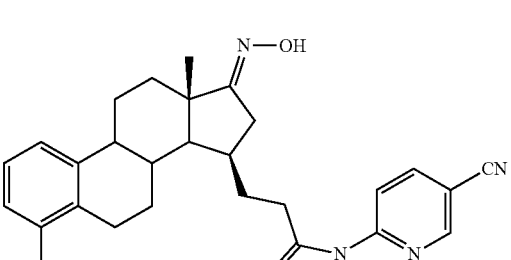 148
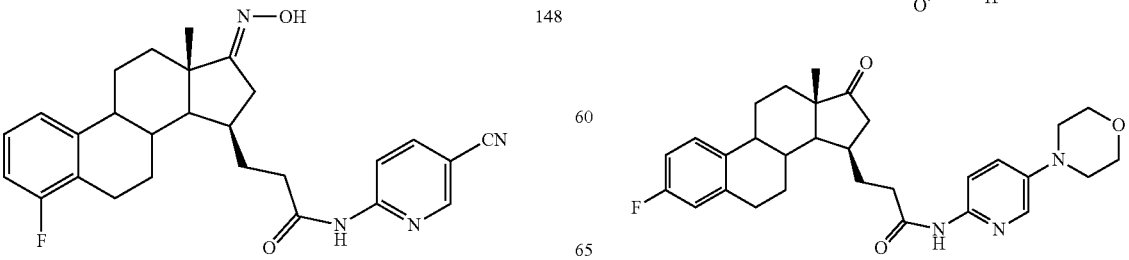 153

TABLE 1-continued
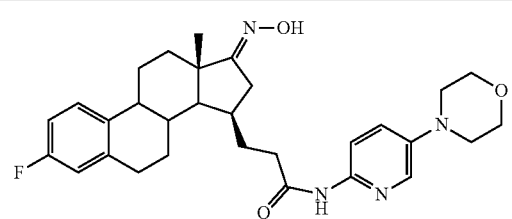 [SMILES: C[C@]12CCC3c4ccc(F)cc4CCC3C1[C@H](CCC(=O)Nc1ccc(N3CCOCC3)cn1)C/C2=N\O] 154
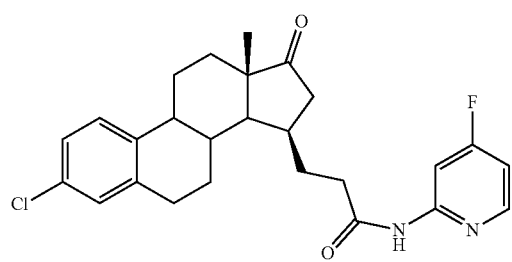 [SMILES: C[C@]12CCC3c4ccc(Cl)cc4CCC3C1[C@H](CCC(=O)Nc1cc(F)ccn1)CC2=O] 155
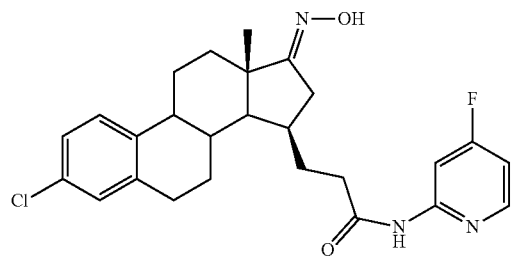 [SMILES: C[C@]12CCC3c4ccc(Cl)cc4CCC3C1[C@H](CCC(=O)Nc1cc(F)ccn1)C/C2=N\O] 156
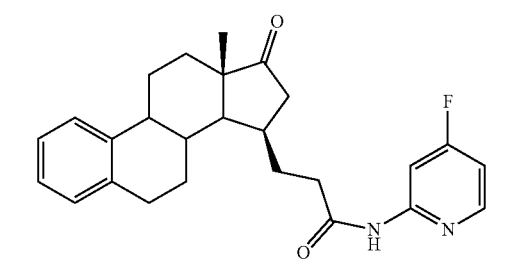 [SMILES: C[C@]12CCC3c4ccccc4CCC3C1[C@H](CCC(=O)Nc1cc(F)ccn1)CC2=O] 157
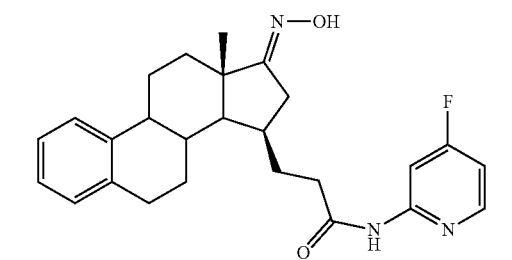 [SMILES: C[C@]12CCC3c4ccccc4CCC3C1[C@H](CCC(=O)Nc1cc(F)ccn1)C/C2=N\O] 158
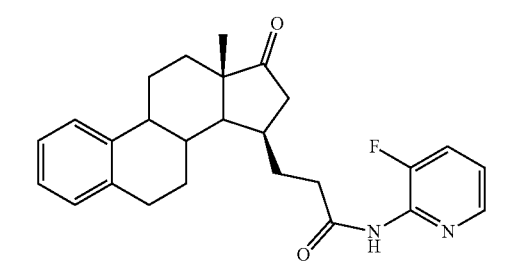 [SMILES: C[C@]12CCC3c4ccccc4CCC3C1[C@H](CCC(=O)Nc1ncccc1F)CC2=O] 159
TABLE 1-continued
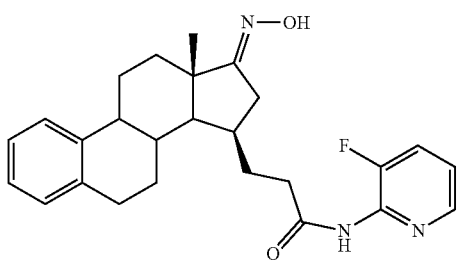 [SMILES: C[C@]12CCC3c4ccccc4CCC3C1[C@H](CCC(=O)Nc1ncccc1F)C/C2=N\O] 160
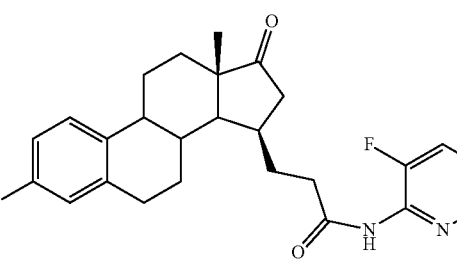 161
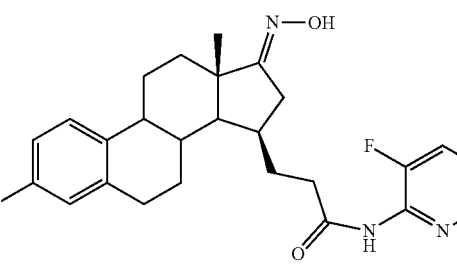 162
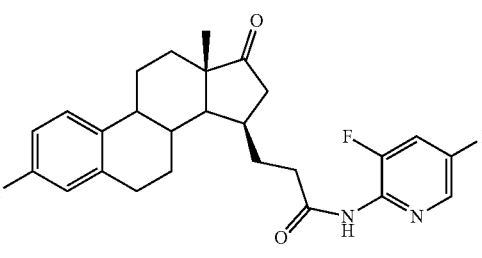 163
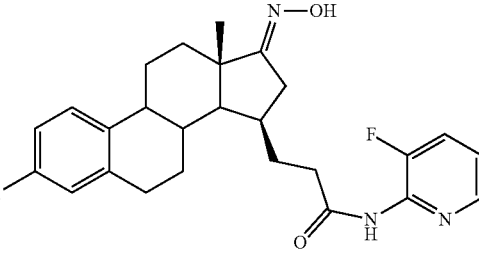 164
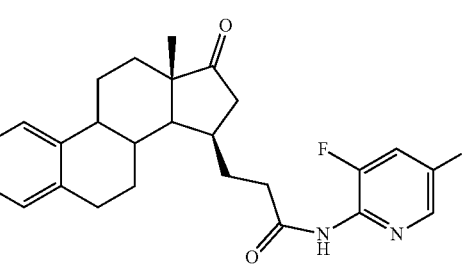 165

TABLE 1-continued
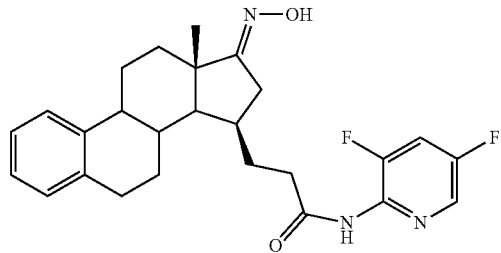 [SMILES: C[C@]12CCC3c4ccccc4CCC3C1[C@H](CCC(=O)Nc1ncc(F)cc1F)C/C2=N\O]
166
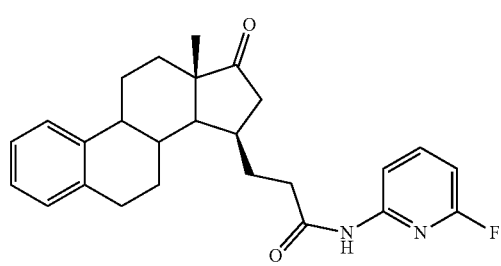 [SMILES: C[C@]12CCC3c4ccccc4CCC3C1[C@H](CCC(=O)Nc1cccc(F)n1)CC2=O]
167
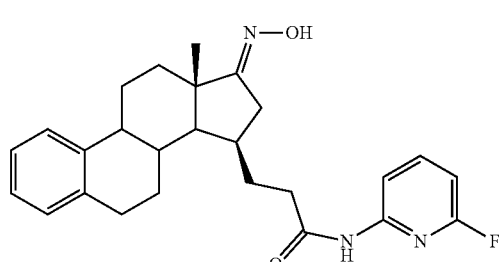
168
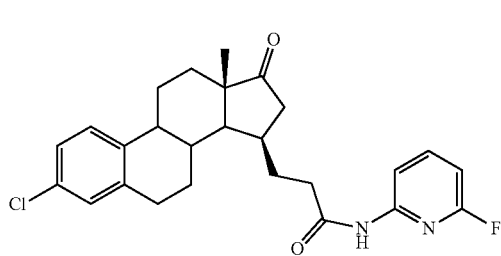 [SMILES: C[C@]12CCC3c4ccc(Cl)cc4CCC3C1[C@H](CCC(=O)Nc1cccc(F)n1)CC2=O]
169
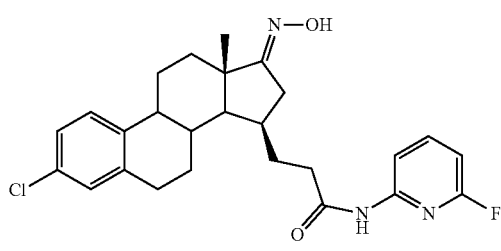 [SMILES: C[C@]12CCC3c4ccc(Cl)cc4CCC3C1[C@H](CCC(=O)Nc1cccc(F)n1)C/C2=N\O]
170
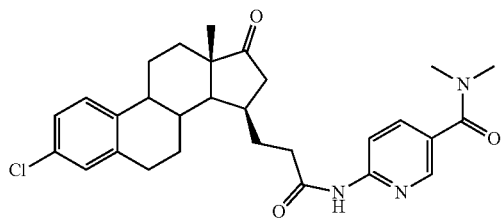 [SMILES: CN(C)C(=O)c1ccc(NC(=O)CC[C@@H]2CC(=O)[C@@]3(C)CCC4c5ccc(Cl)cc5CCC4C23)nc1]
171
TABLE 1-continued
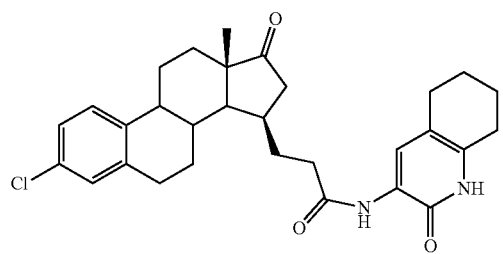 [SMILES: C[C@]12CCC3c4ccc(Cl)cc4CCC3C1[C@H](CCC(=O)Nc1cc3c([nH]c1=O)CCCC3)CC2=O]
172
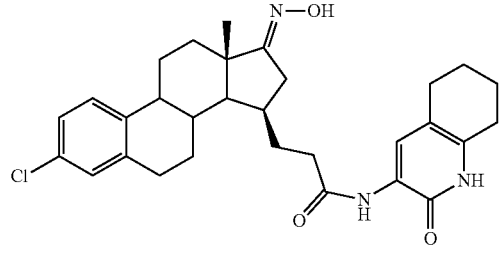 [SMILES: C[C@]12CCC3c4ccc(Cl)cc4CCC3C1[C@H](CCC(=O)Nc1cc3c([nH]c1=O)CCCC3)C/C2=N\O]
173
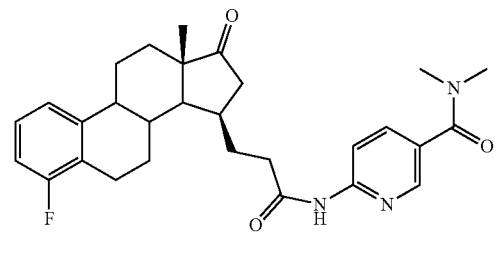 [SMILES: CN(C)C(=O)c1ccc(NC(=O)CC[C@@H]2CC(=O)[C@@]3(C)CCC4c5cccc(F)c5CCC4C23)nc1]
174
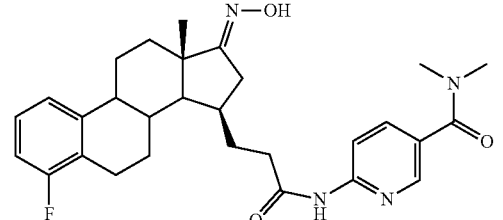
175
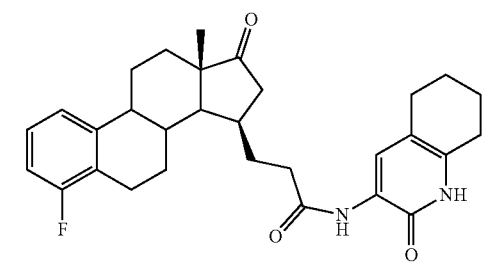 [SMILES: C[C@]12CCC3c4cccc(F)c4CCC3C1[C@H](CCC(=O)Nc1cc3c([nH]c1=O)CCCC3)CC2=O]
176
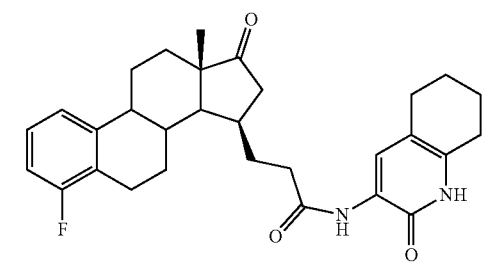 [SMILES: C[C@]12CCC3c4cccc(F)c4CCC3C1[C@H](CCC(=O)Nc1cc3c([nH]c1=O)CCCC3)CC2=O]
177

TABLE 1-continued

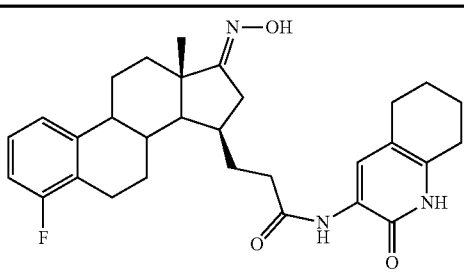

178

Compounds of this invention are also useful in the form of acid or base addition salts, hydrates, or solvates thereof.

GENERAL PREPARATION METHODS

Compounds of the present invention may be prepared by methods known in the art.

The following examples illustrate the preparation of compounds of formula (I).

Preparation of Synthesis Starting Materials and Precursors

Preparation of the Starting Material Acid IX

Compound SM-IX was synthesized from Estrone (Scheme 1.). Methods of Horwitz et al (*J. Med. Chem.,* 1986, 29 (5), 692-698) yielded amine SM-III which was fluorinated using conditions of Labrie et al. WO 2008124922. The fluoride SM-IV was converted to enone SM-VI by silylation/oxidation method of Kobayashi et (Tetrahedron, 71(35), 5918-5924; 2015). The allylation, hydroboration and oxidation of SM-VI to SM-IX was performed as in patents WO2005/047303 and WO2006/125800.

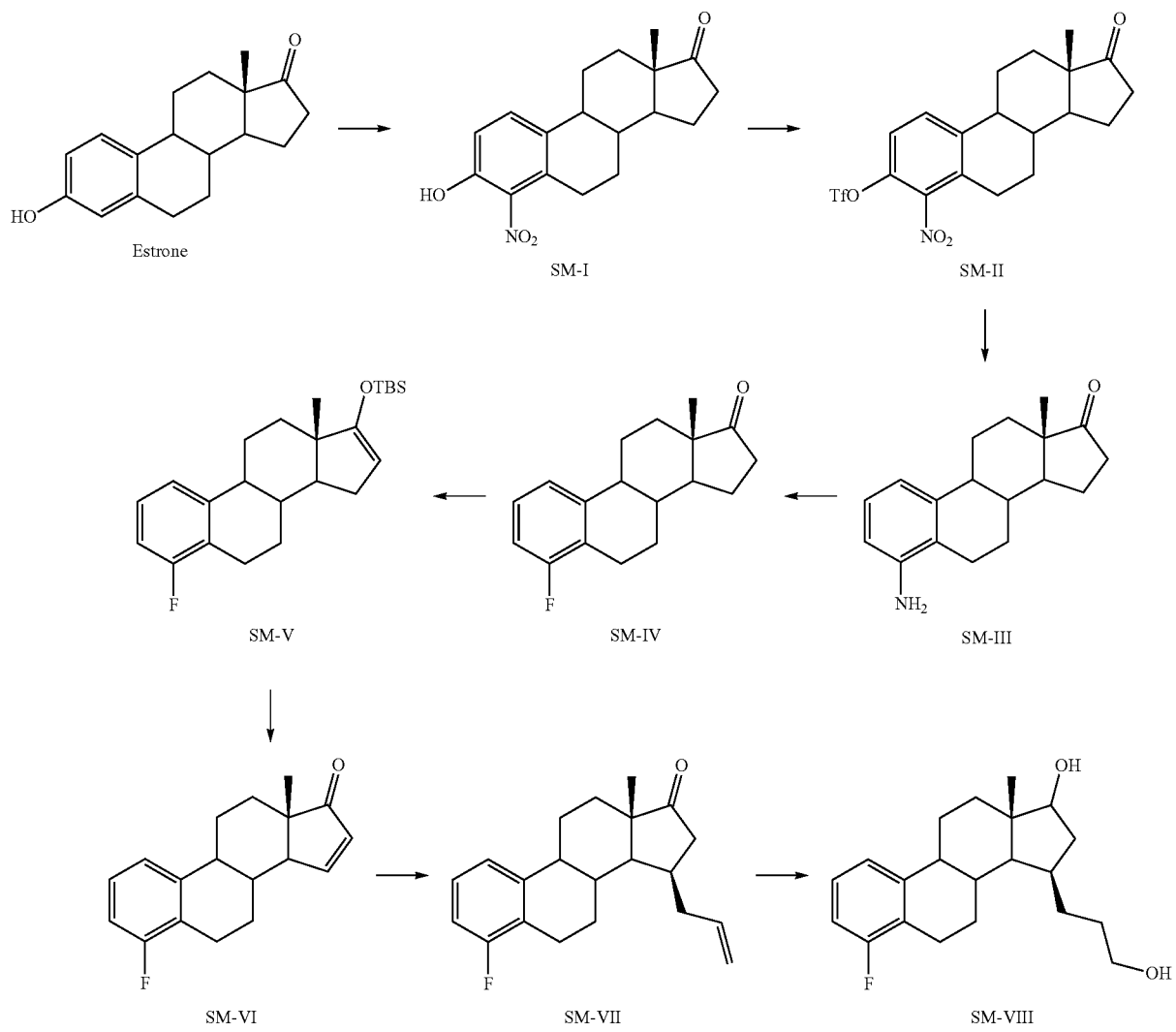

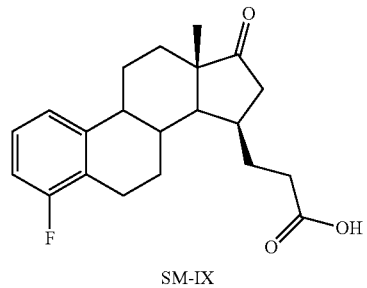

SM-IX

Compound SM-IV

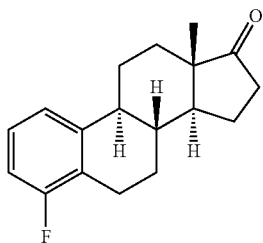

A solution of Compound SM-III (11.00 g, 40.8 mmol, 100 mol-%) in dichloromethane (430 mL) was added to neat boron trifluoride diethyl etherate (7.9 mL, 64.20 mmol, 157 mol-%) while stirring at −15° C. under nitrogen (approx 10-15 mins addition time). The reaction mixture was stirred for 15 min. at −15° C. before a solution of tert-butyl nitrite (5.9 mL, 49.80 mmol, 122 mol-%) in dichloromethane (50 mL) was added to it dropwise over a period of 10 min. The reaction mixture was stirred for another 15 min. at −15° C., and afterwards at 0-5° C. for 30 min.

The solution was added to n-pentane (2.25 L) on order to give a beige precipitate. The liquors were decanted away and the residue was washed with more n-pentane (400 mL). The beige solid (12.00 g) was dried in vacuo at room temperature overnight.

The crude material was purified by flash column chromatography using n-hexanes and ethyl acetate (10-30%) as solvent system. The desired product was isolated as a cream solid. The yield of Compound SM-IV was 70% (7.82 g).

$^1$H NMR (400 MHz, CDCl$_3$) δ ppm 0.91 (s, 3H, —CH$_3$), 1.34-1.70 (m, 6H), 1.93-1.99 (m, 1H), 2.04-2.21 (m, 3H), 2.27-2.46 (m, 2H), 2.48-2.56 (m, 1H), 2.66-2.77 (m, 1H), 2.95-3.03 (m, 1H), 6.84-6.90 (m, 1H, —ArH), 7.06-7.16 (m, 2H, 2×—ArH).

Compound SM-V

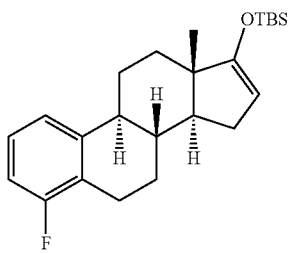

tert-Butyldimethylsilyl triflate (7.1 mL, 31.10 mmol, 110 mol-%) was added dropwise, over a period of 20 min., to a stirred solution of Compound SM-IV (7.70 g, 28.27 mmol, 100 mol-%) and triethylamine (6.0 mL, 42.72 mmol, 151 mol-%) in dichloromethane (75 mL) at room temperature under nitrogen. The reaction mixture was stirred at room temperature for 2 h.

The reaction mixture was diluted with dichloromethane (95 mL) and it was washed with a saturated aqueous solution of sodium bicarbonate (2×70 mL) and brine (70 mL). The organic layer was dried over sodium sulfate, filtered and concentrated under reduced pressure in order to afford the desired Example as a cream solid. The yield of Compound SM-V was quantitative (11.42 g). This Example was used in the next reaction without further purification.

$^1$H NMR (400 MHz, CDCl$_3$) δ ppm 0.14-0.19 (m, 6H, 2×—CH$_3$), 0.86 (s, 3H, —CH$_3$), 0.94 (s, 9H, 3×—CH$_3$), 1.21-1.62 (m, 5H), 1.78-2.06 (m, 3H), 2.08-2.16 (m, 1H), 2.25-2.38 (m, 2H), 2.64-2.88 (m, 1H), 2.90-2.99 (m, 1H), 4.48 (dd, 1H, J=3.1, 1.5 Hz), 6.82-6.88 (m, 1H, —ArH), 7.05-7.13 (m, 2H, 2×—ArH).

Compound SM-VI

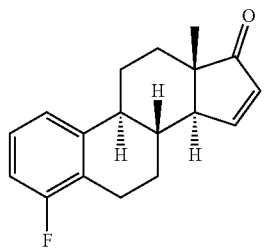

A mixture of Compound SM-V (11.42 g, 28.27 mmol, 100 mol-%) and palladium acetate (0.63 g, 2.83 mmol, 10 mol-%) in dimethylsulfoxide (75 mL) and dichloromethane (50 mL) was stirred at 35° C. under an oxygen atmosphere (balloon) for 16 h. After that time, starting material was still present by tlc. So, more palladium acetate (126 mg, 0.56 mmol, 2 mol-%) was added to the mixture and it was stirred for another 7 h at 35° C. After that time, TLC shown the reaction had reached completion.

The reaction mixture was cooled to room temperature and it was poured into a saturated aqueous solution of sodium bicarbonate (300 mL). The mixture was extracted with ethyl acetate (400 mL). The organic layer was washed with water (300 mL) and brine (200 mL) and it was dried over sodium sulfate, filtered and concentrated under reduced pressure in order to afford an orange/brown solid.

The crude material was purified by flash column chromatography using n-hexanes and ethyl acetate (0-30%) as solvent system. The desired product was isolated as a pinkish/white solid and it was dried in the vacuum oven. The yield of Compound SM-VI was 72% (5.50 g).

$^1$H NMR (400 MHz, CDCl$_3$) δ ppm 1.11 (s, 3H, —CH$_3$), 1.46-1.58 (m, 1H), 1.66-1.88 (m, 3H), 1.97-2.07 (m, 1H), 2.23-2.31 (m, 1H), 2.35-2.54 (m, 3H), 2.72-2.84 (m, 1H), 3.03 (dd, 1H, J=17.9, 6.4 Hz), 6.11 (dd, 1H, J=6.0, 3.2 Hz), 6.83-6.92 (m, 1H, —ArH), 7.05-7.18 (m, 2H, 2×—ArH), 7.63-7.66 (m, 1H).

MS m/z (ES$^+$): 271 (M+H).

Compound SM-VII

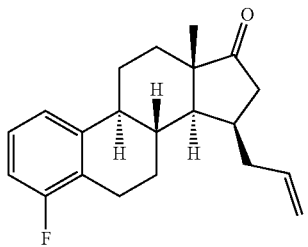

A dry three-neck flask was charged under a nitrogen atmosphere with copper iodide (7.90 g, 41.48 mmol, 350 mol-%), lithium chloride (1.76 g, 41.48 mmol, 350 mol-%) and anhydrous tetrahydrofuran (60 mL). The mixture was stirred for 20 min. at room temperature and it was cooled to −70° C. Allyl magnesium bromide (41.5 mL, 41.48 mmol, 350 mol-%) was then added dropwise, keeping the temperature under −70° C. Chlorotrimethylsilane (5.3 mL, 41.48 mmol, 350 mol-%) was added dropwise to the reaction mixture, keeping the temperature at −70° C., followed by the addition of a solution of Compound SM-VI (3.20 g, 11.85 mmol, 350 mol-%) in anhydrous tetrahydrofuran (60 mL), which was added dropwise keeping the temperature bellow −65° C. The reaction mixture was allowed to warm slowly to room temperature whist stirring overnight.

The mixture was poured into a saturated aqueous solution of ammonium chloride (75 mL) and it was extracted with ethyl acetate (3×70 mL). The combined extracts were washed with 1M HCl (2×50 mL), water (2×50 mL) and diluted aqueous ammonia solution (5×25 mL) (until the solution was colourless). The organic layer was dried over sodium sulfate, filtered and concentrated under reduced pressure. The crude material was purified by flash column chromatography using n-hexanes and ethyl acetate (10%) as solvent system. The yield of Compound SM-VII was 77% (2.85 g).

$^1$H NMR (400 MHz, CDCl$_3$) δ ppm 1.05 (s, 3H, —CH$_3$), 1.40-1.57 (m, 3H), 1.71-1.82 (m, 2H), 1.89-1.96 (m, 1H), 2.04-2.20 (m, 2H), 2.31-2.50 (m, 6H), 2.72-2.84 (m, 1H), 2.94-3.03 (m, 1H), 5.02-5.08 (m, 2H, CH=C$\underline{H}_2$), 5.69-5.81 (m, 1H, C$\underline{H}$=CH$_2$), 6.88 (t, 1H, ArH, J=8.7 Hz), 7.05-7.16 (m, 2H, 2×ArH).

Compound SM-VIII

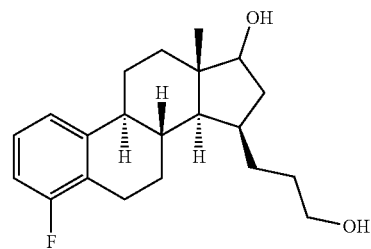

A dry, nitrogen flushed, flask was charged with Compound SM-VII (2.85 g, 9.13 mmol, 100 mol-%) and anhydrous tetrahydrofuran (70 mL). A 1 M solution of borane THF complex (18.3 mL, 18.30 mmol, 200 mol-%) was added dropwise to the previous solution. The resulting reaction mixture was heated until it was gently refluxing and it was stirred for 1 h. After that time, the reaction mixture was cooled in an ice-bath to −5° C. and a 3M aqueous solution of sodium hydroxide (28 mL) was added to it very cautiously. After the addition was complete and the effervescence ceased, hydrogen peroxide 30% (28 mL) was added and the mixture was gently refluxed for 2 h.

The reaction mixture was cooled to room temperature and was extracted with ethyl acetate (3×70 mL). The combined extracts were washed with water (2×50 mL) and brine (50 mL), dried over sodium sulfate, filtered and concentrated under reduced pressure in order to afford the desired Example. The yield of Compound SM-VIII was quantitative (3.09 g).

$^1$H NMR (400 MHz, CDCl$_3$) δ ppm 0.82 (s, 3H, —CH$_3$), 1.13-1.64 (m, 9H), 1.81-1.88 (m, 1H), 1.91-2.06 (m, 2H), 2.16-2.27 (m, 2H), 2.30-2.39 (m, 1H), 2.63-2.74 (m, 1H), 2.81-2.89 (m, 1H), 3.54-3.69 (m, 3H), 6.76-6.82 (m, 1H, —ArH), 6.98-7.08 (m, 2H, 2×—ArH).

Acid SM-IX: [3-((13S,15R)-4-fluoro-13-methyl-17-oxo-7,8,9,11,12,13,14,15,16,17-decahydro-6H-cyclopenta[a]phenanthren-15-yl)propanoic Acid]

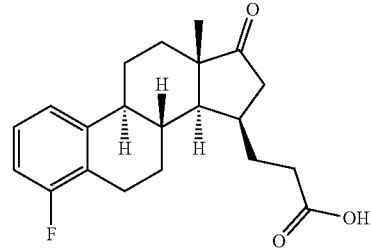

Periodic acid (5.15 g, 22.60 mmol, 500 mol-%) and chromium trioxide (23 mg, 0.23 mmol, 5.0 mol-%) were dissolved in a mixture of acetonitrile (36 mL) and water (12 mL). The solution was cooled to 0° C. in an ice/salt bath. A slurry of Compound SM-VIII (1.5 g, 4.52 mmol, 100 mol-%) in acetonitrile (30 mL) was added to the previous solution over a period of 40 min. whilst maintaining the temperature at or below 0° C. The reaction mixture was stirred for 1 h at 0° C., then the mixture was slowly warmed to room temperature and it was stirred for a further 3.5 h.

The reaction mixture was poured into aqueous sodium phosphate dibasic (~5 g in 100 mL) and it was extracted with ethyl acetate (3×60 mL). The organic extracts were combined and washed with a 5% aqueous solution of sodium bisulfite (2×40 mL), water (50 mL and brine (50 mL), dried over sodium sulfate, filtered and concentrated under reduced pressure.

The crude material was purified by flash column chromatography using n-hexanes, ethyl acetate (10-30%) and acetic acid (1%) as solvent system, in order to afford a white solid. The solid was dissolved in toluene (50 mL) and stirred for 15 min. Solvent was removed in vacuo and the solid was dried under vacuum at 50° C. in order to afford the desired product as a white solid. The crude yield of Compound SM-IX acid was 71% (1.11 g).

$^1$H NMR (400 MHz, CDCl$_3$) δ ppm 0.99 (s, 3H, —CH$_3$), 1.31-1.53 (m, 3H), 1.55-1.78 (m, 3H), 1.83-2.00 (m, 2H), 2.09-2.17 (m, 1H), 2.23-2.47 (m, 7H), 2.68-2.80 (m, 1H), 2.88-2.97 (m, 1H), 6.81 (t, 1H, —ArH, J=8.6 Hz), 6.98-7.10 (m, 2H, 2×—ArH).

MS m/z (ES−): 343 (M−H).

Preparation of the Starting Material Acid SM-XV

C-3 Fluoro SM-XV was synthesized from Estrone (Scheme 2.) via the Compound SM-X, which may be synthesized as disclosed in Messinger et al. Mol Cell Endocrinol. 2009 (301) 216-224. The detailed synthesis of compound X starting from estrone has been described in WO2008065100, WO2005/047303 and WO2006/125800. The acid SM-X was methylated by heating in methanol in the presence of sulphuric acid followed by triflation. Bis-tributyltin derivative SM-XIII was prepared from the corresponding triflate SM-XII followed by fluorination to XIV in 75% yield, (ref. WO 2010059943 and Furuya et al., JACS 2009, 13 (15), 1662). Several estrone deoxyfluorination methods are available (Labrie, Fernand et al. PCT Int. Appl., 9946279, 16 Sep. 1999; Labrie, Fernand et al. PCT Int. Appl., 2004089971, 21 Oct. 2004).

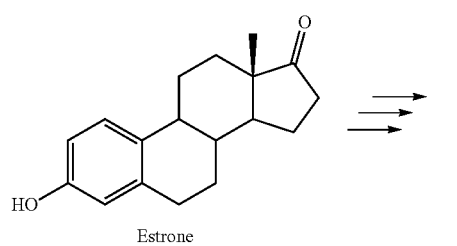

Estrone

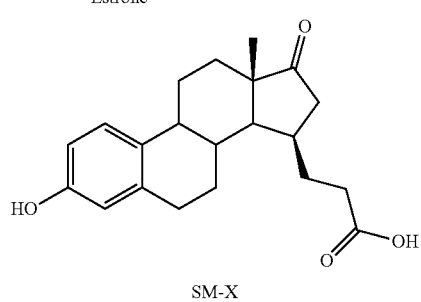

SM-X

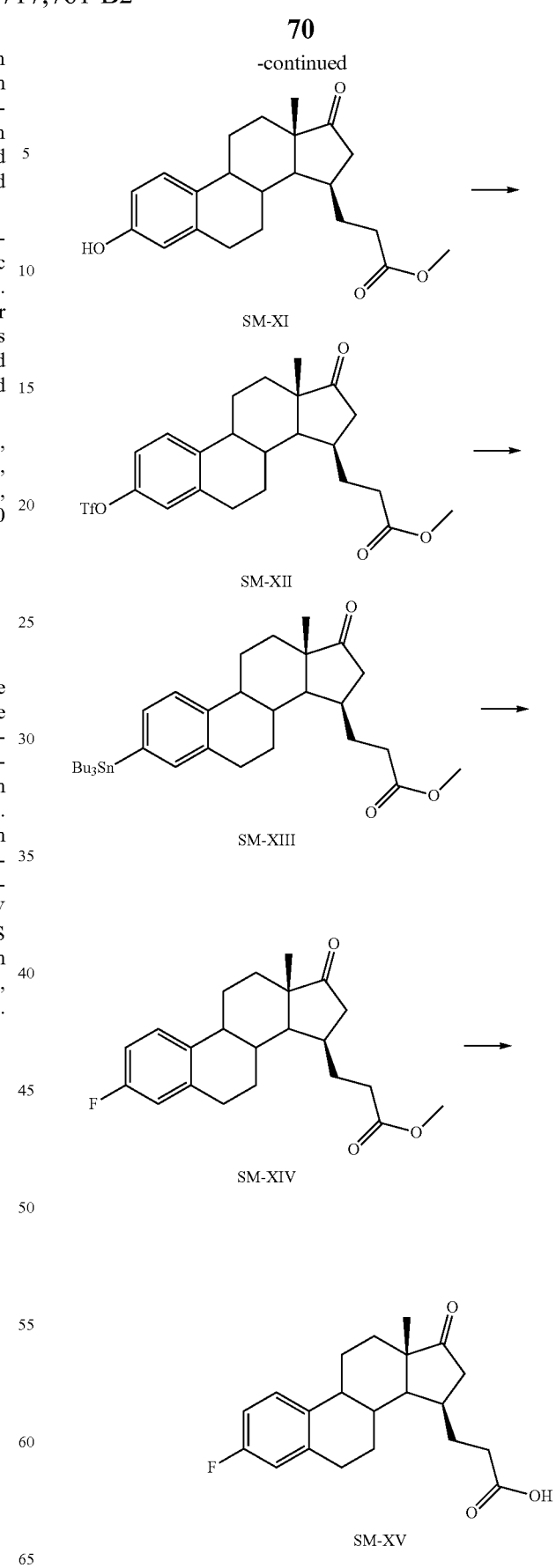

Compound XIII

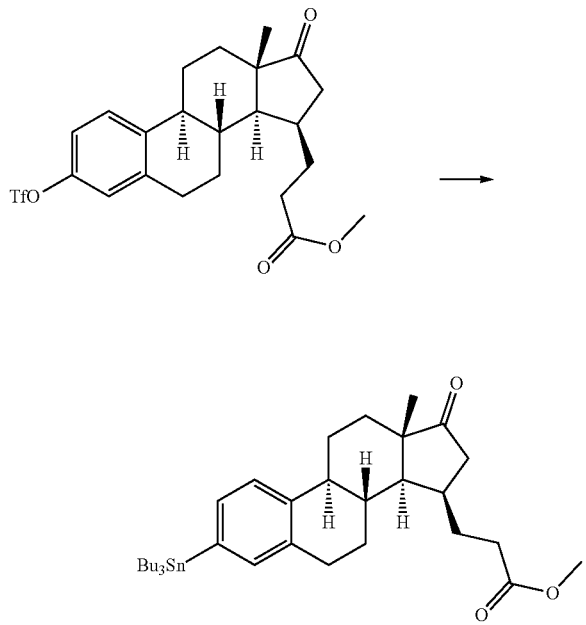

To a screw-cap sealed tube was added Compound SM-XII (10.0 g, 20.47 mmol, 100 mol-%) and 1,4-dioxane (120 mL). Bistributyltin (230.7 mL, 40.99 mmol, 200 mol-%) and LiCl (4.2 g, 102.3 mmol, 500 mol-%) were added to reaction mixture. The reaction mixture was degassed with argon gas for 10 min then added Pd(PPh₃)4 (1.41 g, 1.22 mmol, 6 mol-%) to it. The tube was sealed under nitrogen and the mixture was stirred and heated at 100° C. in a preheated oil bath for 4 hours. The reaction progress was monitored by TLC and LC-MS. The mixture was cooled to room temperature and quenched with water (100 mL), extracted with ethyl acetate (2×200 mL), then filtered through celite, washing well with ethyl acetate. The solvents were concentrated under reduced pressure to leave brown viscous oil. The crude was purified by flash chromatography (40 g snap) eluting with a gradient of 0 to 10% ethyl acetate in hexanes to give the Compound SM-XIII.

¹H NMR (400 MHz, CDCl₃) δ ppm: 7.29-7.19 (m, 3H), 3.69 (s, 3H), 2.95 (bs, 2H), 2.42-0.87 (m, 46H). MS m/z (ES+): poor ionization.

Compound SM-XIV

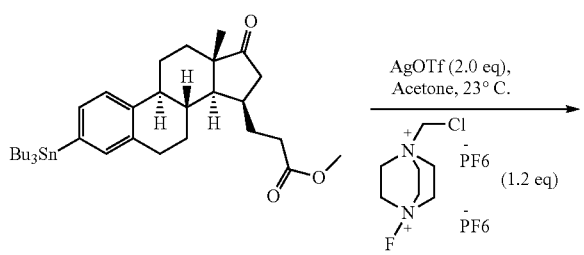

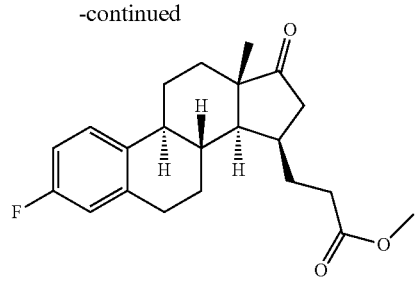

To a stirred solution of Compound SM-XIII (14.0 g, 22.2 mmol, 1.0 eq) in acetone (140 mL) was added AgOTf (11.41 g, 44.4 mmol, 2.0 eq) at room temperature. The reaction mixture was cooled to 0° C. and added 1-Chloromethyl-4-fluoro-1,4-diazoniabicyclo[2.2.2]octane bis(hexafluorophosphate) (12.53 g, 26.6 mmol, 1.2 eq) and the reaction mixture was stirred for 40 min. The reaction progress was monitored by TLC. The reaction mass was quenched with water (100 mL) and extracted with ethyl acetate (2×150 mL). The organic layer was dried over sodium sulphate, filtered and concentrated under reduced pressure to afford the crude compound. The crude compound was purified by flash chromatography using 40 g snap and eluted with 0-20% ethyl acetate in hexane. The combined organic portions were concentrated in vacuo to afford the desired Compound SM-XIV (6.0 g, 75.9%) as white solid.

¹H NMR (400 MHz, DMSO-d6) δ ppm: 7.30-7.27 (m, 1H), 7.10-7.08 (d, 1H, J=8 Hz), 6.94-6.89 (m, 1H), 3.59 (s, 3H), 2.87 (bs, 2H), 2.45-2.07 (m, 8H), 1.86-1.32 (m, 8H), 0.95 (s, 3H). MS m/z (ES+): poor ionization.

Compound SM-XV

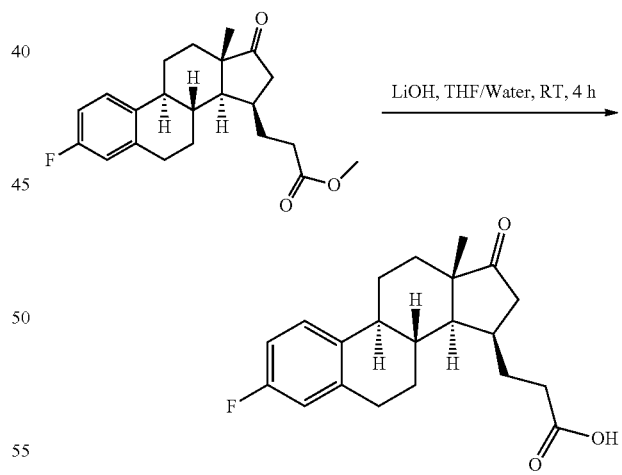

To a stirred solution of compound Compound SM-XIV (6.0 g, 16.7 mmol, 1.0 eq) in THF (60 mL), water (10.5 mL) and was added LiOH.H₂O (1.41 g, 33.5, 2.0 eq) at RT. The reaction mixture was stirred RT for 4 h. The reaction progress was monitored by TLC and LC-MS. The reaction mixture was cooled to 10° C., and neutralized with 1 N HCl (pH=6) and extracted with ethyl acetate (2×50 mL). The organic layer was dried over sodium sulphate, filtered and concentrated under reduced pressure to afford the off white. The compound was triturated with n-pentane (2×10 mL) to give 5.4 g white solid, which was purified by prep HPLC purification to afford Compound SM-XV (2.2 g, 38.19%) as a white solid.

¹H NMR (400 MHz, DMSO-d6) δ ppm: 12.06 (s, 1H), 7.29-7.27 (d, 1H, J=8 Hz), 7.16-7.14 (d, 2H, J=8 Hz), 2.87 (bs, 2H), 2.37-2.12 (m, 8H), 1.82-1.67 (m, 4H), 1.55-1.38 (m, 4H), 0.84 (s, 3H). MS m/z (ES+): 343.23 (M–H).

Acid SM-XVII

The Triflate SM-XII in scheme 3 was prepared followed by methods of Messinger et al, WO 2008065100. SM-XII was converted to chloro derivative SM-XVI by using t-Bu-BrettPhos in the presence of tris(dibenzylideneacetone)dipalladium(0) (Pan et al., Organic Letters, 13(18), 4974-4976; 2011) followed by LiOH treatment in THF:water affording the desired acid SM-XVII.

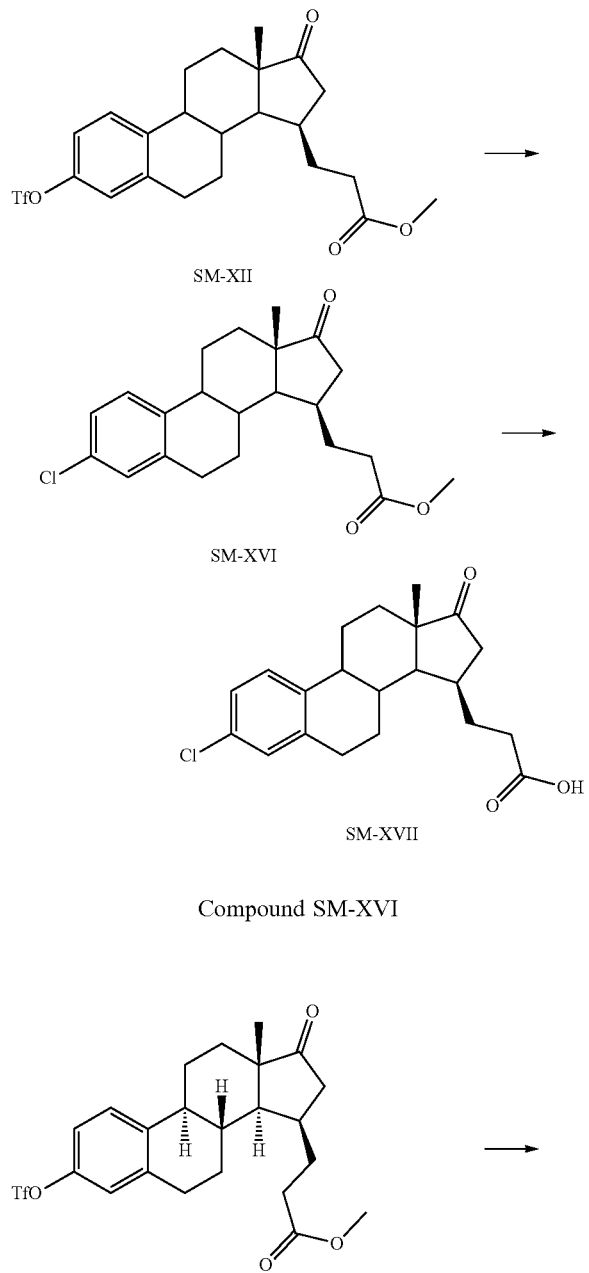

Compound SM-XVI

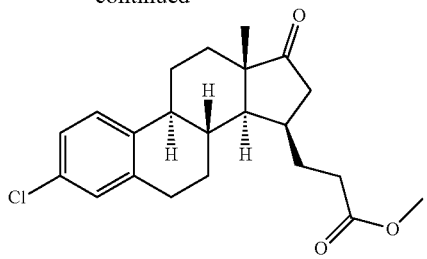

To a screw-cap sealed tube was added tris(dibenzylideneacetone)dipalladium(0) (0.084 g, 0.092 mmol, 3 mol-%) and t-BuBrettPhos (0.133 g, 0.27 mmol, 9 mol-%) and 1,4-dioxane (10 mL) and the tube was sealed under nitrogen. The mixture was stirred and heated at 130° C. in a preheated oil bath for 3 minutes. The catalyst mixture was cooled to room temperature and this mixture was added to a solution of the Compound SM-XII (1.5 g, 3.04 mmol, 100 mol-%) in 1,4-dioxane (11 mL), potassium chloride (0.908 g, 12.28 mmol, 400 mol-%) and potassium fluoride (0.178 g, 3.0 mmol, 100 mol-%). The mixture was then stirred and heated at 130° C. in a preheated oil bath for 3 hours. The reaction progress was monitored by TLC and LC-MS. The mixture was cooled to room temperature and then filtered through celite, washing well with ethyl acetate. The solvents were concentrated under reduced pressure to leave brown viscous oil. The crude was purified by flash chromatography (40 g snap) eluting with a gradient of 0 to 20% to afford the SM-Compound XVI.

¹H NMR (400 MHz, DMSO-d6) δ ppm: 7.29-7.27 (d, 1H, J=8 Hz), 7.16-7.14 (d, 2H, J=8 Hz), 3.59 (s, 3H), 2.87 (bs, 2H), 2.41-2.07 (m, 8H), 1.85-1.38 (m, 8H), 0.95 (s, 3H). MS m/z (ES+): poor ionization.

Compound SM-XVII

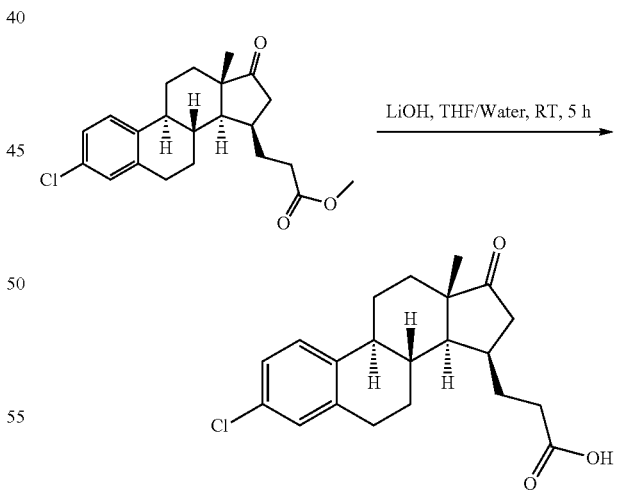

To a stirred solution of Compound SM-XVI (1.7 g, 4.54 mmol, 1.0 eq) in THF:MeOH:Water (12.5 mL, 2:2:1) and was added LiOH.H₂O (0.572 g, 13.6, 3.0 eq) at RT. The reaction mixture was heated at 80° C. for 1.5 h. The reaction progress was monitored by TLC and LC-MS. The reaction mixture was cooled to RT, diluted with water 10 mL and washed with ethyl acetate 3×3 mL. The aqueous layer was neutralized with 1 N HCl (pH=6) and extracted with ethyl acetate (2×50 mL). The organic layer was dried over sodium sulphate, filtered and concentrated under reduced pressure to afford the off white. The compound was triturated with n-pentane (2×10 mL) to afford the desired compound SM-XVII (1.3 g, 79%) as a white solid.

$^1$H NMR (400 MHz, DMSO-d6) δ ppm: 12.06 (s, 1H), 7.29-7.27 (d, 1H, J=8 Hz), 7.16-7.14 (d, 2H, J=8 Hz), 2.87 (bs, 2H), 2.37-2.12 (m, 8H), 1.82-1.67 (m, 4H), 1.55-1.38 (m, 4H), 0.84 (s, 3H). MS m/z (ES+): 358.9 (M–H).

Preparation of the Starting Material Acid SM-XXVI

Compound SM-XXVI was synthesized from Estrone via the triflate SM-XVIII, which was prepared by methods of Messinger et al, WO 2008065100. The C15-C16 SM-XXIII was prepared according to methods described in WO2008065100. The allylation, hydroboration and oxidation of SM-XXIII to SM-XXVI was performed as in patents WO2005/047303 and WO2006/125800.

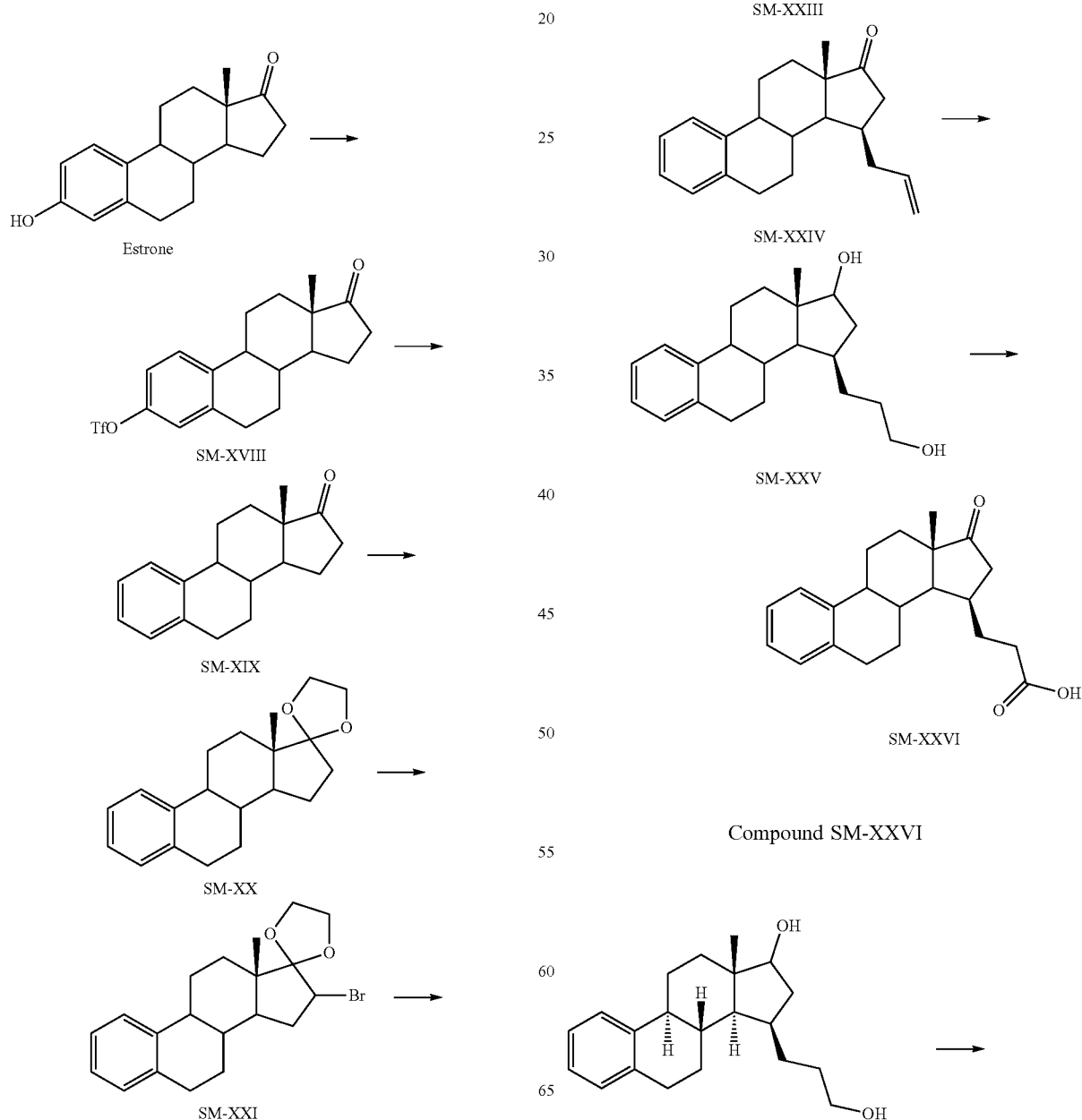

Compound SM-XXVI

-continued

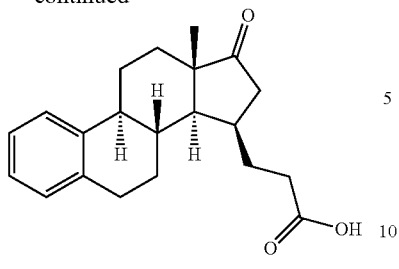

To a stirred solution of (8R,9S,13S,14S,15R)-15-(3-hydroxypropyl)-13-methyl-7,8,9,11,12,13,14,15,16,17-decahydro-6H-cyclopenta[a]phenanthren-17-ol (44.0 g 0.140 mol) in acetone (875 mL) and the resulting solution was cooled to 0° C. In another RBF, Jones reagent was prepared by dissolving the chromic acid (35 g, 0.350 mol) in water (350 mL) and con. Sulphuric acid (41.14 g, 0.420 mol). The Jones reagent prepared was added to the above alcoholic derivative maintaining the temperature at 0-2° C. The addition was completed in 45 minutes. The reaction mass was maintained at 0-2° C. for 2-3 h. Progress of the reaction was monitored by TLC. The reaction mass was then quenched using ice cold water (875 mL), the sticky material was filtered and dissolved in 3N NaOH solution (200 mL). The mixture was extracted with ethyl acetate (3×200 mL). The aqueous layer was neutralized with aqueous 2N HCl (pH=6) and extracted with ethyl acetate (3×200 ml). The combined organic layer was washed with brine (200 mL), dried over anhydrous sodium sulphate and solvent was evaporated under vacuum to obtain solid compound 3-((8R,9S,13S,14S,15R)-13-methyl-17-oxo-7,8,9,11,12,13,14,15,16,17-decahydro-6H-cyclopenta[a]phenanthren-15-yl)propanoic acid (24 g, 52%) as a white solid.

$^1$H NMR (400 MHz, DMSO-d6) δ ppm: 12.0 (s, 1H), 7.27-7.25 (d, 1H, J=8 Hz), 7.13-7.05 (m, 3H), 2.87 (bs, 2H), 2.41-2.10 (m, 8H), 1.87-1.36 (m, 8H), 0.95 (s, 3H).

MS m/z (ES+): 325.23 (M−H).

General Information

Commercial grade reagents and solvents were used without further purification. Thin-layer chromatography (TLC) was performed on Merck-plates; pre-coated aluminium sheets. Visualization of plates was done the following techniques: 1) ultraviolet illumination (254 nm), 2) dipping the plate into anisaldehyde or vanilline solution followed by heating. 1H-NMR spectra were measured with a Bruker DPX (200 MHz) spectrometer with the solvent as indicated.

Oxime compounds of the invention may be prepared from the corresponding C-17 carbonyl derivatives.

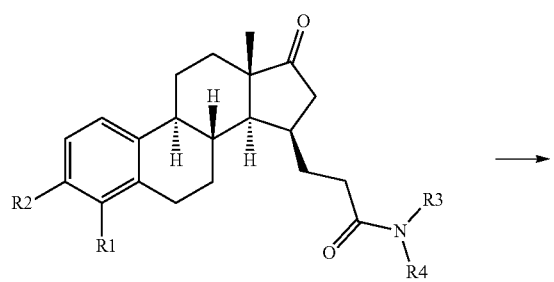

-continued

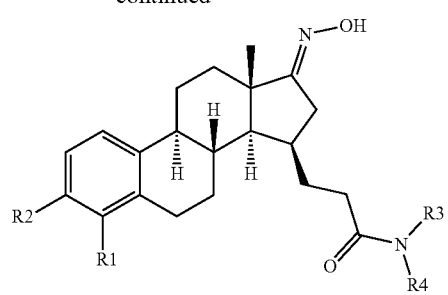

Preparation of C-17 Carbonyl and Oxime Compounds

Compound 1

3-((13S,15R)-4-fluoro-13-methyl-17-oxo-7,8,9,11,12,13,14,15,16,17-decahydro-6H-cyclopenta[a]phenanthren-15-yl)-N-(5-methylisoxazol-3-yl)propanamide

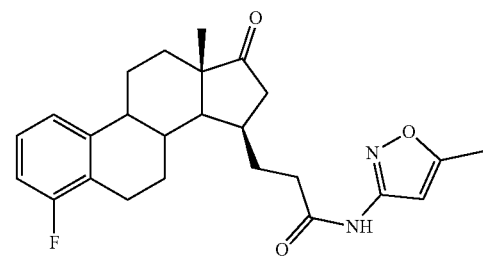 [SMILES: Cc1cc(NC(=O)CC[C@@H]2CC(=O)[C@@]3(C)CCC4c5cccc(F)c5CCC4C23)no1]

To the solution of Acid SM-IX (750 mg, 2.18 mmol, 100 mol-%) in dry DCM (10 ml) under nitrogen atmosphere was added 3-amino-5-methylisoxazole (427 mg, 4.36 mmol, 200 mol-%) and pyridine (526 µl, 6.53 mmol, 300 mol-%). T3P (50 w-% in EtOAc) (2.6 ml, 4.36 mmol, 200 mol-%) was added dropwise and the reaction mixture stirred at rt for four hours. DCM (10 ml) and 10% NaHCO₃ (30 ml) were added. The water phase was extracted twice with DCM (2×10 ml). The organic phases were combined and washed with 0.1 N HCl solution (3×30 ml), water (3×30 ml) and finally with brine (3×30 ml) and dried with sodium sulfate. The crude yield of compound 1 was 95% (875 mg).

$^1$H NMR (200 MHz, DMSO-d6): 0.97 (s, 3H), 1.24-2.46 (m, 16H), 2.37 (s, 3H), 2.58-3.01 (m, 2H), 6.64 (s, 1H), 6.88-7.06 (m, 1H), 7.07-7.25 (m, 2H), 10.88 (s, 1H).

Compound 2

3-((13S,15R,E)-4-fluoro-17-(hydroxyimino)-13-methyl-7,8,9,11,12,13,14,15,16,17-decahydro-6H-cyclopenta[a]phenanthren-15-yl)-N-(5-methylisoxazol-3-yl)propanamide

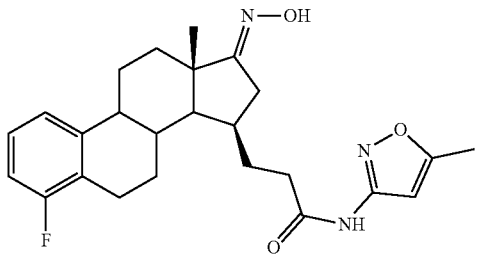 [SMILES: Cc1cc(NC(=O)CC[C@@H]2C/C(=N\O)[C@@]3(C)CCC4c5cccc(F)c5CCC4C23)no1]

A suspension of compound 1 (850 mg, 2.00 mmol, 100 mol-%), hydroxylamine hydrochloride (278 mg, 4.00 mmol, 200 mol-%) and pyridine (0.65 ml, 8.00 mmol, 400 mol-%) in abs. ethanol (15 ml) was stirred at 50° C. under nitrogen atmosphere for 2.5 hours. The solvent was evaporated. The precipitate was dissolved in ethyl acetate (15 ml) and washed with water (15 ml). The water phase was extracted twice with ethyl acetate (15 ml). The organic phases were combined and washed with dilute 0.1 N HCl solution (3×40 ml), 0.25 N HCl (2×40 ml), water (3×40 ml) and finally with brine (3×40 ml), and dried with sodium sulfate. The yield of compound 2 after trituration with heptane:ethanol was 96% (841 mg).

$^1$H NMR (200 MHz, DMSO-d$_6$): 1.02 (s, 3H), 1.24-2.47 (m, 15H), 2.37 (s, 3H), 2.57-2.99 (m, 3H), 6.64 (s, 1H), 6.89-7.05 (m, 1H), 7.07-7.25 (m, 2H), 10.19 (s, 1H), 10.89 (s, 1H). MS m/z (TOF ES$^+$): 462 (M+Na).

Compound 3

3-((13S,15R)-4-fluoro-13-methyl-17-oxo-7,8,9,11,12,13,14,15,16,17-decahydro-6H-cyclopenta[a]phenanthren-15-yl)-N-(6-methoxypyridazin-3-yl)propanamide

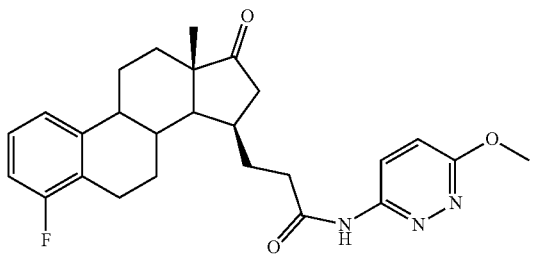 [SMILES: COc1ccc(NC(=O)CC[C@@H]2CC(=O)[C@@]3(C)CCC4c5cccc(F)c5CCC4C23)nn1]

To the solution of Acid SM-IX (70 mg, 0.20 mmol, 100 mol-%) in dry DMF (2 ml) under nitrogen atmosphere was added 1-hydroxybenzotriazole hydrate (HOBt) (60 mg, 0.45 mmol, 220 mol-%), 1-(3-dimethylaminopropyl)-3-ethylcarbodiimide hydrochloride (EDCl) (86 mg, 0.45 mmol, 220 mol-%) and 3-amino-6-methoxypyridazine (51 mg, 0.41 mmol, 200 mol-%). The reaction mixture was stirred at +50° C. for 3.5 hours. Water (3 ml) was added to the reaction mixture. The solid precipitate was filtered and washed several times with water and finally with heptane to yield 56 mg of crude product. Purification was done by flash chromatography. Amount of product compound 3 was 36 mg.

$^1$H-NMR (200 MHz, DMSO-d6): 0.98 (s, 3H), 1.20-2.47 (m, 16H), 2.60-2.97 (m, 2H), 3.98 (s, 3H), 6.89-7.06 (m, 1H), 7.08-7.21 (m, 2H), 7.25 (d, 1H), 8.26 (d, 1H), 10.94 (br s, 1H).

Compound 4

3-((13S,15R,E)-4-fluoro-17-(hydroxyimino)-13-methyl-7,8,9,11,12,13,14,15,16,17-decahydro-6H-cyclopenta[a]phenanthren-15-yl)-N-(6-methoxypyridazin-3-yl)propanamide

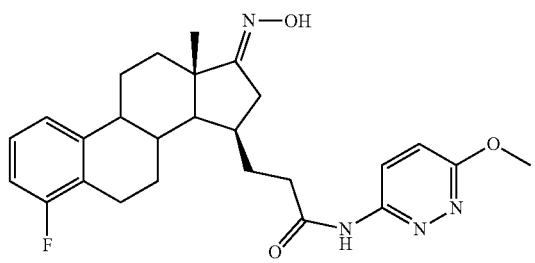

A suspension of compound 3 (25 mg, 0.06 mmol, 100 mol-%), hydroxylamine hydrochloride (8 mg, 0.11 mmol, 200 mol-%) and pyridine (18 µl, 0.22 mmol, 400 mol-%) in abs. ethanol (2 ml) was stirred at 40-50° C. under nitrogen atmosphere for 4.5 hours. The solvent was evaporated. The precipitate was dissolved in DCM (5 ml) and washed with water (5 ml). The water phase was extracted twice with DCM (5 ml). The organic phases were combined and washed with 0.1 N HCl solution (3×5 ml), water (4×5 ml) and finally with brine (3×5 ml), and dried with sodium sulfate. The crude product was purified by flash chromatography. The amount of product compound 4 was 15 mg.

$^1$H-NMR (200 MHz, DMSO-d$_6$): 1.03 (s, 3H), 1.18-2.45 (m, 15H), 2.57-3.00 (m, 3H), 3.98 (s, 3H), 6.86-7.05 (m, 1H), 7.07-7.21 (m, 2H), 7.24 (d, 1H), 8.26 (d, 1H), 10.19 (br s, 1H), 10.95 (br s, 1H). MS m/z (TOF ES+): 460 (M+1)

Compound 5

3-((13S,15R)-4-fluoro-13-methyl-17-oxo-7,8,9,11,12,13,14,15,16,17-decahydro-6H-cyclopenta[a]phenanthren-15-yl)-N-(5-methoxypyridin-2-yl)propanamide

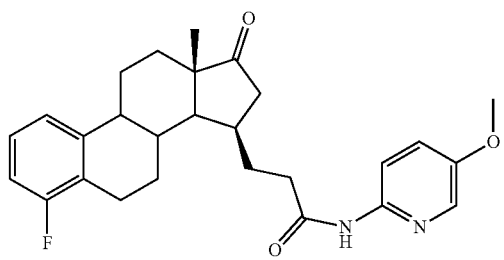 [SMILES: COc1ccc(NC(=O)CC[C@@H]2CC(=O)[C@@]3(C)CCC4c5cccc(F)c5CCC4C23)nc1]

To the solution of Acid SM-IX (50 mg, 0.15 mmol, 100 mol-%) in dry DMF (2 ml) was added 1-hydroxybenzotriazole hydrate (HOBt) (43 mg, 0.32 mmol, 220 mol-%) and 1-(3-dimethylaminopropyl)-3-ethylcarbodiimide hydrochloride (EDCl) (61 mg, 0.32 mmol, 220 mol-%), and finally 5-methoxypyridine-2-amine (38 mg, 0.29 mmol, 200 mol-%). The reaction mixture was stirred at +50° C. for two hours. Water (2 ml) was added to the reaction mixture. The solid precipitate was filtered and washed several times with water. The crude yield of compound 5 was 80% (52 mg).

$^1$H-NMR (200 MHz, CDCl$_3$): 1.07 (s, 3H), 1.35-2.53 (m, 16H), 2.72-3.03 (m, 2H), 3.85 (s, 3H), 6.83-6.92 (m, 1H), 7.05-7.18 (m, 2H), 7.24-7.30 (m, 1H), 7.92-8.01 (m, 2H), 8.15 (d, 1H).

Compound 6

3-((13S,15R,E)-4-fluoro-17-(hydroxyimino)-13-methyl-7,8,9,11,12,13,14,15,16,17-decahydro-6H-cyclopenta[a]phenanthren-15-yl)-N-(5-methoxypyridin-2-yl)propanamide

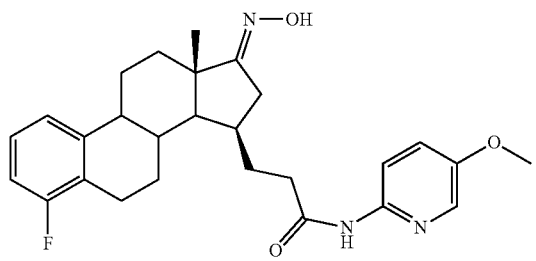

A suspension of compound 5 (30 mg, 0.07 mmol, 100 mol-%), hydroxylamine hydrochloride (9.2 mg, 0.13 mmol, 200 mol-%) and pyridine (32 µl, 0.40 mmol, 600 mol-%) in abs. ethanol (2 ml) was refluxed under nitrogen atmosphere for one hour. The solvent was evaporated. The precipitate was dissolved in ethyl acetate (5 ml) and washed with water (5 ml). The water phase was extracted twice with ethyl acetate (5 ml). The organic phases were combined and washed with dilute 0.25N HCl solution (3×10 ml), water (3×10 ml) and finally with brine (3×20 ml), and dried with sodium sulfate. The crude yield of compound 6 was 94% (29 mg).

$^1$H-NMR (200 MHz, CDCl$_3$): 1.15 (s, 3H), 1.34-2.43 (m, 16H), 2.79-3.03 (m, 3H), 3.84 (s, 3H), 6.81-6.89 (m, 1H), 7.07-7.16 (m, 2H), 7.32 (d, 1H), 7.94 (br s, 1H), 8.21 (d, 1H), 8.83 (br s, 1H). MS m/z 466 (M+1)

Compound 7

3-((13S,15R)-4-fluoro-13-methyl-17-oxo-7,8,9,11,12,13,14,15,16,17-decahydro-6H-cyclopenta[a]phenanthren-15-yl)-N-(5-fluoropyridin-2-yl)propanamide

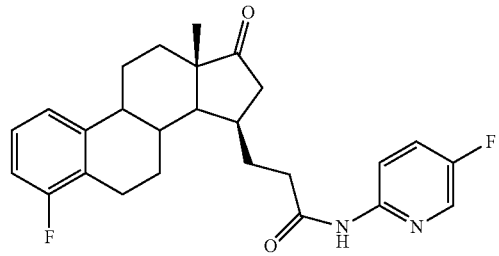 [SMILES: C[C@]12CCC3c4cccc(F)c4CCC3C1[C@H](CCC(=O)Nc1ccc(F)cn1)CC2=O]

To the solution of Acid SM-IX (500 mg, 1.45 mmol, 100 mol-%) in dry THF (10 ml) under nitrogen atmosphere was added 2-amino-5-fluoropyridine (325 mg, 2.90 mmol, 200 mol-%) and pyridine (351 µl, 4.36 mmol, 300 mol-%). T3P (50 w-% in EtOAc) (1.73 ml, 2.90 mmol, 200 mol-%) was added dropwise and the reaction mixture stirred at rt for three hours. Solvent was evaporated and residue dissolved in ethyl acetate (15 ml) and washed with 10% NaHCO$_3$ (30 ml). The water phase was extracted twice with ethyl acetate (2×15 ml). The organic phases were combined and washed with 0.1 N HCl solution (3×30 ml), water (3×30 ml) and finally with brine (2×30 ml) and dried with sodium sulfate. The Example was used in the next step without further purification. The crude yield of compound 7 was 99% (631 mg).

$^1$H NMR (200 MHz, DMSO-d$_6$): 0.98 (s, 3H), 1.24-2.46 (m, 16H), 2.59-3.03 (m, 2H), 6.90-7.05 (m, 1H), 7.06-7.22 (m, 2H), 7.73 (td, 1H), 8.15 (dd, 1H), 8.32 (d, 1H), 10.63 (s, 1H). MS m/z (TOF ES+): 439 (M+1)

Compound 8

3-((13S,15R,E)-4-fluoro-17-(hydroxyimino)-13-methyl-7,8,9,11,12,13,14,15,16,17-decahydro-6H-cyclopenta[a]phenanthren-15-yl)-N-(5-fluoropyridin-2-yl)propanamide

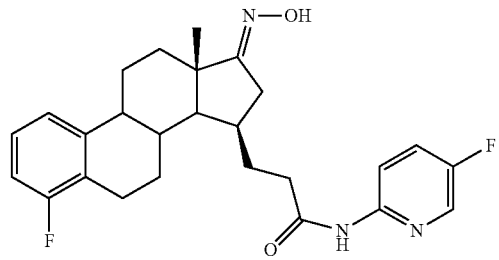 [SMILES: C[C@]12CCC3c4cccc(F)c4CCC3C1[C@H](CCC(=O)Nc1ccc(F)cn1)C/C2=N\O]

A suspension of compound 7 (1.07 g, 2.44 mmol, 100 mol-%), hydroxylamine hydrochloride (339 mg, 4.88 mmol, 200 mol-%) and pyridine (790 µl, 9.76 mmol, 400 mol-%) in abs. ethanol (15 ml) was stirred at 40° C. under nitrogen atmosphere for 1.5 hours. The solvent was evaporated. The precipitate was dissolved in ethyl acetate (15 ml) and washed with water (15 ml). The water phase was extracted twice with ethyl acetate (15 ml). The organic phases were combined and washed with dilute 0.1 N HCl solution (3×40 ml), water (4×40 ml) and finally with brine (3×40 ml), and dried with sodium sulfate. The crude yield of the compound 8 was 92% (1.02 g).

$^1$H NMR (200 MHz, DMSO-d6): 1.03 (s, 3H), 1.12-2.44 (m, 15H), 2.58-3.01 (m, 3H), 6.89-7.04 (m, 1H), 7.05-7.24 (m, 2H), 7.72 (td, 1H), 8.15 (dd, 1H), 8.31 (d, 1H), 10.19 (s, 1H), 10.64 (s, 1H). MS m/z (TOF ES+): 454 (M+1)

Compound 9

3-((13S,15R)-4-fluoro-13-methyl-17-oxo-7,8,9,11,12,13,14,15,16,17-decahydro-6H-cyclopenta[a]phenanthren-15-yl)-N-(oxetan-3-yl)propanamide

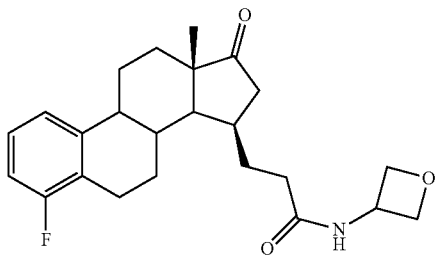 [SMILES: C[C@]12CCC3c4cccc(F)c4CCC3C1[C@H](CCC(=O)NC1COC1)CC2=O]

Acid SM-IX (56.9 mg, 0.17 mmol, 100 mol-%) was dissolved in dry DCM (2 ml). Oxetane-3-amine hydrochloride (30 mg, 0.26 mmol, 150 mmol-%), N-methylmorpholino (57 μl, 0.52 mmol, 300 mol-%) and HOBt (40 mg, 0.30 mmol, 170 mol-%) were added to the reaction mixture, stirred for 5 minutes and then cooled with ice bath. EDCl (73 mg, 0.38 mmol, 220 mol-%) was added and allowed to warm at room temperature. After stirring overnight, the reaction mixture was diluted with DCM, washed with 1N HCl-solution (3×10 ml), water (3×10 ml) and finally with brine (3×10 ml). Dried with sodium sulphate. The solvent was evaporated and the crude product was purified by chromatography producing the compound 9 in 59% yield.

$^1$H-NMR (200 MHz, CDCl$_3$): 1.05 (s, 3H), 1.45-2.49 (m, 16H), 2.71-3.06 (m, 2H), 4.50 (t, 2H), 4.95 (t, 2H), 5.06 (t, 1H), 6.02 (m, 1H), 6.84-6.92 (m, 1H), 7.05-7.18 (m, 2H).

Compound 10

3-((13S,15R,E)-4-fluoro-17-(hydroxyimino)-13-methyl-7,8,9,11,12,13,14,15,16,17-decahydro-6H-cyclopenta[a]phenanthren-15-yl)-N-(oxetan-3-yl)propanamide

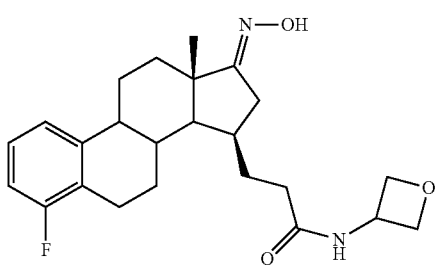 [SMILES: C[C@]12CCC3c4cccc(F)c4CCC3C1[C@H](CCC(=O)NC1COC1)C/C2=N\O]

Compound 10 was prepared in 96% yield from compound 9 by the same method as with Example 2.

$^1$H-NMR (200 MHz, CDCl$_3$): 1.11 (s, 3H), 1.36-2.45 (m, 16H), 2.69-3.03 (m, 2H), 4.50 (t, 2H), 4.95 (t, 2H), 5.07 (t, 1H), 6.14 (m, 1H), 6.82-6.91 (m, 1H), 7.04-7.20 (m, 2H), 8.33 (br s, 1H).

Compound 11

3-((13S,15R)-4-fluoro-13-methyl-17-oxo-7,8,9,11,12,13,14,15,16,17-decahydro-6H-cyclopenta[a]phenanthren-15-yl)-N-methyl-(oxetan-3-yl)propanamide

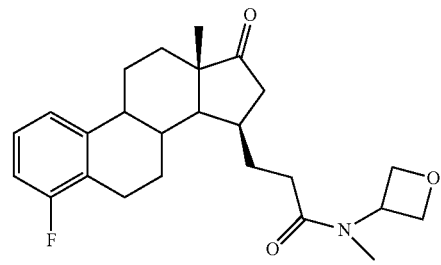 [SMILES: CN(C(=O)CC[C@@H]1CC(=O)[C@@]2(C)CCC3c4cccc(F)c4CCC3C12)C1COC1]

Compound 11 was prepared by the same method as with compound 9 using by using acid SM-IX and N-methyl-3-oxetanamine as amine. Reaction time was for 2 hours producing product in 78% yield.

$^1$H NMR (200 MHz, DMSO-d$_6$): 0.96 (s, 3H), 1.15-2.47 (m, 16H), 2.60-2.98 (m, 2H), 3.00, 3.05 (2×s, 3H), 4.50-4.80 (m, 4H), 5.15-5.40 (m, 1H), 6.90-7.05 (m, 1H), 7.10-7.25 (m, 2H).

Compound 12

3-((13S,15R,E)-4-fluoro-17-(hydroxyimino)-13-methyl-7,8,9,11,12,13,14,15,16,17-decahydro-6H-cyclopenta[a]phenanthren-15-yl)-N-methyl-(oxetan-3-yl)propanamide

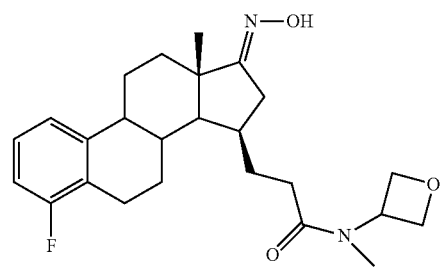 [SMILES: CN(C(=O)CC[C@@H]1C/C(=N\O)[C@@]2(C)CCC3c4cccc(F)c4CCC3C12)C1COC1]

Compound 12 was prepared from the compound 11 by the same method as with compound 2 by stirring at 50° C. for 2 hours, producing product in 18% yield after chromatographic purification.

$^1$H NMR (200 MHz, CDCl$_3$): 1.12 (s, 3H), 1.30-2.55 (m, 15H), 2.60-3.05 (m, 3H), 3.16 (s, 3H), 4.60-4.92 (m, 4H, isomers), 5.05-5.65 (m, 1H), 6.80-6.95 (m, 1H), 7.00-7.20 (m, 2H), 7.23 (br s, 1H).

Compound 13

(13S,15R)-4-fluoro-13-methyl-15-(3-oxo-3-(pyrrolidin-1-yl)propyl)-6,7,8,9,11,12,13,14,15,16-decahydro-17H-cyclopenta[a]phenanthren-17-one

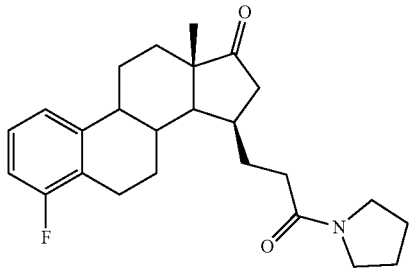 [SMILES: C[C@]12CCC3c4cccc(F)c4CCC3C1[C@H](CCC(=O)N1CCCC1)CC2=O]

Compound 13 was synthesized in 54% yield by the method used in the preparation of the compound 1 by using acid SM-IX and pyrrolidine as starting materials in 5.5 hours reaction time.

$^1$H NMR (200 MHz, CDCl$_3$): 1.07 (s, 3H), 1.20-2.55 (m, 20H), 2.70-3.10 (m, 2H), 3.30-3.55 (m, 4H), 6.80-6.95 (m, 1H), 7.00-7.22 (m, 2H).

Compound 14

3-((13S,15R,E)-4-fluoro-17-(hydroxyimino)-13-methyl-7,8,9,11,12,13,14,15,16,17-decahydro-6H-cyclopenta[a]phenanthren-15-yl)-1-(pyrrolidin-1-yl)propan-1-one

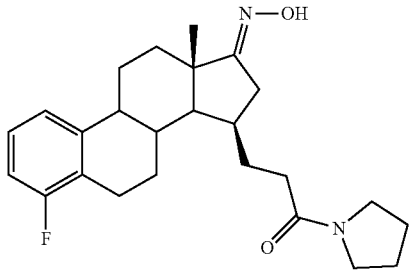 [SMILES: C[C@]12CCC3c4cccc(F)c4CCC3C1[C@H](CCC(=O)N1CCCC1)C/C2=N\O]

Compound 14 was prepared in 72% yield from compound 13 by the same method as with compound 2 in 3 hours reaction time.

$^1$H NMR (200 MHz, CDCl$_3$): 1.13 (s, 3H), 1.25-2.55 (m, 19H), 2.68-3.10 (m, 3H), 3.30-3.55 (m, 4H), 6.80-6.95 (m, 1H), 7.00-7.22 (m, 2H), 7.52 (br s, 1H).

Compound 15

3-((13S,15R)-4-fluoro-13-methyl-17-oxo-7,8,9,11,12,13,14,15,16,17-decahydro-6H-cyclopenta[a]phenanthren-15-yl)-N-(6-methylpyridazin-3-yl)propanamide

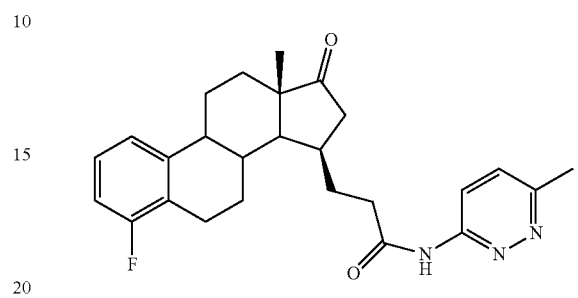

Compound 15 was synthesized in 83% yield by the method used in the preparation of the compound 9 in THF by using acid SM-IX and 3-amino-6-methylpyridazine as starting materials in 4 hours reaction time.

$^1$H-NMR (200 MHz, DMSO-d6): 0.98 (s, 3H), 1.20-2.47 (m, 16H), 2.55 (s, 3H), 2.70-2.95 (m, 2H), 6.89-7.06 (m, 1H), 7.08-7.25 (m, 2H), 7.54 (d, 1H), 8.23 (d, 1H), 11.05 (s, 1H).

Compound 16

3-((13S,15R,E)-4-fluoro-17-(hydroxyimino)-13-methyl-7,8,9,11,12,13,14,15,16,17-decahydro-6H-cyclopenta[a]phenanthren-15-yl)-N-(6-methylpyridazin-3-yl)propanamide

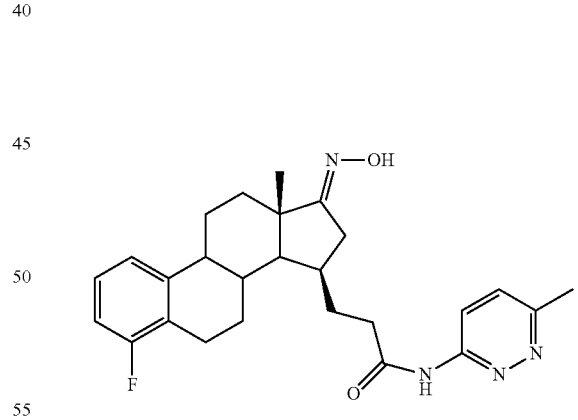

Example 16 was prepared in 59% yield from compound 15 by the same method as with Example 2 in 2.5 hours reaction time.

$^1$H-NMR (200 MHz, DMSO-d$_6$): 1.03 (s, 3H), 1.15-2.47 (m, 15H), 2.55 (s, 3H), 2.60-2.95 (m, 3H), 6.89-7.06 (m, 1H), 7.08-7.25 (m, 2H), 7.54 (d, 1H), 8.23 (d, 1H), 10.20 (s, 1H), 11.06 (s, 1H).

Compound 17

3-((13S,15R)-4-fluoro-13-methyl-17-oxo-7,8,9,11,12,13,14,15,16,17-decahydro-6H-cyclopenta[a]phenanthren-15-yl)-N-(1,3,4-thiadiazol-2-yl)propanamide

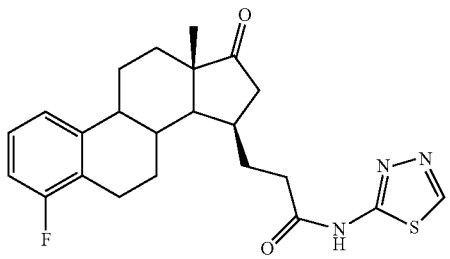 [SMILES: C[C@]12CCC3c4cccc(F)c4CCC3C1[C@H](CCC(=O)Nc1nncs1)CC2=O]

Compound 17 was synthesized in 61% yield by the method used in the preparation of the compound 9 in THF by using acid SM-IX and 2-amino-1,3,4-thiadiazole as starting materials in 5.5 hours reaction time.

$^1$H-NMR (200 MHz, CDCl$_3$): 1.03 (s, 3H), 1.20-3.05 (m, 18H), 6.80-6.95 (m, 1H), 7.03-7.18 (m, 2H), 8.82 (s, 1H), 13.67 (br s, 1H).

Compound 18

3-((13S,15R,E)-4-fluoro-17-(hydroxyimino)-13-methyl-7,8,9,11,12,13,14,15,16,17-decahydro-6H-cyclopenta[a]phenanthren-15-yl)-N-(1,3,4-thiadiazol-2-yl)propanamide

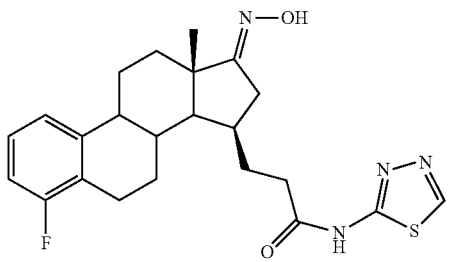 [SMILES: C[C@]12CCC3c4cccc(F)c4CCC3C1[C@H](CCC(=O)Nc1nncs1)C/C2=N\O]

Example 18 was prepared in 94% yield from compound 17 by the same method as with Example 2 in 2.5 hours reaction time.

$^1$H-NMR (200 MHz, DMSO-d6): 1.03 (s, 3H), 1.20-2.47 (m, 15H), 2.55-2.95 (m, 3H), 6.90-7.05 (m, 1H), 7.10-7.23 (m, 2H), 9.15 (s, 1H), 10.20 (s, 1H), 12.59 (br s, 1H).

Compound 19

3-((13S,15R)-4-fluoro-13-methyl-17-oxo-7,8,9,11,12,13,14,15,16,17-decahydro-6H-cyclopenta[a]phenanthren-15-yl)-N-(pyridazine-3-yl)propanamide

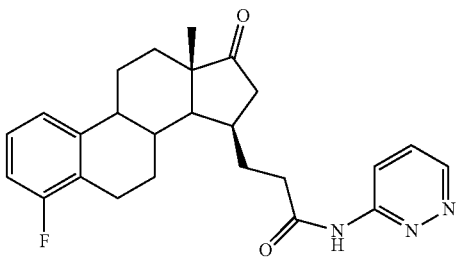 [SMILES: C[C@]12CCC3c4cccc(F)c4CCC3C1[C@H](CCC(=O)Nc1cccnn1)CC2=O]

Compound 19 was synthesized in 42% yield by the method used in the preparation of the compound 3 by using acid SM-IX and 3-aminopyridazine as starting materials in 2 hours reaction time, crystallized from ethanol.

$^1$H-NMR (200 MHz, DMSO-d6): 0.99 (s, 3H), 1.36-2.45 (m, 16H), 2.78-2.91 (m, 2H), 6.92-6.97 (m, 1H), 7.15-7.23 (m, 2H), 7.67 (dd, 1H), 8.33 (d, 1H), 8.95 (d, 1H), 11.14 (s, 1H).

Compound 20

3-((13S,15R,E)-4-fluoro-17-(hydroxyimino)-13-methyl-7,8,9,11,12,13,14,15,16,17-decahydro-6H-cyclopenta[a]phenanthren-15-yl)-N-(pyridazine-3-yl)propanamide

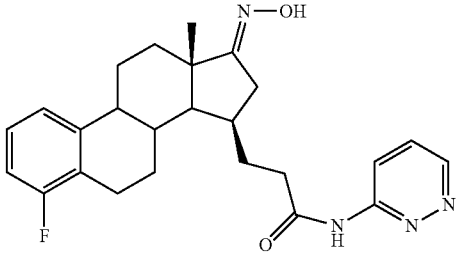 [SMILES: C[C@]12CCC3c4cccc(F)c4CCC3C1[C@H](CCC(=O)Nc1cccnn1)C/C2=N\O]

Compound 20 was prepared from Compound 19 by the same method as with Compound 2.

$^1$H-NMR (200 MHz, CDCl$_3$): 1.12 (s, 3H), 1.33-3.00 (m, 19H), 6.81-6.84 (m, 1H), 7.04-7.13 (m, 2H), 7.54 (d, 1H), 8.63 (dd, 1H), 8.97 (dd, 1H), 10.95 (br s, 1H).

Compound 21

N-(4,5-dihydrothiazol-2-yl)-3-((13S,15R)-4-fluoro-13-methyl-17-oxo-7,8,9,11,12,13,14,15,16,17-decahydro-6H-cyclopenta[a]phenanthren-15-yl)propanamide

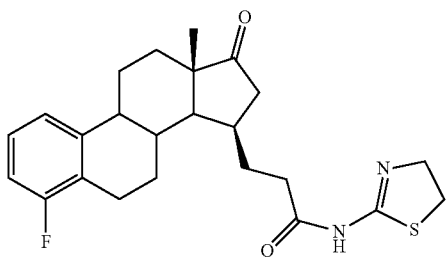 [SMILES: C[C@]12CCC3c4cccc(F)c4CCC3C1[C@H](CCC(=O)NC1=NCCS1)CC2=O]

Compound 21 was synthesized in 74% yield by the method used in the preparation of the compound 3 by using acid SM-IX and 2-amino-2-thiazoline as starting materials in 2 hours reaction time.

$^1$H-NMR (200 MHz, CDCl$_3$): 1.06 (s, 3H), 1.39-2.72 (m, 17H), 2.80-3.05 (m, 2H), 3.30 (t, 2H), 3.94 (t, 2H), 6.84-6.92 (m, 1H), 7.05-7.22 (m, 2H).

Compound 22

N-(4,5-dihydrothiazol-2-yl)-3-((13S,15R,E)-4-fluoro-17-(hydroxyimino)-13-methyl-7,8,9,112,13,14,15,16,17-decahydro-6H-cyclopenta[a]phenanthren-15-yl)propanamide

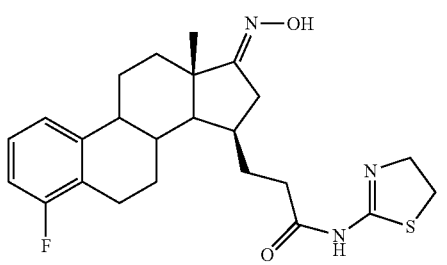 [SMILES: C[C@]12CCC3c4cccc(F)c4CCC3C1[C@H](CCC(=O)NC1=NCCS1)C/C2=N\O]

Example 22 was prepared from compound 21 by the same method as with Example 2 in 2 hours reaction time.

Compound 23

N,N-diethyl-3-((13S,15R)-4-fluoro-13-methyl-17-oxo-7,8,9,11,12,13,14,15,16,17-decahydro-6H-cyclopenta[a]phenanthren-15-yl)propanamide

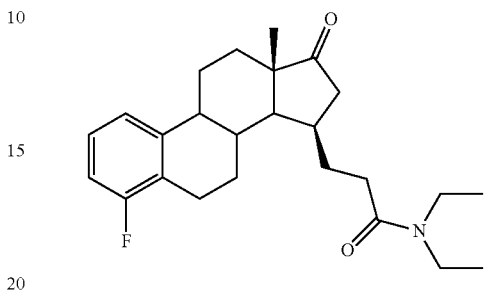

Compound 23 was synthesized in 97% yield by the same method as with compound 3 using acid SM-IX and diethylamine as an amine in two hours reaction time.

$^1$H-NMR (200 MHz, DMSO-d6): 0.97 (s, 3H), 1.01 (t, 3H), 1.11 (t, 3H), 1.20-2.47 (m, 16H), 2.60-2.99 (m, 2H), 3.15-3.40 (m, 4H), 6.90-7.06 (m, 1H), 7.08-7.25 (m, 2H).

Compound 24

N,N-diethyl-3-((13S,15R,E)-4-fluoro-17-(hydroxyimino)-13-methyl-7,8,9,11,12,13,14,15,16,17-decahydro-6H-cyclopenta[a]phenanthren-15-yl)propanamide

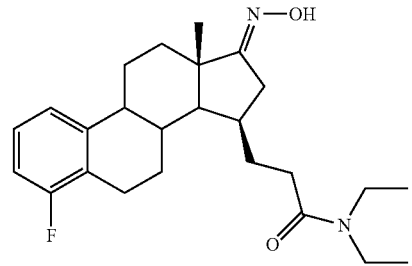 [SMILES: CCN(CC)C(=O)CC[C@@H]1C/C(=N\O)[C@@]2(C)CCC3c4cccc(F)c4CCC3C12]

Example 24 was prepared in 20% yield from the compound 23 by the same method as with Example 2 by stirring at 50° C. for 2.5 hours.

$^1$H-NMR (200 MHz, CDCl$_3$): 1.12 (s, 3H), 1.05-1.24 (m, 6H), 1.25-2.55 (m, 15H), 2.60-3.05 (m, 3H), 3.20-3.53 (m, 4H), 6.80-6.92 (m, 1H), 7.03-7.20 (m, 2H), 8.33 (s, 1H).

Compound 25

3-((13S,15R)-3-fluoro-13-methyl-17-oxo-7,8,9,11,12,13,14,15,16,17-decahydro-6H-cyclopenta[a]phenanthren-15-yl)-N-(5-fluoropyridin-2-yl)propanamide

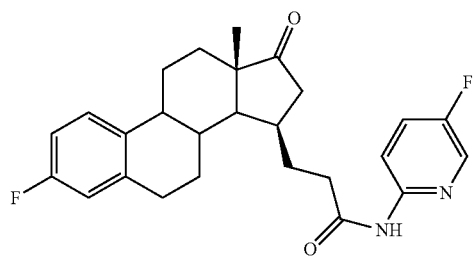 [SMILES: C[C@]12CCC3c4ccc(F)cc4CCC3C1[C@H](CCC(=O)Nc1ccc(F)cn1)CC2=O]

Compound 25 was synthesized by the method used in the preparation of the compound 1 by using acid SM-XV and 2-amino-5-fluoropyridine as starting materials. Reaction time was four hours.

$^1$H NMR (200 MHz, DMSO-d6): 0.98 (s, 3H), 1.22-2.45 (m, 16H), 2.80-2.95 (m, 2H), 6.83-7.03 (m, 2H), 7.20-7.39 (m, 1H), 7.73 (td, 1H), 8.14 (dd, 1H), 8.31 (d, 1H), 10.62 (s, 1H).

Compound 26

3-((13S,15R,E)-3-fluoro-17-(hydroxyimino)-13-methyl-7,8,9,11,12,13,14,15,16,17-decahydro-6H-cyclopenta[a]phenanthren-15-yl)-N-(5-fluoropyridin-2-yl)propanamide

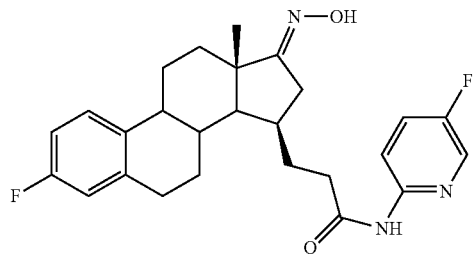 [SMILES: C[C@]12CCC3c4ccc(F)cc4CCC3C1[C@H](CCC(=O)Nc1ccc(F)cn1)C/C2=N\O]

Example 26 was prepared in 94% yield from the compound 25 by the same method as with Example 2 in three hours reaction time.

$^1$H NMR (200 MHz, DMSO-d6): 1.03 (s, 3H), 1.12-2.48 (m, 15H), 2.57-2.78 (m, 1H), 2.80-2.95 (m, 2H), 6.79-7.01 (m, 2H), 7.18-7.38 (m, 1H), 7.72 (td, 1H), 8.15 (dd, 1H), 8.31 (d, 1H), 10.18 (s, 1H), 10.64 (s, 1H).

MS m/z (TOF ES+): 454 (M+1).

Compound 27

3-((13S,15R)-3-fluoro-13-methyl-17-oxo-7,8,9,11,12,13,14,15,16,17-decahydro-6H-cyclopenta[a]phenanthren-15-yl)-N-(5-methoxypyridin-2-yl)propanamide

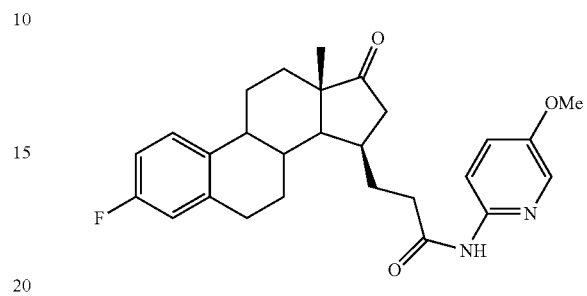

Compound 27 was synthesized in 62% yield by the method used in the preparation of the compound 3 by using acid SM-XV and 5-methoxypyridine-2-amine as starting materials in three hours reaction time.

$^1$H-NMR (200 MHz, CDCl$_3$): 1.07 (s, 3H), 1.39-2.50 (m, 16H), 2.94 (m, 2H), 3.85 (s, 3H), 6.79-6.88 (m, 2H), 7.19-7.30 (m, 2H), 7.90 (br s, 1H), 7.95 (d, 1H), 8.14 (d, 1H).

Compound 28

3-((13S,15R,E)-3-fluoro-17-(hydroxyimino)-13-methyl-7,8,9,11,12,13,14,15,16,17-decahydro-6H-cyclopenta[a]phenanthren-15-yl)-N-(5-methoxypyridin-2-yl)propanamide

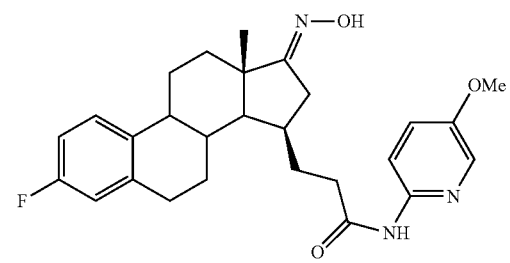 [SMILES: COc1ccc(NC(=O)CC[C@@H]2C/C(=N\O)[C@@]3(C)CCC4c5ccc(F)cc5CCC4C23)nc1]

Example 28 was prepared in 96% yield from compound 27 by the same method as with Example 2 in one hour reaction time.

$^1$H-NMR (200 MHz, CDCl$_3$): 1.15 (s, 3H), 1.40-2.70 (m, 16H), 2.88-3.02 (m, 3H), 3.85 (s, 3H), 6.77-6.90 (m, 2H), 7.18-7.32 (m, 2H), 7.95 (d, 1H), 8.16 (d, 1H), 8.37 (br s, 1H), 8.63 (br s, 1H). MS m/z (TOF ES+): 466 (M+1)

Compound 29

3-((13S,15R)-3-fluoro-13-methyl-17-oxo-7,8,9,11,12,13,14,15,16,17-decahydro-6H-cyclopenta[a]phenanthren-15-yl)-N-(6-methoxypyridazin-3-yl)propanamide

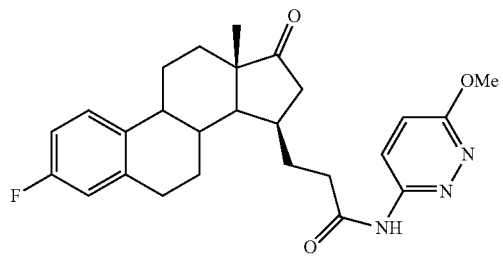 [SMILES: COc1ccc(NC(=O)CC[C@@H]2CC(=O)[C@@]3(C)CCC4c5ccc(F)cc5CCC4C23)nn1]

Compound 29 was synthesized in four hours reaction time by the method used in the preparation of the compound 3 by using acid SM-XV and 3-amino-6-methoxypyridazine as starting materials.

$^1$H-NMR (200 MHz, DMSO-d6): 0.98 (s, 3H), 1.20-2.47 (m, 16H), 2.75-3.02 (m, 2H), 3.98 (s, 3H), 6.83-7.03 (m, 2H), 7.17-7.39 (m, 2H), 8.25 (d, 1H), 10.94 (br s, 1H).

Compound 30

3-((13S,15R,E)-3-fluoro-17-(hydroxyimino)-13-methyl-7,8,9,11,12,13,14,15,16,17-decahydro-6H-cyclopenta[a]phenanthren-15-yl)-N-(6-methoxypyridazin-3-yl)propanamide

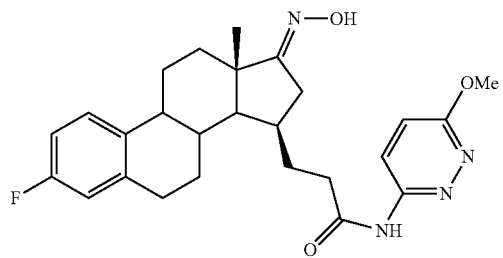 [SMILES: COc1ccc(NC(=O)CC[C@@H]2C/C(=N\O)[C@@]3(C)CCC4c5ccc(F)cc5CCC4C23)nn1]

Example 30 was prepared from compound 29 by the same method as with Example 2 in four hours reaction time.

$^1$H-NMR (200 MHz, DMSO-d6): 1.03 (s, 3H), 1.11-2.47 (m, 15H), 2.58-2.78 (m, 1H), 2.78-2.96 (m, 2H), 3.98 (s, 3H), 6.75-7.02 (m, 2H), 7.13-7.39 (m, 2H), 8.25 (d, 1H), 10.19 (br s, 1H), 10.95 (br s, 1H). MS m/z (TOF ES+): 467 (M+1).

Compound 31

3-((13S,15R)-3-fluoro-13-methyl-17-oxo-7,8,9,11,12,13,14,15,16,17-decahydro-6H-cyclopenta[a]phenanthren-15-yl)-N-(6-methylpyridazin-3-yl)propanamide

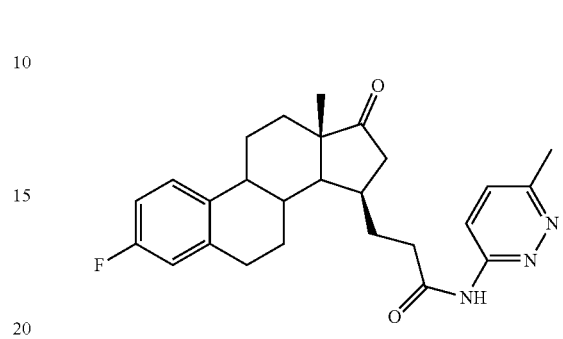

Compound 31 was synthesized in 62% yield by the method used in the preparation of the compound 3 by using acid SM-XV and 3-amino-6-methylpyridazine as starting materials, by using THF as a solvent in five hours reaction time.

$^1$H-NMR (200 MHz, DMSO-d6): 0.98 (s, 3H), 1.12-2.46 (m, 16H), 2.55 (s, 3H), 2.80-3.00 (m, 2H), 6.81-7.02 (m, 2H), 7.21-7.37 (m, 1H), 7.54 (d, 1H), 8.22 (d, 1H), 11.04 (br s, 1H).

Compound 32

3-((13S,15R,E)-3-fluoro-17-(hydroxyimino)-13-methyl-7,8,9,11,12,13,14,15,16,17-decahydro-6H-cyclopenta[a]phenanthren-15-yl)-N-(6-methylpyridazin-3-yl)propanamide

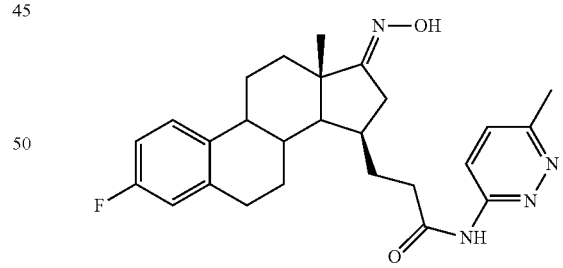

Compound 32 was prepared from Compound 31 by the same method as with Compound 2 in three hours reaction time.

$^1$H-NMR (200 MHz, DMSO-d6): 1.03 (s, 3H), 1.11-2.44 (m, 15H), 2.55 (s, 3H), 2.59-2.77 (m, 1H), 2.78-2.96 (m, 2H), 6.79-7.03 (m, 2H), 7.29 (br t, 1H), 7.54 (d, 1H), 8.22 (d, 1H), 10.18 (s, 1H), 10.95 (s, 1H). MS m/z (TOF ES+): 451 (M+1)

Compound 33

3-((13S,15R)-3-fluoro-13-methyl-17-oxo-7,8,9,11,12,13,14,15,16,17-decahydro-6H-cyclopenta[a]phenanthren-15-yl)-N-(pyridazin-3-yl)propanamide

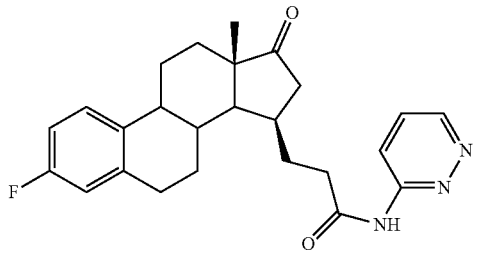 [SMILES: C[C@]12CCC3c4ccc(F)cc4CCC3C1[C@H](CCC(=O)Nc1cccnn1)CC2=O]

Compound 33 was synthesized by the method used in the preparation of the Compound 1 by using acid SM-XV and 3-aminopyridazine as starting materials. Additional amount (70-100 mol-%) of reagents were added after 5.5 hours and stirring continued overnight.

$^1$H NMR (200 MHz, DMSO-d6): 0.99 (s, 3H), 1.11-2.47 (m, 16H), 2.80-2.95 (m, 2H), 6.81-7.03 (m, 2H), 7.20-7.38 (m, 1H), 7.67 (dd, 1H), 8.32 (dd, 1H), 8.95 (dd, 1H), 11.13 (s, 1H).

Compound 34

3-((13S,15R,E)-3-fluoro-17-(hydroxyimino)-13-methyl-7,8,9,11,12,13,14,15,16,17-decahydro-6H-cyclopenta[a]phenanthren-15-yl)-N-(pyridazin-3-yl)propanamide

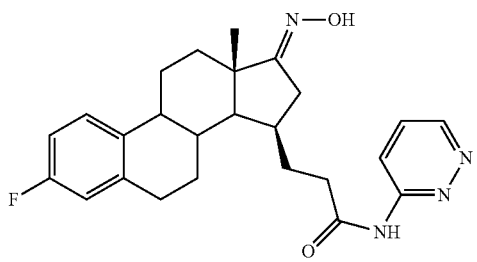 [SMILES: C[C@]12CCC3c4ccc(F)cc4CCC3C1[C@H](CCC(=O)Nc1cccnn1)C/C2=N\O]

Compound 34 was prepared in 96% yield from Compound 33 by the same method as with Compound 2 in 1.5 hour reaction time.

$^1$H-NMR (200 MHz, DMSO-d6): 1.04 (s, 3H), 1.11-2.47 (m, 15H), 2.58-2.79 (m, 1H), 2.78-2.96 (m, 2H), 6.83-7.02 (m, 2H), 7.29 (br t, 1H), 7.66 (dd, 1H), 8.33 (dd, 1H), 8.94 (dd, 1H), 10.19 (s, 1H), 11.15 (s, 1H). MS m/z (TOF ES+): 419 (M–H$_2$O+1).

Compound 35

3-((13S,15R)-3-fluoro-13-methyl-17-oxo-7,8,9,11,12,13,14,15,16,17-decahydro-6H-cyclopenta[a]phenanthren-15-yl)-N-methyl-N-(oxetan-3-yl)propanamide

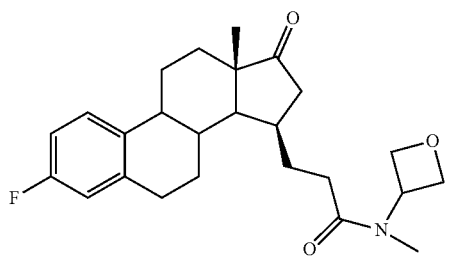 [SMILES: CN(C(=O)CC[C@@H]1CC(=O)[C@@]2(C)CCC3c4ccc(F)cc4CCC3C12)C1COC1]

Compound 35 was synthesized in 96% yield by the method used in the preparation of the Compound 9 by using acid SM-XV and N-methyl-3-oxetanamine as starting materials in 4 hours reaction time.

$^1$H NMR (200 MHz, DMSO-d6): 0.96 (s, 3H), 1.12-2.45 (m, 16H), 2.80-2.95 (m, 2H), 2.95-3.13 (s, 3H), 4.43-4.84 (m, 4H), 5.12-5.40 (m, 1H), 6.82-7.03 (m, 2H), 7.20-7.38 (m, 1H).

Compound 36

3-((13S,15R,E)-3-fluoro-17-(hydroxyimino)-13-methyl-7,8,9,11,12,13,14,15,16,17-decahydro-6H-cyclopenta[a]phenanthren-15-yl)-N-methyl-N-(oxetan-3-yl)propanamide

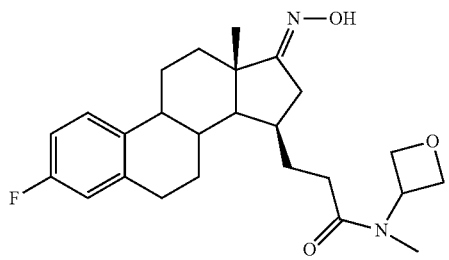 [SMILES: CN(C(=O)CC[C@@H]1C/C(=N\O)[C@@]2(C)CCC3c4ccc(F)cc4CCC3C12)C1COC1]

Compound 36 was prepared in 23% yield from Compound 35 by the same method as with Compound 2 in four hour reaction time.

$^1$H NMR (200 MHz, CDCl$_3$): 1.12 (s, 3H), 1.27-2.61 (m, 15H), 2.75-3.09 (m, 3H), 3.16 (s, 3H) 4.58-4.90 (m, 4H), 5.05-5.61 (m, 1H), 6.67-6.95 (m, 2H), 7.17-7.26 (m, 1H), 7.91 (br s, 1H).

Compound 37

3-((13S,15R)-3-fluoro-13-methyl-17-oxo-7,8,9,11,12,13,14,15,16,17-decahydro-6H-cyclopenta[a]phenanthren-15-yl)-N-(1,3,4-thiadiazol-2-yl)propanamide

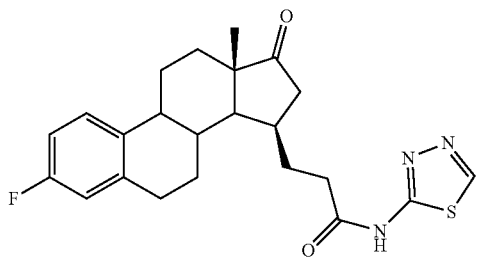 [SMILES: C[C@]12CCC3c4ccc(F)cc4CCC3C1[C@H](CCC(=O)Nc1nncs1)CC2=O]

Compound 37 was synthesized in 52% yield by the method used in the preparation of the compound 9 by using acid SM-XV and 2-amino-1,3,4-thiadiazole as starting materials in 6 hours reaction time.

$^1$H NMR (200 MHz, DMSO-d6): 0.98 (s, 3H), 1.20-2.70 (m, 16H), 2.80-2.95 (m, 2H), 6.85-7.03 (m, 2H), 7.22-7.38 (m, 1H), 9.15 (s, 1H), 12.56 (br s, 1H).

Compound 38

3-((13S,15R,E)-3-fluoro-17-(hydroxyimino)-13-methyl-7,8,9,11,12,13,14,15,16,17-decahydro-6H-cyclopenta[a]phenanthren-15-yl)-N-(1,3,4-thiadiazol-2-yl)propanamide

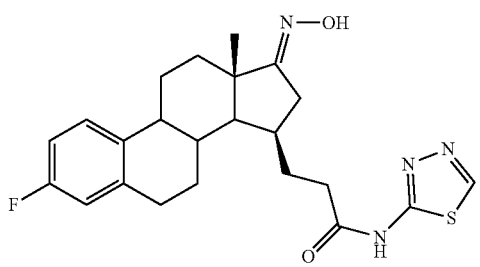 [SMILES: C[C@]12CCC3c4ccc(F)cc4CCC3C1[C@H](CCC(=O)Nc1nncs1)C/C2=N\O]

Compound 38 was prepared in 96% yield from Compound 37 by the same method as with Compound 2 in two hours reaction time.

$^1$H NMR (200 MHz, DMSO-d6): 1.03 (s, 3H), 1.20-2.80 (m, 16H), 2.80-2.95 (m, 2H), 6.85-7.03 (m, 2H), 7.22-7.38 (m, 1H), 9.14 (s, 1H), 10.19 (s, 1H), 12.57 (br s, 1H). MS m/z (TOF ES+): 425 (M−H$_2$O+1)

Compound 39

N,N-diethyl-3-((13S,15R)-3-fluoro-13-methyl-17-oxo-7,8,9,11,12,13,14,15,16,17-decahydro-6H-cyclopenta[a]phenanthren-15-yl)propanamide

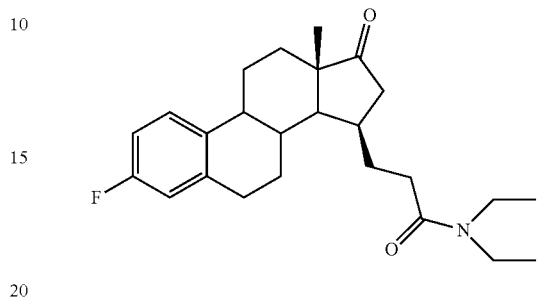

Compound 39 was synthesized in 52% yield by the method used in the preparation of the compound 3 by using acid SM-XV and diethylamine as starting materials in 4 hours reaction time.

$^1$H NMR (200 MHz, CDCl$_3$): 1.07 (s, 3H), 1.08-1.24 (m, 6H), 1.31-2.57 (m, 16H), 2.78-3.11 (m, 2H), 3.19-3.57 (m, 4H), 6.73-6.92 (m, 2H), 7.20 (br d, 1H).

Compound 40

N,N-diethyl-3-((13S,15R,E)-3-fluoro-17-(hydroxyimino)-13-methyl-7,8,9,11,12,13,14,15,16,17-decahydro-6H-cyclopenta[a]phenanthren-15-yl)propanamide

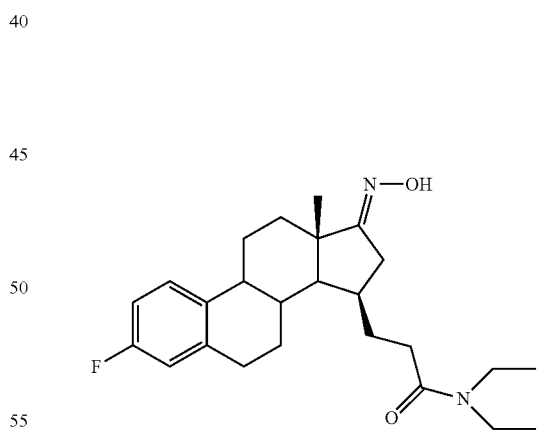

Compound 40 was prepared in 76% yield from Compound 39 by the same method as with Compound 2 in five hours reaction time.

$^1$H NMR (200 MHz, CDCl$_3$): 1.13 (s, 3H), 1.08-1.24 (m, 6H), 1.31-2.57 (m, 15H), 2.78-3.11 (m, 3H), 3.19-3.57 (m, 4H), 6.73-6.92 (m, 2H), 7.04 (br s, 1H), 7.18-7.25 (m, 1H).

Compound 41

3-((13S,15R)-3-fluoro-13-methyl-17-oxo-7,8,9,11,12,13,14,15,16,17-decahydro-6H-cyclopenta[a]phenanthren-15-yl)-N-(5-isopropylpyridin-2-yl)propanamide

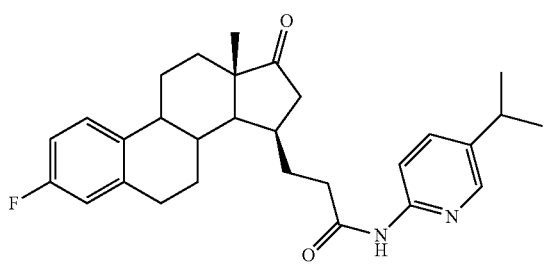 [SMILES: CC(C)c1ccc(NC(=O)CC[C@@H]2CC(=O)[C@@]3(C)CCC4c5ccc(F)cc5CCC4C23)nc1]

Compound 41 was synthesized in 60% yield by the method used in the preparation of the compound 1 by using acid SM-XV and 2-amino-5-isopropylpyridine as starting materials in overnight reaction time.

$^1$H NMR (200 MHz, DMSO-d6): 0.98 (s, 3H), 1.20 (d, 6H), 1.28-2.49 (m, 16H), 2.74-3.02 (m, 3H), 6.79-7.03 (m, 2H), 7.19-7.39 (m, 1H), 7.66 (d, 1H), 8.02 (d, 1H), 8.19 (s, 1H), 10.43 (s, 1H).

Compound 42

3-((13S,15R,E)-3-fluoro-17-(hydroxyimino)-13-methyl-7,8,9,11,12,13,14,15,16,17-decahydro-6H-cyclopenta[a]phenanthren-15-yl)-N-(5-isopropylpyridin-2-yl)propanamide

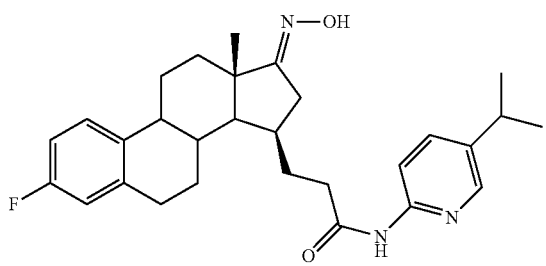 [SMILES: CC(C)c1ccc(NC(=O)CC[C@@H]2C/C(=N\O)[C@@]3(C)CCC4c5ccc(F)cc5CCC4C23)nc1]

Compound 42 was prepared in 64% yield from Compound 41 by the same method as with Compound 2 in four hours reaction time.

$^1$H NMR (200 MHz, DMSO-d6): 1.03 (s, 3H), 1.20 (d, 6H), 1.28-2.49 (m, 15H), 2.50-2.74 (m, 1H), 2.75-3.02 (m, 3H), 6.79-7.03 (m, 2H), 7.19-7.39 (m, 1H), 7.65 (dd, 1H), 8.02 (d, 1H), 8.19 (d, 1H), 10.18 (s, 1H), 10.45 (s, 1H).

Compound 43

3-((13S,15R)-3-chloro-13-methyl-17-oxo-7,8,9,11,12,13,14,15,16,17-decahydro-6H-cyclopenta[a]phenanthren-15-yl)-N-(pyridazine-3-yl)propanamide

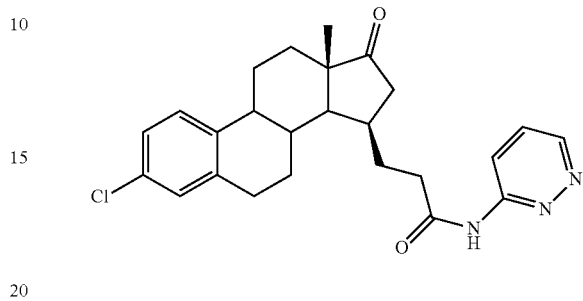

Acid SM-XVII (100 mg, 0.28 mmol, 100 mol-%) was dissolved in dry DCM (2 ml). SOCl$_2$ (40 µl, 200 mol-%) was added under nitrogen atmosphere to the reaction mixture and refluxed for 30 minutes followed by additional amount of SOCl$_2$ (20 µl) with continuing refluxion for 1.5 hours. Anhydrous pyridine (112 µl, 500 mol-%) and 3-aminopyridazine (54 mg, 200 mol-%) were dissolved in dry DCM/DMF (1 ml, vol 1:1) and added dropwise to the reaction mixture. After stirring at room temperature until the reaction was completed, the reaction mixture was diluted with DCM followed by dilute HCl-solution, water and brine, dried with sodium sulfate. Solvents were evaporated and the precipitate was purified by chromatography producing Compound 43 in 25% yield.

$^1$H-NMR (200 MHz, CDCl$_3$): 1.06 (s, 3H), 1.38-2.75 (m, 16H), 2.90 (m, 2H), 7.09-7.22 (m, 3H), 7.54 (dd, 1H), 8.63 (d, 1H), 8.93 (d, 1H), 10.95 (br s, 1H).

Compound 44

3-((13S,15R,E)-3-chloro-17-(hydroxyimino)-13-methyl-7,8,9,11,12,13,14,15,16,17-decahydro-6H-cyclopenta[a]phenanthren-15-yl)-N-(pyridazine-3-yl)propanamide

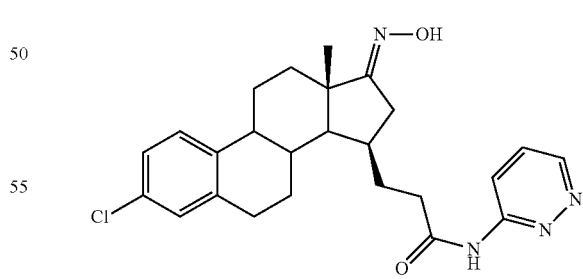

Compound 44 was prepared from Compound 43 by the same method as with Compound 2 by stirring at room temperature overnight.

$^1$H-NMR (200 MHz, CDCl$_3$): 1.10 (s, 3H), 1.31-2.99 (m, 16H), 2.90 (m, 2H), 7.07-7.21 (m, 3H), 7.54 (dd, 1H), 8.14 (br s, 1H), 8.61 (d, 1H), 8.96 (d, 1H), 10.75 (br s, 1H). MS m/z (TOF ES+): 475/477 (M+Na)

Compound 45

3-((13S,15R)-3-chloro-13-methyl-17-oxo-7,8,9,11,12,13,14,15,16,17-decahydro-6H-cyclopenta[a]phenanthren-15-yl)-N-(4,5-dihydrothiazol-2-yl)propanamide

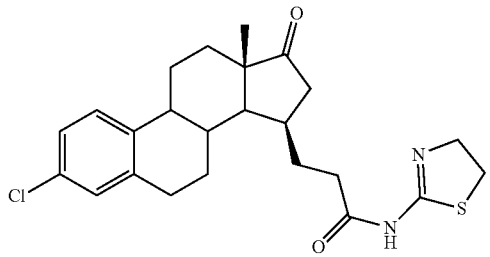 [SMILES: C[C@]12CCC3c4ccc(Cl)cc4CCC3C1[C@H](CCC(=O)NC1=NCCS1)CC2=O]

Compound 45 was prepared from the acid SM-XVII by the same method as with Compound 9 by stirring at room temperature for three hours.

¹H-NMR (200 MHz, CDCl₃): 1.05 (s, 3H), 1.50-2.56 (m, 17H), 2.94 (m, 2H), 3.35 (dd, 2H), 3.97 (dd, 2H), 7.09-7.22 (m, 3H).

Compound 46

3-((13S,15R,E)-3-chloro-17-(hydroxyimino)-13-methyl-7,8,9,11,12,13,14,15,16,17-decahydro-6H-cyclopenta[a]phenanthren-15-yl)-N-(4,5-dihydrothiazol-2-yl)propanamide

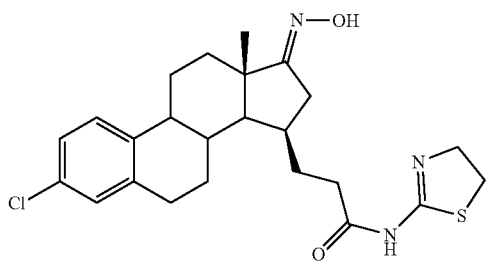 [SMILES: C[C@]12CCC3c4ccc(Cl)cc4CCC3C1[C@H](CCC(=O)NC1=NCCS1)C/C2=N\O]

Compound 46 was prepared from Compound 45 by the same method as with Compound 2.

¹H-NMR (200 MHz, CDCl₃): 1.08 (s, 3H), 1.54-2.41 (m, 18H), 2.91-3.20 (m, 6H), 7.07-7.21 (m, 3H). MS m/z 460/462 Compound 47 (13S,15R)-3-chloro-13-methyl-15-(3-oxo-3-(8-oxa-2-azaspiro[4.5]decan-2-yl)propyl)-6,7,8,9,11,12,13,14,15,16-decahydro-17H-cyclopenta[a]phenanthren-17-one

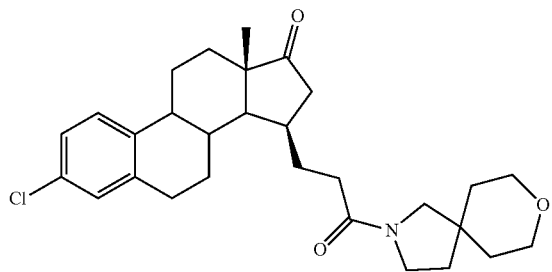 [SMILES: C[C@]12CCC3c4ccc(Cl)cc4CCC3C1[C@H](CCC(=O)N1CCC3(CCOCC3)C1)CC2=O]

Compound 47 was prepared in 94% yield from acid SM-XVII by the same method as with Compound 9 using 8-oxa-2-aza-spiro(4,5)decane hydrochloride as amine. Reaction time was 4.5 hours.

¹H NMR (200 MHz, DMSO-d6): 0.96 (s, 3H), 1.11-2.45 (m, 22H), 2.75-3.00 (m, 2H), 3.20 (s, 1H), 3.30-3.70 (m, 7H), 7.08-7.22 (m, 2H), 7.25-7.38 (m, 1H).

Compound 48

3-((13S,15R,E)-3-chloro-17-(hydroxyimino)-13-methyl-7,8,9,11,12,13,14,15,16,17-decahydro-6H-cyclopenta[a]phenanthren-15-yl)-1-(8-oxa-2-azaspiro[4.5]decan-2-yl)propan-1-one

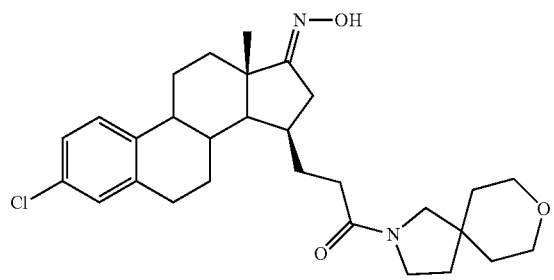 [SMILES: C[C@]12CCC3c4ccc(Cl)cc4CCC3C1[C@H](CCC(=O)N1CCC3(CCOCC3)C1)C/C2=N\O]

Compound 48 was prepared in 92% yield from Compound 47 by the same method as with Compound 2 by refluxing 5.5 hours.

¹H NMR (200 MHz, DMSO-d6): 1.01 (s, 3H), 1.20-2.45 (m, 21H), 2.50-2.75 (m, 1H), 2.75-3.00 (m, 2H), 3.20 (s, 1H), 3.30-3.70 (m, 7H), 7.08-7.22 (m, 2H), 7.25-7.38 (m, 1H), 10.17 (s, 1H).

Compound 49

3-((13S,15R)-3-chloro-13-methyl-17-oxo-7,8,9,11,12,13,14,15,16,17-decahydro-6H-cyclopenta[a]phenanthren-15-yl)-N-(6-methoxypyridazin-3-yl)propanamide

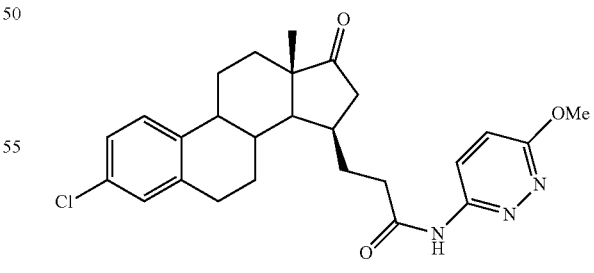

Compound 49 was prepared in 56% yield from acid SM-XVII by the same method as with Compound 3 by stirring at +50° C. for several days.

¹H-NMR (200 MHz, CDCl₃): 1.06 (s, 3H), 1.45-2.43 (m, 15H), 2.67 (m, 2H), 2.92 (m, 2H), 4.07 (s, 3H), 7.04-7.22 (m, 4H), 8.47 (d, 1H), 10.0 (br s, 1H).

Compound 50

3-((13S,15R,E)-3-chloro-17-(hydroxyimino)-13-methyl-7,8,9,11,12,13,14,15,16,17-decahydro-6H-cyclopenta[a]phenanthren-15-yl)-N-(6-methoxy-pyridazin-3-yl)propanamide

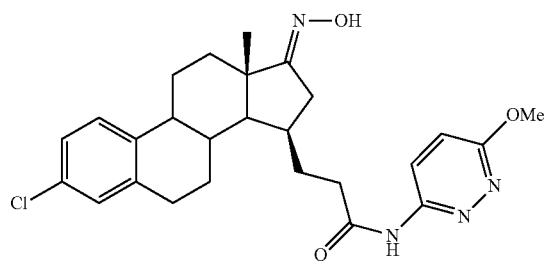 [SMILES: COc1ccc(NC(=O)CC[C@@H]2C/C(=N\O)[C@@]3(C)CCC4c5ccc(Cl)cc5CCC4C23)nn1]

Compound 50 was prepared in 36% yield from Compound 49 by the same method as with Compound 2 by refluxing for two hours.

$^1$H-NMR (200 MHz, CDCl$_3$): 1.07 (s, 3H), 1.50-3.03 (m, 20H), 4.09 (s, 3H), 7.03-7.21 (m, 4H), 8.51 (d, 1H), 9.01 (br s, 1H), 10.89 (br s, 1H). MS m/z (TOF ES+): 483/485 (M+)

Compound 51

3-((13S,15R)-3-chloro-13-methyl-17-oxo-7,8,9,11,12,13,14,15,16,17-decahydro-6H-cyclopenta[a]phenanthren-15-yl)-N,N-diethylpropanamide

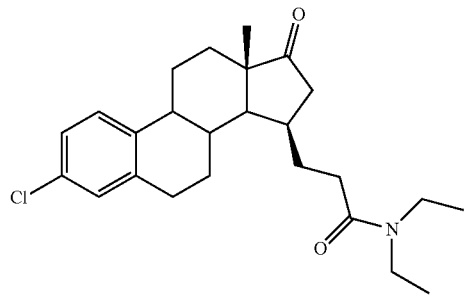 [SMILES: CCN(CC)C(=O)CC[C@@H]1CC(=O)[C@@]2(C)CCC3c4ccc(Cl)cc4CCC3C12]

Compound 51 was prepared in 63% yield from acid SM-XVII and diethylamine as an amide by the same method as with Compound 9 by stirring at room temperature overnight.

$^1$H-NMR (200 MHz, CDCl$_3$): 1.07 (s, 3H), 1.15 (td, 6H), 1.44-2.40 (m, 16H), 2.93 (m, 2H), 3.34 (m, 4H), 7.09-7.23 (m, 3H).

Compound 52

3-((13S,15R,E)-3-chloro-17-(hydroxyimino)-13-methyl-7,8,9,11,12,13,14,15,16,17-decahydro-6H-cyclopenta[a]phenanthren-15-yl)-N,N-diethylpropanamide

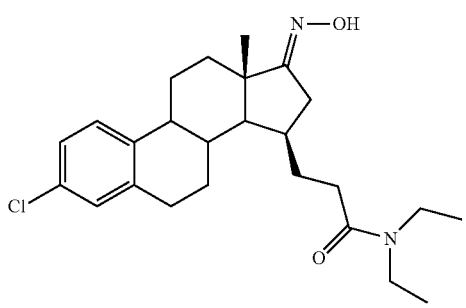 [SMILES: CCN(CC)C(=O)CC[C@@H]1C/C(=N\O)[C@@]2(C)CCC3c4ccc(Cl)cc4CCC3C12]

Compound 52 was prepared in 98% yield from Compound 51 by the same method as with Compound 2 by refluxing for three hours.

$^1$H-NMR (200 MHz, CDCl$_3$): 1.12 (s, 3H), 1.16 (td, 6H), 1.34-2.44 (m, 16H), 2.83-2.97 (m, 3H), 3.34 (m, 4H), 7.08-7.22 (m, 3H).

Compound 53

3-((13S,15R)-3-chloro-13-methyl-17-oxo-7,8,9,11,12,13,14,15,16,17-decahydro-6H-cyclopenta[a]phenanthren-15-yl)-N-(5-methylisoxazol-3-yl)propanamide

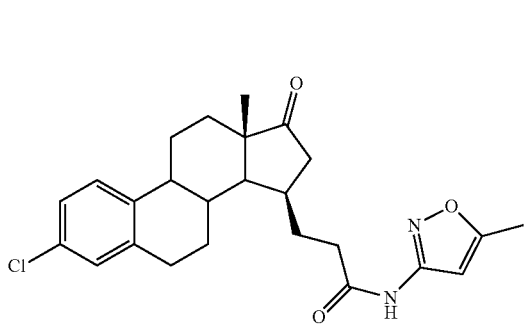 [SMILES: Cc1cc(NC(=O)CC[C@@H]2CC(=O)[C@@]3(C)CCC4c5ccc(Cl)cc5CCC4C23)no1]

Compound 53 was synthesized in 94% yield from acid SM-XVII by the same method as with Compound 1 in DCM using 3-amino-5-methylisoxazole as amine. Reaction time was 6 hours.

$^1$H NMR (200 MHz, DMSO-d6): 0.97 (s, 3H), 1.15-2.45 (m, 16H), 2.37 (s, 3H), 2.80-3.00 (m, 2H), 6.64 (s, 1H), 7.08-7.22 (m, 2H), 7.25-7.38 (m, 1H), 10.88 (br s, 1H).

Compound 54

3-((13S,15R,E)-3-chloro-17-(hydroxyimino)-13-methyl-7,8,9,11,12,13,14,15,16,17-decahydro-6H-cyclopenta[a]phenanthren-15-yl)-N-(5-methylisoxazol-3-yl)propanamide

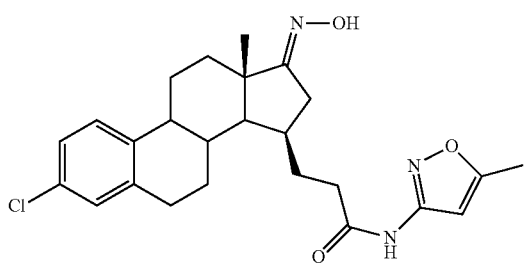 [SMILES: Cc1cc(NC(=O)CC[C@@H]2C/C(=N\O)[C@@]3(C)CCC4c5ccc(Cl)cc5CCC4C23)no1]

Compound 54 was prepared in 92% yield from Compound 53 by the same method as with Compound 2 by refluxing 2 hours.

$^1$H NMR (200 MHz, DMSO-d6): 1.02 (s, 3H), 1.15-2.45 (m, 15H), 2.37 (s, 3H), 2.55-2.75 (m, 1H), 2.80-3.00 (m, 2H), 6.64 (s, 1H), 7.08-7.22 (m, 2H), 7.25-7.38 (m, 1H), 10.19 (s, 1H), 10.89 (br s, 1H).

Compound 55

3-((13S,15R)-3-chloro-13-methyl-17-oxo-7,8,9,11,12,13,14,15,16,17-decahydro-6H-cyclopenta[a]phenanthren-15-yl)-N-(4-methoxypyridin-2-yl)propanamide

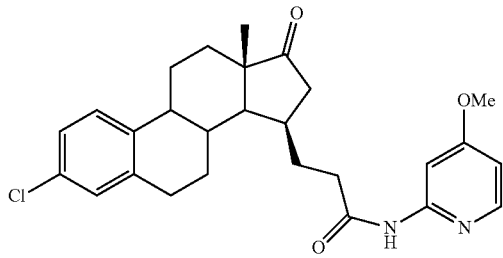 [SMILES: COc1ccnc(NC(=O)CC[C@@H]2CC(=O)[C@@]3(C)CCC4c5ccc(Cl)cc5CCC4C23)c1]

Compound 55 was prepared in 51% yield from acid SM-XVII by the same method as with Compound 9 using 2-amino-4-methoxypyridine as amine and stirring reaction overnight at rt.

$^1$H NMR (200 MHz, DMSO-d6): 0.98 (s, 3H), 1.15-2.45 (m, 16H), 2.80-3.00 (m, 2H), 3.80 (s, 3H), 6.65-6.75 (dd, 1H), 7.08-7.22 (m, 2H), 7.25-7.38 (m, 1H), 7.72-7.73 (d, 1H), 8.12 (d, 1H), 10.47 (br s, 1H).

Compound 56

3-((13S,15R,E)-3-chloro-17-(hydroxyimino)-13-methyl-7,8,9,11,12,13,14,15,16,17-decahydro-6H-cyclopenta[a]phenanthren-15-yl)-N-(4-methoxypyridin-2-yl)propanamide

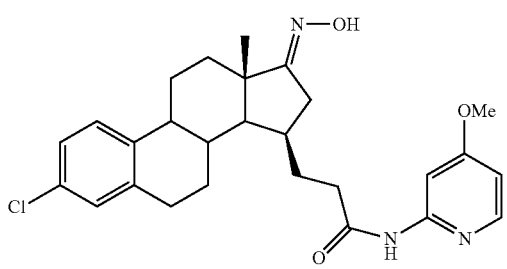 [SMILES: COc1ccnc(NC(=O)CC[C@@H]2C/C(=N\O)[C@@]3(C)CCC4c5ccc(Cl)cc5CCC4C23)c1]

Compound 56 was prepared in 84% yield from Compound 55 by the same method as with Compound 2 by refluxing 1.5 hours.

$^1$H NMR (200 MHz, DMSO-d6): 1.03 (s, 3H), 1.15-2.45 (m, 15H), 2.55-2.75 (m, 1H), 2.80-3.00 (m, 2H), 3.80 (s, 3H), 6.65-6.75 (dd, 1H), 7.08-7.22 (m, 2H), 7.25-7.38 (m, 1H), 7.72-7.73 (d, 1H), 8.12 (d, 1H), 10.19 (s, 1H), 10.48 (br s, 1H).

Compound 57

3-((13S,15R)-3-chloro-13-methyl-17-oxo-7,8,9,11,12,13,14,15,16,17-decahydro-6H-cyclopenta[a]phenanthren-15-yl)-N-(5-fluoropyridin-2-yl)propanamide

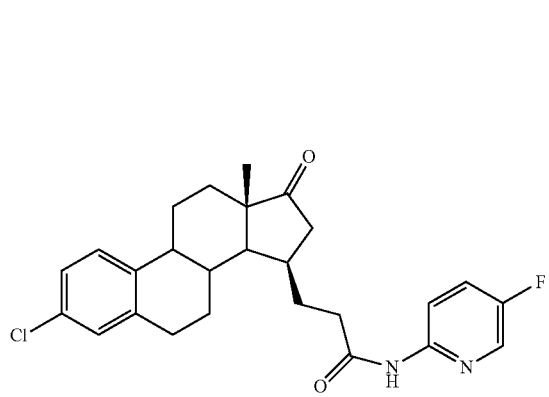 [SMILES: C[C@]12CCC3c4ccc(Cl)cc4CCC3C1[C@H](CCC(=O)Nc1ccc(F)cn1)CC2=O]

Compound 57 was synthesized from acid SM-XVII by the same method as with Compound 1 in DCM. Reaction time was four hours.

$^1$H NMR (200 MHz, DMSO-d6): 0.98 (s, 3H), 1.22-2.47 (m, 16H), 2.75-3.02 (m, 2H), 7.06-7.22 (m, 2H), 7.22-7.37 (m, 1H), 7.72 (td, 1H), 8.14 (dd, 1H), 8.31 (d, 1H), 10.62 (s, 1H).

Compound 58

3-((13S,15R,E)-3-chloro-17-(hydroxyimino)-13-methyl-7,8,9,11,12,13,14,15,16,17-decahydro-6H-cyclopenta[a]phenanthren-15-yl)-N-(5-fluoropyridin-2-yl)propanamide

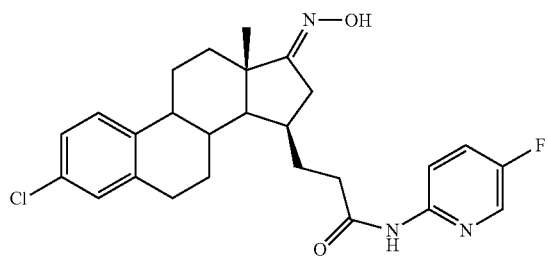 [SMILES: C[C@]12CCC3c4ccc(Cl)cc4CCC3C1[C@H](CCC(=O)Nc1ccc(F)cn1)C/C2=N\O]

Compound 58 was prepared from Compound 57 by the same method as with Compound 2. Reaction time was 2 hours at 50° C.

$^1$H NMR (200 MHz, DMSO-d6): 1.03 (s, 3H), 1.23-2.46 (m, 15H), 2.56-2.77 (m, 1H), 2.80-2.95 (m, 2H), 7.10-7.32 (m, 2H), 7.23-7.36 (m, 1H), 7.72 (td, 1H), 8.15 (dd, 1H), 8.31 (d, 1H), 10.19 (s, 1H), 10.63 (s, 1H).

MS m/z (TOF ES+): 470 (M+1)

Compound 59

3-((13S,15R)-3-chloro-13-methyl-17-oxo-7,8,9,11,12,13,14,15,16,17-decahydro-6H-cyclopenta[a]phenanthren-15-yl)-N-(3-methylpyridin-2-yl)propanamide

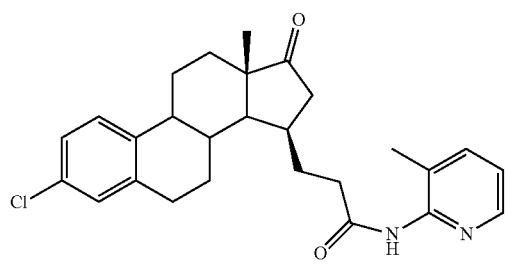 [SMILES: Cc1cccnc1NC(=O)CC[C@@H]1CC(=O)[C@@]2(C)CCC3c4ccc(Cl)cc4CCC3C12]

Compound 59 was synthesized in 54% yield from acid SM-XVII by the same method as with Compound 1 in DCM using 3-methylpyridin-2-amine as amine. Reaction was first stirred for 3 hours, then additional amount (100 mol-%) of amine and T3P were added and stirring continued overnight. Finally reaction was refluxed for 4 hours.

$^1$H NMR (200 MHz, DMSO-d6): 0.98 (s, 3H), 1.15-2.45 (m, 16H), 2.15 (s, 3H), 2.80-3.00 (m, 2H), 7.10-7.25 (m, 3H), 7.26-7.33 (m, 1H), 7.66 (d, 1H), 8.24 (d, 1H), 10.00 (br s, 1H).

Compound 60

3-((13S,15R,E)-3-chloro-17-(hydroxyimino)-13-methyl-7,8,9,11,12,13,14,15,16,17-decahydro-6H-cyclopenta[a]phenanthren-15-yl)-N-(3-methylpyridin-2-yl)propanamide

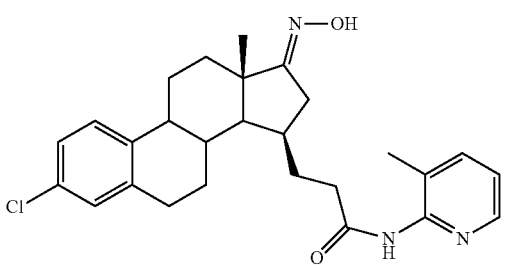 [SMILES: Cc1cccnc1NC(=O)CC[C@@H]1C/C(=N\O)[C@@]2(C)CCC3c4ccc(Cl)cc4CCC3C12]

Compound 60 was prepared in 93% yield from Compound 59 by the same method as with Compound 2 by stirring at 50° C. for 2 hours.

$^1$H NMR (200 MHz, DMSO-d6): 1.03 (s, 3H), 1.15-2.45 (m, 15H), 2.15 (s, 3H), 2.60-2.79 (m, 1H), 2.80-3.00 (m, 2H), 7.10-7.25 (m, 3H), 7.26-7.33 (m, 1H), 7.66 (d, 1H), 8.24 (d, 1H), 10.01 (br s, 1H), 10.20 (s, 1H).

Compound 61

3-((13S,15R)-3-chloro-13-methyl-17-oxo-7,8,9,11,12,13,14,15,16,17-decahydro-6H-cyclopenta[a]phenanthren-15-yl)-N-(3-fluoropyridin-2-yl)propanamide

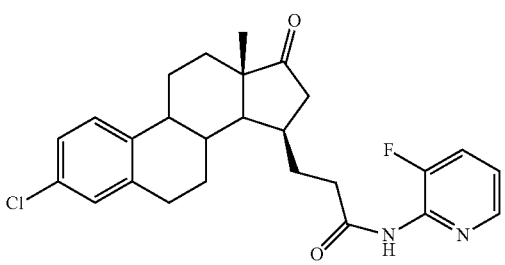 [SMILES: C[C@]12CCC3c4ccc(Cl)cc4CCC3C1[C@H](CCC(=O)Nc1ncccc1F)CC2=O]

Compound 61 was synthesized from acid SM-XVII by the same method as with Compound 1 in DCM. Reaction time was three hours.

$^1$H NMR (200 MHz, DMSO-d6): 0.98 (s, 3H), 1.20-2.47 (m, 16H), 2.80-2.90 (m, 2H), 7.10-7.23 (m, 2H), 7.23-7.42 (m, 2H), 7.76 (dd, 1H), 8.24 (dd, 1H), 10.28 (s, 1H).

Compound 62

3-((13S,15R,E)-3-chloro-17-(hydroxyimino)-13-methyl-7,8,9,11,12,13,14,15,16,17-decahydro-6H-cyclopenta[a]phenanthren-15-yl)-N-(3-fluoropyridin-2-yl)propanamide

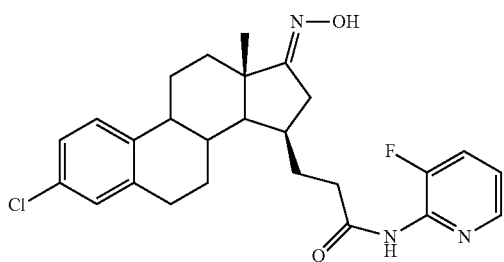 [SMILES: C[C@]12CCC3c4ccc(Cl)cc4CCC3C1[C@H](CCC(=O)Nc1ncccc1F)C/C2=N\O]

Compound 62 was prepared from Compound 61 by the same method as with Compound 2. Reaction time was 2.5 hours at 50° C.

$^1$H NMR (200 MHz, DMSO-d6): 1.03 (s, 3H), 1.12-2.46 (m, 15H), 2.56-2.77 (m, 1H), 2.80-2.95 (m, 2H), 7.10-7.22 (m, 2H), 7.23-7.42 (m, 2H), 7.76 (td, 1H), 8.24 (dd, 1H), 10.19 (s, 1H), 10.29 (s, 1H).

Compound 63

3-((13S,15R)-3-chloro-13-methyl-17-oxo-7,8,9,11,12,13,14,15,16,17-decahydro-6H-cyclopenta[a]phenanthren-15-yl)-N-(5-methyloxazol-2-yl)propanamide

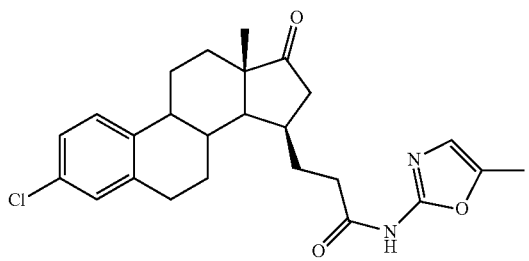 [SMILES: Cc1cnc(NC(=O)CC[C@@H]2CC(=O)[C@@]3(C)CCC4c5ccc(Cl)cc5CCC4C23)o1]

Compound 63 was prepared in 52% yield from acid SM-XVII by the same method as with Compound 3 using 2-amino-5-methyloxazole as amine. Reaction time was 3 hours.

$^1$H NMR (200 MHz, DMSO-d6): 0.97 (s, 3H), 1.15-2.47 (m, 19H), 2.80-2.90 (m, 2H), 6.68 (s, 1H), 7.10-7.23 (m, 2H), 7.24-7.35 (m, 1H), 10.95 (br s, 1H).

Compound 64

3-((13S,15R,E)-3-chloro-17-(hydroxyimino)-13-methyl-7,8,9,11,12,13,14,15,16,17-decahydro-6H-cyclopenta[a]phenanthren-15-yl)-N-(5-methyloxazol-2-yl)propanamide

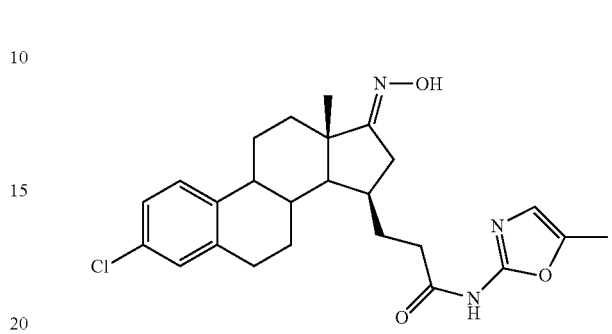

Compound 64 was prepared in 89% yield from Compound 63 by the same method as with Compound 2. Reaction time was 2.5 hours.

$^1$H NMR (200 MHz, DMSO-d6): 1.02 (s, 3H), 1.15-2.47 (m, 18H), 2.55-2.75 (m, 1H), 2.80-2.90 (m, 2H), 6.68 (s, 1H), 7.10-7.23 (m, 2H), 7.24-7.35 (m, 1H), 10.19 (s, 1H), 10.96 (br s, 1H).

Compound 65

3-((13S,15R)-3-chloro-13-methyl-17-oxo-7,8,9,11,12,13,14,15,16,17-decahydro-6H-cyclopenta[a]phenanthren-15-yl)-N-(5-methoxypyridin-2-yl)propanamide

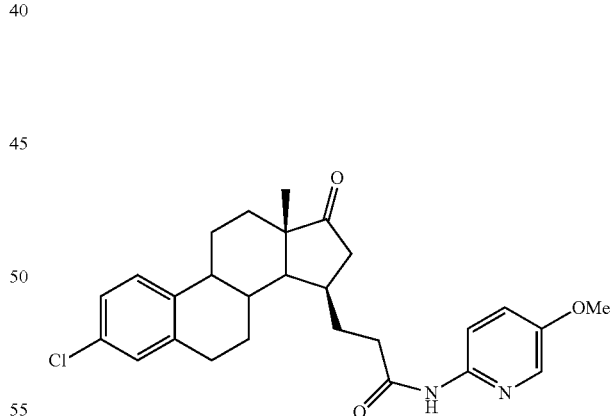

Compound 65 was prepared in 62% yield from acid SM-XVII by the same method as with Compound 3 by stirring at +50° C. for two hours.

$^1$H-NMR (200 MHz, DMSO-d6): 0.97 (s, 3H), 1.35-2.42 (m, 16H), 2.89 (m, 2H), 3.80 (s, 3H), 7.15 (br s, 2H), 7.31-7.44 (m, 2H), 8.02 (m, 2H), 10.37 (br s, 1H).

Compound 66

3-((13S,15R,E)-3-chloro-17-(hydroxyimino)-13-methyl-7,8,9,11,12,13,14,15,16,17-decahydro-6H-cyclopenta[a]phenanthren-15-yl)-N-(5-methoxypyridin-2-yl)propanamide

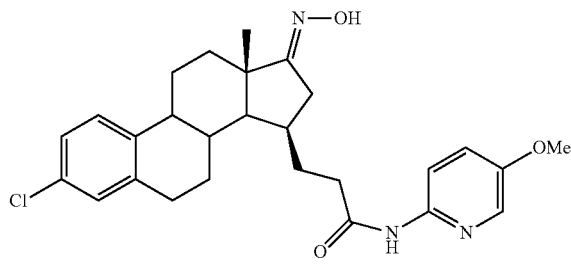 [SMILES: COc1ccc(NC(=O)CC[C@@H]2C/C(=N\O)[C@@]3(C)CCC4c5ccc(Cl)cc5CCC4C23)nc1]

Compound 66 was prepared in 93% yield from Compound 65 by the same method as with Compound 2 by refluxing for 2.5 hours.

$^1$H-NMR (200 MHz, DMSO-d6): 1.03 (s, 3H), 1.38-2.45 (m, 16H), 2.86 (m, 2H), 3.80 (s, 3H), 7.14 (br s, 2H), 7.27-7.44 (2×m, 2H), 8.03 (m, 2H), 10.18 (br s, 1H), 10.38 (br s, 1H). MS m/z (TOF ES+): 482/484 (M+)

Compound 67

3-((13S,15R)-3-chloro-13-methyl-17-oxo-7,8,9,11,12,13,14,15,16,17-decahydro-6H-cyclopenta[a]phenanthren-15-yl)-N-(pyridin-2-yl)propanamide

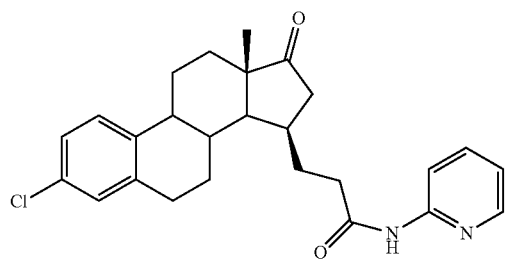 [SMILES: C[C@]12CCC3c4ccc(Cl)cc4CCC3C1[C@H](CCC(=O)Nc1ccccn1)CC2=O]

Compound 67 was prepared in 41% yield from acid SM-XVII by the same method as with Compound 3 by stirring at +50° C. for 5 hours and then overnight at room temperature.

$^1$H-NMR (200 MHz, CDCl$_3$): 1.05 (s, 3H), 1.37-2.60 (m, 16H), 2.92 (m, 2H), 7.03-7.15 (m, 4H), 7.73 (t, 1H), 8.19-8.28 (m, 2H), 8.58 (br s, 1H).

Compound 68

3-((13S,15R,E)-3-chloro-17-(hydroxyimino)-13-methyl-7,8,9,11,12,13,14,15,16,17-decahydro-6H-cyclopenta[a]phenanthren-15-yl)-N-(pyridin-2-yl)propanamide

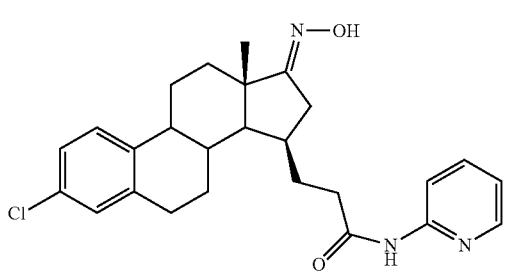 [SMILES: C[C@]12CCC3c4ccc(Cl)cc4CCC3C1[C@H](CCC(=O)Nc1ccccn1)C/C2=N\O]

Compound 68 was prepared in 90% yield from Compound 67 by the same method as with Compound 2 by refluxing for one hour.

$^1$H-NMR (200 MHz, CDCl$_3$): 1.14 (s, 3H), 1.42-2.58 (m, 16H), 2.88-3.03 (m, 3H), 7.07 (br s, 3H), 7.18 (m, 1H), 7.74 (t, 1H), 8.26 (d, 2H), 8.97 (br s, 1H), 9.66 (br s, 1H). MS m/z (TOF ES+): 452/454 (M+)

Compound 69

3-((13S,15R)-3-chloro-13-methyl-17-oxo-7,8,9,11,12,13,14,15,16,17-decahydro-6H-cyclopenta[a]phenanthren-15-yl)-N-(4-methylpyridin-2-yl)propanamide

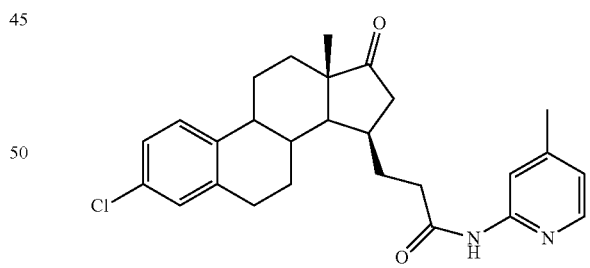

Compound 69 was prepared in 40% yield from acid SM-XVII by the same method as with Compound 43 by stirring at room temperature for 1.5 hours.

$^1$H-NMR (200 MHz, CDCl$_3$): 1.06 (s, 3H), 1.44-2.54 (m, 19H), 2.91 (m, 2H), 6.89 (d, 1H), 7.09-7.22 (m, 3H), 8.06 (br s, 1H), 8.13 (d, 1H), 8.49 (br s, 1H).

Compound 70

3-((13S,15R,E)-3-chloro-17-(hydroxyimino)-13-methyl-7,8,9,11,12,13,14,15,16,17-decahydro-6H-cyclopenta[a]phenanthren-15-yl)-N-(4-methylpyridin-2-yl)propanamide

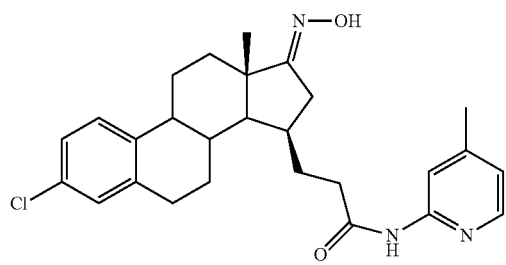 [SMILES: Cc1ccnc(NC(=O)CC[C@@H]2C/C(=N\O)[C@@]3(C)CCC4c5ccc(Cl)cc5CCC4C23)c1]

Compound 70 was prepared in 46% yield from Compound 69. by the same method as with Compound 2 by refluxing for one hour.

$^1$H-NMR (200 MHz, CDCl$_3$): 1.15 (s, 3H), 1.44-2.51 (m, 21H), 2.91 (m, 2H), 6.89 (d, 1H), 7.08-7.22 (m, 3H), 8.08-8.13 (m, 2H), 8.54 (br s, 1H), 8.83 (br s, 1H).

Compound 71

3-((13S,15R)-3-chloro-13-methyl-17-oxo-7,8,9,11,12,13,14,15,16,17-decahydro-6H-cyclopenta[a]phenanthren-15-yl)-N-(5-cyanopyridin-2-yl)propanamide

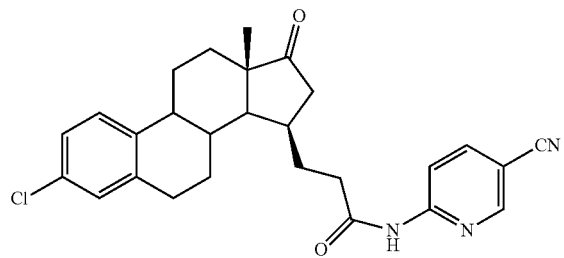 [SMILES: C[C@]12CCC3c4ccc(Cl)cc4CCC3C1[C@H](CCC(=O)Nc1ccc(C#N)cn1)CC2=O]

Compound 71 was prepared in 37% yield from acid SM-XVII by the same method as with Compound 43 by stirring at room temperature for 1.5 hours.

$^1$H-NMR (200 MHz, CDCl$_3$): 1.07 (s, 3H), 1.46-2.42 (m, 16H), 2.93 (m, 2H), 7.10-7.19 (m, 3H), 7.93-8.08 (m, 2H), 8.35 (d, 1H), 8.56 (s, 1H).

Compound 72

3-((13S,15R,E)-3-chloro-17-(hydroxyimino)-13-methyl-7,8,9,11,12,13,14,15,16,17-decahydro-6H-cyclopenta[a]phenanthren-15-yl)-N-(5-cyanopyridin-2-yl)propanamide

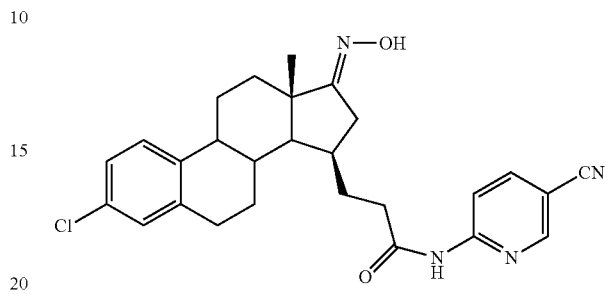

Compound 72 was prepared in 96% yield from Compound 71 by the same method as with Compound 2 by refluxing for two hour.

$^1$H-NMR (200 MHz, CDCl$_3$): 1.14 (s, 3H), 1.42-2.70 (m, 17H), 2.91 (m, 3H), 7.09-7.22 (m, 3H), 7.96 (d, 1H), 8.38 (d, 1H), 8.56 (s, 1H). MS m/z (TOF ES+): 477/479 (M+)

Compound 73

3-((13S,15R)-3-chloro-13-methyl-17-oxo-7,8,9,11,12,13,14,15,16,17-decahydro-6H-cyclopenta[a]phenanthren-15-yl)-N-(pyrazin-2-yl)propanamide

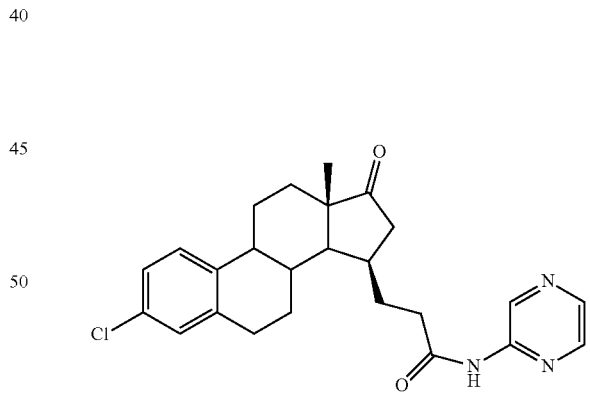

Compound 73 was synthesized in 50% yield from acid SM-XVII by the same method as with Compound 1 in DCM using aminopyrazine as amine. Reaction time was 5 hours.

$^1$H NMR (200 MHz, DMSO-d6): 0.98 (s, 3H), 1.15-2.65 (m, 16H), 2.80-2.90 (m, 2H), 7.10-7.23 (m, 2H), 7.24-7.35 (m, 1H), 8.30-8.45 (m, 2H), 9.35 (s, 1H), 10.81 (br s, 1H).

Compound 74

3-((13S,15R,E)-3-chloro-17-(hydroxyimino)-13-methyl-7,8,9,11,12,13,14,15,16,17-decahydro-6H-cyclopenta[a]phenanthren-15-yl)-N-(pyrazin-2-yl)propanamide

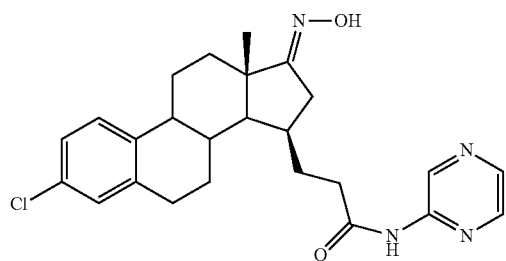 [SMILES: C[C@]12CCC3c4ccc(Cl)cc4CCC3C1[C@H](CCC(=O)Nc1cnccn1)C/C2=N\O]

Compound 74 was prepared in 92% yield from Compound 73 by the same method as with Compound 2 by stirring at 40° C. for 2.5 hours.

$^1$H NMR (200 MHz, DMSO-d6): 1.03 (s, 3H), 1.15-2.79 (m, 16H), 2.80-2.90 (m, 2H), 7.10-7.23 (m, 2H), 7.24-7.35 (m, 1H), 8.30-8.45 (m, 2H), 9.35 (s, 1H), 10.19 (s, 1H), 10.82 (br s, 1H).

Compound 75

3-((13S,15R)-3-chloro-13-methyl-17-oxo-7,8,9,11,12,13,14,15,16,17-decahydro-6H-cyclopenta[a]phenanthren-15-yl)-N-(6-methylpyridazin-3-yl)propanamide

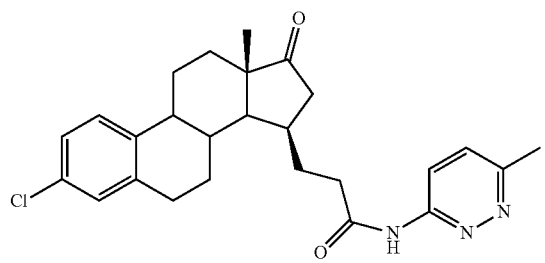 [SMILES: Cc1ccc(NC(=O)CC[C@@H]2CC(=O)[C@@]3(C)CCC4c5ccc(Cl)cc5CCC4C23)nn1]

Compound 75 was synthesized from acid SM-XVII by the same method as with Compound 9 in THF. Reaction time was 5 hours.

$^1$H-NMR (200 MHz, DMSO-d6): 0.98 (s, 3H), 1.22-2.47 (m, 16H), 2.55 (s, 3H), 2.80-3.00 (m, 2H), 7.08-7.22 (m, 2H), 7.22-7.37 (m, 1H), 7.54 (d, 1H), 8.22 (d, 1H), 11.04 (br s, 1H).

Compound 76

3-((13S,15R,E)-3-chloro-17-(hydroxyimino)-13-methyl-7,8,9,11,12,13,14,15,16,17-decahydro-6H-cyclopenta[a]phenanthren-15-yl)-N-(6-methyl-pyridazin-3-yl)propanamide

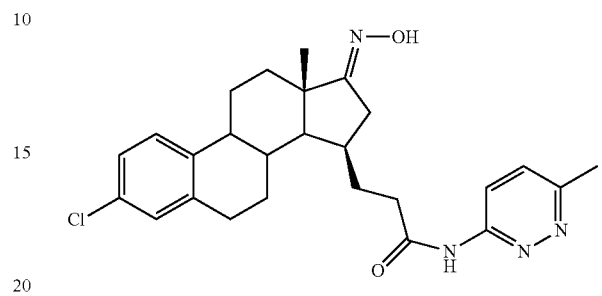

Compound 76 was prepared from Compound 75 by the same method as with Compound 2. Reaction time was 4.5 hours at 40° C. and overnight at rt.

$^1$H-NMR (200 MHz, DMSO-d6): 1.03 (s, 3H), 1.12-2.47 (m, 15H), 2.55 (s, 3H), 2.59-2.79 (m, 1H), 2.78-2.96 (m, 2H), 7.05-7.22 (m, 2H), 7.23-7.34 (m, 1H), 7.54 (d, 1H), 8.22 (d, 1H), 10.19 (s, 1H), 11.05 (s, 1H).

Compound 77

3-((13S,15R)-3-chloro-13-methyl-17-oxo-7,8,9,11,12,13,14,15,16,17-decahydro-6H-cyclopenta[a]phenanthren-15-yl)-N-(5-morpholinopyridin-2-yl)propanamide

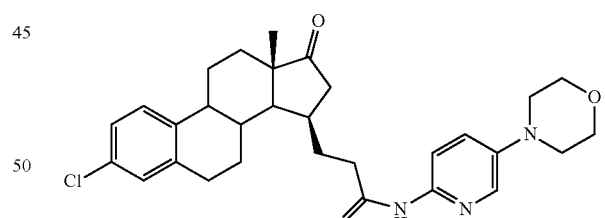

Compound 77 was synthesized in 69& yield from acid SM-XVII by the same method as with Compound 1 in DCM using triethylamine as base and 5-morpholinopyridin-2-amine as amine. Reaction time was 4.5 hours.

$^1$H-NMR (200 MHz, DMSO-d6): 0.97 (s, 3H), 1.15-2.47 (m, 16H), 2.80-3.00 (m, 2H), 3.01-3.15 (m, 4H), 3.70-3.80 (m, 4H), 7.08-7.22 (m, 2H), 7.23-7.35 (m, 1H), 7.37-7.45 (m, 1H), 7.90-8.10 (m, 2H), 10.28 (s, 1H).

117

Compound 78

3-((13S,15R,E)-3-chloro-17-(hydroxyimino)-13-methyl-7,8,9,11,12,13,14,15,16,17-decahydro-6H-cyclopenta[a]phenanthren-15-yl)-N-(5-morpholinopyridin-2-yl)propanamide

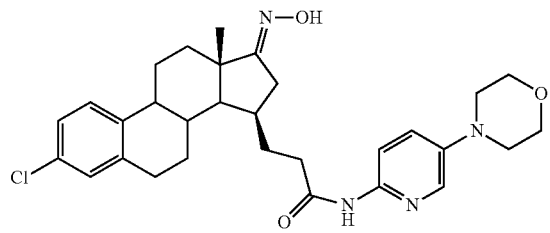 [SMILES: C[C@]12CCC3c4ccc(Cl)cc4CCC3C1[C@H](CCC(=O)Nc1ccc(N3CCOCC3)cn1)C/C2=N\O]

Compound 78 was prepared in 66% yield from Compound 77 by the same method as with Compound 2 Reaction time was 7 hours at 40-50° C. and overnight at rt.

¹H-NMR (200 MHz, DMSO-d6): 1.02 (s, 3H), 1.15-2.47 (m, 15H), 2.50-2.75 (m, 1H), 2.80-2.95 (m, 2H), 3.01-3.15 (m, 4H), 3.70-3.80 (m, 4H), 7.08-7.22 (m, 2H), 7.23-7.35 (m, 1H), 7.37-7.45 (m, 1H), 7.90-8.10 (m, 2H), 10.18 (s, 1H), 10.29 (s, 1H).

Compound 79

N-methyl-3-((13S,15R)-13-methyl-17-oxo-7,8,9,11,12,13,14,15,16,17-decahydro-6H-cyclopenta[a]phenanthren-15-yl)-N-(tetrahydro-2H-pyran-4-yl)propanamide

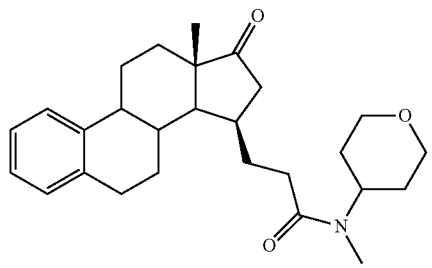 [SMILES: CN(C(=O)CC[C@@H]1CC(=O)[C@@]2(C)CCC3c4ccccc4CCC3C12)C1CCOCC1]

Compound 79 was prepared in 37% yield from acid SM-XXVI by the same method as with Compound 9 using methyl-(tetrahydro-pyran-4-yl)-amine hydrochloride as amine. Reaction time was 4 hours.

¹H NMR (200 MHz, DMSO-d6): 0.97 (s, 3H), 1.14-2.48 (m, 20H), 2.60-2.90 (m, 5H), 3.26-3.51 (m, 2H), 3.79-4.04 (m, 2H), 4.40-4.60 (m, 1H), 7.00-7.19 (m, 3H), 7.27 (br d, 1H). MS m/z (TOF ES⁺): 424 (M+1)

118

Compound 80

3-((13S,15R,E)-17-(hydroxyimino)-13-methyl-7,8,9,11,12,13,14,15,16,17-decahydro-6H-cyclopenta[a]phenanthren-15-yl)-N-methyl-N-(tetrahydro-2H-pyran-4-yl)propanamide

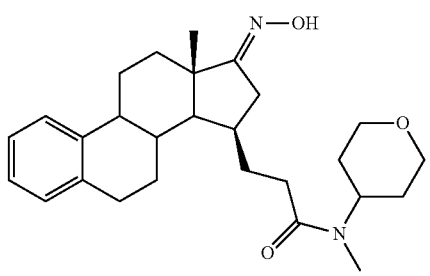 [SMILES: CN(C(=O)CC[C@@H]1C/C(=N\O)[C@@]2(C)CCC3c4ccccc4CCC3C12)C1CCOCC1]

Compound 80 was prepared in 88% yield from Compound 79 by the same method as with Compound 2 using 6 eq of pyridine and refluxing for two hours.

¹H NMR (200 MHz, DMSO-d6): 1.02 (s, 3H), 1.10-2.45 (m, 19H), 2.50-2.90 (m, 6H), 3.21-3.57 (m, 2H), 3.76-4.00 (m, 2H), 4.40-4.60 (m, 1H), 7.00-7.19 (m, 3H), 7.27 (br d, 1H), 10.16 (m, 1H).

Compound 81

3-((13S,15R)-13-methyl-17-oxo-7,8,9,11,12,13,14,15,16,17-decahydro-6H-cyclopenta[a]phenanthren-15-yl)-N-(pyridazin-3-yl)propanamide

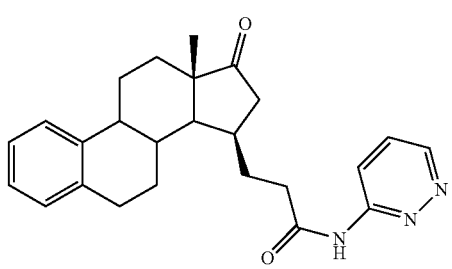 [SMILES: C[C@]12CCC3c4ccccc4CCC3C1[C@H](CCC(=O)Nc1cccnn1)CC2=O]

Compound 81 was prepared in 36% yield from acid SM-XXVI by the same method as with Compound 43 using 3-aminopyridazine as an amine.

¹H-NMR (200 MHz, CDCl₃): 1.06 (s, 3H), 1.46-3.00 (m, 17H), 7.10-7.18 (m, 3H), 7.23-7.31 (m, 2H), 7.51 (dd, 1H), 8.62 (dd, 1H), 8.94 (dd, 1H), 10.73 (br s, 1H).

Compound 82

3-((13S,15R,E)-17-(hydroxyimino)-13-methyl-7,8,9,11,12,13,14,15,16,17-decahydro-6H-cyclopenta[a]phenanthren-15-yl)-N-(pyridazin-3-yl)propanamide

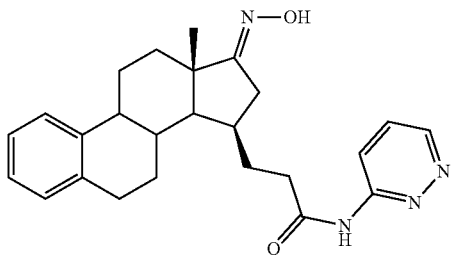 [SMILES: C[C@]12CCC3c4ccccc4CCC3C1[C@H](CCC(=O)Nc1cccnn1)C/C2=N\O]

Compound 82 was prepared in yield 70% from Compound 81 by the same method as with Compound 2
¹H-NMR (200 MHz, CDCl₃): 1.11 (s, 3H), 1.59-2.66 (m, 16H), 2.87-3.00 (m, 2H), 7.11 (m, 3H), 7.24-7.35 (br s, 1H), 7.53 (dd, 1H), 8.25 (br s, 1H), 8.62 (d, 1H), 8.95 (d, 1H), 10.77 (br s, 1H).

Compound 83

N-(5-methoxypyridin-2-yl)-3-((13S,15R)-13-methyl-17-oxo-7,8,9,11,12,13,14,15,16,17-decahydro-6H-cyclopenta[a]phenanthren-15-yl)propanamide

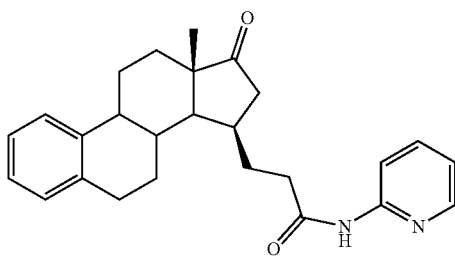

Compound 83 was synthesized in 40% yield from acid SM-XXVI by the same method as with Compound 3 refluxing for two hours.

¹H NMR (200 MHz, CDCl₃): 1.07 (s, 3H), 1.40-2.57 (m, 17H), 2.96 (m, 2H), 3.85 (s, 3H), 7.13-7.18 (m, 3H), 7.24-7.30 (m, 2H), 7.96 (d, 1H), 8.15 (d, 1H).

Compound 84

3-((13S,15R,E)-17-(hydroxyimino)-13-methyl-7,8,9,11,12,13,14,15,16,17-decahydro-6H-cyclopenta[a]phenanthren-15-yl)-N-(5-methoxypyridin-2-yl)propanamide

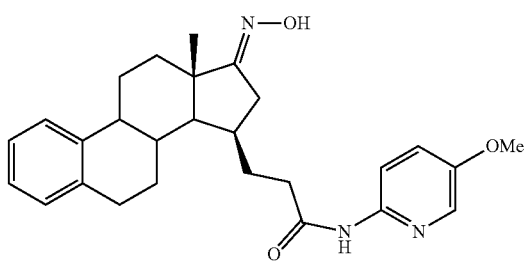 [SMILES: COc1ccc(NC(=O)CC[C@@H]2C/C(=N\O)[C@@]3(C)CCC4c5ccccc5CCC4C23)nc1]

Compound 84 was prepared in 82% yield from Compound 83 by the same method as with Compound 2 by refluxing for two hours.

¹H-NMR (200 MHz, CDCl₃): 1.15 (s, 3H), 1.42-2.52 (m, 16H), 2.92 (m, 3H), 3.84 (s, 3H), 7.12-7.16 (m, 3H), 7.30 (m, 1H), 7.96 (d, 1H), 8.15 (d, 1H), 8.44 (br s, 1H), 8.77 (br s, 1H). MS m/z (TOF ES+): 448 (M+1)

Compound 85

3-((13S,15R)-13-methyl-17-oxo-7,8,9,11,12,13,14,15,16,17-decahydro-6H-cyclopenta[a]phenanthren-15-yl)-N-(5-(4-methylpiperazin-1-yl)pyridin-2-yl)propanamide

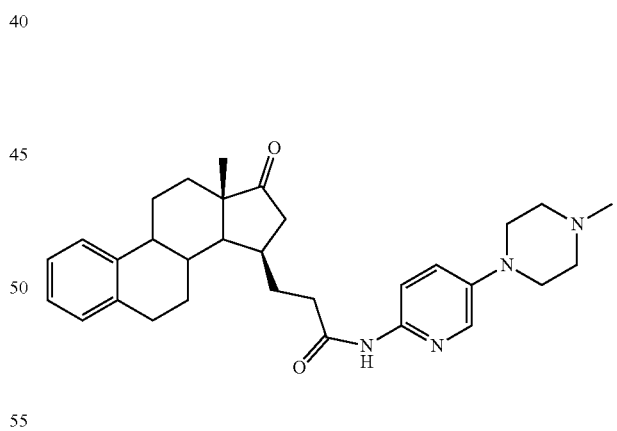

Compound 85 was synthesized in 29% yield from acid SM-XXVI by the same method as with Compound 1 in DCM using trietylamine as base. Reaction time was 3.5 hours.

¹H NMR (200 MHz, DMSO-d6): 0.98 (s, 3H), 1.10-2.50 (m, 23H), 2.80-2.95 (m, 2H), 3.01-3.19 (m, 4H), 7.03-7.19 (m, 3H), 7.27 (br d, 1H), 7.35-7.43 (m, 1H), 7.90-8.02 (m, 2H), 10.26 (s, 1H).

Compound 86

3-((13S,15R,E)-17-(hydroxyimino)-13-methyl-7,8,9,11,12,13,14,15,16,17-decahydro-6H-cyclopenta[a]phenanthren-15-yl)-N-(5-(4-methylpiperazin-1-yl)pyridin-2-yl)propanamide

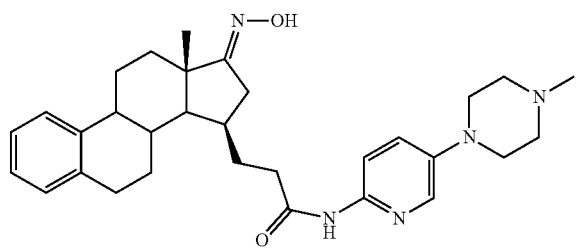 [SMILES: CN1CCN(c2ccc(NC(=O)CC[C@@H]3C/C(=N\O)[C@@]4(C)CCC5c6ccccc6CCC5C34)nc2)CC1]

Compound 86 was prepared in 11% yield from Compound 85 by the same method as with Compound 2 Reaction was stirred 2 hours at 50° C.

$^1$H NMR (200 MHz, CDCl$_3$): 1.13 (s, 3H), 1.25-2.55 (m, 19H), 2.56-2.65 (m, 4H), 2.80-3.07 (m, 2H), 3.12-3.30 (m, 4H), 7.03-7.22 (m, 3H), 7.25-7.35 (m, 2H), 7.91 (d, 1H), 8.11 (d, 1H). MS m/z (TOF ES+): 516 (M+1)

Compound 87

3-((13S,15R)-13-methyl-17-oxo-7,8,9,11,12,13,14,15,16,17-decahydro-6H-cyclopenta[a]phenanthren-15-yl)-N-(4-methylpyridin-2-yl)propanamide

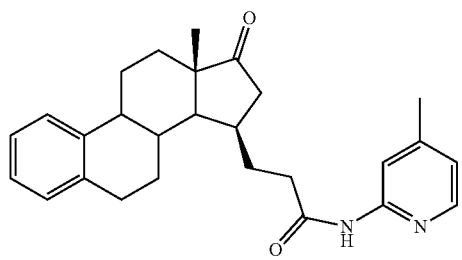

Compound 87 was synthesized in 27% yield from acid SM-XXVI by the same method as with Compound 3 in THF using 200 mol-% of EDCl and HOBT. Reaction time was 6 hours.

$^1$H NMR (200 MHz, DMSO-d6): 0.98 (s, 3H), 1.12-2.48 (m, 19H), 2.80-2.95 (m, 2H), 6.92 (d, 1H), 7.02-7.19 (m, 3H), 7.27 (br d, 1H), 7.95 (s, 1H), 8.15 (d, 1H), 10.41 (s, 1H).

Compound 88

3-((13S,15R,E)-17-(hydroxyimino)-13-methyl-7,8,9,11,12,13,14,15,16,17-decahydro-6H-cyclopenta[a]phenanthren-15-yl)-N-(4-methylpyridin-2-yl)propanamide

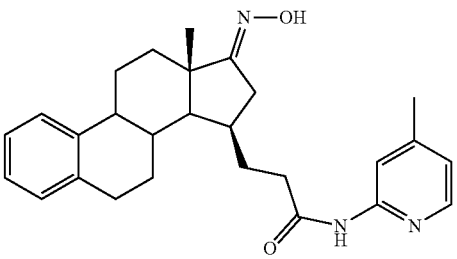 [SMILES: Cc1ccnc(NC(=O)CC[C@@H]2C/C(=N\O)[C@@]3(C)CCC4c5ccccc5CCC4C23)c1]

Compound 88 was prepared in 48% yield from Compound 87 by the same method as with Compound 2. Reaction time was 1.5 hours at 50° C.

$^1$H NMR (200 MHz, DMSO-d6): 1.04 (s, 3H), 1.12-2.47 (m, 18H), 2.58-2.76 (m, 1H), 2.80-2.95 (m, 2H), 6.92 (d, 1H), 7.02-7.19 (m, 3H), 7.27 (br d, 1H), 7.96 (s, 1H), 8.15 (d, 1H), 10.18 (s, 1H), 10.43 (s, 1H). MS m/z (TOF ES+): 432 (M+1)

Compound 89

3-((13S,15R)-13-methyl-17-oxo-7,8,9,11,12,13,14,15,16,17-decahydro-6H-cyclopenta[a]phenanthren-15-yl)-N-(5-morpholinopyridin-2-yl)propanamide

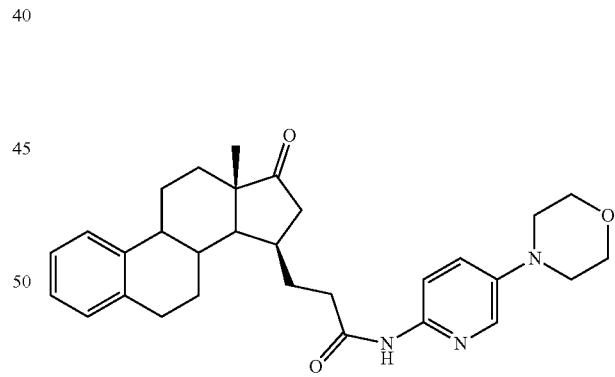

Compound 89 was synthesized in 29% yield from acid SM-XXVI by the same method as with Compound 1 in DCM using trietylamine as base. Reaction time was five hours.

$^1$H NMR (200 MHz, DMSO-d6): 0.98 (s, 3H), 1.10-2.46 (m, 16H), 2.80-2.95 (m, 2H), 3.01-3.19 (m, 4H), 3.63-3.84 (m, 4H), 7.03-7.19 (m, 3H), 7.27 (br d, 1H), 7.40 (dd, 1H), 7.88-8.07 (m, 2H), 10.28 (s, 1H).

Compound 90

3-((13S,15R,E)-17-(hydroxyimino)-13-methyl-7,8,9,11,12,13,14,15,16,17-decahydro-6H-cyclopenta[a]phenanthren-15-yl)-N-(5-morpholinopyridin-2-yl)propanamide

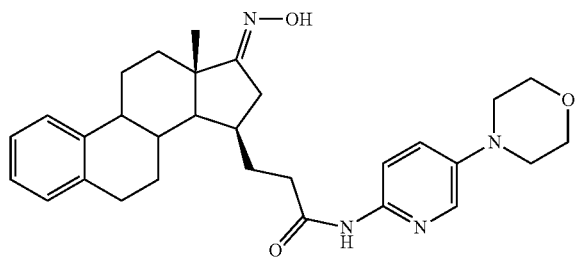 [SMILES: C[C@]12CCC3c4ccccc4CCC3C1[C@H](CCC(=O)Nc1ccc(N3CCOCC3)cn1)C/C2=N\O]

Compound 90 was prepared in 55% yield from Compound 89 by the same method as with Compound 2. Reaction time was 5 hours at +50° C.

$^1$H NMR (200 MHz, DMSO-d6): 1.03 (s, 3H), 1.23-2.46 (m, 15H), 2.56-2.75 (m, 1H), 2.80-2.95 (m, 2H), 3.02-3.14 (m, 4H), 3.65-3.84 (m, 4H), 6.99-7.18 (m, 3H), 7.26 (br d, 1H), 7.40 (dd, 1H), 7.89-8.07 (m, 2H), 10.17 (s, 1H), 10.30 (s, 1H).

Compound 91

N,N-dimethyl-6-(3-((13S,15R)-13-methyl-17-oxo-7,8,9,11,12,13,14,15,16,17-decahydro-6H-cyclopenta[a]phenanthren-15-yl)propanamido)nicotinamide

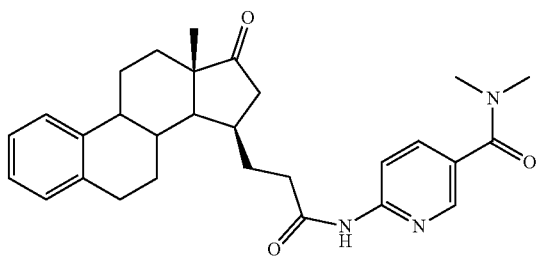

Compound 91 was synthesized in 12% yield from acid SM-XXVI by the same method as with Compound 1 in DCM using triethylamine as base.

Reaction time was 6 hours.

$^1$H NMR (200 MHz, CDCl$_3$) 1.08 (s, 3H) 1.13-2.67 (m, 16H) 2.91-3.01 (m, 2H) 3.08 (br s, 6H) 7.06-7.22 (m, 3H) 7.23-7.39 (m, 1H) 7.81 (dd, 1H), 8.15 (br s, 1H), 8.25 (d, 1H) 8.39 (d, 1H)

Compound 92

6-(3-((13S,15R,E)-17-(hydroxyimino)-13-methyl-7,8,9,11,12,13,14,15,16,17-decahydro-6H-cyclopenta[a]phenanthren-15-yl)propanamido)-N,N-dimethyl-nicotinamide

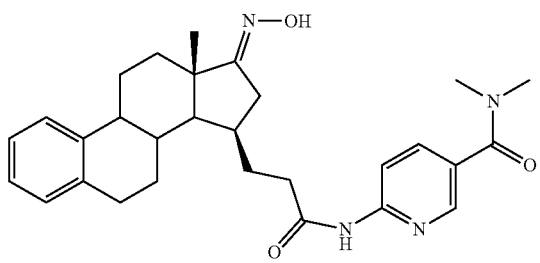 [SMILES: CN(C)C(=O)c1ccc(NC(=O)CC[C@@H]2C/C(=N\O)[C@@]3(C)CCC4c5ccccc5CCC4C23)nc1]

Compound 92 was prepared in quantitative yield from Compound 91 by the same method as with Compound 2. Reaction time was 1.5 hour at 50° C.

$^1$H NMR (200 MHz, CDCl$_3$) 1.15 (s, 3H) 1.21-2.73 (m, 15H) 2.82-3.03 (m, 3H) 3.09 (br s, 6H) 7.05-7.23 (m, 3H) 7.25-7.37 (m, 1H) 7.82 (dd, 1H) 8.28 (d, 1H) 8.40 (d, 1H), 8.61 (br s, 1H)

Compound 93

3-((13S,15R)-13-methyl-17-oxo-7,8,9,11,12,13,14,15,16,17-decahydro-6H-cyclopenta[a]phenanthren-15-yl)-N-(2-oxo-1,2,5,6,7,8-hexahydroquinolin-3-yl)propanamide

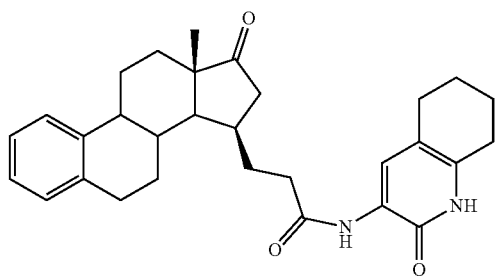 [SMILES: C[C@]12CCC3c4ccccc4CCC3C1[C@H](CCC(=O)Nc1cc3c([nH]c1=O)CCCC3)CC2=O]

Compound 93 was synthesized in 22% yield from acid SM-XXVI by the same method as with Compound 3. Reaction time was 2.5 hours.

$^1$H NMR (200 MHz, DMSO-d6): 0.97 (s, 3H), 1.10-2.48 (m, 24H), 2.76-2.95 (m, 2H), 7.02-7.19 (m, 3H), 7.26 (m, 1H), 8.01 (s, 1H), 9.15 (s, 1H), 11.68 (br s, 1H).

Compound 94

3-((13S,15R,E)-17-(hydroxyimino)-13-methyl-7,8,9,11,12,13,14,15,16,17-decahydro-6H-cyclopenta[a]phenanthren-15-yl)-N-(2-oxo-1,2,5,6,7,8-hexahydroquinolin-3-yl)propanamide

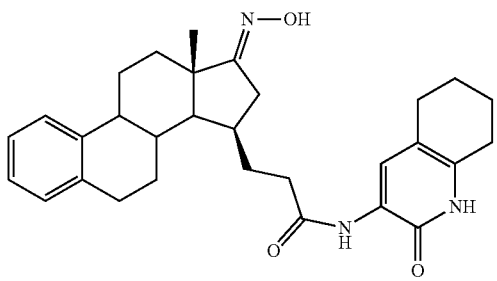 [SMILES: C[C@]12CCC3c4ccccc4CCC3C1[C@H](CCC(=O)Nc1cc3c([nH]c1=O)CCCC3)C/C2=N\O]

Compound 94 was prepared in 74% yield form Compound 93 by the same method as with Compound 2. Reaction time was 2 hours at 50° C.

¹H NMR (200 MHz, CDCl₃) 1.13 (s, 3H), 1.35-2.64 (m, 23H), 2.78-3.08 (m, 3H), 6.90 (br s, 1H), 7.06-7.21 (m, 3H), 7.28-7.41 (m, 1H), 8.19 (br s, 1H) 8.23 (s, 1H), 9.61 (br s, 1H).

Compound 95

N-(5-isopropylpyridin-2-yl)-3-((13S,15R)-13-methyl-17-oxo-7,8,9,11,12,13,14,15,16,17-decahydro-6H-cyclopenta[a]phenanthren-15-yl)propanamide

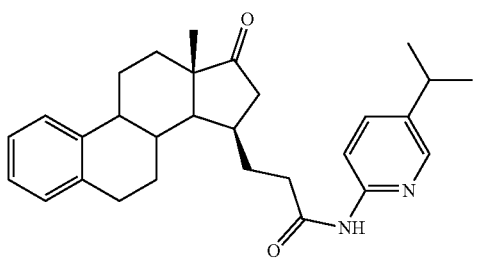 [SMILES: CC(C)c1ccc(NC(=O)CC[C@@H]2CC(=O)[C@@]3(C)CCC4c5ccccc5CCC4C23)nc1]

Compound 95 was synthesized in 37% yield from acid SM-XXVI by the same method as with Compound 9 stirring at room temperature overnight.

¹H-NMR (200 MHz, CDCl₃): 1.07 (s, 3H), 1.24 & 1.28 (2×s, 6H), 1.45-2.58 (m, 16H), 2.95 (m, 3H), 7.13-7.18 (m, 3H), 7.29-7.31 (m, 1H), 7.58 (dd, 1H), 8.07 (d, 1H), 8.14 (br s, 2H).

Compound 96

3-((13S,15R,E)-17-(hydroxyimino)-13-methyl-7,8,9,11,12,13,14,15,16,17-decahydro-6H-cyclopenta[a]phenanthren-15-yl)-N-(5-isopropylpyridin-2-yl)propanamide

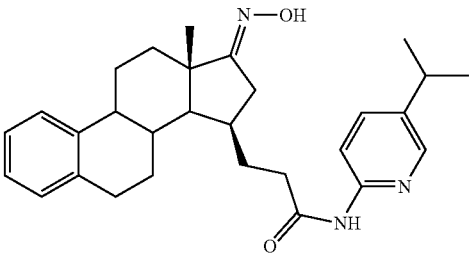 [SMILES: CC(C)c1ccc(NC(=O)CC[C@@H]2C/C(=N\O)[C@@]3(C)CCC4c5ccccc5CCC4C23)nc1]

Compound 96 was prepared in 80% yield from Compound 95 by the same method as with Compound 2 by refluxing for two hours.

¹H-NMR (200 MHz, CDCl₃): 1.16 (s, 3H), 1.24 & 1.27 (2×s, 6H), 1.48-2.53 (m, 16H), 2.94 (m, 3H), 7.11 (m, 3H), 7.26 (m, 1H), 7.60 (d, 1H), 8.16 (m, 2H), 8.89 (br s, 1H). 9.69 (br s, 1H). MS m/z (TOF ES+): 460 (M+1)

Compound 97

N-(5-fluoropyridin-2-yl)-3-((13S,15R)-13-methyl-17-oxo-7,8,9,11,12,13,14,15,16,17-decahydro-6H-cyclopenta[a]phenanthren-15-yl)propanamide

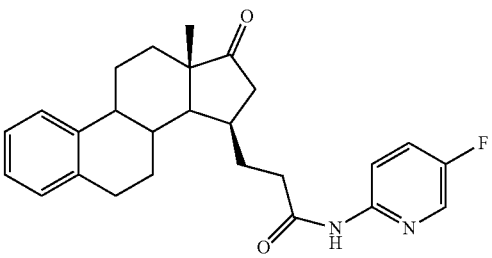 [SMILES: C[C@]12CCC3c4ccccc4CCC3C1[C@H](CCC(=O)Nc1ccc(F)cn1)CC2=O]

Compound 97 was synthesized 14% yield from acid SM-XXVI by the same method as with Compound 1 in DCM using 2-amino-5-fluoropyridine as amine. Reaction time was 4.5 hours.

¹H NMR (200 MHz, CDCl₃): 1.07 (s, 3H), 1.20-2.77 (m, 16H), 2.80-3.15 (m, 2H), 7.06-7.23 (m, 3H), 7.25-7.37 (m, 1H), 7.38-7.52 (m, 1H), 7.90 (br s, 1H), 8.13 (d, 1H), 8.23 (dd, 1H).

Compound 98

N-(5-fluoropyridin-2-yl)-3-((13S,15R,E)-17-(hydroxyimino)-13-methyl-7,8,9,11,12,13,14,15,16,17-decahydro-6H-cyclopenta[a]phenanthren-15-yl)propanamide

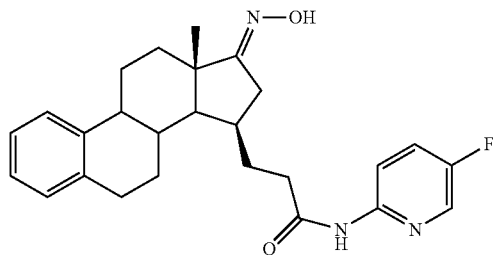 [SMILES: C[C@]12CCC3c4ccccc4CCC3C1[C@H](CCC(=O)Nc1ccc(F)cn1)C/C2=N\O]

Compound 98 was prepared in 75% yield from Compound 97 by the same method as with Compound 2 by stirring at 50° C. for 3 hours.

¹H-NMR (200 MHz, DMSO-d6): 1.03 (s, 3H), 1.14-2.75 (m, 16H), 2.80-3.00 (m, 2H), 6.96-7.20 (m, 3H), 7.21-7.30 (m, 1H), 7.72 (td, 1H), 8.15 (dd, 1H), 8.31 (d, 1H), 10.18 (s, 1H), 10.63 (s, 1H).

Compound 99

N-(5-cyanopyridin-2-yl)-3-((13S,15R)-13-methyl-17-oxo-7,8,9,11,12,13,14,15,16,17-decahydro-6H-cyclopenta[a]phenanthren-15-yl)propanamide

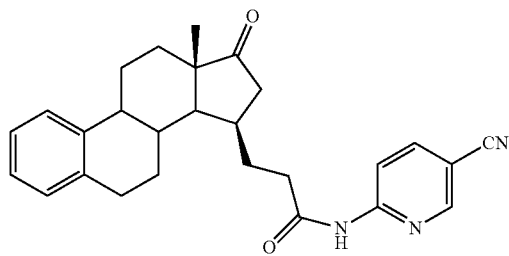 [SMILES: C[C@]12CCC3c4ccccc4CCC3C1[C@H](CCC(=O)Nc1ccc(C#N)cn1)CC2=O]

Compound 99 was synthesized in 39% yield from acid SM-XXVI by the same method as with Compound 1 in DCM using 2-amino-5-cyanopyridine as amine. Reaction time was 5 hours.

¹H NMR (200 MHz, CDCl₃): 1.08 (s, 3H), 1.20-2.70 (m, 16H), 2.80-3.15 (m, 2H), 7.06-7.23 (m, 3H), 7.25-7.37 (m, 1H), 7.95 (dd, 1H), 8.07 (br s, 1H), 8.36 (d, 1H), 8.56 (d, 1H).

Compound 100

N-(5-cyanopyridin-2-yl)-3-((13S,15R,E)-17-(hydroxyimino)-13-methyl-7,8,9,11,12,13,14,15,16,17-decahydro-6H-cyclopenta[a]phenanthren-15-yl)propanamide

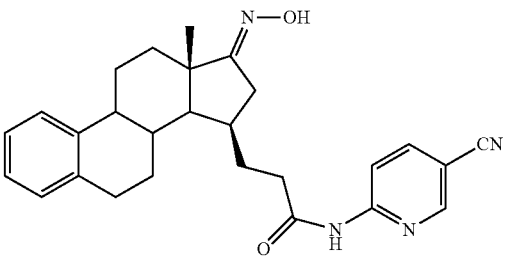 [SMILES: C[C@]12CCC3c4ccccc4CCC3C1[C@H](CCC(=O)Nc1ccc(C#N)cn1)C/C2=N\O]

Compound 100 was prepared in 33% yield from Compound 99 by the same method as with Compound 2 by stirring at 50° C. for 3 hours.

¹H NMR (200 MHz, CDCl₃): 1.14 (s, 3H), 1.35-2.70 (m, 15H), 2.80-3.15 (m, 3H), 7.06-7.23 (m, 3H), 7.25-7.37 (m, 1H), 7.85 (s, 1H), 7.95 (dd, 1H), 8.28 (br s, 1H), 8.37 (d, 1H), 8.56 (d, 1H).

Compound 101

N-(3-hydroxypyridin-2-yl)-3-((13S,15R)-13-methyl-17-oxo-7,8,9,11,12,13,14,15,16,17-decahydro-6H-cyclopenta[a]phenanthren-15-yl)propanamide

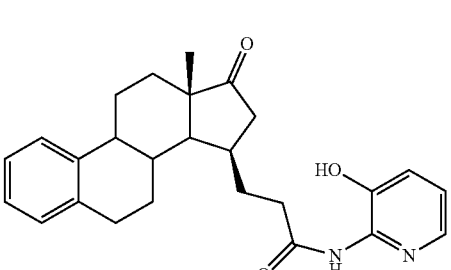

Compound 101 was prepared in 6% yield from acid SM-XXVI by the same method as with Compound 9 using 2-amino-3-hydroxypyridine as amine. Reaction time was 5 hours.

¹H NMR (200 MHz, CDCl₃+MeOH-d₄): 1.08 (s, 3H), 1.20-2.72 (m, 16H), 2.80-3.15 (m, 2H), 7.06-7.23 (m, 4H), 7.25-7.38 (m, 2H), 7.84 (dd, 1H).

Compound 102

3-((13S,15R,E)-17-(hydroxyimino)-13-methyl-7,8,9,11,12,13,14,15,16,17-decahydro-6H-cyclopenta[a]phenanthren-15-yl)-N-(3-hydroxypyridin-2-yl)propanamide

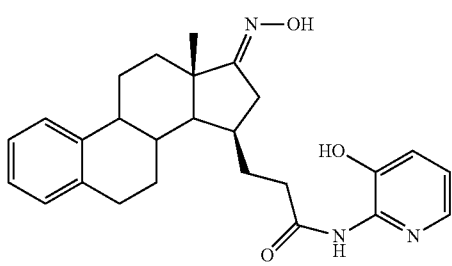 [SMILES: C[C@]12CCC3c4ccccc4CCC3C1[C@H](CCC(=O)Nc1ncccc1O)C/C2=N\O]

Compound 102 was prepared in 34% yield from Compound 101 by the same method as with Compound 2 by stirring at 50° C. for 3 hours.

$^1$H NMR (200 MHz, CDCl$_3$): 1.13 (s, 3H), 1.20-2.72 (m, 15H), 2.80-3.15 (m, 3H), 7.06-7.23 (m, 4H), 7.25-7.36 (m, 1H), 7.39 (dd, 1H), 7.88 (dd, 1H), 9.29 (br s, 1H), 10.31 (br s, 1H).

Compound 103

3-((13S,15R)-13-methyl-17-oxo-7,8,9,11,12,13,14,15,16,17-decahydro-6H-cyclopenta[a]phenanthren-15-yl)-N-(pyridin-2-yl)propanamide

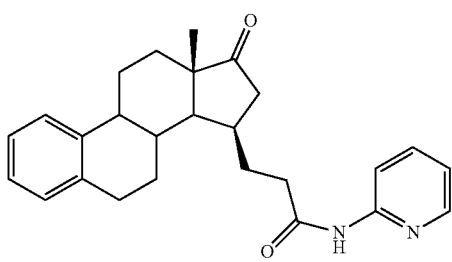 [SMILES: C[C@]12CCC3c4ccccc4CCC3C1[C@H](CCC(=O)Nc1ccccn1)CC2=O]

Compound 103 was prepared in 16% yield from acid SM-XXVI by the same method as with Compound 3 using 2-aminopyridine as an amine. Reaction time was 6.5 hours.

$^1$H-NMR (200 MHz, DMSO-d6): 0.99 (s, 3H), 1.14-2.45 (m, 16H), 2.80-3.00 (m, 2H), 7.00-7.15 (m, 4H), 7.21-7.30 (m, 1H), 7.70-7.82 (m, 1H), 8.10 (d, 1H), 8.28-8.33 (m, 1H), 10.50 (s, 1H).

Compound 104

3-((13S,15R,E)-17-(hydroxyimino)-13-methyl-7,8,9,11,12,13,14,15,16,17-decahydro-6H-cyclopenta[a]phenanthren-15-yl)-N-(pyridin-2-yl)propanamide

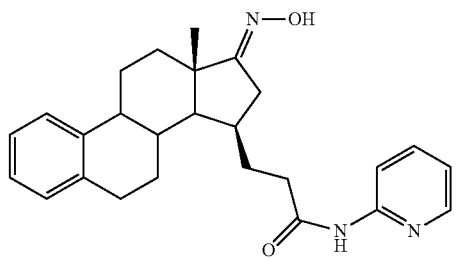 [SMILES: C[C@]12CCC3c4ccccc4CCC3C1[C@H](CCC(=O)Nc1ccccn1)C/C2=N\O]

Compound 104 was prepared in 58% yield from Compound 103 by the same method as with Compound 2 by stirring at 50° C. for 1 hour.

$^1$H NMR (200 MHz, CDCl$_3$+MeOH-d$_4$): 1.15 (s, 3H), 1.20-2.70 (m, 15H), 2.80-3.10 (m, 3H), 7.00-7.17 (m, 4H), 7.21-7.35 (m, 1H), 7.68-7.82 (m, 1H), 8.20-8.33 (m, 2H), 8.72 (br s, 1H), 9.16 (br s, 1H).

Compound 105

N-(4-methoxypyridin-2-yl)-3-((13S,15R)-13-methyl-17-oxo-7,8,9,11,12,13,14,15,16,17-decahydro-6H-cyclopenta[a]phenanthren-15-yl)propanamide

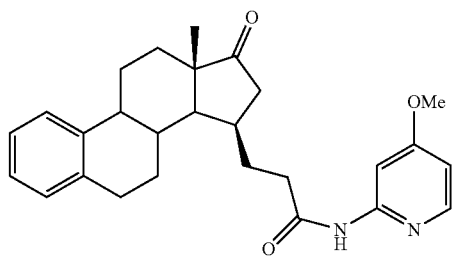 [SMILES: COc1ccnc(NC(=O)CC[C@@H]2CC(=O)[C@@]3(C)CCC4c5ccccc5CCC4C23)c1]

Compound 105 was prepared in 17% yield from acid SM-XXVI by the same method as with Compound 9 using 2-amino-4-methoxypyridine as an amine. Reaction was stirred overnight.

$^1$H NMR (200 MHz, CDCl$_3$): 1.07 (s, 3H), 1.20-2.60 (m, 16H), 2.80-3.15 (m, 2H), 3.88 (s, 3H), 6.60 (dd, 1H), 7.06-7.23 (m, 3H), 7.25-7.37 (m, 1H), 7.83 (d, 1H), 8.05 (d, 1H), 8.09 (br s, 1H).

Compound 106

3-((13S,15R,E)-17-(hydroxyimino)-13-methyl-7,8,9,11,12,13,14,15,16,17-decahydro-6H-cyclopenta[a]phenanthren-15-yl)-N-(4-methoxypyridin-2-yl)propanamide

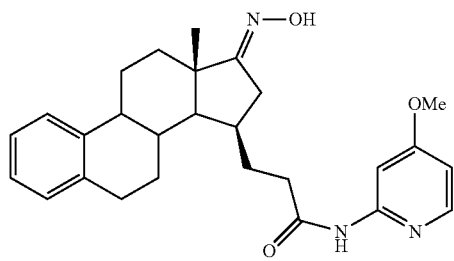 [SMILES: COc1ccnc(NC(=O)CC[C@@H]2C/C(=N\O)[C@@]3(C)CCC4c5ccccc5CCC4C23)c1]

Compound 106 was prepared in 90% yield from Compound 105 by the modified method as with Compound 2 by using methanol as a co-solvent and stirring at rt for 3 hours.

$^1$H NMR (200 MHz, CDCl$_3$): 1.15 (s, 3H), 1.20-2.65 (m, 15H), 2.80-3.15 (m, 3H), 3.88 (s, 3H), 6.60 (dd, 1H), 7.06-7.23 (m, 3H), 7.25-7.37 (m, 1H), 7.86 (d, 1H), 8.05 (d, 1H), 8.60 (br s, 1H), 8.78 (br s, 1H).

Compound 107

3-((13S,15R)-13-methyl-17-oxo-7,8,9,11,12,13,14,15,16,17-decahydro-6H-cyclopenta[a]phenanthren-15-yl)-N-(5-methyloxazol-2-yl)propanamide

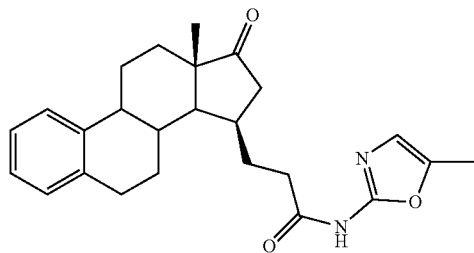 [SMILES: Cc1cnc(NC(=O)CC[C@@H]2CC(=O)[C@@]3(C)CCC4c5ccccc5CCC4C23)o1]

Compound 107 was prepared in 26% yield from acid SM-XXVI by the same method as with Compound 3 using 2-amino-5-methyloxazole as an amine. Reaction time was 2.5 hours.

$^1$H-NMR (200 MHz, DMSO-d6): 0.98 (s, 3H), 1.14-2.45 (m, 19H), 2.80-2.98 (m, 2H), 6.69 (s, 1H), 7.05-7.20 (m, 3H), 7.20-7.30 (m, 1H), 10.96 (br s, 1H).

Compound 108

3-((13S,15R,E)-17-(hydroxyimino)-13-methyl-7,8,9,11,12,13,14,15,16,17-decahydro-6H-cyclopenta[a]phenanthren-15-yl)-N-(5-methyloxazol-2-yl)propanamide

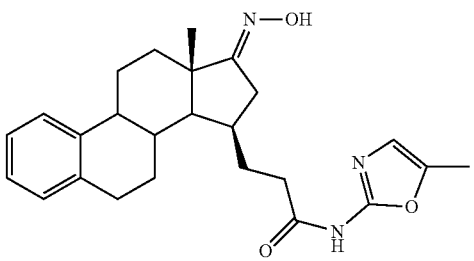 [SMILES: Cc1cnc(NC(=O)CC[C@@H]2C/C(=N\O)[C@@]3(C)CCC4c5ccccc5CCC4C23)o1]

Compound 108 was prepared in quantitative yield from Compound 107 by the same method as with Compound 2 by stirring at 50° C. for 1.5 hours.

$^1$H-NMR (200 MHz, DMSO-d6): 1.03 (s, 3H), 1.20-2.75 (m, 19H), 2.80-2.95 (m, 2H), 6.69 (s, 1H), 7.05-7.20 (m, 3H), 7.20-7.30 (m, 1H), 10.18 (s, 1H), 10.96 (br s, 1H).

Compound 109

3-((13S,15R,E)-13-methyl-17-oxo-7,8,9,11,12,13,14,15,16,17-decahydro-6H-cyclopenta[a]phenanthren-15-yl)-N-(5-methylisoxazol-3-yl)propanamide

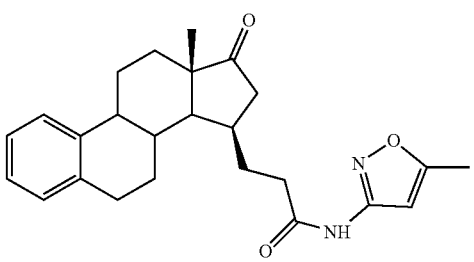 [SMILES: Cc1cc(NC(=O)CC[C@@H]2CC(=O)[C@@]3(C)CCC4c5ccccc5CCC4C23)no1]

Compound 109 was prepared in 22% yield from Acid XXVI by the same method as with Compound 1 in the presence of triethylamine using 3-amino-5-methylisoxazole as an amine. Reaction time was 5 hours.

$^1$H-NMR (200 MHz, CDCl$_3$): 0.97 (s, 3H), 1.29-2.44 (m, 19H), 2.86 (m, 2H), 6.63 (s, 1H), 7.09-7.25 (m, 3H), 7.28 (m, 1H), 10.88 (s, 1H). MS m/z (TOF ES+): 407 (M+1), 429 (M+Na).

Compound 110

3-((13S,15R,E)-17-hydroxyimino)-13-methyl-7,8,9,11,12,13,14,15,16,17-decahydro-H-cyclopenta[a]phenanthren-15-yl)-N-(5-methylisoxazol-3-yl)propanamide

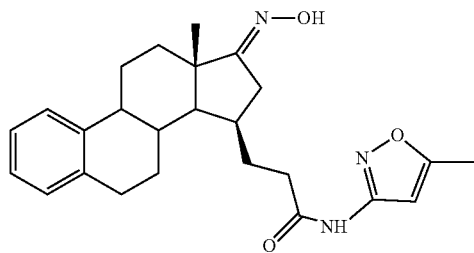 [SMILES: Cc1cc(NC(=O)CC[C@@H]2C/C(=N\O)[C@@]3(C)CCC4c5ccccc5CCC4C23)no1]

Compound 110 was prepared from Compound 109 by the same method as with Compound 2.

¹H-NMR (200 MHz, CDCl$_3$): 1.12 (s, 3H), 1.37-2.66 (m, 18H), 2.86-3.00 (m, 2H), 6.76 (s, 1H), 7.09-7.20 (m, 3H), 7.30-7.31 (m, 1H), 7.49 (br s, 1H), 10.18 (s, 1H), 9.49 (br s, 1H). MS m/z (TOF ES+): 422 (M+1).

Compound 111

3-((13S,15R)-4-fluoro-13-methyl-17-oxo-7,8,9,11,12,13,14,15,16,17-decahydro-6H-cyclopenta[a]phenanthren-15-yl)-N-(5-isopropylpyridin-2-yl)propanamide

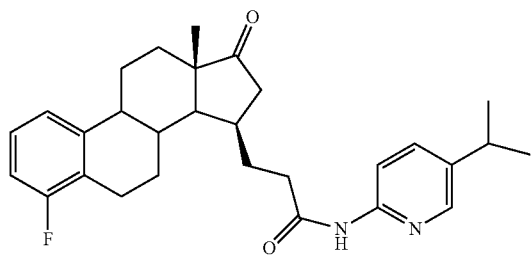 [SMILES: CC(C)c1ccc(NC(=O)CC[C@@H]2CC(=O)[C@@]3(C)CCC4c5cccc(F)c5CCC4C23)nc1]

Compound 111 was synthesized in 20% yield after chromatographic purification by the method used in the preparation of the compound 1 in THF by using acid SM-IX and 2-amino-5-isopropylpyridine as starting materials in 4 hours reaction time.

¹H-NMR (200 MHz, CDCl$_3$): 1.07 (s, 3H), 1.25 (s, 3H), 1.28 (s, 3H), 1.34-2.60 (m, 17H), 2.72-3.05 (m, 2H), 6.83-6.92 (m, 1H), 7.05-7.18 (m, 2H), 7.57-7.63 (m, 1H), 8.09-8.17 (m, 2H), 8.49 (br s, 1H).

Compound 112

3-((13S,15R,E)-4-fluoro-17-(hydroxyimino)-13-methyl-7,8,9,11,12,13,14,15,16,17-decahydro-6H-cyclopenta[a]phenanthren-15-yl)-N-(5-isopropylpyridin-2-yl)propanamide

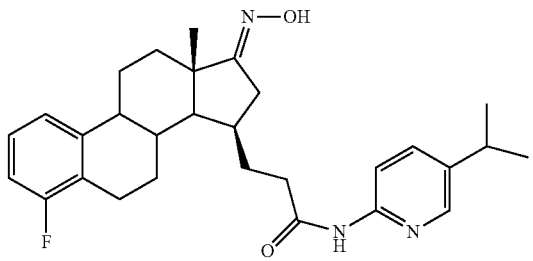 [SMILES: CC(C)c1ccc(NC(=O)CC[C@@H]2C/C(=N\O)[C@@]3(C)CCC4c5cccc(F)c5CCC4C23)nc1]

Compound 112 was prepared in 70% yield from the compound 111 by the same method as with Example 2 in 1.5 hours reaction time.

¹H-NMR (200 MHz, CDCl$_3$): 1.15 (s, 3H), 1.24 (s, 3H), 1.28 (s, 3H), 1.34-2.60 (m, 16H), 2.72-3.05 (m, 3H), 6.82-6.92 (m, 1H), 7.05-7.18 (m, 2H), 7.57-7.64 (m, 1H), 8.09-8.19 (m, 2H), 8.84 (br s, 1H).

Compound 113

3-((13S,15R)-4-fluoro-13-methyl-17-oxo-7,8,9,11,12,13,14,15,16,17-decahydro-6H-cyclopenta[a]phenanthren-15-yl)-N-(5-morpholinopyridin-2-yl)propanamide

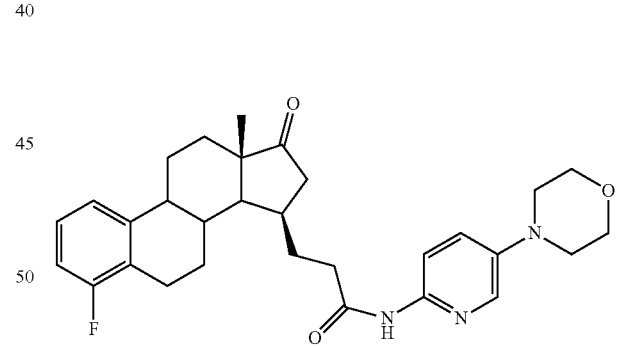

Compound 113 was synthesized in 82% yield after chromatographic purification by the method used in the preparation of the compound 1 in DCM by using acid SM-IX and 5-morpholinopyridin-2-amine as starting materials and triethylamine as base in 2 hours reaction time.

¹H-NMR (400 MHz, DMSO-d6): 0.98 (s, 3H), 1.30-2.46 (m, 16H), 2.63-2.80 (m, 1H), 2.81-2.96 (m, 1H), 3.03-3.15 (m, 4H), 3.68-3.80 (m, 4H), 6.90-7.03 (m, 1H), 7.10-7.22 (m, 2H), 7.40 (dd, 1H), 7.95-8.01 (m, 2H), 10.29 (s, 1H).

Compound 114

3-((13S,15R,E)-4-fluoro-17-(hydroxyimino)-13-methyl-7,8,9,11,12,13,14,15,16,17-decahydro-6H-cyclopenta[a]phenanthren-15-yl)-N-(5-morpholinopyridin-2-yl)propanamide

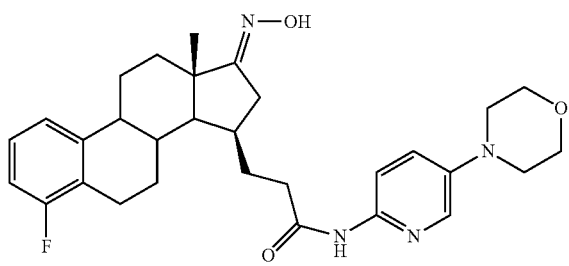 [SMILES: C[C@]12CCC3c4cccc(F)c4CCC3C1[C@H](CCC(=O)Nc1ccc(N3CCOCC3)cn1)C/C2=N\O]

Compound 114 was prepared in 65% yield after chromatographic purification from the compound 113 by the same method as with Example 2 in 6.5 hours reaction time at 50-80° C. Reaction needed 300 mol-% of hydroxylamine hydrochloride and 800 mol-% of pyridine.

$^1$H-NMR (400 MHz, DMSO-d6): 1.03 (s, 3H), 1.30-2.46 (m, 15H), 2.63-2.80 (m, 2H), 2.81-2.96 (m, 1H), 3.03-3.15 (m, 4H), 3.68-3.80 (m, 4H), 6.90-7.03 (m, 1H), 7.10-7.22 (m, 2H), 7.40 (dd, 1H), 7.95-8.01 (m, 2H), 10.18 (s, 1H), 10.30 (s, 1H).

Compound 115

3-((13S,15R)-4-fluoro-13-methyl-17-oxo-7,8,9,11,12,13,14,15,16,17-decahydro-6H-cyclopenta[a]phenanthren-15-yl)-N-(5-(4-methylpiperazin-1-yl)pyridin-2-yl)propanamide

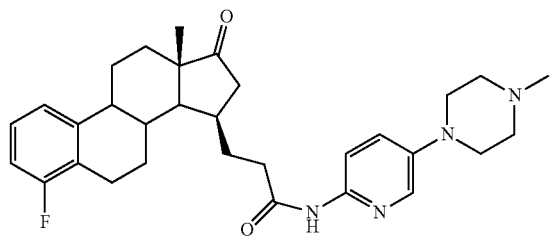 [SMILES: CN1CCN(c2ccc(NC(=O)CC[C@@H]3CC(=O)[C@@]4(C)CCC5c6cccc(F)c6CCC5C34)nc2)CC1]

Compound 115 was synthesized in 83% yield after chromatographic purification by the method used in the preparation of the compound 1 in DCM by using acid SM-IX and 1-methyl-4-(6-aminopyridin-3-yl)piperazine as starting materials and triethylamine as base in 2 hours reaction time.

$^1$H-NMR (400 MHz, DMSO-d6): 0.98 (s, 3H), 1.30-2.42 (m, 16H), 2.21 (s, 3H), 2.43-2.48 (m, 4H), 2.63-2.80 (m, 1H), 2.81-2.96 (m, 1H), 3.05-3.15 (m, 4H), 6.93-7.03 (m, 1H), 7.10-7.22 (m, 2H), 7.39 (dd, 1H), 7.92-8.00 (m, 2H), 10.27 (s, 1H).

Compound 116

3-((13S,15R,E)-4-fluoro-17-(hydroxyimino)-13-methyl-7,8,9,11,12,13,14,15,16,17-decahydro-6H-cyclopenta[a]phenanthren-15-yl)-N-(5-(4-methylpiperazin-1-yl)pyridin-2-yl)propanamide

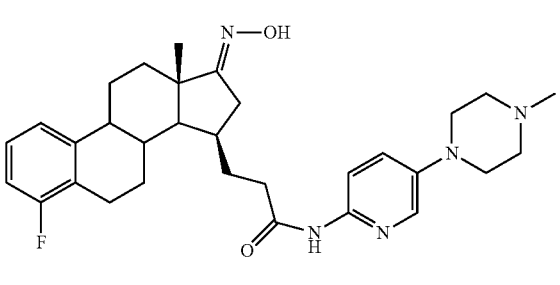 [SMILES: CN1CCN(c2ccc(NC(=O)CC[C@@H]3C/C(=N\O)[C@@]4(C)CCC5c6cccc(F)c6CCC5C34)nc2)CC1]

Compound 116 was prepared in 90% yield from the compound 115 by the same method as with Example 2 in 2 hours reaction time.

$^1$H-NMR (400 MHz, DMSO-d6): 1.03 (s, 3H), 1.30-2.42 (m, 15H), 2.22 (s, 3H), 2.43-2.48 (m, 4H), 2.63-2.80 (m, 2H), 2.81-2.96 (m, 1H), 3.05-3.15 (m, 4H), 6.93-7.00 (m, 1H), 7.10-7.22 (m, 2H), 7.39 (dd, 1H), 7.92-8.00 (m, 2H), 10.19 (s, 1H), 10.28 (s, 1H). MS m/z (TOF ES+): 534 (M+1)

Compound 117

3-((13S,15R)-4-fluoro-13-methyl-17-oxo-7,8,9,11,12,13,14,15,16,17-decahydro-6H-cyclopenta[a]phenanthren-15-yl)-N-methylpropanamide

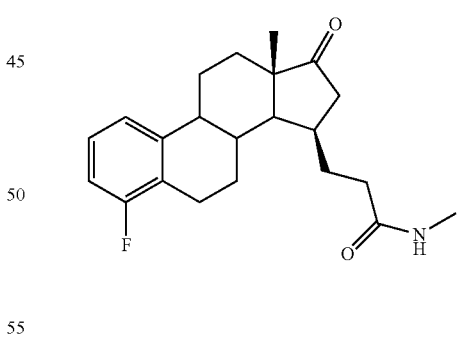

Compound 117 was synthesized in 44% yield after chromatographic purification by the method used in the preparation of the compound 9 by using acid SM-IX and methylamine hydrochloride as starting materials in 2 hours reaction time.

$^1$H-NMR (200 MHz, DMSO-d6): 0.96 (s, 3H), 1.28-2.42 (m, 16H), 2.55/2.58 (2×s, 3H, isomers), 2.63-2.96 (m, 2H), 6.93-7.03 (m, 1H), 7.10-7.25 (m, 2H), 7.70-7.80 (m, 1H).

Compound 118

3-((13S,15R,E)-4-fluoro-17-(hydroxyimino)-13-methyl-7,8,9,11,12,13,14,15,16,17-decahydro-6H-cyclopenta[a]phenanthren-15-yl)-N-methylpropanamide

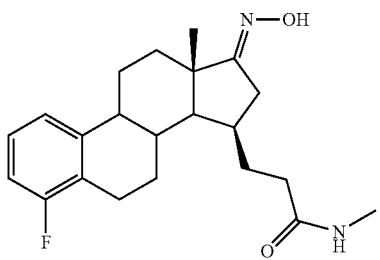 [SMILES: CNC(=O)CC[C@@H]1C/C(=N\O)[C@@]2(C)CCC3c4cccc(F)c4CCC3C12]

Compound 118 was prepared in 97% yield from the compound 117 by the same method as with Example 2 in 1.5 hours reaction time.

$^1$H-NMR (200 MHz, DMSO-d6): 1.01 (s, 3H), 1.28-2.45 (m, 15H), 2.55/2.57 (2×s, 3H, isomers), 2.62-2.96 (m, 3H), 6.90-7.03 (m, 1H), 7.10-7.25 (m, 2H), 7.70-7.82 (m, 1H), 10.18 (s, 1H).

Compound 119

3-((13S,15R)-4-fluoro-13-methyl-17-oxo-7,8,9,11,12,13,14,15,16,17-decahydro-6H-cyclopenta[a]phenanthren-15-yl)-N,N-dimethylpropanamide

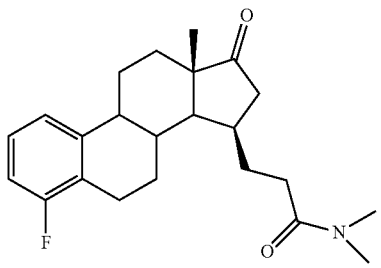 [SMILES: CN(C)C(=O)CC[C@@H]1CC(=O)[C@@]2(C)CCC3c4cccc(F)c4CCC3C12]

Compound 119 was synthesized in 85% yield by the method used in the preparation of the compound 9 by using acid SM-IX and dimethylamine hydrochloride as starting materials in 2 hours reaction time.

$^1$H-NMR (200 MHz, DMSO-d6): 0.97 (s, 3H), 1.28-2.40 (m, 16H), 2.62-2.94 (m, 2H), 2.82 (s, 3H), 2.97 (s, 3H), 6.90-7.03 (m, 1H), 7.10-7.25 (m, 2H).

Compound 120

3-((13S,15R,E)-4-fluoro-17-(hydroxyimino)-13-methyl-7,8,9,11,12,13,14,15,16,17-decahydro-6H-cyclopenta[a]phenanthren-15-yl)-N,N-dimethylpropanamide

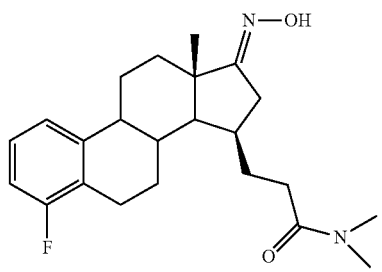 [SMILES: CN(C)C(=O)CC[C@@H]1C/C(=N\O)[C@@]2(C)CCC3c4cccc(F)c4CCC3C12]

Compound 120 was prepared in 32% yield from the compound 119 by the same method as with Example 2 in 1 hour reaction time.

$^1$H-NMR (200 MHz, CDCl$_3$): 1.13 (s, 3H), 1.24-2.60 (m, 15H), 2.62-3.00 (m, 3H), 2.97 (s, 3H), 3.03 (s, 3H), 6.80-6.92 (m, 1H), 7.04-7.18 (m, 2H), 8.34 (br s, 1H).

Compound 121

3-((13S,15R)-4-fluoro-13-methyl-17-oxo-7,8,9,11,12,13,14,15,16,17-decahydro-6H-cyclopenta[a]phenanthren-15-yl)-N-(tetrahydro-2H-pyran-4-yl)propanamide

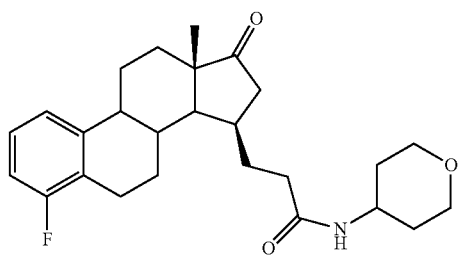 [SMILES: C[C@]12CCC3c4cccc(F)c4CCC3C1[C@H](CCC(=O)NC1CCOCC1)CC2=O]

Compound 121 was synthesized in 56% yield after chromatographic purification by the method used in the preparation of the compound 9 by using acid SM-IX and 4-aminotetrahydropyran as starting materials in 5 hours reaction time.

$^1$H-NMR (400 MHz, DMSO-d6): 0.96 (s, 3H), 1.30-2.41 (m, 20H), 2.67-2.76 (m, 1H), 2.85-2.90 (m, 1H), 3.29-3.30 (m, 2H), 3.70-3.77 (m, 1H), 3.80-3.83 (m, 2H), 6.94-7.00 (m, 1H), 7.10-7.22 (m, 2H), 7.84 (d, 1H).

Compound 122

3-((13S,15R,E)-4-fluoro-17-(hydroxyimino)-13-methyl-7,8,9,11,12,13,14,15,16,17-decahydro-6H-cyclopenta[a]phenanthren-15-yl)-N-(tetrahydro-2H-pyran-4-yl)propanamide

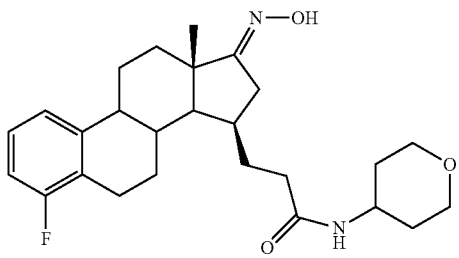 [SMILES: C[C@]12CCC3c4cccc(F)c4CCC3C1[C@H](CCC(=O)NC1CCOCC1)C/C2=N\O]

Compound 122 was prepared in quantitative yield from the compound 121 by the same method as with Example 2 in 1.5 hours reaction time.

¹H-NMR (400 MHz, DMSO-d6): 1.01 (s, 3H), 1.28-2.40 (m, 19H), 2.60-2.76 (m, 2H), 2.82-2.90 (m, 1H), 3.29-3.30 (m, 2H), 3.70-3.77 (m, 1H), 3.80-3.83 (m, 2H), 6.94-7.00 (m, 1H), 7.10-7.20 (m, 2H), 7.86 (d, 1H), 10.18 (s, 1H).

Compound 123

N-cyclohexyl-3-((13S,15R)-4-fluoro-13-methyl-17-oxo-7,8,9,11,12,13,14,15,16,17-decahydro-6H-cyclopenta[a]phenanthren-15-yl)propanamide

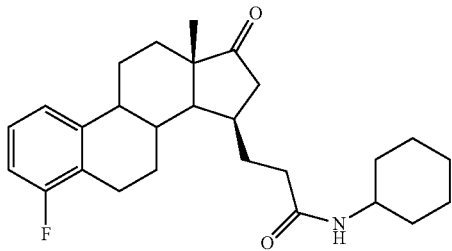 [SMILES: C[C@]12CCC3c4cccc(F)c4CCC3C1[C@H](CCC(=O)NC1CCCCC1)CC2=O]

Compound 123 was synthesized in 64% yield after chromatographic purification by the method used in the preparation of the compound 9 by using acid SM-IX and cyclohexylamine as starting materials in 2 hours reaction time.

¹H-NMR (400 MHz, DMSO-d6): 0.95 (s, 3H), 1.10-2.41 (m, 26H), 2.67-2.76 (m, 1H), 2.84-2.91 (m, 1H), 3.50-3.53 (m, 1H), 6.94-7.00 (m, 1H), 7.10-7.22 (m, 2H), 7.71 (br d, 1H).

Compound 124

N-Cyclohexyl-3-((13S,15R,E)-4-fluoro-17-(hydroxyimino)-13-methyl-7,8,9,11,12,13,14,15,16,17-decahydro-6H-cyclopenta[a]phenanthren-15-yl)propanamide

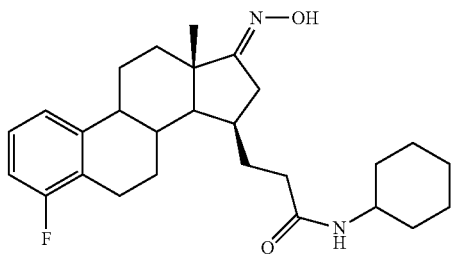 [SMILES: C[C@]12CCC3c4cccc(F)c4CCC3C1[C@H](CCC(=O)NC1CCCCC1)C/C2=N\O]

Compound 124 was prepared in 73% yield after chromatographic purification from the compound 123 by the same method as with Example 2 in 1 hour reaction time.

¹H-NMR (400 MHz, DMSO-d6): 1.00 (s, 3H), 1.10-2.40 (m, 25H), 2.59-2.76 (m, 2H), 2.82-2.90 (m, 1H), 3.45-3.55 (m, 1H), 6.94-7.00 (m, 1H), 7.10-7.20 (m, 2H), 7.72 (br d, 1H), 10.17 (s, 1H).

Compound 125

3-((13S,15R)-4-fluoro-13-methyl-17-oxo-7,8,9,11,12,13,14,15,16,17-decahydro-6H-cyclopenta[a]phenanthren-15-yl)-N-(pyrazin-2-yl)propanamide

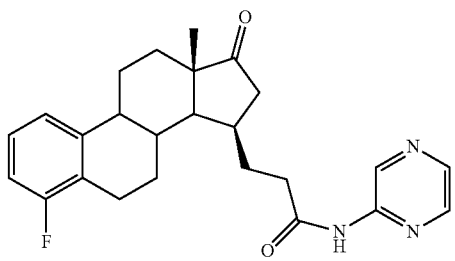 [SMILES: C[C@]12CCC3c4cccc(F)c4CCC3C1[C@H](CCC(=O)Nc1cnccn1)CC2=O]

Compound 125 was synthesized in 53% yield after chromatographic purification by the method used in the preparation of the compound 1 in DCM by using acid SM-IX and aminopyrazine as starting materials in 5 hours reaction time.

¹H-NMR (400 MHz, DMSO-d6): 0.99 (s, 3H), 1.30-2.60 (m, 16H), 2.69-2.78 (m, 1H), 2.84-2.92 (m, 1H), 6.94-7.00 (m, 1H), 7.12-7.20 (m, 2H), 8.33-8.40 (m, 2H), 9.35 (s, 1H), 10.81 (s, 1H).

Compound 126

3-((13S,15R,E)-4-fluoro-17-(hydroxyimino)-13-methyl-7,8,9,11,12,13,14,15,16,17-decahydro-6H-cyclopenta[a]phenanthren-15-yl)-N-(pyrazin-2-yl)propanamide

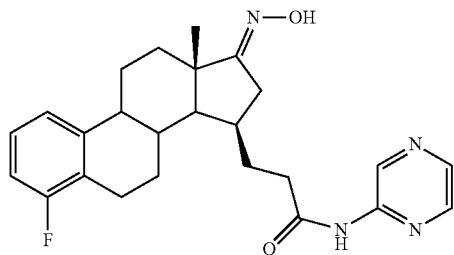 [SMILES: C[C@]12CCC3c4cccc(F)c4CCC3C1[C@H](CCC(=O)Nc1cnccn1)C/C2=N\O]

Compound 126 was prepared in 48% yield from the compound 125 by the same method as with Example 2 in 2.5 hours reaction time.

$^1$H-NMR (400 MHz, CDCl$_3$): 1.15 (s, 3H), 1.34-2.65 (m, 15H), 2.72-2.87 (m, 1H), 2.90-3.00 (m, 2H), 6.82-6.90 (m, 1H), 7.05-7.15 (m, 2H), 8.15 (s, 1H), 8.10-8.20 (br s, 1H), 8.24-8.26 (m, 1H), 8.36-8.38 (m, 1H), 9.56 (s, 1H).

Compound 127

(13S,15R)-4-fluoro-13-methyl-15-(3-oxo-3-(8-oxa-2-azaspiro[4.5]decan-2-yl)propyl)-6,7,8,9,11,12,13,14,15,16-decahydro-17H-cyclopenta[a]phenanthren-17-one

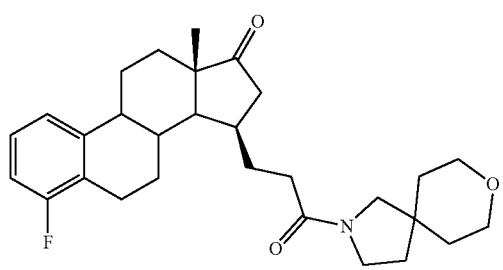 [SMILES: C[C@]12CCC3c4cccc(F)c4CCC3C1[C@H](CCC(=O)N1CCC3(CCOCC3)C1)CC2=O]

Compound 127 was synthesized in 93% yield by the method used in the preparation of the compound 9 by using acid SM-IX and 8-oxa-2-azaspiro(4,5)decane hydrochloride as starting materials in 4 hours reaction time.

$^1$H-NMR (400 MHz, DMSO-d6): 0.97 (s, 3H), 1.30-2.45 (m, 22H), 2.65-2.76 (m, 1H), 2.84-2.91 (m, 1H), 3.19-3.22 (m, 1H), 3.29-3.42 (m, 2H), 3.46-3.65 (m, 5H), 6.94-7.00 (m, 1H), 7.10-7.22 (m, 2H).

Compound 128

3-((13S,15R,E)-4-fluoro-17-(hydroxyimino)-13-methyl-7,8,9,11,12,13,14,15,16,17-decahydro-6H-cyclopenta[a]phenanthren-15-yl)-1-(8-oxa-2-azaspiro[4:5]decan-2-yl)propan-1-one

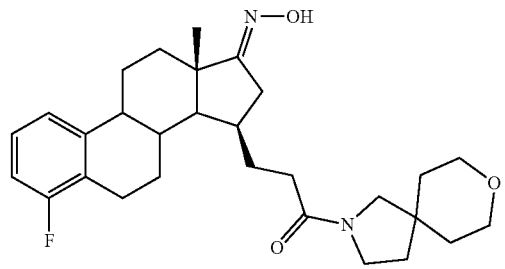 [SMILES: C[C@]12CCC3c4cccc(F)c4CCC3C1[C@H](CCC(=O)N1CCC3(CCOCC3)C1)C/C2=N\O]

Compound 128 was prepared in 90% yield from the compound 127 by the same method as with Example 2 in 2 hours reaction time.

$^1$H-NMR (400 MHz, DMSO-d6): 1.02 (s, 3H), 1.30-2.45 (m, 21H), 2.60-2.75 (m, 2H), 2.82-2.91 (m, 1H), 3.19-3.22 (m, 1H), 3.29-3.42 (m, 2H), 3.46-3.65 (m, 5H), 6.94-7.00 (m, 1H), 7.10-7.22 (m, 2H), 10.17 (s, 1H).

Compound 129

3-((13S,15R)-4-fluoro-13-methyl-17-oxo-7,8,9,11,12,13,14,15,16,17-decahydro-6H-cyclopenta[a]phenanthren-15-yl)-N-(4-methylpyridin-2-yl)propanamide

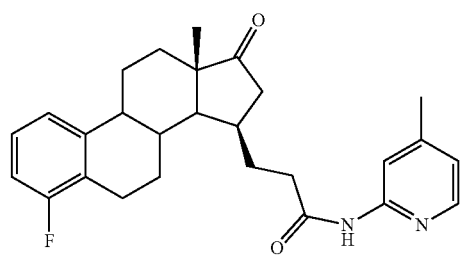 [SMILES: Cc1ccnc(NC(=O)CC[C@@H]2CC(=O)[C@@]3(C)CCC4c5cccc(F)c5CCC4C23)c1]

Compound 129 was synthesized in 37% yield after chromatographic purification by the method used in the preparation of the compound 3 in THF by using 200 mol-% of EDCl and HOBT and acid SM-IX and 2-amino-4-methylpyridine as starting materials in 4.5 hours reaction time.

$^1$H-NMR (400 MHz, DMSO-d6): 0.98 (s, 3H), 1.30-2.48 (m, 16H), 2.30 (s, 3H), 2.65-2.78 (m, 1H), 2.80-2.92 (m, 1H), 6.90-6.93 (m, 1H), 6.94-7.00 (m, 1H), 7.10-7.21 (m, 2H), 7.95 (s, 1H), 8.13-8.17 (m, 1H), 10.42 (s, 1H).

Compound 130

3-((13S,15R,E)-4-fluoro-17-(hydroxyimino)-13-methyl-7,8,9,11,12,13,14,15,16,17-decahydro-6H-cyclopenta[a]phenanthren-15-yl)-N-(4-methylpyridin-2-yl)propanamide

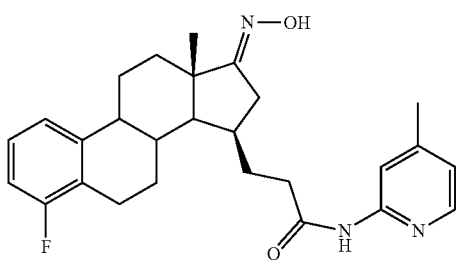 [SMILES: Cc1ccnc(NC(=O)CC[C@@H]2C/C(=N\O)[C@@]3(C)CCC4c5cccc(F)c5CCC4C23)c1]

Compound 130 was prepared in 81% yield from the compound 129 by the same method as with Example 2 in 2 hours reaction time.

$^1$H-NMR (400 MHz, DMSO-d6): 1.03 (s, 3H), 1.30-2.48 (m, 15H), 2.30 (s, 3H), 2.62-2.78 (m, 2H), 2.80-2.92 (m, 1H), 6.90-6.93 (m, 1H), 6.94-7.00 (m, 1H), 7.10-7.21 (m, 2H), 7.95 (s, 1H), 8.13-8.17 (m, 1H), 10.19 (s, 1H), 10.43 (s, 1H).

Compound 131

3-((13S,15R)-4-fluoro-13-methyl-17-oxo-7,8,9,11,12,13,14,15,16,17-decahydro-6H-cyclopenta[a]phenanthren-15-yl)-N-(4-methoxypyridin-2-yl)propanamide

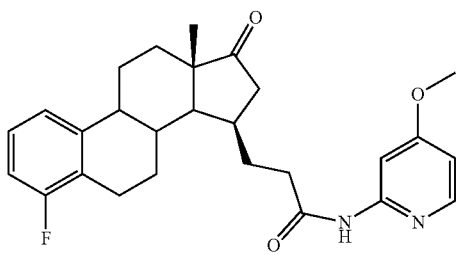 [SMILES: COc1ccnc(NC(=O)CC[C@@H]2CC(=O)[C@@]3(C)CCC4c5cccc(F)c5CCC4C23)c1]

Compound 131 was synthesized in 47% yield after chromatographic purification by the method used in the preparation of the compound 3 in THF by using acid SM-IX and 2-amino-4-methoxypyridine as starting materials in 10 hours and overnight at room temperature. Reaction needed 250 mol-% of amine, EDCl and HOBT.

$^1$H-NMR (400 MHz, DMSO-d6): 0.98 (s, 3H), 1.30-2.48 (m, 16H), 2.65-2.78 (m, 1H), 2.80-2.92 (m, 1H), 3.81 (s, 3H), 6.68-6.72 (m, 1H), 6.94-7.00 (m, 1H), 7.10-7.21 (m, 2H), 7.73 (s, 1H), 8.10-8.13 (m, 1H), 10.47 (s, 1H).

Compound 132

3-((13S,15R,E)-4-fluoro-17-(hydroxyimino)-13-methyl-7,8,9,11,12,13,14,15,16,17-decahydro-6H-cyclopenta[a]phenanthren-15-yl)-N-(4-methoxypyridin-2-yl)propanamide

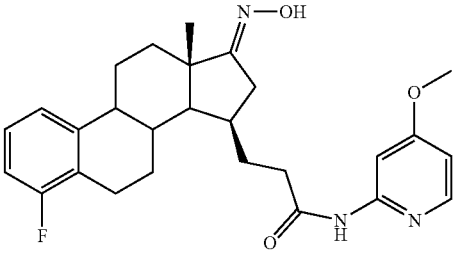 [SMILES: COc1ccnc(NC(=O)CC[C@@H]2C/C(=N\O)[C@@]3(C)CCC4c5cccc(F)c5CCC4C23)c1]

Compound 132 was prepared in 60% yield from the compound 131 by the same method as with Example 2 in 1 hour reaction time.

$^1$H-NMR (400 MHz, DMSO-d6): 1.03 (s, 3H), 1.30-2.48 (m, 15H), 2.59-2.78 (m, 2H), 2.80-2.92 (m, 1H), 3.81 (s, 3H), 6.68-6.72 (m, 1H), 6.94-7.00 (m, 1H), 7.10-7.21 (m, 2H), 7.74 (s, 1H), 8.10-8.13 (m, 1H), 10.19 (s, 1H), 10.49 (s, 1H).

Compound 133

3-((13S,15R)-3-fluoro-13-methyl-17-oxo-7,8,9,11,12,13,14,15,16,17-decahydro-6H-cyclopenta[a]phenanthren-15-yl)-N-(5-methylisoxazol-3-yl)propanamide

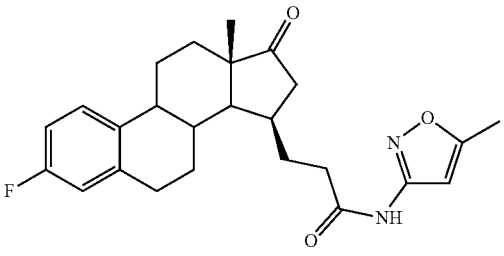 [SMILES: Cc1cc(NC(=O)CC[C@@H]2CC(=O)[C@@]3(C)CCC4c5ccc(F)cc5CCC4C23)no1]

Compound 133 was synthesized in quantitative yield by the method used in the preparation of the compound 1 in DCM by using acid SM-XV and 3-amino-5-methylisoxazole as starting materials in 4.5 hours reaction time.

$^1$H-NMR (200 MHz, DMSO-d6): 0.97 (s, 3H), 1.25-2.45 (m, 16H), 2.36 (s, 3H), 2.80-2.95 (m, 2H), 6.63 (s, 1H), 6.83-7.00 (m, 2H), 7.24-7.35 (m, 1H), 10.88 (br s, 1H).

Compound 134

3-((13S,15R,E)-3-fluoro-17-(hydroxyimino)-13-methyl-7,8,9,11,12,13,14,15,16,17-decahydro-6H-cyclopenta[a]phenanthren-15-yl)-N-(5-methylisoxazol-3-yl)propanamide

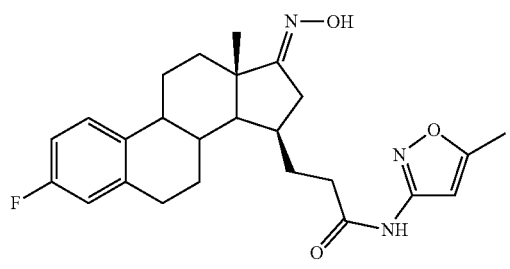 [SMILES: Cc1cc(NC(=O)CC[C@@H]2C/C(=N\O)[C@@]3(C)CCC4c5ccc(F)cc5CCC4C23)no1]

Compound 134 was prepared in 78% yield from the compound 133 by the same method as with Example 2 in two hours reaction time.

$^1$H-NMR (200 MHz, DMSO-d6): 1.02 (s, 3H), 1.25-2.45 (m, 15H), 2.37 (s, 3H), 2.58-2.74 (m, 1H), 2.80-2.95 (m, 2H), 6.64 (s, 1H), 6.87-7.00 (m, 2H), 7.24-7.35 (m, 1H), 10.18 (s, 1H), 10.89 (br s, 1H).

Compound 135

(13S,15R)-4-fluoro-13-methyl-15-(3-morpholino-3-oxopropyl)-6,7,8,9,11,12,13,14,15,16-decahydro-17H-cyclopenta[a]phenanthren-17-one

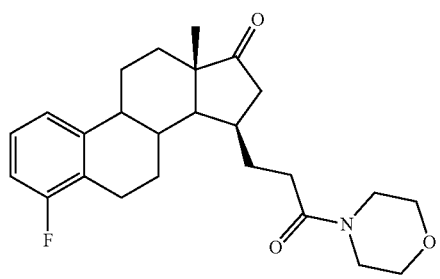 [SMILES: C[C@]12CCC3c4cccc(F)c4CCC3C1[C@H](CCC(=O)N1CCOCC1)CC2=O]

Compound 135 was synthesized in 83% yield by the method used in the preparation of Compound 3 in DMF by using acid SM-IX and morpholine as starting materials in two hours reaction time.

$^1$H-NMR (200 MHz, DMSO-d$_6$): 0.97 (s, 3H), 1.35-2.37 (m, 15H), 2.76-2.92 (m, 3H), 3.45 (br s, 4H), 3.55 (br s 4H), 6.93-7.02 (m, 1H), 7.16-7.23 (m, 2H).

Compound 136

3-((13S,15R,E)-4-fluoro-17-(hydroxyimino)-13-methyl-7,8,9,11,12,13,14,15,16,17-decahydro-6H-cyclopenta[a]phenanthren-15-yl)-1-morpholinopropan-1-one

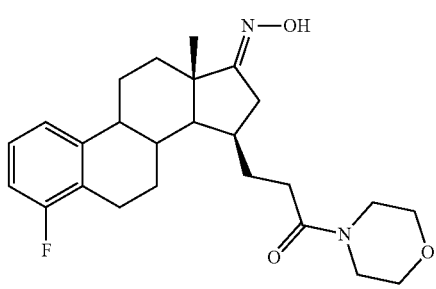 [SMILES: C[C@]12CCC3c4cccc(F)c4CCC3C1[C@H](CCC(=O)N1CCOCC1)C/C2=N\O]

Compound 136 was prepared in 79% yield from the compound 135 by the same method as with Compound 2 in 1 hour reaction time.

$^1$H-NMR (200 MHz, CDCl$_3$): 1.13 (s, 3H), 1.35-3.03 (m, 18H), 3.46-3.51 (m, 2H), 3.66-3.72 (m, 6H), 6.82-6.90 (m, 1H), 7.05-7.19 (m, 2H), 8.23 (br s, 1H).

Compound 137

3-((13S,15R)-4-fluoro-13-methyl-17-oxo-7,8,9,11,12,13,14,15,16,17-decahydro-6H-cyclopenta[a]phenanthren-15-yl)-N-(pyridin-2-yl)propanamide

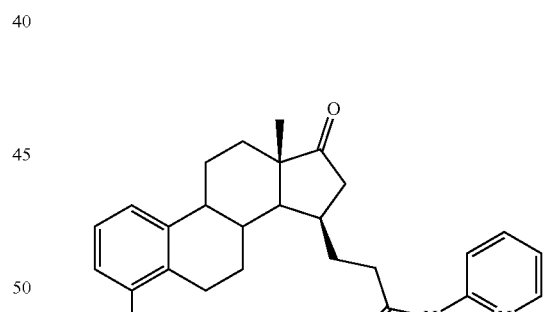

Compound 137 was synthesized in 51% yield by the method used in the preparation of Compound 3 in DMF by using acid SM-IX and 2-aminopyridine as starting materials in overnight reaction time.

$^1$H-NMR (400 MHz, DMSO-d$_6$): 0.98 (s, 3H), 1.34-1.47 (m, 3H), 1.59-1.68 (m, 4H), 1.78-1.90 (m, 1H), 2.17-2.46 (m, 8H), 2.68-2.82 (m, 2H), 6.95-6.99 (m, 1H), 7.07-7.13 (m, 1H), 7.14-7.20 (m, 2H), 7.76 (dd, 1H), 8.10 (d, 1H), 8.30 (dd, 1H), 10.50 (s, 1H).

Compound 138

3-((13S,15R,E)-4-fluoro-17-(hydroxyimino)-13-methyl-7,8,9,11,12,13,14,15,16,17-decahydro-6H-cyclopenta[a]phenanthren-15-yl)-N-(pyridin-2-yl)propanamide

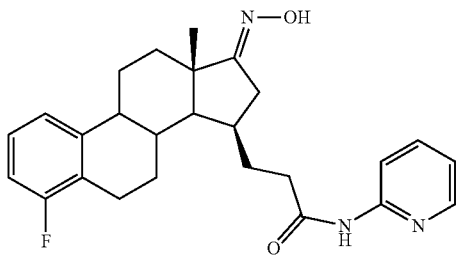 [SMILES: C[C@]12CCC3c4cccc(F)c4CCC3C1[C@H](CCC(=O)Nc1ccccn1)C/C2=N\O]

Compound 138 was prepared in 89% yield from the compound 137 by the same method as with Compound 2 in 1 hour reaction time.

$^1$H-NMR (400 MHz, DMSO-d$_6$): 1.03 (s, 3H), 1.36-1.77 (m, 8H), 2.08-2.45 (m, 7H), 2.63-2.76 (m, 2H), 2.82-2.89 (m, 1H), 6.94-6.98 (m, 1H), 7.07 (m, 1H), 7.14-7.19 (m, 2H), 7.74 (dd, 1H), 8.10 (d, 1H), 8.30 (d, 1H), 10.19 (s, 1H), 10.52 (s, 1H).

Compound 139

3-((13S,15R)-4-fluoro-13-methyl-17-oxo-7,8,9,11,12,13,14,15,16,17-decahydro-6H-cyclopenta[a]phenanthren-15-yl)-N-(4-fluoropyridin-2-yl)propanamide

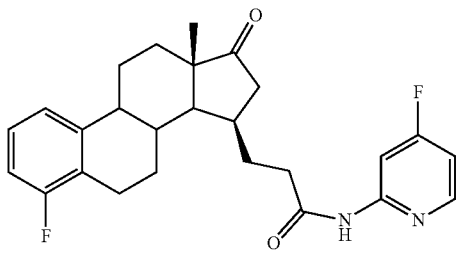 [SMILES: C[C@]12CCC3c4cccc(F)c4CCC3C1[C@H](CCC(=O)Nc1cc(F)ccn1)CC2=O]

Compound 139 was synthesized in 83% yield by the method used in the preparation of the Compound 1 in THF by using acid SM-IX and 2-amino-4-fluoropyridine as starting materials in overnight reaction time.

$^1$H-NMR (400 MHz, DMSO-d$_6$): 0.98 (s, 3H), 1.36-1.46 (m, 3H), 1.58-1.74 (m, 4H), 1.89-1.94 (m, 1H), 2.16-2.43 (m, 7H), 2.68-2.91 (m, 3H), 6.95-7.04 (m, 2H), 7.05-7.20 (m, 2H), 7.93 (dd, 1H), 8.34 (dd, 1H), 10.83 (s, 1H).

Compound 140

3-((13S,15R,E)-4-fluoro-17-(hydroxyimino)-13-methyl-7,8,9,11,12,13,14,15,16,17-decahydro-6H-cyclopenta[a]phenanthren-15-yl)-N-(4-fluoropyridin-2-yl)propanamide

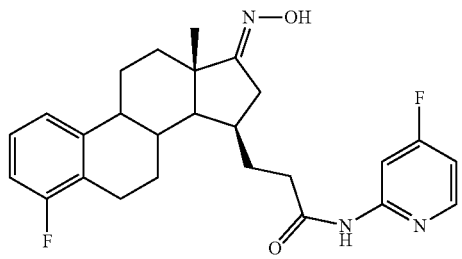 [SMILES: C[C@]12CCC3c4cccc(F)c4CCC3C1[C@H](CCC(=O)Nc1cc(F)ccn1)C/C2=N\O]

Compound 140 was prepared in 77% yield from Compound 139 by the same method as with Compound 2 in two hours reaction time.

$^1$H-NMR (400 MHz, DMSO-d$_6$): 1.03 (s, 3H), 1.35-1.71 (m, 6H), 1.81-1.91 (m, 2H), 2.08-2.14 (m, 2H), 2.30-2.47 (m, 5H), 2.65-2.90 (m, 3H), 6.94-7.04 (m, 2H), 7.10-7.19 (m, 2H), 7.93 (dd, 1H), 8.35 (dd, 1H), 10.19 (s, 1H), 10.84 (s, 1H).

Compound 141

3-((13S,15R)-4-fluoro-13-methyl-17-oxo-7,8,9,11,12,13,14,15,16,17-decahydro-6H-cyclopenta[a]phenanthren-15-yl)-N-(3-fluoropyridin-2-yl)propanamide

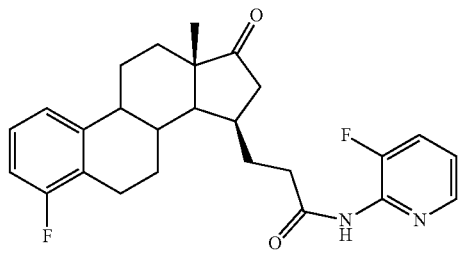 [SMILES: C[C@]12CCC3c4cccc(F)c4CCC3C1[C@H](CCC(=O)Nc1ncccc1F)CC2=O]

Compound 141 was synthesized in 96% yield by the method used in the preparation of the Compound 1 in THF by using acid SM-IX and 2-amino-3-fluoropyridine as starting materials in overnight reaction time.

$^1$H-NMR (400 MHz, DMSO-d$_6$): 0.98 (s, 3H), 1.34-1.98 (m, 8H), 2.18-2.47 (m, 8H), 2.68-2.77 (m, 1H), 2.84-2.90 (m, 1H), 6.97 (m, 1H), 7.10-7.20 (m, 2H), 7.34 (m, 1H), 7.77 (dd, 1H), 8.24 (d, 1H), 10.28 (s, 1H).

Compound 142

3-((13S,15R,E)-4-fluoro-17-(hydroxyimino)-13-methyl-7,8,9,11,12,13,14,15,16,17-decahydro-6H-cyclopenta[a]phenanthren-15-yl)-N-(3-fluoropyridin-2-yl)propanamide

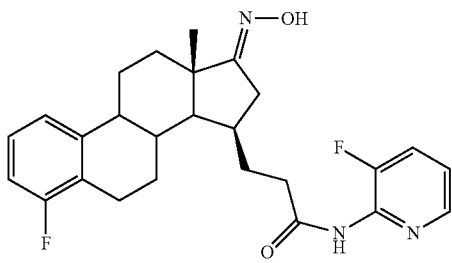 [SMILES: C[C@]12CCC3c4cccc(F)c4CCC3C1[C@H](CCC(=O)Nc1ncccc1F)C/C2=N\O]

Compound 142 was prepared in 69% yield from Compound 141 by the same method as with Compound 2 in 1 hour reaction time.

$^1$H-NMR (400 MHz, DMSO-d$_6$): 1.04 (s, 3H), 1.33-1.70 (m, 6H), 1.88-2.46 (m, 9H), 2.66-2.90 (m, 3H), 6.94-6.98 (m, 1H), 7.10-7.17 (m, 2H), 7.35 (m, 1H), 7.76 (dd, 1H), 8.24 (d, 1H), 10.19 (s, 1H), 10.28 (s, 1H).

Compound 143

3-((13S,15R)-4-fluoro-13-methyl-17-oxo-7,8,9,11,12,13,14,15,16,17-decahydro-6H-cyclopenta[a]phenanthren-15-yl)-N-(6-fluoropyridin-2-yl)propanamide

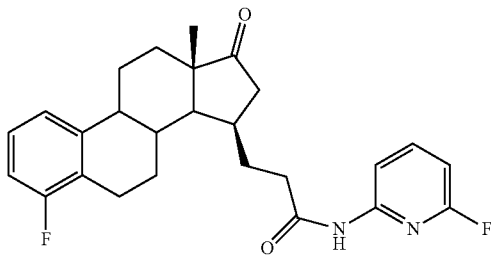 [SMILES: C[C@]12CCC3c4cccc(F)c4CCC3C1[C@H](CCC(=O)Nc1cccc(F)n1)CC2=O]

Compound 143 was synthesized in 88% yield by the method used in the preparation of the Compound 1 in THF by using acid SM-IX and 2-amino-6-fluoropyridine as starting materials in two hours reaction time.

$^1$H-NMR (400 MHz, DMSO-d$_6$): 0.98 (s, 3H), 1.35-1.46 (m, 3H), 1.57-1.77 (m, 4H), 1.93 (m, 1H), 2.16-2.47 (m, 8H), 2.68-2.90 (m, 2H), 6.83 (dd, 1H), 6.97 (dd, 1H), 7.12-7.20 (m, 2H), 7.95 (dd, 1H), 8.01 (d, 1H), 10.69 (s, 1H).

Compound 144

3-((13S,15R,E)-4-fluoro-17-(hydroxyimino)-13-methyl-7,8,9,11,12,13,14,15,16,17-decahydro-6H-cyclopenta[a]phenanthren-15-yl)-N-(6-fluoropyridin-2-yl)propanamide

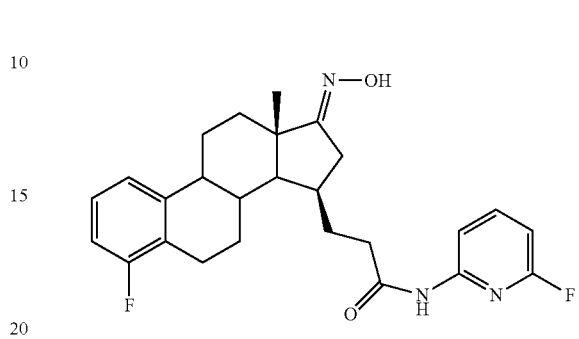

Compound 144 was prepared in 79% yield from Compound 143 by the same method as with Compound 2 in 1 hour reaction time.

$^1$H-NMR (400 MHz, DMSO-d$_6$): 1.03 (s, 3H), 1.30-1.68 (m, 6H), 1.84-1.91 (m, 2H), 2.09-2.16 (m, 2H), 2.31-2.47 (m, 5H), 2.65-2.88 (m, 3H), 6.83 (dd, 1H), 6.96 (m, 1H), 7.12-7.19 (m, 2H), 7.94 (dd, 1H), 8.02 (dd, 1H), 10.19 (s, 1H), 10.71 (s, 1H).

Compound 145

N-(3,5-difluoropyridin-2-yl)-3-((13S,15R)-4-fluoro-13-methyl-17-oxo-7,8,9,11,12,13,14,15,16,17-decahydro-6H-cyclopenta[a]phenanthren-15-yl)propanamide

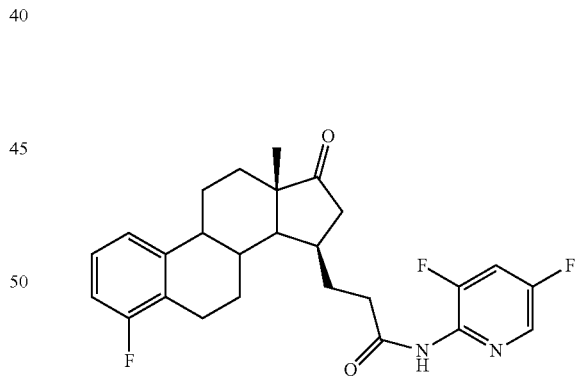

Compound 145 was synthesized in 91% yield by the method used in the preparation of the Compound 1 in THF by using acid SM-IX and 2-amino-3,5-difluoropyridine as starting materials in two hours reaction time.

$^1$H-NMR (400 MHz, DMSO-d$_6$): 0.98 (s, 3H), 1.34-1.47 (m, 4H), 1.58-1.83 (m, 4H), 1.90-1.95 (m, 1H), 2.17-2.55 (m, 9H), 2.67-2.90 (m, 2H), 6.97 (dd, 1H), 8.01 (dd, 1H), 8.34 (d, 1H), 10.31 (s, 1H).

Compound 146

N-(3,5-difluoropyridin-2-yl)-3-((13S,15R,E)-4-fluoro-17-(hydroxyimino)-13-methyl-7,8,9,11,12,13,14,15,16,17-decahydro-6H-cyclopenta[a]phenanthren-15-yl)propanamide

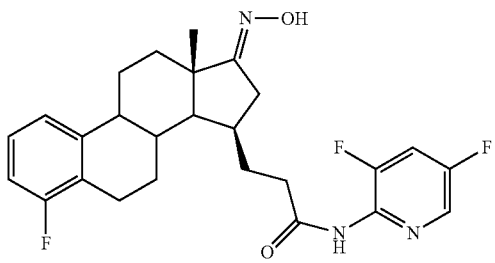 [SMILES: C[C@]12CCC3c4cccc(F)c4CCC3C1[C@H](CCC(=O)Nc1ncc(F)cc1F)C/C2=N\O]

Compound 146 was prepared in 84% yield from Compound 145 by the same method as with Compound 2 in 1 hour reaction time.

$^1$H-NMR (400 MHz, DMSO-$d_6$): 1.03 (s, 3H), 1.30-1.68 (m, 6H), 1.88-1.91 (m, 2H), 2.13-2.18 (m, 2H), 2.31-2.45 (m, 5H), 2.66-2.88 (m, 3H), 6.96 (m, 1H), 7.12-7.19 (m, 2H), 8.01 (dd, 1H), 8.34 (dd, 1H), 10.19 (s, 1H), 10.32 (s, 1H).

Compound 147

N-(5-cyanopyridin-2-yl)-3-((13S,15R)-4-fluoro-13-methyl-17-oxo-7,8,9,11,12,13,14,15,16,17-decahydro-6H-cyclopenta[a]phenanthren-15-yl)propanamide

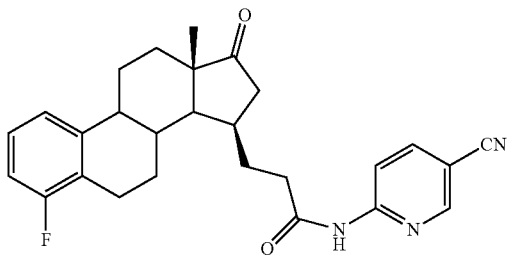 [SMILES: C[C@]12CCC3c4cccc(F)c4CCC3C1[C@H](CCC(=O)Nc1ccc(C#N)cn1)CC2=O]

Compound 147 was synthesized in 85% yield by the method used in the preparation of the Compound 1 in THF by using acid SM-IX and 2-amino-5-cyanopyridine as starting materials in overnight reaction time.

$^1$H-NMR (400 MHz, DMSO-$d_6$): 0.98 (s, 3H), 1.36-1.97 (m, 8H), 2.17-2.43 (m, 7H), 2.58 (m, 1H), 2.68-2.90 (m, 2H), 6.97 (dd, 1H), 7.12-7.20 (m, 2H), 8.25 (m, 2H), 8.78 (d, 1H), 11.04 (s, 1H).

Compound 148

N-(5-cyanopyridin-2-yl)-3-((13S,15R,E)-4-fluoro-17-(hydroxyimino)-13-methyl-7,8,9,11,12,13,14,15,16,17-decahydro-6H-cyclopenta[a]phenanthren-15-yl)propanamide

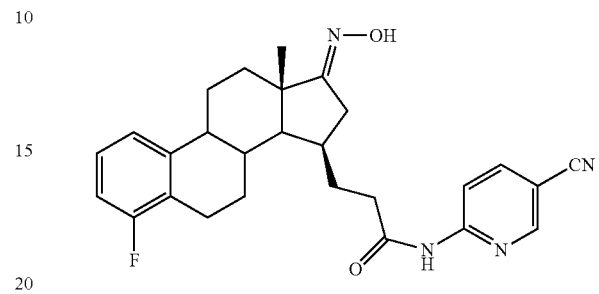

Compound 148 was prepared in 71% yield from the compound 147 by the same method as with Compound 2 in 1 reaction time.

$^1$H-NMR (400 MHz, DMSO-$d_6$): 1.03 (s, 3H), 1.30-1.66 (m, 6H), 1.88-2.43 (m, 8H), 2.63-2.87 (m, 4H), 6.94-6.98 (m, 1H), 7.14-7.19 (m, 2H), 8.24 (s, 2H), 8.78 (d, 1H), 10.19 (s, 1H), 11.06 (s, 1H).

Compound 149

3-((13S,15R)-3-fluoro-13-methyl-17-oxo-7,8,9,11,12,13,14,15,16,17-decahydro-6H-cyclopenta[a]phenanthren-15-yl)-N-(3-fluoropyridin-2-yl)propanamide

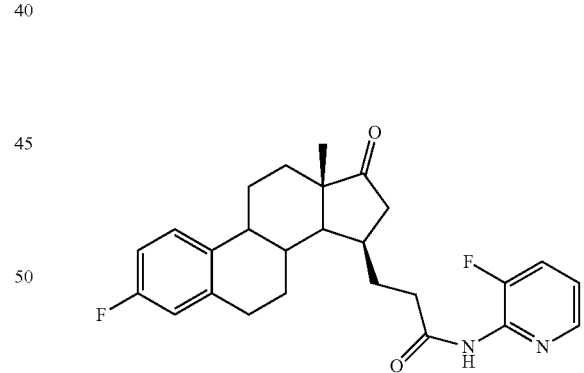

Compound 149 was synthesized in 92% yield by the method used in the preparation of the Compound 1 in THF by using acid SM-XV and 2-amino-3-fluoropyridine as starting materials in overnight reaction time.

$^1$H-NMR (400 MHz, DMSO-$d_6$): 0.98 (s, 3H), 1.35-1.46 (m, 3H), 1.58-1.75 (m, 4H), 1.89-1.92 (m, 1H), 2.11-2.14 (m, 1H), 2.27-2.48 (m, 7H), 2.88 (m, 2H), 6.92 (m, 2H), 7.27-7.36 (m, 2H), 7.76 (dd, 1H), 8.24 (d, 1H), 10.27 (s, 1H).

Compound 150a 3-((13S,15R,E)-3-fluoro-17-(hydroxyimino)-13-methyl-7,8,9,11,12,13,14,15,16,17-decahydro-6H-cyclopenta[a]phenanthren-15-yl)-N-(3-fluoropyridin-2-yl)propanamide

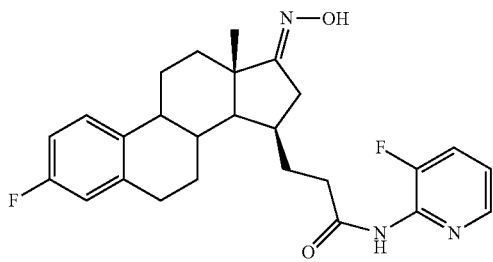 [SMILES: C[C@]12CCC3c4ccc(F)cc4CCC3C1[C@H](CCC(=O)Nc1ncccc1F)C/C2=N\O]

Compound 150 was prepared from Compound 149 by the same method as with Compound 2 in 1 hour reaction time. E- and Z-isomers (compounds 150a and 150b, respectively) was isolated by chromatographic purification.

Compound 150a: E-Isomer, Yield 58%

$^1$H-NMR (400 MHz, CDCl$_3$): 1.14 (s, 3H), 1.43-1.75 (m 7H), 2.00-2.11 (m, 2H), 2.19 (m, 1H), 2.27-2.36 (m, 3H), 2.51 (d, 1H), 2.59 (m, 1H), 2.78 (m, 1H), 2.90-2.97 (m, 3H), 6.78-6.84 (m, 2H), 7.14 (m, 1H), 7.21 (m, 1H), 7.48 (dd, 1H), 8.00 (br s, 1H), 8.20 (d, 1H).

Compound 150b: Z-Isomer, Yield 4%

3-((13S,15R,Z)-3-fluoro-17-(hydroxyimino)-13-methyl-7,8,9,11,12,13,14,15,16,17-decahydro-6H-cyclopenta[a]phenanthren-15-yl)-N-(3-fluoropyridin-2-yl)propanamide

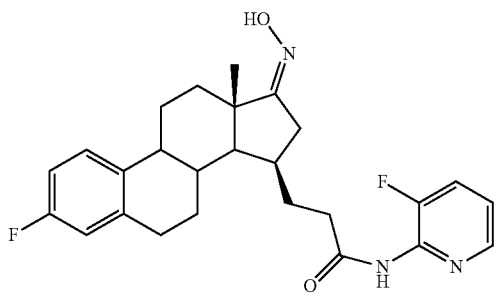 [SMILES: C[C@]12CCC3c4ccc(F)cc4CCC3C1[C@H](CCC(=O)Nc1ncccc1F)C/C2=N/O]

$^1$H-NMR (400 MHz, CDCl$_3$): 1.31 (s, 3H), 1.43-1.87 (m, 7H), 2.16 (m, 2H), 2.30-2.38 (m, 4H), 2.53 (d, 1H), 2.60-3.04 (m, 5H), 6.81-6.85 (m, 2H), 7.16-7.24 (m, 2H), 7.53 (m, 1H), 8.17 (d, 1H), 9.74 (br s, 1H).

Compound 151

N-(3,5-difluoropyridin-2-yl)-3-((13S,15R)-3-fluoro-13-methyl-17-oxo-7,8,9,11,12,13,14,15,16,17-decahydro-6H-cyclopenta[a]phenanthren-15-yl)propanamide

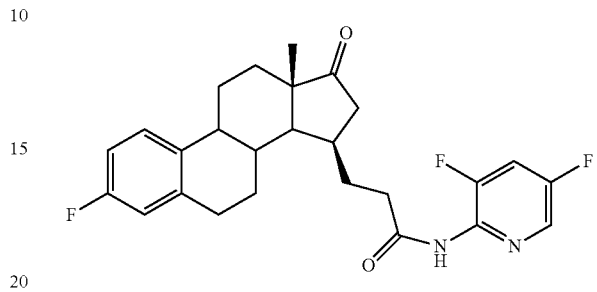

Compound 151 was synthesized in 96% yield by the method used in the preparation of the Compound 1 in THF by using acid SM-XV and 2-amino-3,5-difluoropyridine as starting materials in 3 hours reaction time.

$^1$H-NMR (400 MHz, DMSO-d$_6$): 0.98 (s, 3H), 1.34-1.74 (m, 7H), 1.88-1.96 (m, 1H), 2.11-2.48 (m, 8H), 2.88 (m, 2H), 6.92 (m, 2H), 7.29 (dd, 1H), 8.01 (dd, 1H), 8.34 (d, 1H), 10.31 (s, 1H).

Compound 152

N-(3,5-difluoropyridin-2-yl)-3-((13S,15R, E)-3-fluoro-17-(hydroxyimino)-13-methyl-7,8,9,11,12,13,14,15,16,17-decahydro-6H-cyclopenta[a]phenanthren-15-yl)propanamide

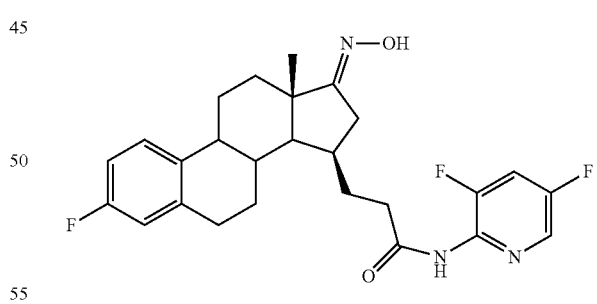

Compound 152 was prepared in 55% yield from Compound 151 by the same method as with Compound 2 in 30 minutes reaction time.

$^1$H-NMR (400 MHz, DMSO-d$_6$): 1.03 (s, 3H), 1.35-1.65 (m, 6H), 1.85-2.44 (m, 9H), 2.66-2.73 (m, 1H), 2.86 (m, 2H), 6.89-6.94 (m, 2H), 7.29 (m, 1H), 8.00 (dd, 1H), 8.34 (d, 1H), 10.19 (s, 1H), 10.32 (s, 1H).

155

Compound 153

3-((13S,15R)-3-fluoro-13-methyl-17-oxo-7,8,9,11,12,13,14,15,16,17-decahydro-6H-cyclopenta[a]phenanthren-15-yl)-N-(5-morpholinopyridin-2-yl)propanamide

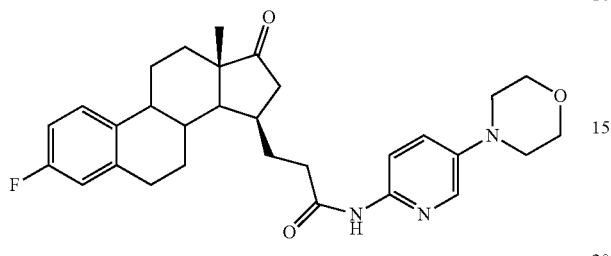

Compound 153 was synthesized in 63% yield after chromatographic purification by the method used in the preparation of the compound 1 in DCM by using acid SM-XV and 5-morpholinopyridin-2-amine as starting materials and triethylamine as a base in 2 hours reaction time.

$^1$H-NMR (400 MHz, DMSO-d6): 0.98 (s, 3H), 1.30-2.47 (m, 16H), 2.81-2.96 (m, 2H), 3.06-3.12 (m, 4H), 3.70-3.78 (m, 4H), 6.90-6.95 (m, 2H), 7.25-7.32 (t, 1H), 7.40 (dd, 1H), 7.95-8.01 (m, 2H), 10.28 (s, 1H).

Compound 154

3-((13S,15R,E)-3-fluoro-17-(hydroxyimino)-13-methyl-7,8,9,11,12,13,14,15,16,17-decahydro-6H-cyclopenta[a]phenanthren-15-yl)-N-(5-morpholinopyridin-2-yl)propanamide

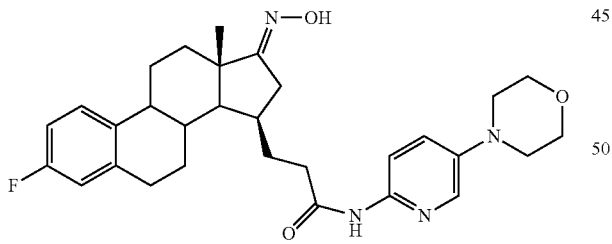

Compound 154 was prepared in 65% yield after chromatographic purification from the compound 153 by the same method as with Example 2 at 50-70° C. in 4 hours reaction time.

$^1$H-NMR (400 MHz, DMSO-d6): 1.03 (s, 3H), 1.30-2.47 (m, 15H), 2.60-2.70 (m, 1H), 2.81-2.96 (m, 2H), 3.06-3.12 (m, 4H), 3.70-3.78 (m, 4H), 6.90-6.95 (m, 2H), 7.25-7.32 (t, 1H), 7.40 (dd, 1H), 7.95-8.01 (m, 2H), 10.17 (s, 1H), 10.29 (s, 1H).

156

Compound 155

3-((13S,15R)-3-chloro-13-methyl-17-oxo-7,8,9,11,12,13,14,15,16,17-decahydro-6H-cyclopenta[a]phenanthren-15-yl)-N-(4-fluoropyridin-2-yl)propanamide

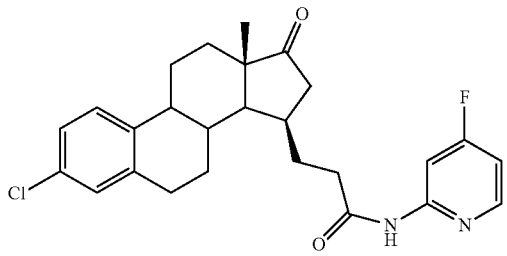 [SMILES: C[C@]12CCC3c4ccc(Cl)cc4CCC3C1[C@H](CCC(=O)Nc1cc(F)ccn1)CC2=O]

Compound 155 was synthesized in 90% yield by the method used in the preparation of the compound 1 in THF by using acid SM-XVII and 2-amino-4-fluoropyridine as starting materials in 4 hours reaction time.

$^1$H-NMR (400 MHz, DMSO-d6): 0.98 (s, 3H), 1.30-2.47 (m, 16H), 2.81-2.96 (m, 2H), 7.00-7.06 (m, 1H), 7.14-7.17 (m, 2H), 7.27-7.31 (m, 1H), 7.92 (dd, 1H), 8.30-8.37 (m, 1H), 10.82 (s, 1H).

Compound 156

3-((13S,15R,E)-3-chloro-17-(hydroxyimino)-13-methyl-7,8,9,11,12,13,14,15,16,17-decahydro-6H-cyclopenta[a]phenanthren-15-yl)-N-(4-fluoropyridin-2-yl)propanamide

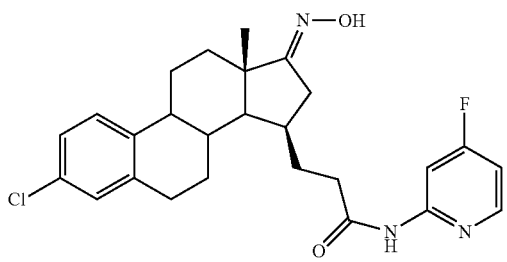 [SMILES: C[C@]12CCC3c4ccc(Cl)cc4CCC3C1[C@H](CCC(=O)Nc1cc(F)ccn1)C/C2=N\O]

Compound 156 was prepared in 41% yield after chromatographic purification from the compound 155 by the same method as with Example 2 in 2 hours reaction time.

$^1$H-NMR (400 MHz, CDCl$_3$): 1.15 (s, 3H), 1.35-2.65 (m, 15H), 2.81-3.00 (m, 3H), 6.80-6.83 (m, 1H), 7.08-7.11 (m, 2H), 7.15-7.21 (m, 1H), 8.04 (dd, 1H), 8.20-8.25 (m, 1H), 8.50 (br s, 1H), 8.52 (br s, 1H).

157

Compound 157

N-(4-fluoropyridin-2-yl)-3-((13S,15R)-13-methyl-17-oxo-7,8,9,11,12,13,14,15,16,17-decahydro-6H-cyclopenta[a]phenanthren-15-yl)propanamide

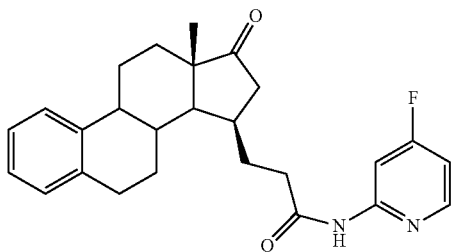 [SMILES: C[C@]12CCC3c4ccccc4CCC3C1[C@H](CCC(=O)Nc1cc(F)ccn1)CC2=O]

Compound 157 was synthesized in 78% yield by the method used in the preparation of the compound 1 in THF by using acid SM-XXVI and 290 mol-% of 2-amino-4-fluoropyridine as starting materials in overnight reaction time.

$^1$H-NMR (400 MHz, DMSO-d6): 0.98 (s, 3H), 1.30-2.47 (m, 16H), 2.81-2.96 (m, 2H), 7.00-7.06 (m, 1H), 7.07-7.16 (m, 3H), 7.25-7.30 (m, 1H), 7.92 (dd, 1H), 8.30-8.37 (m, 1H), 10.82 (s, 1H).

Compound 158

N-(4-fluoropyridin-2-yl)-3-((13S,15R,E)-17-(hydroxyimino)-13-methyl-7,8,9,11,12,13,14,15,16,17-decahydro-6H-cyclopenta[a]phenanthren-15-yl)propanamide

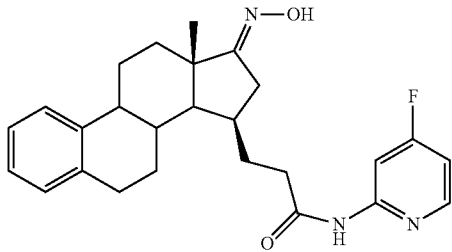 [SMILES: C[C@]12CCC3c4ccccc4CCC3C1[C@H](CCC(=O)Nc1cc(F)ccn1)C/C2=N\O]

Compound 158 was prepared in 68% yield from the compound 157 by the same method as with Example 2 in 1.5 hours reaction time.

$^1$H-NMR (400 MHz, DMSO-d6): 1.03 (s, 3H), 1.30-2.45 (m, 15H), 2.60-2.72 (m, 1H), 2.81-2.96 (m, 2H), 7.00-7.06 (m, 1H), 7.07-7.16 (m, 3H), 7.25-7.30 (m, 1H), 7.92 (dd, 1H), 8.30-8.37 (m, 1H), 10.18 (s, 1H), 10.84 (s, 1H).

158

Compound 159

N-(3-fluoropyridin-2-yl)-3-((13S,15R)-13-methyl-17-oxo-7,8,9,11,12,13,14,15,16,17-decahydro-6H-cyclopenta[a]phenanthren-15-yl)propanamide

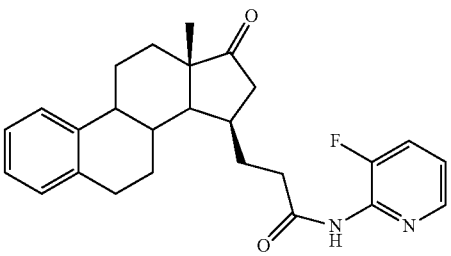 [SMILES: C[C@]12CCC3c4ccccc4CCC3C1[C@H](CCC(=O)Nc1ncccc1F)CC2=O]

Compound 159 was synthesized in 88% yield by the method used in the preparation of the compound 1 in THF by using acid SM-XXVI and 2-amino-3-fluoropyridine as starting materials in overnight reaction time.

$^1$H-NMR (400 MHz, DMSO-d6): 0.99 (s, 3H), 1.30-2.47 (m, 16H), 2.81-2.96 (m, 2H), 7.05-7.16 (m, 3H), 7.26-7.28 (m, 1H), 7.30-7.37 (m, 1H), 7.73-7.79 (m, 1H), 8.23-8.25 (m, 1H), 10.27 (s, 1H).

Compound 160

N-(3-fluoropyridin-2-yl)-3-((13S,15R,E)-17-(hydroxyimino)-13-methyl-7,8,9,11,12,13,14,15,16,17-decahydro-6H-cyclopenta[a]phenanthren-15-yl)propanamide

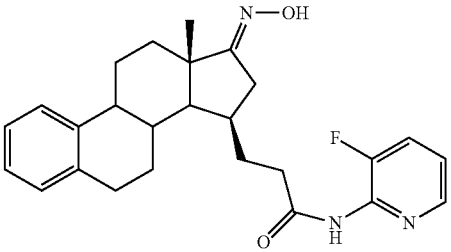 [SMILES: C[C@]12CCC3c4ccccc4CCC3C1[C@H](CCC(=O)Nc1ncccc1F)C/C2=N\O]

Compound 160 was prepared in 95% yield from the compound 159 by the same method as with Example 2 in 1 hour reaction time.

$^1$H-NMR (400 MHz, DMSO-d6): 1.04 (s, 3H), 1.30-2.47 (m, 15H), 2.65-2.74 (m, 1H), 2.80-2.96 (m, 2H), 7.05-7.16 (m, 3H), 7.26-7.28 (m, 1H), 7.30-7.37 (m, 1H), 7.73-7.79 (m, 1H), 8.23-8.25 (m, 1H), 10.18 (s, 1H), 10.28 (s, 1H).

Compound 161

3-((13S,15R)-3-chloro-13-methyl-17-oxo-7,8,9,11,12,13,14,15,16,17-decahydro-6H-cyclopenta[a]phenanthren-15-yl)-N-(3-fluoropyridin-2-yl)propanamide

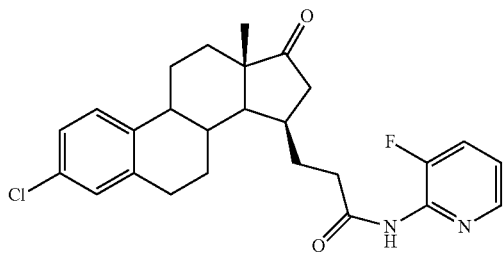 [SMILES: C[C@]12CCC3c4ccc(Cl)cc4CCC3C1[C@H](CCC(=O)Nc1ncccc1F)CC2=O]

Compound 161 was synthesized in 81% yield by the method used in the preparation of the compound 1 in THF by using acid SM-XVII and 2-amino-3-fluoropyridine as starting materials in overnight reaction time.

$^1$H-NMR (400 MHz, DMSO-d6): 0.98 (s, 3H), 1.30-2.47 (m, 16H), 2.81-2.94 (m, 2H), 7.15-7.16 (m, 2H), 7.28-7.30 (m, 1H), 7.32-7.36 (m, 1H), 7.73-7.79 (m, 1H), 8.23-8.25 (d, 1H), 10.27 (s, 1H).

Compound 162

3-((13S,15R,E)-3-chloro-17-(hydroxyimino)-13-methyl-7,8,9,11,12,13,14,15,16,17-decahydro-6H-cyclopenta[a]phenanthren-15-yl)-N-(3-fluoropyridin-2-yl)propanamide

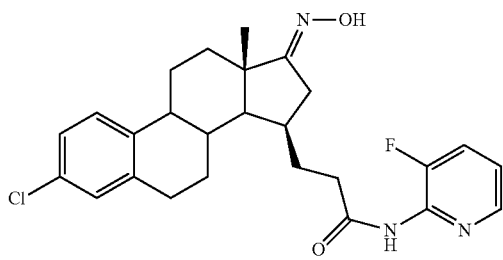 [SMILES: C[C@]12CCC3c4ccc(Cl)cc4CCC3C1[C@H](CCC(=O)Nc1ncccc1F)C/C2=N\O]

Compound 162 was prepared in 88% yield from the compound 161 by the same method as with Example 2 in 2.5 hours reaction time.

$^1$H-NMR (400 MHz, DMSO-d6): 1.03 (s, 3H), 1.30-2.47 (m, 15H), 2.65-2.73 (m, 1H), 2.81-2.94 (m, 2H), 7.14-7.16 (m, 2H), 7.28-7.30 (m, 1H), 7.31-7.36 (m, 1H), 7.73-7.77 (m, 1H), 8.23-8.24 (d, 1H), 10.19 (s, 1H), 10.28 (s, 1H).

Compound 163

3-((13S,15R)-3-chloro-13-methyl-17-oxo-7,8,9,11,12,13,14,15,16,17-decahydro-6H-cyclopenta[a]phenanthren-15-yl)-N-(3,5-difluoropyridin-2-yl)propanamide

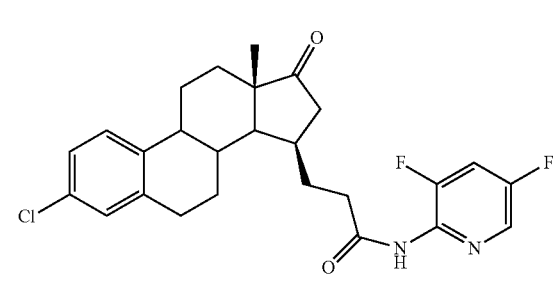 [SMILES: C[C@]12CCC3c4ccc(Cl)cc4CCC3C1[C@H](CCC(=O)Nc1ncc(F)cc1F)CC2=O]

Compound 163 was synthesized in 90% yield by the method used in the preparation of the compound 1 in THF by using acid SM-XVII and 2-amino-3,5-difluoropyridine as starting materials in 5 hours reaction time.

$^1$H-NMR (400 MHz, DMSO-d6): 0.98 (s, 3H), 1.30-2.47 (m, 16H), 2.80-2.94 (m, 2H), 7.15-7.16 (m, 2H), 7.28-7.30 (m, 1H), 7.98-8.03 (m, 1H), 8.34-8.35 (m, 1H), 10.31 (s, 1H).

Compound 164

3-((13S,15R,E)-3-chloro-17-(hydroxyimino)-13-methyl-7,8,9,11,12,13,14,15,16,17-decahydro-6H-cyclopenta[a]phenanthren-15-yl)-N-(3,5-difluoropyridin-2-yl)propanamide

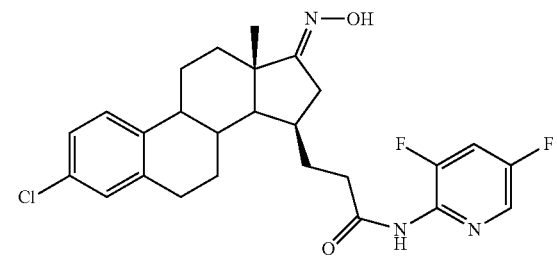 [SMILES: C[C@]12CCC3c4ccc(Cl)cc4CCC3C1[C@H](CCC(=O)Nc1ncc(F)cc1F)C/C2=N\O]

Compound 164 was prepared in 93% yield from the compound 163 by the same method as with Example 2 in 4 hours reaction time.

$^1$H-NMR (400 MHz, DMSO-d6): 1.03 (s, 3H), 1.30-2.47 (m, 15H), 2.65-2.74 (m, 1H), 2.80-2.94 (m, 2H), 7.14-7.16 (m, 2H), 7.28-7.30 (m, 1H), 7.98-8.03 (m, 1H), 8.34-8.35 (m, 1H), 10.19 (s, 1H), 10.32 (s, 1H).

Compound 165

N-(3,5-difluoropyridin-2-yl)-3-((13S,15R)-13-methyl-17-oxo-7,8,9,11,12,13,14,15,16,17-decahydro-6H-cyclopenta[a]phenanthren-15-yl)propanamide

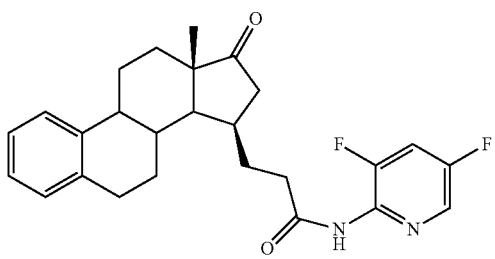 [SMILES: C[C@]12CCC3c4ccccc4CCC3C1[C@H](CCC(=O)Nc1ncc(F)cc1F)CC2=O]

Compound 165 was synthesized in 90% yield by the method used in the preparation of the compound 1 in THF by using acid SM-XXVI and 2-amino-3,5-difluoropyridine as starting materials in overnight reaction time.

$^1$H-NMR (400 MHz, DMSO-d6): 0.98 (s, 3H), 1.30-2.47 (m, 16H), 2.80-2.94 (m, 2H), 7.05-7.15 (m, 3H), 7.26-7.28 (m, 1H), 7.98-8.03 (m, 1H), 8.34-8.35 (m, 1H), 10.31 (s, 1H).

Compound 166

N-(3,5-difluoropyridin-2-yl)-3-((13S,15R,E)-17-(hydroxyimino)-13-methyl-7,8,9,11,12,13,14,15,16,17-decahydro-6H-cyclopenta[a]phenanthren-15-yl)propanamide

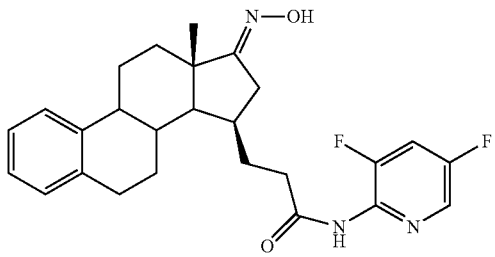 [SMILES: C[C@]12CCC3c4ccccc4CCC3C1[C@H](CCC(=O)Nc1ncc(F)cc1F)C/C2=N\O]

Compound 166 was prepared in 71% yield after chromatographic purification from the compound 165 by the same method as with Example 2 in 3 hours reaction time.

$^1$H-NMR (400 MHz, DMSO-d6): 1.04 (s, 3H), 1.30-2.47 (m, 15H), 2.65-2.74 (m, 1H), 2.80-2.94 (m, 2H), 7.05-7.15 (m, 3H), 7.26-7.28 (m, 1H), 7.98-8.03 (m, 1H), 8.34-8.35 (m, 1H), 10.18 (s, 1H), 10.32 (s, 1H).

Compound 167

N-(6-fluoropyridin-2-yl)-3-((13S,15R)-13-methyl-17-oxo-7,8,9,11,12,13,14,15,16,17-decahydro-6H-cyclopenta[a]phenanthren-15-yl)propanamide

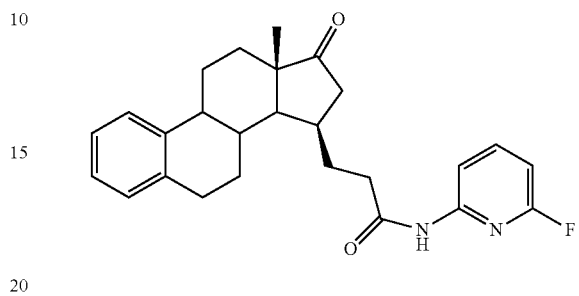

Compound 167 was synthesized in 92% yield by the method used in the preparation of the compound 1 in THF by using acid SM-XXVI and 2-amino-6-fluoropyridine as starting materials in 4 hours reaction time.

$^1$H-NMR (400 MHz, DMSO-d6): 0.98 (s, 3H), 1.30-2.47 (m, 16H), 2.80-2.95 (m, 2H), 6.83 (dd, 1H), 7.05-7.15 (m, 3H), 7.26-7.28 (m, 1H), 7.91-7.97 (m, 1H), 8.00-8.03 (m, 1H), 10.69 (s, 1H).

Compound 168

N-(6-fluoropyridin-2-yl)-3-((13S,15R,E)-17-(hydroxyimino)-13-methyl-7,8,9,11,12,13,14,15,16,17-decahydro-6H-cyclopenta[a]phenanthren-15-yl)propanamide

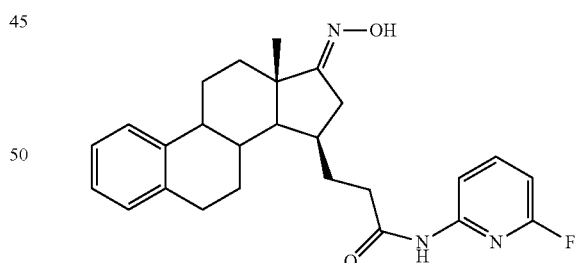

Compound 168 was prepared in 85% yield from the compound 167 by the same method as with Example 2 in 2 hours reaction time.

$^1$H-NMR (400 MHz, DMSO-d6): 1.03 (s, 3H), 1.30-2.47 (m, 15H), 2.60-2.71 (m, 1H), 2.80-2.95 (m, 2H), 6.83 (dd, 1H), 7.05-7.15 (m, 3H), 7.26-7.28 (m, 1H), 7.91-7.97 (m, 1H), 8.00-8.03 (m, 1H), 10.18 (s, 1H), 10.70 (s, 1H).

Compound 169

3-((13S,15R)-3-chloro-13-methyl-17-oxo-7,8,9,11,12,13,14,15,16,17-decahydro-6H-cyclopenta[a]phenanthren-15-yl)-N-(6-fluoropyridin-2-yl)propanamide

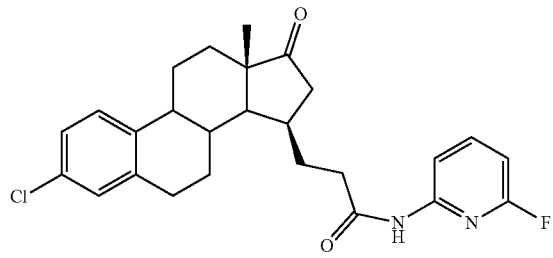 [SMILES: C[C@]12CCC3c4ccc(Cl)cc4CCC3C1[C@H](CCC(=O)Nc1cccc(F)n1)CC2=O]

Compound 169 was synthesized in 71% yield by the method used in the preparation of the compound 1 in THF by using acid SM-XVII and 2-amino-6-fluoropyridine as starting materials in overnight reaction time.

$^1$H-NMR (400 MHz, DMSO-d6): 0.97 (s, 3H), 1.30-2.47 (m, 16H), 2.80-2.95 (m, 2H), 6.83 (dd, 1H), 7.14-7.17 (m, 2H), 7.28-7.31 (m, 1H), 7.91-7.97 (m, 1H), 8.00-8.03 (m, 1H), 10.68 (s, 1H).

Compound 170

3-((13S,15R,E)-3-chloro-17-(hydroxyimino)-13-methyl-7,8,9,11,12,13,14,15,16,17-decahydro-6H-cyclopenta[a]phenanthren-15-yl)-N-(6-fluoropyridin-2-yl)propanamide

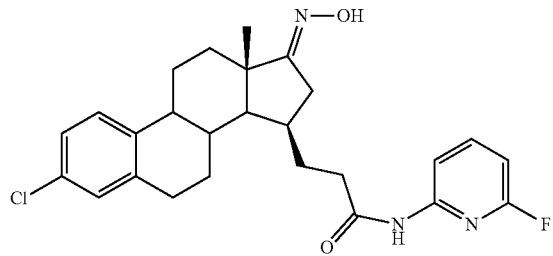 [SMILES: C[C@]12CCC3c4ccc(Cl)cc4CCC3C1[C@H](CCC(=O)Nc1cccc(F)n1)C/C2=N\O]

Compound 170 was prepared in 73% yield from the compound 169 by the same method as with Example 2 in 3 hours reaction time.

$^1$H-NMR (400 MHz, DMSO-d6): 1.02 (s, 3H), 1.30-2.47 (m, 15H), 2.60-2.70 (m, 1H), 2.80-2.95 (m, 2H), 6.83 (dd, 1H), 7.13-7.17 (m, 2H), 7.27-7.30 (m, 1H), 7.90-7.97 (m, 1H), 8.00-8.03 (m, 1H), 10.18 (s, 1H), 10.70 (s, 1H).

Compound 171

6-(3-((13S,15R)-3-chloro-13-methyl-17-oxo-7,8,9,11,12,13,14,15,16,17-decahydro-6H-cyclopenta[a]phenanthren-15-yl)propanamido)-N,N-dimethylnicotinamide

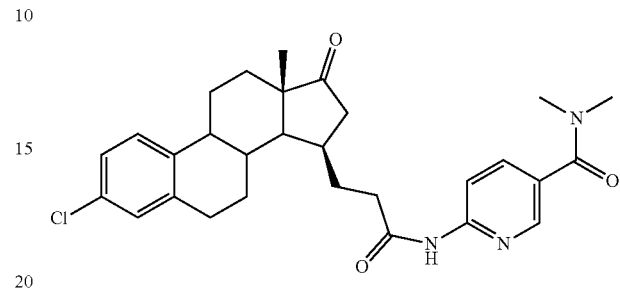

Compound 171 was synthesized in 85% yield by the method used in the preparation of the compound 1 in THF by using acid SM-XVII and 6-amino-N,N-dimethylpyridine-3-carboxamide as starting materials in overnight reaction time.

$^1$H-NMR (400 MHz, DMSO-d6): 0.98 (s, 3H), 1.30-2.47 (m, 16H), 2.80-2.95 (m, 2H), 2.97 (s, 6H), 7.14-7.17 (m, 2H), 7.28-7.31 (m, 1H), 7.85 (dd, 1H), 8.14 (d, 1H), 8.38 (d, 1H), 10.71 (s, 1H).

Compound 172

6-(3-((13S,15R,E)-3-chloro-17-(hydroxyimino)-13-methyl-7,8,9,11,12,13,14,15,16,17-decahydro-6H-cyclopenta[a]phenanthren-15-yl)propanamido)-N,N-dimethylnicotinamide

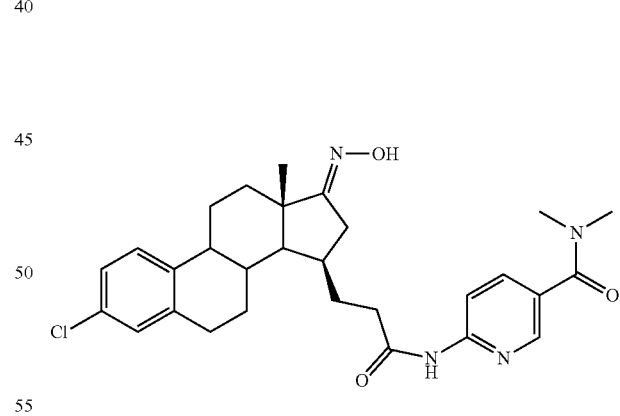

Compound 172 was prepared in 78% yield from the compound 171 by the same method as with Example 2 in 1 hour reaction time.

$^1$H-NMR (400 MHz, DMSO-d6): 1.03 (s, 3H), 1.30-2.47 (m, 15H), 2.60-2.72 (m, 1H), 2.80-2.95 (m, 2H), 2.98 (s, 6H), 7.14-7.17 (m, 2H), 7.28-7.31 (m, 1H), 7.85 (dd, 1H), 8.14 (d, 1H), 8.38 (d, 1H), 10.18 (s, 1H), 10.73 (s, 1H).

Compound 173

3-((13S,15R)-3-chloro-13-methyl-17-oxo-7,8,9,11,12,13,14,15,16,17-decahydro-6H-cyclopenta[a]phenanthren-15-yl)-N-(2-oxo-1,2,5,6,7,8-hexahydroquinolin-3-yl)propanamide

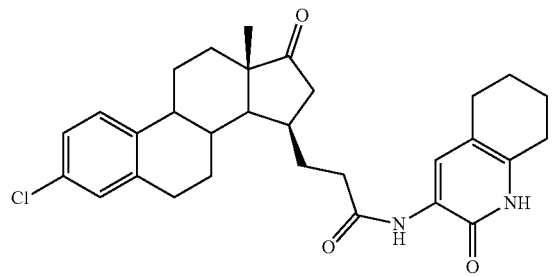 [SMILES: C[C@]12CCC3c4ccc(Cl)cc4CCC3C1[C@H](CCC(=O)Nc1cc3c([nH]c1=O)CCCC3)CC2=O]

Compound 173 was synthesized in 79% yield by the method used in the preparation of the compound 1 in THF by using acid SM-XVII and 3-amino-1,2,5,6,7,8-hexahydroquinolin-2-one as starting materials in overnight reaction time.

$^1$H-NMR (400 MHz, DMSO-d6): 0.97 (s, 3H), 1.30-2.47 (m, 24H), 2.80-2.95 (m, 2H), 7.14-7.17 (m, 2H), 7.28-7.31 (m, 1H), 8.01 (s, 1H), 9.14 (s, 1H), 11.68 (s, 1H).

Compound 174

3-((13S,15R,E)-3-chloro-17-(hydroxyimino)-13-methyl-7,8,9,11,12,13,14,15,16,17-decahydro-6H-cyclopenta[a]phenanthren-15-yl)-N-(2-oxo-1,2,5,6,7,8-hexahydroquinolin-3-yl)propanamide

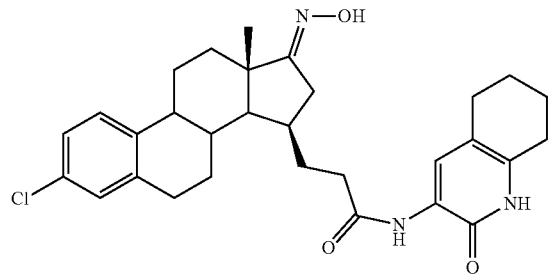 [SMILES: C[C@]12CCC3c4ccc(Cl)cc4CCC3C1[C@H](CCC(=O)Nc1cc3c([nH]c1=O)CCCC3)C/C2=N\O]

Compound 174 was prepared in 83% yield from the compound 173 by the same method as with Example 2 in 3 hours reaction time.

$^1$H-NMR (400 MHz, DMSO-d6): 1.02 (s, 3H), 1.29-2.47 (m, 23H), 2.59-2.68 (m, 1H), 2.80-2.94 (m, 2H), 7.14-7.17 (m, 2H), 7.28-7.31 (m, 1H), 8.01 (s, 1H), 9.16 (s, 1H), 10.17 (s, 1H), 11.67 (br s, 1H).

Compound 175

6-(3-((13S,15R)-4-fluoro-13-methyl-17-oxo-7,8,9,11,12,13,14,15,16,17-decahydro-6H-cyclopenta[a]phenanthren-15-yl)propanamido)-N,N-dimethylnicotinamide

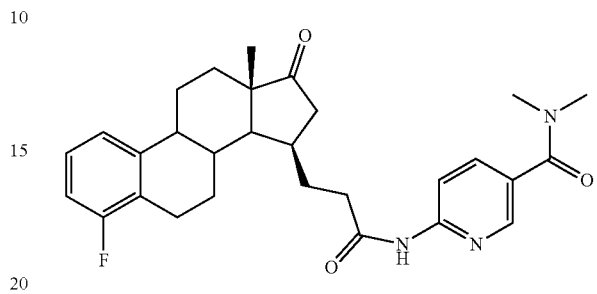

Compound 175 was synthesized in quantitative yield by the method used in the preparation of the compound 1 in THF by using acid SM-IX and 6-amino-N,N-dimethylpyridine-3-carboxamide as starting materials in overnight reaction time.

$^1$H-NMR (400 MHz, DMSO-d6): 0.98 (s, 3H), 1.30-2.47 (m, 16H), 2.66-2.94 (m, 2H), 2.98 (s, 6H), 6.94-7.00 (m, 1H), 7.12-7.21 (m, 2H), 7.85 (dd, 1H), 8.14 (d, 1H), 8.38 (d, 1H), 10.72 (s, 1H).

Compound 176

6-(3-((13S,15R,E)-4-fluoro-17-(hydroxyimino)-13-methyl-7,8,9,11,12,13,14,15,16,17-decahydro-6H-cyclopenta[a]phenanthren-15-yl)propanamido)-N,N-dimethylnicotinamide

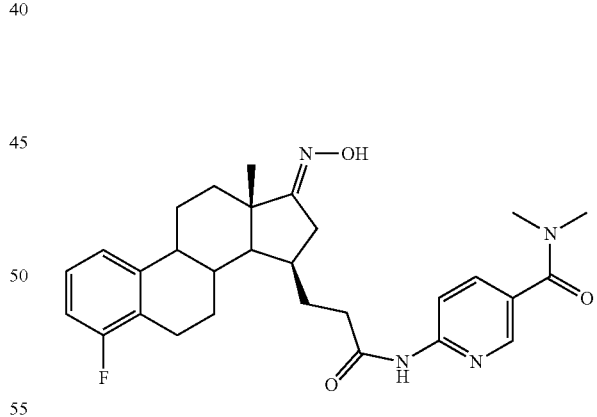

Compound 176 was prepared in 91% yield from the compound 175 by the same method as with Example 2 in 1 hour reaction time.

$^1$H-NMR (400 MHz, DMSO-d6): 1.04 (s, 3H), 1.30-2.47 (m, 15H), 2.63-2.94 (m, 3H), 2.98 (s, 6H), 6.93-7.00 (m, 1H), 7.08-7.21 (m, 2H), 7.85 (dd, 1H), 8.15 (d, 1H), 8.38 (d, 1H), 10.19 (s, 1H), 10.73 (s, 1H).

Compound 177

3-((13S,15R)-4-fluoro-13-methyl-17-oxo-7,8,9,11,12,13,14,15,16,17-decahydro-6H-cyclopenta[a]phenanthren-15-yl)-N-(2-oxo-1,2,5,6,7,8-hexahydroquinolin-3-yl)propanamide

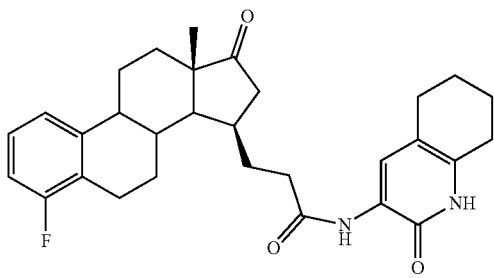 [SMILES: C[C@]12CCC3c4cccc(F)c4CCC3C1[C@H](CCC(=O)Nc1cc3c([nH]c1=O)CCCC3)CC2=O]

Compound 177 was synthesized in 86% yield by the method used in the preparation of the compound 1 in THF by using acid SM-IX and 3-amino-1,2,5,6,7,8-hexahydroquinolin-2-one as starting materials in overnight reaction time.

$^1$H-NMR (400 MHz, DMSO-d6): 0.97 (s, 3H), 1.30-2.47 (m, 24H), 2.65-2.93 (m, 2H), 6.94-7.00 (m, 1H), 7.12-7.21 (m, 2H), 8.01 (s, 1H), 9.15 (s, 1H), 11.68 (br s, 1H).

Compound 178

3-((13S,15R,E)-4-fluoro-17-(hydroxyimino)-13-methyl-7,8,9,11,12,13,14,15,16,17-decahydro-6H-cyclopenta[a]phenanthren-15-yl)-N-(2-oxo-1,2,5,6,7,8-hexahydroquinolin-3-yl)propanamide

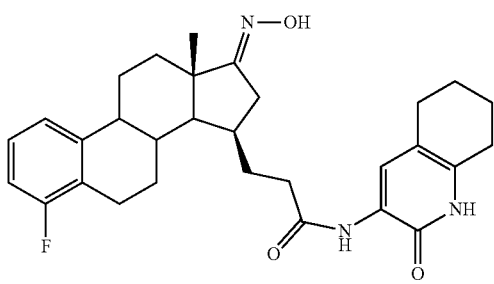

Compound 178 was prepared in 78% yield from the compound 177 by the same method as with Example 2 in 2 hours reaction time.

$^1$H-NMR (400 MHz, DMSO-d6): 1.02 (s, 3H), 1.30-2.47 (m, 23H), 2.58-2.93 (m, 3H), 6.94-7.00 (m, 1H), 7.10-7.21 (m, 2H), 8.02 (s, 1H), 9.17 (s, 1H), 10.17 (s, 1H), 11.67 (br s, 1H).

Pharmacological Tests

The following tests are provided to demonstrate the present invention in illustrative way and should not be considered as limiting in the scope of invention. Further, the concentrations of the compound in the assays are exemplary and should not be taken as limiting. A person skilled in the art may define pharmaceutically relevant concentrations with method known in the art.

Inhibition of 17β-Hydroxysteroid Dehydrogenase Type 1 Enzyme

17β-HSD1 production and isolation: Recombinant baculovirus was generated by the "Bac to Bac Expression System" (Invitrogen). Recombinant bacmid was transfected to Sd9 insect cells using "Cellfectin Reagent" (Invitrogen). 60 h later cells were harvested; the microsomal fraction was isolated as described by Puranen, T. J., Poutanen, M. H., Peltoketo, H. E., Vihko, P. T. and Vihko, R. K. (1994) Site-directed mutagenesis of the putative active site of human 17 β-hydroxysteroid dehydrogenase type 1. Biochem. J. 304: 289-293. Aliquots were stored frozen until determination of enzymatic activity.

Assay—Inhibition of Recombinant Human 17β-HSD1:

Recombinant protein (1 μg/ml) was incubated in 20 mM KH2PO4 pH 7.4 with 30 nM estrone (including 800 000 cpm/ml of $^3$H-estrone) and 1 mM NADPH for 30 min at RT, in the presence of the potential inhibitor at concentrations 1 μM or 0.1 μM. Inhibitor stock solutions were prepared in DMSO. Final concentration of DMSO was adjusted to 1% in all samples. The enzyme reaction was stopped by addition of 10% trichloroacetic acid (final concentration). Samples were centrifuged in a microtiter plate at 4000 rpm for 10 min. Supernatants were applied to reverse phase HPLC on a Waters Symmetry C18 column, equipped with a Waters Sentry Guard column. Isocratic HPLC runs were performed at RT at a flow rate of 1 ml/min in acetonitrile:water 48:52 as running solvent. Radioactivity was monitored in the eluate by a Scintillation Analyzer. Total radioactivity for estrone and estradiol were determined in each sample and percent conversion of estrone to estradiol was calculated according to the following formula:

$$\% \text{ conversion} = 100 \times \frac{\{(\text{cpm estradiol in sample with inhibitor})/[(\text{cpm estrone in sample with inhibitor}) + (\text{cpm estradiol in sample with inhibitor})]\}}{[(\text{cpm estradiol in sample without inhibitor})/[(\text{cpm estrone in sample without inhibitor}) + (\text{cpm estradiol in sample without inhibitor})]\}}.$$

Percent inhibition was calculated flowingly: % inhibition=100−% conversion

The values % inhibition were determined for exemplified compounds and the results are summarized in Table 2.

Inhibition of the 17β-Hydroxysteroid Dehydrogenase Type 2 Enzyme

17β-HSD2 Production and Isolation:

Similarly to 17β-HSD1 the Recombinant baculovirus was generated by the "Bac to Bac Expression System" (Invitrogen). Recombinant bacmid was transfected to Sd9 insect cells using "Cellfectin Reagent" (Invitrogen). 60 h later cells were harvested and supernatant were fractionated by the following protocol:

cells were dissolved into 40 ml of A-buffer (40 mM TRIS, pH 8.0, 20% glycerol, 20 μM NAD, 0.4 mM PMSF, 150 mM NaCl, 0.5% dodecyl-β-maltoside+protease inhibitor cocktail)
cells were sonicated
lysate was incubated on ice for 15 min
lysate was centrifuged 5000 rpm 15 min, +4° C.
centrifugation of the supernatant 180 000 g 30 min, +4° C.

pellet was dissolved into 8 ml of A-buffer
not resuspended material was removed by centrifugation 5000 rpm 15 min, +4° C.
the clear supernatant was divided into 100 µl aliquots and were stored frozen until determination of enzymatic activity.

The amount of 17β-HSD2 was analysed by immunoblotting and total protein concentration of each extract batch was determined.

Assay—Inhibition of Recombinant Human 17β-HSD2:

Recombinant protein (4 µg/ml) was incubated in 20 mM $KH_2PO_4$ pH 8.5 with 50 nM estradiol (including 800 000 cpm/ml of $^3H$-estradiol) and 1 mM NADH for 30 min at RT, in the presence of the potential inhibitor at concentrations 1 µM or 0.1 µM. Inhibitor stock solutions were prepared in DMSO. Final concentration of DMSO was adjusted to 1% in all samples. The enzyme reaction was stopped by addition of 10% trichloroacetic acid (final concentration). Samples were centrifuged in a microtiter plate at 4000 rpm for 10 min. Supernatants were applied to reverse phase HPLC on a Waters Symmetry C18 column, equipped with a Waters Sentry Guard column. Isocratic HPLC runs were performed at RT at a flow rate of 1 ml/min in acetonitrile:water 48:52 as running solvent. Radioactivity was monitored in the eluate by a Scintillation Analyzer. Total radioactivity for estrone and estradiol were determined in each sample and percent conversion of estradiol to estrone was calculated according to the following formula:

$$\% \text{ conversion} = 100 \times \frac{\{(\text{cpm estrone in sample with inhibitor})/[(\text{cpm estradiol in sample with inhibitor}) + (\text{cpm estrone in sample with inhibitor})]\}}{[(\text{cpm estrone in sample without inhibitor})/[(\text{cpm estradiol in sample without inhibitor}) + (\text{cpm estrone in sample without inhibitor})]\}}$$

Percent inhibition was calculated flowingly: % inhibition=100–% conversion

The values % inhibition were determined for exemplified compounds and the results are summarized in Table 2.

Inhibition of the Estrone to Estradiol Conversion in a Rabbit Tissue Homogenate

The assay is based on an enzymatic reaction where HSD1 enzyme that is expressed in rabbit placenta tissue converts its natural substance estrone (E1) to estradiol (E2) in the presence of a co-factor β-NADPH.

Homogenization of Rabbit Placenta Tissue:

Weight a piece of the frozen tissue into a Precellys ck28 bead tube. Add buffer solution (20 mM $KH_2PO_4$ with 1 mM EDTA, pH 7.4) in 1:2 ratio (e.g. 300 mg of tissue: 600 µl reaction buffer solution). Insert the bead tubes to homogenizer and homogenize 2×30 s. 6000 rpm. Centrifuged 5 min., 2600 rpm at +4° C. and collect supernatant. Aliquots of homogenate are stored in −80° C.

Assay—Inhibition of E1 to E2 Conversion in Rabbit Placenta Tissue:

The reaction takes place in a buffer solution (20 mM $KH_2PO_4$ with 1 mM EDTA, pH 7.4), including appropriate amount of rabbit placenta homogenate, co-factor (1 mM β-NADPH), Substrate (30 nM estrone), labelled substrate as tracer (5 nM [$^3H$]-estrone). During a 30-minute incubation part of the estrone is converted to estradiol. The reaction is stopped by lowering the pH to 1 with 10% trichloro acetic acid (TCA). The substrate and conversion products are analyzed by HPLC and a Scintillation counter analyzer. Total radioactivity for estrone and estradiol were determined in each sample and percent conversion of estrone to estradiol was calculated according to the following formula:

$$\% \text{ conversion} = 100 \times \frac{\{(\text{cpm estradiol in sample with inhibitor})/[(\text{cpm estrone in sample with inhibitor}) + (\text{cpm estradiol in sample with inhibitor})]\}}{[(\text{cpm estradiol in sample without inhibitor})/[(\text{cpm estrone in sample without inhibitor}) + (\text{cpm estradiol in sample without inhibitor})]\}}$$

Percent inhibition was calculated flowingly: % inhibition=100–% conversion. The values % inhibition were determined for exemplified compounds and the results are summarized in Table 2.

Metabolic Stability Assay

The in vitro metabolic stability of the compounds of the invention was determined for exemplified compounds using human hepatocyte incubations. Study compounds were incubated 0, 10, 20, 40 and 60 min at 37° C. Samples were collected at all time points and compounds were detected by LC-MS/MS analysis. The percent compound remaining is calculated by comparing the peak area of the parent compound at each time point to time zero. In vitro metabolic stability was determined as half life (T½), which was determined by regression analysis of the percent parent disappearance vs. time curve. The results are summarized in Table 2.

Pharmacological Test Results

TABLE 2

| # | HSD1__ inhibition % @100 nM | HSD2__ inhibition % @1 µM | Rabbit placenta inhibition % @100 nM | Human hepatocytes MetStab T1__ 2 min |
|---|---|---|---|---|
| 2 | 83 | 9 | 75 | 38 |
| 4 | 87 | 13 | 89 | 42 |
| 6 | 92 | 1 | 79 | 67 |
| 8 | 90 | 2 | 37 | 52 |
| 10 | 30 | 5 | 18 | |
| 12 | 73 | 2 | 5 | |
| 14 | 53 | 4 | 14 | |
| 16 | 79 | 9 | 81 | |
| 18 | 68 | 14 | 62 | |
| 20 | 80 | 0 | 50 | 17 |
| 24 | 85 | 12 | 18 | |
| 26 | 49 | 8 | 10 | |
| 28 | 74 | 7 | 48 | |
| 30 | 40 | 3 | 79 | |
| 32 | 35 | 9 | 55 | |
| 34 | 23 | 9 | 16 | |
| 36 | 33 | 10 | 12 | |
| 38 | 21 | 3 | 19 | |
| 40 | 46 | 6 | 6 | |
| 42 | 96 | −5 | 41 | 78 |
| 44 | 20 | 2 | 11 | |
| 46 | 55 | 0 | 50 | |
| 48 | 30 | −2 | 1 | |
| 50 | 37 | −2 | 42 | |
| 52 | 64 | 2 | 6 | |
| 54 | 47 | 0 | 10 | |
| 56 | 63 | 3 | 0 | 334 |
| 58 | 60 | 18 | 1 | |
| 60 | 38 | 2 | 4 | |
| 62 | 45 | −8 | 3 | |
| 64 | 26 | 0 | 5 | |
| 66 | 72 | 23 | 14 | |
| 68 | 67 | 3 | 12 | |

TABLE 2-continued

| # | HSD1_ inhibition % @100 nM | HSD2_ inhibition % @1 μM | Rabbit placenta inhibition % @100 nM | Human hepatocytes MetStab T1_ 2 min |
|---|---|---|---|---|
| 70 | 81 | 4 | −7 | |
| 72 | 52 | 7 | 26 | |
| 74 | 27 | 2 | 13 | |
| 76 | 33 | 4 | 56 | |
| 78 | 76 | 1 | 37 | |
| 80 | 32 | 4 | 3 | |
| 82 | 17 | 7 | 18 | |
| 84 | 73 | −15 | 35 | 35 |
| 86 | 61 | 6 | 51 | |
| 88 | 65 | −2 | 10 | |
| 90 | 82 | −6 | 47 | 83 |
| 92 | 37 | 9 | 15 | |
| 94 | 63 | 0 | 8 | |
| 96 | 84 | −4 | 51 | 46 |
| 98 | 60 | 0 | 4 | 28 |
| 100 | 51 | −2 | 12 | |
| 102 | 57 | 20 | 1 | |
| 104 | 64 | −13 | 9 | |
| 106 | 76 | 2 | 5 | 31 |
| 108 | 54 | 5 | 20 | 21 |
| 110 | 33 | −4 | 35 | 26 |
| 112 | 96 | 7 | 67 | 29 |
| 114 | 100 | 7 | 75 | 40 |
| 116 | 85 | 26 | 76 | |
| 118 | 43 | 2 | −1 | |
| 120 | 57 | 2 | 9 | |
| 122 | 67 | 6 | 4 | |
| 124 | 86 | 4 | 4 | |
| 126 | 53 | 3 | 26 | |
| 128 | 59 | 6 | 2 | |
| 130 | 92 | 14 | 40 | |
| 132 | 87 | 6 | 27 | |
| 134 | 75 | −3 | 46 | |
| 136 | 39 | −1 | 18 | |
| 138 | 89 | | 36 | |
| 140 | 86 | 6 | 24 | |
| 142 | 93 | −1 | 34 | |
| 144 | 74 | 10 | 24 | |
| 146 | 92 | 8 | 63% @ 1000 nM | |
| 148 | 90 | 9 | 35 | |
| 150a | 74 | 0 | 10 | |
| 150b | 30 | 6 | 3 | |
| 152 | 56 | 2 | 6 | |
| 154 | 83 | 7 | 38 | |
| 156 | 47 | 10 | 3 | |
| 158 | 36 | 4 | 12 | |
| 160 | 66 | 5 | 10 | |
| 162 | 44 | 10 | 7 | |
| 164 | 40 | 11 | 5 | |
| 166 | 56 | 7 | 3 | |
| 168 | 26 | 9 | 6 | |
| 170 | 34 | 12 | 13 | |
| 172 | 45 | 9 | 9 | |
| 174 | 84 | 12 | 10 | |
| 176 | 87 | 5 | 34 | |
| 178 | 95 | 9 | 23 | |

UTILITY OF THE INVENTION

Compounds of the invention show selective inhibitory potential of the 17β-HSD1 enzyme and little or no inhibitory activity to the 17β-HSD2 enzyme and therefore, and may be useful for the treatment of a steroid hormone dependent disease or disorder, in particular for treatment and prevention of several diseases and conditions that include, but are not limited to, breast cancer, prostate carcinoma, ovarian cancer, uterine cancer, endometrial cancer, endometrial hyperplasia, endometriosis, uterine fibroids, adenomyosis, polycystic ovarian syndrome, dysmenorrhea, menorrhagia, metrorrhagia, contraception, prostadynia, benign prostatic hyperplasia, urinary dysfunction, lower urinary tract symptoms, chronic prostatitis/chronic pelvic pain syndrome (CP/CPPS), systemic lupus erythematosus (SLE), multiple sclerosis, obesity, rheumatoid arthritis, chronic obstructive pulmonary disease (COPD), lung cancer, colon cancer, tissue wounds, skin wrinkles and cataracts.

Further, compounds of the present invention may be useful for the treatment of diseases and disorders associated with increased levels of estradiol and which may be prevented, treated, and/or ameliorated by an inhibitor of 17β-HSD1 enzyme.

"Treatment or prevention" as used herein includes prophylaxis, or prevention of, as well as lowering the individual's risk of falling ill with the named disorder or condition, or alleviation, amelioration, elimination, or cure of the said disorder once it has been established.

Compounds of the present invention may be administered in an effective amount within the dosage range of about 0.1 μg/kg to about 300 mg/kg, preferably between 1.0 μg/kg to 10 mg/kg body weight. Compounds of the present invention may be administered in a single daily dose, or the total daily dosage may be administered in divided doses of two, three or four times daily.

"An effective amount" refers to an amount of a compound that confers a therapeutic effect on the treated subject. The therapeutic effect may be objective (i.e. measurable by some test or marker) or subjective (i.e. subject gives an indication of or feels an effect). Such treatment need not necessarily completely ameliorate the condition of disease. Further, such treatment or prevention can be used in conjunction with other traditional treatments for reducing the condition known to those skilled in the art.

Compounds of the invention are most preferably used alone or in combination i.e. administered simultaneously, separately or sequentially with other active ingredients, e.g. pharmaceutically active compounds or biologic products. The amounts of the compound(s) of the invention, particularly a compound of Formula (I), (Ia) or (Ib), or pharmaceutically acceptable salts thereof, and the other active ingredient(s) and the relative timings of administration will be selected in order to achieve the desired combined therapeutic effect. Compounds of the invention may be administered by various routes, for example, parenteral, subcutaneous, intravenous, intraarticular, intrathecal, intramuscular, intraperitoneal, topical, and by intradermal injections, and via transdermal, rectal, buccal, oromucosal, nasal, ocular routes and via inhalation and via implant.

Compounds may be formulated into a suitable composition; suitable administration forms include, for example, solutions, dispersions, suspensions, powders, capsules, tablets, pills, controlled release capsules, controlled release tablets and controlled release pills. In addition to the pharmacologically active compounds, the pharmaceutical compositions of the compounds can contain suitable pharmaceutically acceptable carriers comprising excipients and auxiliaries that facilitate processing of the active compounds into preparations that can be used pharmaceutically.

Skilled artisans possess the knowledge and skill in the art to enable them to select suitable pharmaceutically acceptable excipients in appropriate amounts for use in the invention. In addition, there are a number of resources that are available to the skilled artisan which describe pharmaceutically acceptable excipients and may be useful in selecting suitable pharmaceutically acceptable excipients.

Suitable pharmaceutically acceptable excipients include but are not limited to the following types of excipients: diluents (for example starches, mannitol), fillers (for example lactose, microcrystalline cellulose or calcium hydrogen phosphate), binders (for example pre-gelatised corn starch, polyvinylpyrrolidone or methylcellulose), additives (for example magnesium stearate, talc, silica), disintegrants (for example potato starch), lubricants (for example sodium lauryl sulphate), glidants (for example fumed silica, talc, magnesium carbonate), granulating agents (for example water, ethanol), coating agents (for example hydroxypropyl methylcellulose, gelatin, waxes, shellac, plastics, plant fibers), wetting agents (for example sorbitan monopalmitate, poloxamer 407), solvents (for example water), co-solvents (for example ethanol, propylene glycol), suspending agents (for example sorbitol, cellulose derivatives, edible hydrogenated fats), emulsifiers (for example lecithin or acacia), sweeteners (for example sucrose), flavoring agents (for example cherry, lime), flavor masking agents (for example vanilla, citrus), coloring agents (for example titanium oxide), anti-caking agents (for example silicon dioxide), humectants (for example glycerine, sorbitol), chelating agents (for example EDTA salts, histidine, aspartic acid), plasticizers (for example tributyl citrate, diethyl phthalate), viscosity increasing agents (for example methylcellulose), antioxidants (for example (ascorbic acid, cysteine), preservatives (for example methyl or propyl phydroxybenzoates, sorbic acid or ascorbic acid), stabilizers (for example polysorbate 20 & 80, poloxamer 407), surfactants (for example polyethylene glycol, polysorbate 80), and buffering agents (for example sodium and potassium phosphates, citrate, acetate, carbonate or glycine buffers de-pending on the targeted pH-range). The skilled artisan will appreciate that certain pharmaceutically acceptable excipients may serve more than one function and may serve alternative functions depending on how much of the excipient is present in the composition and what other ingredients are present in the composition.

The pharmaceutical compositions of the invention are prepared using techniques and methods known to those skilled in the art. Pharmaceutical compositions of the invention include, but are not limited to, for parenteral and topical administration that include, but are not limited to, sterile aqueous or non-aqueous solvents, suspensions and emulsions. Examples of non-aqueous solvents are propylene glycol, polyethylene glycol, vegetable oil, fish oil, and injectable organic esters. Aqueous carriers include, but are not limited to, water, water-alcohol solutions, including saline and buffered medial parenteral vehicles including sodium chloride solution, Ringer's dextrose solution, dextrose plus sodium chloride solution, Ringer's solution containing lactose, or fixed oils. Intravenous vehicles include, but are not limited to, fluid and nutrient replenishers, electrolyte replenishers, such as those based on Ringer's dextrose and the like. Aqueous compositions according to the invention may comprise suitable buffer agents, such as sodium and potassium phosphates, citrate, acetate, carbonate or glycine buffers depending on the targeted pH-range. The use of sodium chloride as a tonicity adjuster is also useful. Compositions may include other excipients, such as stabilizing agents or preservatives. Useful stabilizing excipients include surfactants (polysorbate 20 & 80, poloxamer 407), polymers (polyethylene glycols, povidones), carbohydrates (sucrose, mannitol, glucose, lactose), alcohols (sorbitol, glycerol propylene glycol, ethylene glycol), suitable proteins (albumin), suitable amino acids (glycine, glutamic acid), fatty acids (ethanolamine), antioxidants (ascorbic acid, cysteine etc.), chelating agents (EDTA salts, histidine, aspartic acid) or metal ions (Ca, Ni, Mg, Mn). Among useful preservative agents are benzyl alcohol, chlorobutanol, benzalkonium chloride and possibly parabens. The pharmaceutical composition according to the present invention may be provided in concentrated form or in form of a powder to be reconstituted on demand. In such cases formulations of powder for solution for injection/infusion excipients mentioned above may be used. In case of lyophilizing, certain cryoprotectants are preferred, including polymers (povidones, polyethylene glycol, dextran), sugars (sucrose, glucose, lactose), amino acids (glycine, arginine, glutamic acid) and albumin. If solution for reconstitution is added to the packaging, it may consist e.g., of pure water for injection or sodium chloride solution or dextrose or glucose solutions.

Furthermore, compounds of formula (I) can be used as synthesis intermediates for the preparation of other compounds, in particular of other pharmaceutically active ingredients, which are obtainable from compounds of formula (I), for example by introduction of substituents or modification of functional groups.

It will be obvious to a person skilled in the art that, as the technology advances, the inventive concept can be implemented in various ways. The invention and its embodiments are not limited to the examples described above but may vary within the scope of the claims.

The invention claimed is:
1. A compound of formula (I)

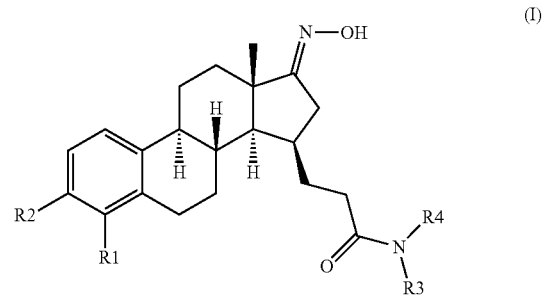

wherein R1 and R2 are each independently selected from the group consisting of H and halogen;
(i) R3 is selected from the group consisting of H and C1-3-alkyl; and
R4 is selected from the group consisting of
C1-3-alkyl,
4- to 6-membered unsubstituted saturated heterocycle comprising 1 heteroatom selected from the group consisting of nitrogen, sulfur, and oxygen,
5-membered partially unsaturated heterocycle comprising 1 nitrogen atom and optionally 1 to 2 further heteroatom(s) selected from the group consisting of nitrogen, sulfur, and oxygen, and being optionally substituted with one or two substituents selected from the group consisting of halogen, CN, C1-3-alkyl, C1-3-(per)haloalkyl, OH, C1-3-alkoxy, C(O)N(C1-3-alkyl)$_2$, and 6-membered saturated heterocycle comprising 1 to 2 heteroatom(s) independently selected from the group consisting of nitrogen, oxygen and sulfur and being optionally substituted with one or two substituent(s) independently selected from the group consisting of halogen, CN, C1-3-alkyl, C1-3-(per)haloalkyl, OH, and C1-3-alkoxy,
5-membered unsubstituted unsaturated or aromatic heterocycle comprising 1 nitrogen atom and 1 to 2 further heteroatom(s) independently selected from the group consisting of nitrogen, sulfur, and oxygen, 5-membered unsaturated or aromatic heterocycle having 1 nitrogen atom and up to 2 further heteroatom(s) independently selected from the group consisting of nitrogen and oxygen with the remaining atoms being carbon, and being substituted with one or two substituent(s) independently selected from the group consisting of halogen, CN, C1-3-alkyl, C1-3-(per)haloalkyl, OH, C1-3-alkoxy, C(O)N(C1-3-alkyl)$_2$, and 6-membered saturated heterocycle containing 1 to 2 heteroatom(s) independently selected from the group consisting of nitrogen, oxygen and sulfur and being optionally substituted with one or two substituent(s) independently selected from the group consisting of halogen, CN, C1-3-alkyl, C1-3-(per)haloalkyl, OH, and C1-3-alkoxy, and 6-membered unsaturated or aromatic heterocycle comprising 1 nitrogen atom and optionally 1 to 2 further heteroatom(s) independently selected from the group consisting of nitrogen, sulfur, and oxygen, and being optionally substituted with one or two substituent(s) independently selected from the group consisting of halogen, CN, C1-3-alkyl, C1-3-(per)haloalkyl, OH, oxo, C1-3-alkoxy, C(O)N(C1-3-alkyl)$_2$, and 6-membered saturated heterocycle comprising 1 to 2 heteroatom(s) independently selected from the group consisting of nitrogen, oxygen and sulfur and being optionally substituted with one or two substituent(s) independently selected from the group consisting of halogen, CN, C1-3-alkyl, C1-3-(per)haloalkyl, OH, and C1-3-alkoxy, or two adjacent substituents may form a 5- or 6-membered saturated fused ring;

or (ii) R3 and R4 form together with the nitrogen atom they are attached to form a group selected from a 5- to 6-membered saturated heterocycle comprising said nitrogen atom and being optionally substituted with a substituent selected from the group consisting of halogen, CN, methyl, C1-3-(per)haloalkyl, OH, and methoxy; and an unsubstituted bicyclic spirocyclic or fused heterocycle containing said nitrogen atom and optionally 1 or 2 further heteroatom(s) selected from a group consisting of nitrogen, oxygen and sulfur;

or a pharmaceutically acceptable salt thereof.

2. A compound as claimed in claim 1, having formula (Ia)

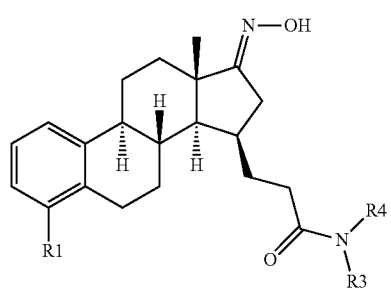

(Ia)

wherein R1 is selected from the group consisting of H and halogen;

(i) R3 is selected from the group consisting of H and C1-3-alkyl; and

R4 is selected from the group consisting of C1-3-alkyl, 4- to 6-membered unsubstituted saturated heterocycle comprising 1 heteroatom selected from the group consisting of nitrogen, sulfur, and oxygen, 5-membered partially unsaturated heterocycle comprising 1 nitrogen atom and optionally 1 to 2 further heteroatom(s) selected from the group consisting of nitrogen, sulfur, and oxygen, and being optionally substituted with one or two substituents selected from the group consisting of halogen, CN, C1-3-alkyl, C1-3-(per)haloalkyl, OH, C1-3-alkoxy, C(O)N(C1-3-alkyl)$_2$, and 6 membered saturated heterocycle comprising 1 to 2 heteroatom(s) independently selected from the group consisting of nitrogen, oxygen and sulfur and being optionally substituted with one or two substituent(s) independently selected from the group consisting of halogen, CN, C1-3-alkyl, C1-3-(per)haloalkyl, OH, and C1-3-alkoxy, 5-membered unsubstituted unsaturated or aromatic heterocycle comprising 1 nitrogen atom and 1 to 2 further heteroatom(s) independently selected from the group consisting of nitrogen, sulfur, and oxygen, 5-membered unsaturated or aromatic heterocycle having 1 nitrogen atom and up to 2 further heteroatom(s) independently selected from the group consisting of nitrogen and oxygen with the remaining atoms being carbon, and being substituted with one or two substituent(s) independently selected from the group consisting of halogen, CN, C1-3-alkyl, C1-3-(per)haloalkyl, OH, C1-3-alkoxy, C(O)N(C1-3-alkyl)$_2$, and 6-membered saturated heterocycle containing 1 to 2 heteroatom(s) independently selected from the group consisting of nitrogen, oxygen and sulfur and being optionally substituted with one or two substituent(s) independently selected from the group consisting of halogen, CN, C1-3-alkyl, C1-3-(per)haloalkyl, OH, and C1-3-alkoxy, and 6-membered unsaturated or aromatic heterocycle comprising 1 nitrogen atom and optionally 1 to 2 further heteroatom(s) independently selected from the group consisting of nitrogen, sulfur, and oxygen, and being optionally substituted with one or two substituent(s) independently selected from the group consisting of halogen, CN, C1-3-alkyl, C1-3-(per)haloalkyl, OH, oxo, C1-3-alkoxy, C(O)N(C1-3-alkyl)$_2$, and 6 membered saturated heterocycle comprising 1 to 2 heteroatom(s) independently selected from the group consisting of nitrogen, oxygen and sulfur and being optionally substituted with one or two substituent(s) independently selected from the group consisting of halogen, CN, C1-3-alkyl, C1-3-(per)haloalkyl, OH, and C1-3-alkoxy, or two adjacent substituents may form a 5- or 6-membered saturated fused ring;

or (ii) R3 and R4 form together with the nitrogen atom they are attached to form a group selected from a 5- to 6-membered saturated heterocycle comprising said nitrogen atom and being optionally substituted with a substituent selected from the group consisting of halogen, CN, methyl, C1-3-(per)haloalkyl, OH, and methoxy; and an unsubstituted bicyclic spirocyclic or fused heterocycle containing said nitrogen atom and optionally 1 or 2 further heteroatom(s) selected from a group consisting of nitrogen, oxygen and sulfur;

or a pharmaceutically acceptable salt thereof.

3. A compound or pharmaceutically acceptable salt as claimed in claim 2, wherein R1 is selected from the group consisting of H, F and Cl.

4. A compound or pharmaceutically acceptable salt as claimed in claim 1, wherein R3 is H or methyl.

5. A compound or pharmaceutically acceptable salt as claimed in claim 4, wherein R3 is H.

6. A compound or pharmaceutically acceptable salt as claimed in claim 1, wherein R4 is selected from a group consisting of

- 5-membered unsubstituted unsaturated or aromatic heterocycle comprising 1 nitrogen atom and 1 to 2 further heteroatom(s) independently selected from the group consisting of nitrogen, sulfur, and oxygen,
- 5-membered unsaturated or aromatic heterocycle having 1 nitrogen atom and up to 2 further heteroatom(s) independently selected from the group consisting of nitrogen and oxygen with the remaining atoms being carbon, and being substituted with one or two substituent(s) independently selected from the group consisting of halogen, CN, C1-3-alkyl, C1-3-(per)haloalkyl, OH, C1-3-alkoxy, C(O)N(C1-3-alkyl)$_2$, and 6-membered saturated heterocycle containing 1 to 2 heteroatom(s) independently selected from the group consisting of nitrogen, oxygen and sulfur and being optionally substituted with one or two substituent(s) independently selected from the group consisting of halogen, CN, C1-3-alkyl, C1-3-(per)haloalkyl, OH, and C1-3-alkoxy, and
- 6-membered unsaturated or aromatic heterocycle comprising 1 nitrogen atom and optionally 1 to 2 further heteroatom(s) independently selected from the group consisting of nitrogen, sulfur, and oxygen, and being optionally substituted with one or two substituent(s) independently selected from the group consisting of halogen, CN, C1-3-alkyl, C1-3-(per)haloalkyl, OH, oxo, C1-3-alkoxy, C(O)N(C1-3-alkyl)$_2$, and 6-membered saturated heterocycle comprising 1 to 2 heteroatom(s) independently selected from the group consisting of nitrogen, oxygen and sulfur and being optionally substituted with one or two substituent(s) independently selected from the group consisting of halogen, CN, C1-3-alkyl, C1-3-(per)haloalkyl, OH, and C1-3-alkoxy, or two adjacent substituents may form a 5- or 6-membered saturated fused ring.

7. A compound or pharmaceutically acceptable salt as claimed in claim 1, wherein R4 is selected from the group consisting of oxetanyl, pyrrolidinyl, piperidinyl, tetrahydropyranyl, dihydrothiazolyl, thiadiazolyl, oxazolyl, methyloxazolyl, pyridinyl, fluoropyridinyl, cyanopyridinyl, methylpyridinyl, dimethylpyridinyl, isopropylpyridinyl, hydroxypyridinyl, methoxypyridinyl, morpholinopyridinyl, methylpiperazinylpyridinyl, pyrazinyl, methylpyridazinyl, and methoxypyridazinyl.

8. A compound or pharmaceutically acceptable salt as claimed in claim 1, wherein R3 and R4 form together with the nitrogen they are attached to a ring selected from the group consisting of pyrrolidinyl, methoxymethylpyrrolidinyl, and oxaazaspiro[4.5]decanyl.

9. A compound as claimed in claim 1, wherein the compound has formula (Ib):

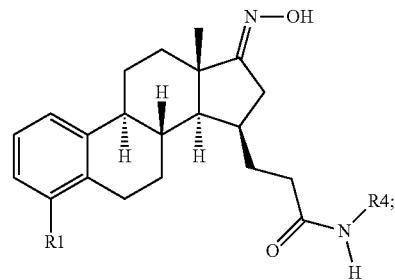

(Ib)

wherein R1 is selected from the group consisting of H and halogen; and

R4 is selected from the group consisting of

C1-3-alkyl, 4- to 6-membered unsubstituted saturated heterocycle comprising 1 heteroatom selected from the group consisting of nitrogen, sulfur, and oxygen, 5-membered partially unsaturated heterocycle comprising 1 nitrogen atom and optionally 1 to 2 further heteroatom(s) selected from the group consisting of nitrogen, sulfur, and oxygen, and being optionally substituted with one or two substituents selected from the group consisting of halogen, CN, C1-3-alkyl, C1-3-(per)haloalkyl, OH, C1-3-alkoxy, C(O)N(C1-3-alkyl)$_2$, and 6-membered saturated heterocycle comprising 1 to 2 heteroatom(s) independently selected from the group consisting of nitrogen, oxygen and sulfur and being optionally substituted with one or two substituent(s) independently selected from the group consisting of halogen, CN, C1-3-alkyl, C1-3-(per)haloalkyl, OH, and C1-3-alkoxy, 5-membered unsubstituted unsaturated or aromatic heterocycle comprising 1 nitrogen atom and 1 to 2 further heteroatom(s) independently selected from the group consisting of nitrogen, sulfur, and oxygen, 5-membered unsaturated or aromatic heterocycle having 1 nitrogen atom and up to 2 further heteroatom(s) independently selected from the group consisting of nitrogen and oxygen with the remaining atoms being carbon, and being substituted with one or two substituent(s) independently selected from the group consisting of halogen, CN, C1-3-alkyl, C1-3-(per)haloalkyl, OH, C1-3-alkoxy, C(O)N(C1-3-alkyl)$_2$, and 6-membered saturated heterocycle containing 1 to 2 heteroatom(s) independently selected from the group consisting of nitrogen, oxygen and sulfur and being optionally substituted with one or two substituent(s) independently selected from the group consisting of halogen, CN, C1-3-alkyl, C1-3-(per)haloalkyl, OH, and C1-3-alkoxy, and 6-membered unsaturated or aromatic heterocycle comprising 1 nitrogen atom and optionally 1 to 2 further heteroatom(s) independently selected from the group consisting of nitrogen, sulfur, and oxygen, and being optionally substituted with one or two substituent(s) independently selected from the group consisting of halogen, CN, C1-3-alkyl, C1-3-(per)haloalkyl, OH, oxo, C1-3-alkoxy, C(O)N(C1-3-alkyl)$_2$, and 6 membered saturated heterocycle comprising 1 to 2 heteroatom(s) independently selected from the group consisting of nitrogen, oxygen and sulfur and being optionally substituted with one or two substituent(s) independently selected from the group consisting of halogen, CN, C1-3-alkyl, C1-3-(per)haloalkyl, OH, and C1-3-alkoxy, or two adjacent substituents may form a 5- or 6-membered saturated fused ring;
or a pharmaceutically acceptable salt thereof.

10. A compound or pharmaceutically acceptable salt as claimed in claim 9, wherein R4 is a 6 membered aromatic heterocycle of formula (A)

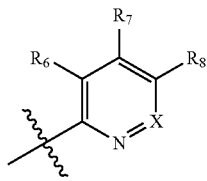

(A)

wherein
X is CR9 or N;
one of R6, R7, R8 is H, and the others are independently selected from a group consisting of H, halogen, CN, C1-3-alkyl, C1-3-(per)haloalkyl, OH, C1-3-alkoxy, and morpholine ring; and
R9 is H or C1-3-alkyl.

11. A compound selected from the group consisting of:
3-((13S,15R,E)-4-fluoro-17-(hydroxyimino)-13-methyl-7,8,9,11,12,13,14,15,16,17-decahydro-6H-cyclopenta[a]phenanthren-15-yl)-N-(5-methylisoxazol-3-yl)propanamide;
3-((13S,15R,E)-4-fluoro-17-(hydroxyimino)-13-methyl-7,8,9,11,12,13,14,15,16,17-decahydro-6H-cyclopenta[a]phenanthren-15-yl)-N-(6-methoxypyridazin-3-yl)propanamide;
3-((13S,15R,E)-4-fluoro-17-(hydroxyimino)-13-methyl-7,8,9,11,12,13,14,15,16,17-decahydro-6H-cyclopenta[a]phenanthren-15-yl)-N-(5-methoxypyridin-2-yl)propanamide;
3-((13S,15R,E)-4-fluoro-17-(hydroxyimino)-13-methyl-7,8,9,11,12,13,14,15,16,17-decahydro-6H-cyclopenta[a]phenanthren-15-yl)-N-(5-fluoropyridin-2-yl)propanamide;
3-((13S,15R,E)-4-fluoro-17-(hydroxyimino)-13-methyl-7,8,9,11,12,13,14,15,16,17-decahydro-6H-cyclopenta[a]phenanthren-15-yl)-N-(oxetan-3-yl)propanamide;
3-((13S,15R,E)-4-fluoro-17-(hydroxyimino)-13-methyl-7,8,9,11,12,13,14,15,16,17-decahydro-6H-cyclopenta[a]phenanthren-15-yl)-N-methyl-(oxetan-3-yl)propanamide;
3-((13S,15R,E)-4-fluoro-17-(hydroxyimino)-13-methyl-7,8,9,11,12,13,14,15,16,17-decahydro-6H-cyclopenta[a]phenanthren-15-yl)-1-(pyrrolidin-1-yl)propan-1-one;
3-((13S,15R,E)-4-fluoro-17-(hydroxyimino)-13-methyl-7,8,9,11,12,13,14,15,16,17-decahydro-6H-cyclopenta[a]phenanthren-15-yl)-N-(6-methylpyridazin-3-yl)propanamide;
3-((13S,15R,E)-4-fluoro-17-(hydroxyimino)-13-methyl-7,8,9,11,12,13,14,15,16,17-decahydro-6H-cyclopenta[a]phenanthren-15-yl)-N-(1,3,4-thiadiazol-2-yl)propanamide;
3-((13S,15R,E)-4-fluoro-17-(hydroxyimino)-13-methyl-7,8,9,11,12,13,14,15,16,17-decahydro-6H-cyclopenta[a]phenanthren-15-yl)-N-(pyridazine-3-yl)propanamide;
N-(4,5-dihydrothiazol-2-yl)-3-((13S,15R,E)-4-fluoro-17-(hydroxyimino)-13-methyl-7,8,9,11,12,13,14,15,16,17-decahydro-6H-cyclopenta[a]phenanthren-15-yl)propanamide;
N,N-diethyl-3-((13S,15R,E)-4-fluoro-17-(hydroxyimino)-13-methyl-7,8,9,11,12,13,14,15,16,17-decahydro-6H-cyclopenta[a]phenanthren-15-yl)propanamide;
3-((13S,15R,E)-3-fluoro-17-(hydroxyimino)-13-methyl-7,8,9,11,12,13,14,15,16,17-decahydro-6H-cyclopenta[a]phenanthren-15-yl)-N-(5-fluoropyridin-2-yl)propanamide;
3-((13S,15R,E)-3-fluoro-17-(hydroxyimino)-13-methyl-7,8,9,11,12,13,14,15,16,17-decahydro-6H-cyclopenta[a]phenanthren-15-yl)-N-(5-methoxypyridin-2-yl)propanamide;
3-((13S,15R,E)-3-fluoro-17-(hydroxyimino)-13-methyl-7,8,9,11,12,13,14,15,16,17-decahydro-6H-cyclopenta[a]phenanthren-15-yl)-N-(6-methoxypyridazin-3-yl)propanamide;
3-((13S,15R,E)-3-fluoro-17-(hydroxyimino)-13-methyl-7,8,9,11,12,13,14,15,16,17-decahydro-6H-cyclopenta[a]phenanthren-15-yl)-N-(6-methylpyridazin-3-yl)propanamide;
3-((13S,15R,E)-3-fluoro-17-(hydroxyimino)-13-methyl-7,8,9,11,12,13,14,15,16,17-decahydro-6H-cyclopenta[a]phenanthren-15-yl)-N-(pyridazin-3-yl)propanamide;
3-((13S,15R,E)-3-fluoro-17-(hydroxyimino)-13-methyl-7,8,9,11,12,13,14,15,16,17-decahydro-6H-cyclopenta[a]phenanthren-15-yl)-N-methyl-N-(oxetan-3-yl)propanamide;
3-((13S,15R,E)-3-fluoro-17-(hydroxyimino)-13-methyl-7,8,9,11,12,13,14,15,16,17-decahydro-6H-cyclopenta[a]phenanthren-15-yl)-N-(1,3,4-thiadiazol-2-yl)propanamide;
N,N-diethyl-3-((13S,15R,E)-3-fluoro-17-(hydroxyimino)-13-methyl-7,8,9,11,12,13,14,15,16,17-decahydro-6H-cyclopenta[a]phenanthren-15-yl)propanamide;
3-((13S,15R,E)-3-fluoro-17-(hydroxyimino)-13-methyl-7,8,9,11,12,13,14,15,16,17-decahydro-6H-cyclopenta[a]phenanthren-15-yl)-N-(5-isopropylpyridin-2-yl)propanamide;
3-((13S,15R,E)-3-chloro-17-(hydroxyimino)-13-methyl-7,8,9,11,12,13,14,15,16,17-decahydro-6H-cyclopenta[a]phenanthren-15-yl)-N-(pyridazine-3-yl)propanamide;
3-((13S,15R,E)-3-chloro-17-(hydroxyimino)-13-methyl-7,8,9,11,12,13,14,15,16,17-decahydro-6H-cyclopenta[a]phenanthren-15-yl)-N-(4,5-dihydrothiazol-2-yl)propanamide;
3-((13S,15R,E)-3-chloro-17-(hydroxyimino)-13-methyl-7,8,9,11,12,13,14,15,16,17-decahydro-6H-cyclopenta[a]phenanthren-15-yl)-1-(8-oxa-2-azaspiro[4.5]decan-2-yl)propan-1-one;
3-((13S,15R,E)-3-chloro-17-(hydroxyimino)-13-methyl-7,8,9,11,12,13,14,15,16,17-decahydro-6H-cyclopenta[a]phenanthren-15-yl)-N-(6-methoxypyridazin-3-yl)propanamide;
3-((13S,15R,E)-3-chloro-17-(hydroxyimino)-13-methyl-7,8,9,11,12,13,14,15,16,17-decahydro-6H-cyclopenta[a]phenanthren-15-yl)-N,N-diethylpropanamide;
3-((13S,15R,E)-3-chloro-17-(hydroxyimino)-13-methyl-7,8,9,11,12,13,14,15,16,17-decahydro-6H-cyclopenta[a]phenanthren-15-yl)-N-(5-methylisoxazol-3-yl)propanamide;

3-((13S,15R,E)-3-chloro-17-(hydroxyimino)-13-methyl-7,8,9,11,12,13,14,15,16,17-decahydro-6H-cyclopenta[a]phenanthren-15-yl)-N-(4-methoxypyridin-2-yl)propanamide;

3-((13S,15R,E)-3-chloro-17-(hydroxyimino)-13-methyl-7,8,9,11,12,13,14,15,16,17-decahydro-6H-cyclopenta[a]phenanthren-15-yl)-N-(5-fluoropyridin-2-yl)propanamide;

3-((13S,15R,E)-3-chloro-17-(hydroxyimino)-13-methyl-7,8,9,11,12,13,14,15,16,17-decahydro-6H-cyclopenta[a]phenanthren-15-yl)-N-(3-methylpyridin-2-yl)propanamide;

3-((13S,15R,E)-3-chloro-17-(hydroxyimino)-13-methyl-7,8,9,11,12,13,14,15,16,17-decahydro-6H-cyclopenta[a]phenanthren-15-yl)-N-(3-fluoropyridin-2-yl)propanamide;

3-((13S,15R,E)-3-chloro-17-(hydroxyimino)-13-methyl-7,8,9,11,12,13,14,15,16,17-decahydro-6H-cyclopenta[a]phenanthren-15-yl)-N-(5-methyloxazol-2-yl)propanamide;

3-((13S,15R,E)-3-chloro-17-(hydroxyimino)-13-methyl-7,8,9,11,12,13,14,15,16,17-decahydro-6H-cyclopenta[a]phenanthren-15-yl)-N-(5-methoxypyridin-2-yl)propanamide;

3-((13S,15R,E)-3-chloro-17-(hydroxyimino)-13-methyl-7,8,9,11,12,13,14,15,16,17-decahydro-6H-cyclopenta[a]phenanthren-15-yl)-N-(pyridin-2-yl)propanamide;

3-((13S,15R,E)-3-chloro-17-(hydroxyimino)-13-methyl-7,8,9,11,12,13,14,15,16,17-decahydro-6H-cyclopenta[a]phenanthren-15-yl)-N-(4-methylpyridin-2-yl)propanamide;

3-((13S,15R,E)-3-chloro-17-(hydroxyimino)-13-methyl-7,8,9,11,12,13,14,15,16,17-decahydro-6H-cyclopenta[a]phenanthren-15-yl)-N-(5-cyanopyridin-2-yl)propanamide;

3-((13S,15R,E)-3-chloro-17-(hydroxyimino)-13-methyl-7,8,9,11,12,13,14,15,16,17-decahydro-6H-cyclopenta[a]phenanthren-15-yl)-N-(pyrazin-2-yl)propanamide;

3-((13S,15R,E)-3-chloro-17-(hydroxyimino)-13-methyl-7,8,9,11,12,13,14,15,16,17-decahydro-6H-cyclopenta[a]phenanthren-15-yl)-N-(6-methylpyridazin-3-yl)propanamide;

3-((13S,15R,E)-3-chloro-17-(hydroxyimino)-13-methyl-7,8,9,11,12,13,14,15,16,17-decahydro-6H-cyclopenta[a]phenanthren-15-yl)-N-(5-morpholinopyridin-2-yl)propanamide;

3-((13S,15R,E)-17-(hydroxyimino)-13-methyl-7,8,9,11,12,13,14,15,16,17-decahydro-6H-cyclopenta[a]phenanthren-15-yl)-N-methyl-N-(tetrahydro-2H-pyran-4-yl)propanamide;

3-((13S,15R,E)-17-(hydroxyimino)-13-methyl-7,8,9,11,12,13,14,15,16,17-decahydro-6H-cyclopenta[a]phenanthren-15-yl)-N-(pyridazin-3-yl)propanamide;

3-((13S,15R,E)-17-(hydroxyimino)-13-methyl-7,8,9,11,12,13,14,15,16,17-decahydro-6H-cyclopenta[a]phenanthren-15-yl)-N-(5-methoxypyridin-2-yl)propanamide;

3-((13S,15R,E)-17-(hydroxyimino)-13-methyl-7,8,9,11,12,13,14,15,16,17-decahydro-6H-cyclopenta[a]phenanthren-15-yl)-N-(5-(4-methylpiperazin-1-yl)pyridin-2-yl)propanamide;

3-((13S,15R,E)-17-(hydroxyimino)-13-methyl-7,8,9,11,12,13,14,15,16,17-decahydro-6H-cyclopenta[a]phenanthren-15-yl)-N-(4-methylpyridin-2-yl)propanamide;

3-((13S,15R,E)-17-(hydroxyimino)-13-methyl-7,8,9,11,12,13,14,15,16,17-decahydro-6H-cyclopenta[a]phenanthren-15-yl)-N-(5-morpholinopyridin-2-yl)propanamide;

6-(3-((13S,15R,E)-17-(hydroxyimino)-13-methyl-7,8,9,11,12,13,14,15,16,17-decahydro-6H-cyclopenta[a]phenanthren-15-yl)propanamido)-N,N-dimethylnicotinamide;

3-((13S,15R,E)-17-(hydroxyimino)-13-methyl-7,8,9,11,12,13,14,15,16,17-decahydro-6H-cyclopenta[a]phenanthren-15-yl)-N-(2-oxo-1,2,5,6,7,8-hexahydroquinolin-3-yl)propanamide;

3-((13S,15R,E)-17-(hydroxyimino)-13-methyl-7,8,9,11,12,13,14,15,16,17-decahydro-6H-cyclopenta[a]phenanthren-15-yl)-N-(5-isopropylpyridin-2-yl)propanamide;

N-(5-fluoropyridin-2-yl)-3-((13S,15R,E)-17-(hydroxyimino)-13-methyl-7,8,9,11,12,13,14,15,16,17-decahydro-6H-cyclopenta[a]phenanthren-15-yl)propanamide;

N-(5-cyanopyridin-2-yl)-3-((13S,15R,E)-17-(hydroxyimino)-13-methyl-7,8,9,11,12,13,14,15,16,17-decahydro-6H-cyclopenta[a]phenanthren-15-yl)propanamide;

3-((13S,15R,E)-17-(hydroxyimino)-13-methyl-7,8,9,11,12,13,14,15,16,17-decahydro-6H-cyclopenta[a]phenanthren-15-yl)-N-(3-hydroxypyridin-2-yl)propanamide;

3-((13S,15R,E)-17-(hydroxyimino)-13-methyl-7,8,9,11,12,13,14,15,16,17-decahydro-6H-cyclopenta[a]phenanthren-15-yl)-N-(pyridin-2-yl)propanamide;

3-((13S,15R,E)-17-(hydroxyimino)-13-methyl-7,8,9,11,12,13,14,15,16,17-decahydro-6H-cyclopenta[a]phenanthren-15-yl)-N-(4-methoxypyridin-2-yl)propanamide;

3-((13S,15R,E)-17-(hydroxyimino)-13-methyl-7,8,9,11,12,13,14,15,16,17-decahydro-6H-cyclopenta[a]phenanthren-15-yl)-N-(5-methyloxazol-2-yl)propanamide;

3-((13S,15R,E)-17-(hydroxyimino)-13-methyl-7,8,9,11,12,13,14,15,16,17-decahydro-6H-cyclopenta[a]phenanthren-15-yl)-N-(5-methylisoxazol-3-yl)propanamide;

3-((13S,15R,E)-4-fluoro-17-(hydroxyimino)-13-methyl-7,8,9,11,12,13,14,15,16,17-decahydro-6H-cyclopenta[a]phenanthren-15-yl)-N-(5-isopropylpyridin-2-yl)propanamide;

3-((13S,15R,E)-4-fluoro-17-(hydroxyimino)-13-methyl-7,8,9,11,12,13,14,15,16,17-decahydro-6H-cyclopenta[a]phenanthren-15-yl)-N-(5-morpholinopyridin-2-yl)propanamide;

3-((13S,15R,E)-4-fluoro-17-(hydroxyimino)-13-methyl-7,8,9,11,12,13,14,15,16,17-decahydro-6H-cyclopenta[a]phenanthren-15-yl)-N-(5-(4-methylpiperazin-1-yl)pyridin-2-yl)propanamide;

3-((13S,15R,E)-4-fluoro-17-(hydroxyimino)-13-methyl-7,8,9,11,12,13,14,15,16,17-decahydro-6H-cyclopenta[a]phenanthren-15-yl)-N-methylpropanamide;

3-((13S,15R,E)-4-fluoro-17-(hydroxyimino)-13-methyl-7,8,9,11,12,13,14,15,16,17-decahydro-6H-cyclopenta[a]phenanthren-15-yl)-N,N-dimethylpropanamide;

3-((13S,15R,E)-4-fluoro-17-(hydroxyimino)-13-methyl-7,8,9,11,12,13,14,15,16,17-decahydro-6H-cyclopenta[a]phenanthren-15-yl)-N-(tetrahydro-2H-pyran-4-yl)propanamide;

N-Cyclohexyl-3-((13S,15R,E)-4-fluoro-17-(hydroxyimino)-13-methyl-7,8,9,11,12,13,14,15,16,17-decahydro-6H-cyclopenta[a]phenanthren-15-yl)propanamide;
3-((13S,15R,E)-4-fluoro-17-(hydroxyimino)-13-methyl-7,8,9,11,12,13,14,15,16,17-decahydro-6H-cyclopenta[a]phenanthren-15-yl)-N-(pyrazin-2-yl)propanamide;
3-((13S,15R,E)-4-fluoro-17-(hydroxyimino)-13-methyl-7,8,9,11,12,13,14,15,16,17-decahydro-6H-cyclopenta[a]phenanthren-15-yl)-1-(8-oxa-2-azaspiro[4.5]decan-2-yl)propan-1-one;
3-((13S,15R,E)-4-fluoro-17-(hydroxyimino)-13-methyl-7,8,9,11,12,13,14,15,16,17-decahydro-6H-cyclopenta[a]phenanthren-15-yl)-N-(4-methylpyridin-2-yl)propanamide;
3-((13S,15R,E)-4-fluoro-17-(hydroxyimino)-13-methyl-7,8,9,11,12,13,14,15,16,17-decahydro-6H-cyclopenta[a]phenanthren-15-yl)-N-(4-methoxypyridin-2-yl)propanamide;
3-((13S,15R,E)-3-fluoro-17-(hydroxyimino)-13-methyl-7,8,9,11,12,13,14,15,16,17-decahydro-6H-cyclopenta[a]phenanthren-15-yl)-N-(5-methylisoxazol-3-yl)propanamide;
3-((13S,15R,E)-4-fluoro-17-(hydroxyimino)-13-methyl-7,8,9,11,12,13,14,15,16,17-decahydro-6H-cyclopenta[a]phenanthren-15-yl)-1-morpholinopropan-1-one;
3-((13S,15R,E)-4-fluoro-17-(hydroxyimino)-13-methyl-7,8,9,11,12,13,14,15,16,17-decahydro-6H-cyclopenta[a]phenanthren-15-yl)-N-(pyridin-2-yl)propanamide;
3-((13S,15R,E)-4-fluoro-17-(hydroxyimino)-13-methyl-7,8,9,11,12,13,14,15,16,17-decahydro-6H-cyclopenta[a]phenanthren-15-yl)-N-(4-fluoropyridin-2-yl)propanamide;
3-((13S,15R,E)-4-fluoro-17-(hydroxyimino)-13-methyl-7,8,9,11,12,13,14,15,16,17-decahydro-6H-cyclopenta[a]phenanthren-15-yl)-N-(3-fluoropyridin-2-yl)propanamide;
3-((13S,15R,E)-4-fluoro-17-(hydroxyimino)-13-methyl-7,8,9,11,12,13,14,15,16,17-decahydro-6H-cyclopenta[a]phenanthren-15-yl)-N-(6-fluoropyridin-2-yl)propanamide;
N-(3,5-difluoropyridin-2-yl)-3-((13S,15R,E)-4-fluoro-17-(hydroxyimino)-13-methyl-7,8,9,11,12,13,14,15,16,17-decahydro-6H-cyclopenta[a]phenanthren-15-yl)propanamide;
N-(5-cyanopyridin-2-yl)-3-((13S,15R,E)-4-fluoro-17-(hydroxyimino)-13-methyl-7,8,9,11,12,13,14,15,16,17-decahydro-6H-cyclopenta[a]phenanthren-15-yl)propanamide;
3-((13S,15R,E)-3-fluoro-17-(hydroxyimino)-13-methyl-7,8,9,11,12,13,14,15,16,17-decahydro-6H-cyclopenta[a]phenanthren-15-yl)-N-(3-fluoropyridin-2-yl)propanamide;
N-(3,5-difluoropyridin-2-yl)-3-((13S,15R,E)-3-fluoro-17-(hydroxyimino)-13-methyl-7,8,9,11,12,13,14,15,16,17-decahydro-6H-cyclopenta[a]phenanthren-15-yl)propanamide;
3-((13S,15R,E)-3-fluoro-17-(hydroxyimino)-13-methyl-7,8,9,11,12,13,14,15,16,17-decahydro-6H-cyclopenta[a]phenanthren-15-yl)-N-(5-morpholinopyridin-2-yl)propanamide;
3-((13S,15R,E)-3-chloro-17-(hydroxyimino)-13-methyl-7,8,9,11,12,13,14,15,16,17-decahydro-6H-cyclopenta[a]phenanthren-15-yl)-N-(4-fluoropyridin-2-yl)propanamide;
N-(4-fluoropyridin-2-yl)-3-((13S,15R,E)-17-(hydroxyimino)-13-methyl-7,8,9,11,12,13,14,15,16,17-decahydro-6H-cyclopenta[a]phenanthren-15-yl)propanamide;
N-(3-fluoropyridin-2-yl)-3-((13S,15R,E)-17-(hydroxyimino)-13-methyl-7,8,9,11,12,13,14,15,16,17-decahydro-6H-cyclopenta[a]phenanthren-15-yl)propanamide;
3-((13S,15R,E)-3-chloro-17-(hydroxyimino)-13-methyl-7,8,9,11,12,13,14,15,16,17-decahydro-6H-cyclopenta[a]phenanthren-15-yl)-N-(3-fluoropyridin-2-yl)propanamide;
3-((13S,15R,E)-3-chloro-17-(hydroxyimino)-13-methyl-7,8,9,11,12,13,14,15,16,17-decahydro-6H-cyclopenta[a]phenanthren-15-yl)-N-(3,5-difluoropyridin-2-yl)propanamide;
N-(3,5-difluoropyridin-2-yl)-3-((13S,15R,E)-17-(hydroxyimino)-13-methyl-7,8,9,11,12,13,14,15,16,17-decahydro-6H-cyclopenta[a]phenanthren-15-yl)propanamide;
N-(6-fluoropyridin-2-yl)-3-((13S,15R,E)-17-(hydroxyimino)-13-methyl-7,8,9,11,12,13,14,15,16,17-decahydro-6H-cyclopenta[a]phenanthren-15-yl)propanamide;
3-((13S,15R,E)-3-chloro-17-(hydroxyimino)-13-methyl-7,8,9,11,12,13,14,15,16,17-decahydro-6H-cyclopenta[a]phenanthren-15-yl)-N-(6-fluoropyridin-2-yl)propanamide;
6-(3-((13S,15R,E)-3-chloro-17-(hydroxyimino)-13-methyl-7,8,9,11,12,13,14,15,16,17-decahydro-6H-cyclopenta[a]phenanthren-15-yl)propanamido)-N,N-dimethylnicotinamide;
3-((13S,15R,E)-3-chloro-17-(hydroxyimino)-13-methyl-7,8,9,11,12,13,14,15,16,17-decahydro-6H-cyclopenta[a]phenanthren-15-yl)-N-(2-oxo-1,2,5,6,7,8-hexahydroquinolin-3-yl)propanamide;
6-(3-((13S,15R,E)-4-fluoro-17-(hydroxyimino)-13-methyl-7,8,9,11,12,13,14,15,16,17-decahydro-6H-cyclopenta[a]phenanthren-15-yl)propanamido)-N,N-dimethylnicotinamide;
3-((13S,15R,E)-4-fluoro-17-(hydroxyimino)-13-methyl-7,8,9,11,12,13,14,15,16,17-decahydro-6H-cyclopenta[a]phenanthren-15-yl)-N-(2-oxo-1,2,5,6,7,8-hexahydroquinolin-3-yl)propanamide;

or a pharmaceutically acceptable salt thereof.

12. The compound as claimed in claim 11 selected from the group consisting of:
3-((13S,15R,E)-4-fluoro-17-(hydroxyimino)-13-methyl-7,8,9,11,12,13,14,15,16,17-decahydro-6H-cyclopenta[a]phenanthren-15-yl)-N-(5-methoxypyridin-2-yl)propanamide;
3-((13S,15R,E)-4-fluoro-17-(hydroxyimino)-13-methyl-7,8,9,11,12,13,14,15,16,17-decahydro-6H-cyclopenta[a]phenanthren-15-yl)-N-(5-fluoropyridin-2-yl)propanamide;

or a pharmaceutically acceptable salt thereof.

13. A method for alleviating the symptoms of or ameliorating a disease or condition selected from the group consisting of: breast cancer, prostate carcinoma, ovarian cancer, uterine cancer, endometrial cancer, endometrial hyperplasia, endometriosis, uterine fibroids, adenomyosis, polycystic ovarian syndrome, dysmenorrhea, menorrhagia, metrorrhagia, contraception, prostadynia, benign prostatic hyperplasia, urinary dysfunction, lower urinary tract symptoms, chronic prostatitis/chronic pelvic pain syndrome (CP/CPPS), obesity, chronic obstructive pulmonary disease (COPD), lung cancer, colon cancer, tissue wounds, skin wrinkles, and cataracts in a patient in need thereof, comprising administering the compound as claimed in claim 1 to the patient, or administering the compound as claimed in claim 1 as a contraceptive.

14. A pharmaceutical composition comprising an effective amount of one or more compounds as claimed in claim 1, together with one or more pharmaceutically acceptable excipient(s).

15. A pharmaceutical composition as claimed in claim 14, further comprising one or more other active ingredients.

16. A method for the preparation of a compound of formula (I) as defined in claim 1, comprising the steps of:

reacting a compound of formula (III)

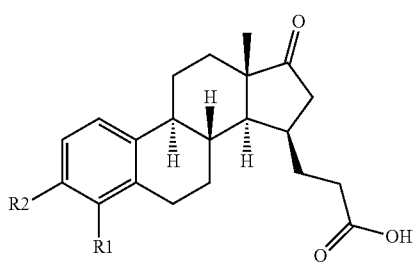

(III)

wherein R1 and R2 are each independently selected from the group consisting of H and halogen;

with a compound of formula (IV)

NR3R4          (IV)

wherein R3 and R4 are as defined for compound of formula (I), in the presence of amide bond forming reagents, to obtain a compound of formula (II), and reacting the obtained compound with

NH$_2$—OH          (V)

or hydrogen halide thereof, in the presence of a base, to obtain a compound of formula (I); and optionally converting the compound of formula (I) to a pharmaceutically acceptable salt thereof.

17. A compound of formula (I)

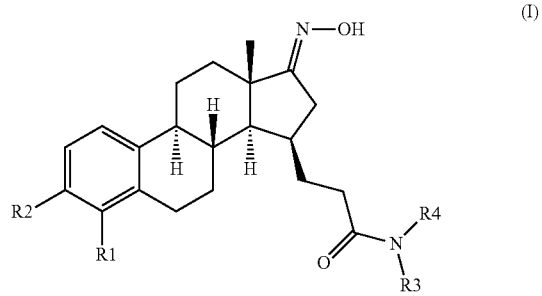

(I)

wherein R1 and R2 are each independently selected from the group consisting of H and halogen;

R3 is selected from the group consisting of H and C1-3-alkyl; and

R4 is selected from the group consisting of oxetanyl, pyrrolidinyl, piperidinyl, tetrahydropyranyl, dihydrothiazolyl, thiadiazolyl, oxazolyl, methyloxazolyl, pyridinyl, fluoropyridinyl, cyanopyridinyl, methylpyridinyl, dimethylpyridinyl, isopropylpyridinyl, hydroxypyridinyl, methoxypyridinyl, morpholinopyridinyl, methylpiperazinylpyridinyl, pyrazinyl, methylpyridazinyl, and methoxypyridazinyl, or a pharmaceutically acceptable salt thereof.

18. A method for alleviating the symptoms of or ameliorating a disease or condition selected from the group consisting of: breast cancer, prostate carcinoma, ovarian cancer, uterine cancer, endometrial cancer, endometrial hyperplasia, endometriosis, uterine fibroids, adenomyosis, polycystic ovarian syndrome, dysmenorrhea, menorrhagia, metrorrhagia, contraception, prostadynia, benign prostatic hyperplasia, urinary dysfunction, lower urinary tract symptoms, chronic prostatitis/chronic pelvic pain syndrome (CP/CPPS), obesity, chronic obstructive pulmonary disease (COPD), lung cancer, colon cancer, tissue wounds, skin wrinkles, and cataracts, in a patient in need thereof, comprising administering the compound as claimed in claim 17 to the patient, or administering the compound as claimed in claim 17 as a contraceptive.

19. A pharmaceutical composition comprising an effective amount of one or more compounds as claimed in claim 17, together with one or more pharmaceutically acceptable excipient(s).

20. A pharmaceutical composition as claimed in claim 19, further comprising one or more other active ingredients.

\* \* \* \* \*